(12) United States Patent
Alexandrino et al.

(10) Patent No.: US 11,566,270 B2
(45) Date of Patent: *Jan. 31, 2023

(54) METHOD FOR THE IN VIVO SYNTHESIS OF 4-HYDROXYMETHYLFURFURAL AND DERIVATIVES THEREOF

(71) Applicant: Braskem S.A., Sao Paulo (BR)

(72) Inventors: Paulo Moises Raduan Alexandrino, Campinas (BR); Iuri Estrada Gouvea, Campinas (BR); Veronica Leite Queiroz, Campinas (BR); Felipe Cicaroni Fernandes, Campinas (BR); Bárbara Mano, Campinas (BR)

(73) Assignee: BRASKEM S.A., Sao Paulo (BR)

( * ) Notice: Subject to any disclaimer, the term of this patent is extended or adjusted under 35 U.S.C. 154(b) by 120 days.

This patent is subject to a terminal disclaimer.

(21) Appl. No.: 17/219,792

(22) Filed: Mar. 31, 2021

(65) Prior Publication Data

US 2021/0238639 A1 Aug. 5, 2021

Related U.S. Application Data

(63) Continuation of application No. 16/806,728, filed on Mar. 2, 2020, now Pat. No. 11,339,414.

(60) Provisional application No. 62/812,904, filed on Mar. 1, 2019.

(51) Int. Cl.

| | | |
|---|---|---|
| *C12P 17/04* | (2006.01) | |
| *C07D 307/68* | (2006.01) | |
| *C12N 9/88* | (2006.01) | |
| *C12N 9/04* | (2006.01) | |
| *C12N 9/02* | (2006.01) | |
| *C12N 9/08* | (2006.01) | |
| *C12N 9/16* | (2006.01) | |

(52) U.S. Cl.
CPC ............ *C12P 17/04* (2013.01); *C07D 307/68* (2013.01); *C12N 9/0006* (2013.01); *C12N 9/0008* (2013.01); *C12N 9/0065* (2013.01); *C12N 9/16* (2013.01); *C12N 9/88* (2013.01); *C12Y 101/01* (2013.01); *C12Y 102/01* (2013.01); *C12Y 101/01001* (2013.01); *C12Y 101/03* (2013.01); *C12Y 102/01003* (2013.01); *C12Y 102/01004* (2013.01); *C12Y 102/01005* (2013.01); *C12Y 207/01* (2013.01); *C12Y 301/03* (2013.01); *C12Y 402/03* (2013.01)

(58) Field of Classification Search
None
See application file for complete search history.

(56) References Cited

FOREIGN PATENT DOCUMENTS

WO WO-2016133384 8/2016

OTHER PUBLICATIONS

Bio-Based Furan Dicarboxylic Acid (FDCA) and Its Polymer Polyethylene Furanoate (PEF). Pep Report 294—IHS Chemical, Dec. 2015.
Bobik, Thomas A., et al. "Structure of the methanofuran/methanopterin-biosynthetic enzyme MJ1099 from *Methanocaldococcus jannaschii*." Acta Crystallographica Section F: Structural Biology Communications 70.11 (2014): 1472-1479.
Bourdet, Aurelie, et al. "Molecular Mobility in Amorphous Biobased Poly (ethylene 2, 5-furandicarboxylate) and Poly (ethylene 2, 4-furandicarboxylate)." Macromolecules 51.5 (2018): 1937-1945.
Brown, Caroline, "The Mechanism of the Enzymatic Synthesis of 2,4-hydroxymethfufural phosphate", University of North Georgia, Honor Thesis, 44, Jan. 1, 2019 (019-01-01), pp. 1-39, XP055700512, Retrieved from the Internet: URL:https://digitalcommons.northgeorgia.edu/cgi/viewcontent.cgi?article=1044&context=honors_theses [retrieved on Jun. 3, 2020] p. 6-p. 14; figures 2, 4, 5.
Carro, Juan, et al., "5-hyrdoxymethylfurfural conversion by fungal aryl-alcohol oxidase and unspecific peroxygenase", FEBS Journal, vol. 282, No. 16, Jan. 8, 2015 (Jan. 8, 2015), pp. 3218-3229, XP055555047, GB ISSN: 1742-464X, DOI: 10.1111/febs.13177 cited in the application abstract p. 3219, right-hand col. paragraph 2—p. 3222, right-hand column, paragraph 3; figures 1-4,7; tables 1,2.
Cui, Min-Shu, et al. "Production of 4-hydroxymethylfurfural from derivatives of biomass-derived glycerol for chemicals and polymers." ACS Sustainable Chemistry & Engineering 4.3 (2016): 1707-1714.
Dijkman, Willem, et al., "Discovery and Characterization of a 5-Hydroxymethylfurfural Oxidase from *Methylovorus sp.* Strain MP688", Applied and Environmental Microbiology, vol. 80, No. 3, Feb. 1, 2014 (Feb. 1, 2014), pp. 1082-1090, XP055700609, U.S. ISSN: 0099-2240, DOI: 10.1128/AEM.03740-13 abstract; figure 1 p. 1084, right-hand column paragraph 4—p. 1087, right hand column, paragraph 1; table 1.
Hossain, Gazi Sakir, et al. "Metabolic engineering of *Raoultella omithinolytica* BF60 for the production of 2,5-furandicarboxylic acid from 5-hydroxymethylfurfural." Applied and environmental microbiology (2016): AEM-02312.

(Continued)

*Primary Examiner* — Robert B Mondesi
*Assistant Examiner* — Todd M Epstein
(74) *Attorney, Agent, or Firm* — Morgan, Lewis & Bockius LLP

(57) ABSTRACT

The present disclosure provides recombinant microorganisms and methods for the production of 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and/or 2,4-FDCA from a carbon source. The method provides for engineered microorganisms that express endogenous and/or exogenous nucleic acid molecules that catalyze the conversion of a carbon source into 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and/or 2,4-FDCA. The disclosure further provides methods of producing polymers derived from 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and/or 2,4-FDCA.

14 Claims, 16 Drawing Sheets

Specification includes a Sequence Listing.

(56) References Cited

OTHER PUBLICATIONS

International Search Report and Written Opinion for Application No. PCT/BR2020/050064, dated Jun. 17, 2020, 16 pages.
Koopman, Frank, et al. "Efficient whole-cell biotransformation of 5-(hydroxymethyl)furfural into FDCA, 2,5-furandicarboxylic acid." Bioresource technology 101.16 (2010): 6291-6296.
Miller, Danielle, et al. "Biosynthesis of the 5-(aminomethyl)-3-furanmethanol moiety of methanofuran." Biochemistry 53.28 (2014): 4635-4647.
Sousa, Andreia F., et al. "Biobased polyesters and other polymers from 2,5-furandicarboxylic acid: a tribute to furan excellency." Polymer chemistry 6.33 (2015): 5961-5983.
Thiyagarajan, Shanmugam, et al. "Biobased furandicarboxylic acids (FDCAs): effects of isomeric substitution on polyester synthesis and properties." Green Chemistry 16.4 (2014): 1957-1966.
Thiyagarajan, Shanmugam, et al. "Concurrent formation of furan-2,5- and furan-2,4-dicarboxylicacid: unexpected aspects of the Henkel reaction", RSC Advances, vol. 3, Jan. 1, 2013 (Jan. 1, 2013), pp. 15678-15686, XP007923218, ISSN: 2046-2069, DOI: 10.1039/C3RA424257J cited in the application abstract; figure 1 Scheme 4.
Wang, Yu, et al. "Industrial production, application, microbial biosynthesis and degradation of furanic compound, hydroxymethylfurfural (HMF)", AIMS Microbiology, vol. 4, No. 2, Jan. 1, 2018 (Jan. 10, 2018), pp. 261-273, XP055700144, ISSN: 2471-1888, DOI: 10.3934/microbiol.2018.2.261 abstract p. 263, paragraph 1; figures 1, 3, 4.
Wang, Yu, et al. "Mechanism of the enzymatic synthesis of 4-(hydroxymethyl)-2-furancarboxaldehyde-phosphate (4-HFC-P) from glyceraldehyde-3-phosphate catalyzed by 4-HFC-P synthase." Biochemistry 54.19 (2015): 2997-3008.
Zaidi, Sami, et al. "Highly transparent films of new copolyesters derived from terephthalic and 2,4-furandicarboxylic acids", Polymer Chemistry, vol. 10, No. 39, Jan. 1, 2019 (Jan. 10, 2019), pp. 5324-5332, XP055700937, ISSN: 1759-9954, DOI: 10.1039/C9PY00844F abstract schema 1 and 2; tables 1, 2.

SEQUENCE LISTING

<160> NUMBER OF SEQ ID NOS: 92

<210> SEQ ID NO 1
<211> LENGTH: 235
<212> TYPE: PRT
<213> ORGANISM: Methanocaldococcus jannaschii MfnB 1

<400> SEQUENCE: 1

Met Ile Leu Leu Val Ser Pro Ile Asp Val Glu Glu Ala Lys Glu Ala
1               5                   10                  15

Ile Ala Gly Gly Ala Asp Ile Ile Asp Val Lys Asn Pro Lys Glu Gly
                20                  25                  30

Ser Leu Gly Ala Asn Phe Pro Trp Met Ile Lys Ala Ile Arg Glu Val
            35                  40                  45

Thr Pro Lys Asp Leu Leu Val Ser Ala Thr Val Gly Asp Val Pro Tyr
        50                  55                  60

Lys Pro Gly Thr Ile Ser Leu Ala Ala Val Gly Ala Ala Ile Ser Gly
65                  70                  75                  80

```
Ala Asp Tyr Ile Lys Val Gly Leu Tyr Gly Val Lys Asn Tyr Tyr Gln
                85                  90                  95

Ala Val Glu Leu Met Lys Asn Val Val Arg Ala Val Lys Asp Ile Asp
            100                 105                 110

Glu Asn Lys Ile Val Val Ala Ala Gly Tyr Ala Asp Ala Tyr Arg Val
        115                 120                 125

Gly Ala Val Glu Pro Leu Ile Val Pro Lys Ile Ala Arg Asp Ala Gly
    130                 135                 140

Cys Asp Val Ala Met Leu Asp Thr Ala Ile Lys Asp Gly Lys Thr Leu
145                 150                 155                 160

Phe Asp Phe Gln Ser Lys Glu Ile Leu Ala Glu Phe Val Asp Glu Ala
                165                 170                 175

His Ser Tyr Gly Leu Lys Cys Ala Leu Ala Gly Ser Ile Lys Lys Glu
            180                 185                 190

His Ile Pro Ile Leu Lys Glu Ile Gly Thr Asp Ile Val Gly Val Arg
        195                 200                 205

Gly Ala Ala Cys Lys Gly Gly Asp Arg Asn Asn Gly Arg Ile Asp Arg
    210                 215                 220

Glu Leu Val Lys Glu Leu Lys Glu Leu Cys Lys
225                 230                 235

<210> SEQ ID NO 2
<211> LENGTH: 235
<212> TYPE: PRT
<213> ORGANISM: Methanocaldococcus fervens MfnB 2

<400> SEQUENCE: 2

Met Ile Leu Leu Val Ser Pro Ile Asp Val Glu Glu Ala Lys Glu Ala
1               5                   10                  15

Ile Ala Gly Gly Ala Asp Ile Ile Asp Val Lys Asn Pro Lys Glu Gly
            20                  25                  30

Ser Leu Gly Ala Asn Phe Pro Trp Met Ile Lys Ala Ile Arg Glu Val
        35                  40                  45

Thr Pro Lys Glu Leu Leu Val Ser Ala Thr Val Gly Asp Val Pro Phe
    50                  55                  60

Lys Pro Gly Thr Ile Ser Leu Ala Ala Val Gly Ala Ala Ile Ser Gly
65                  70                  75                  80

Ala Asp Tyr Ile Lys Val Gly Leu Tyr Gly Val Lys Asn Tyr Tyr Glu
                85                  90                  95

Gly Val Glu Leu Met Lys Asn Val Val Arg Ala Val Lys Asp Ile Asp
            100                 105                 110

Glu Asn Lys Ile Val Val Ala Ala Gly Tyr Ala Asp Ala His Arg Val
        115                 120                 125

Gly Ala Val Glu Pro Leu Ile Ile Pro Lys Ile Ala Arg Asp Ala Gly
    130                 135                 140

Cys Asp Val Ala Met Leu Asp Thr Ala Val Lys Asp Gly Lys Thr Leu
145                 150                 155                 160

Phe Asp Phe Gln Ser Lys Glu Ile Leu Glu Glu Phe Val Gln Glu Ser
                165                 170                 175

His Asp Tyr Gly Leu Lys Cys Ala Leu Ala Gly Ser Ile Lys Lys Glu
            180                 185                 190

His Ile Pro Ile Leu Lys Glu Ile Gly Thr Asp Ile Val Gly Val Arg
        195                 200                 205

Gly Ala Val Cys Lys Gly Gly Asp Arg Asn Asn Gly Arg Ile Asp Arg
```

```
                210                 215                 220
Glu Leu Val Arg Glu Leu Lys Glu Leu Cys Lys
225                 230                 235

<210> SEQ ID NO 3
<211> LENGTH: 234
<212> TYPE: PRT
<213> ORGANISM: Methanocaldococcus vulcanius MfnB 3

<400> SEQUENCE: 3

Met Ile Leu Leu Val Ser Pro Ile Asp Val Asp Glu Ala Arg Glu Ala
1               5                   10                  15

Ile Ala Gly Gly Ala Asp Ile Ile Asp Val Lys Asn Pro Lys Glu Gly
            20                  25                  30

Ser Leu Gly Ala Asn Phe Pro Trp Met Ile Lys Ala Ile Arg Glu Ile
        35                  40                  45

Thr Pro Lys Glu Leu Leu Val Ser Ala Thr Val Gly Asp Val Pro Tyr
    50                  55                  60

Lys Pro Gly Thr Val Ser Leu Ala Ser Val Gly Ala Ala Met Ser Gly
65                  70                  75                  80

Ala Asp Tyr Ile Lys Val Gly Leu Tyr Gly Val Lys Asn Tyr Tyr Glu
                85                  90                  95

Ala Val Glu Leu Met Lys Asn Val Val Arg Ala Val Lys Asp Val Asp
            100                 105                 110

Glu Asn Lys Ile Val Val Ala Ala Gly Tyr Ala Asp Ala His Arg Val
        115                 120                 125

Gly Ala Val Asp Pro Leu Ile Ile Pro Lys Ile Ala Arg Asp Ala Asp
    130                 135                 140

Cys Asp Val Ala Met Leu Asp Thr Ala Ile Lys Asp Gly Lys Thr Leu
145                 150                 155                 160

Phe Asp Phe Gln Ser Lys Glu Ile Leu Glu Glu Phe Val Glu Glu Thr
                165                 170                 175

His Ser Tyr Gly Leu Lys Cys Ala Leu Ala Gly Ser Ile Lys Lys Glu
            180                 185                 190

His Ile Pro Ile Leu Lys Glu Ile Gly Thr Asp Ile Val Gly Val Arg
        195                 200                 205

Gly Ala Val Cys Lys Gly Gly Asp Arg Asn Lys Gly Arg Ile Asp Arg
    210                 215                 220

Asn Leu Val Lys Glu Leu Lys Glu Leu Val
225                 230

<210> SEQ ID NO 4
<211> LENGTH: 234
<212> TYPE: PRT
<213> ORGANISM: Methanocaldococcus infernus  MfnB 3

<400> SEQUENCE: 4

Met Leu Leu Leu Val Ser Pro Ile Asp Val Glu Glu Ala Lys Glu Ala
1               5                   10                  15

Ile Glu Gly Gly Ala Asp Ile Ile Asp Val Lys Asn Pro Lys Glu Gly
            20                  25                  30

Ser Leu Gly Ala Asn Phe Pro Trp Val Ile Arg Glu Val Arg Lys Ile
        35                  40                  45

Thr Pro Lys Ser Leu Leu Val Ser Ala Thr Val Gly Asp Val Pro Tyr
    50                  55                  60

Lys Pro Gly Thr Val Ser Leu Ala Ala Leu Gly Ala Gly Met Ser Gly
```

```
            65                  70                  75                  80
Ala Asp Tyr Ile Lys Val Gly Leu Tyr Gly Val Lys Asn Tyr Asn Gln
                85                  90                  95

Ala Val Glu Leu Met Lys Ser Val Val Lys Ala Val Lys Asp Phe Asp
            100                 105                 110

Asp Asn Lys Ile Val Val Ala Ala Gly Tyr Ala Asp Ala Tyr Arg Val
            115                 120                 125

Gly Ala Val Asp Pro Leu Val Ile Pro Lys Ile Ala Arg Asp Ser Gly
130                 135                 140

Ala Asp Val Ala Met Leu Asp Thr Ala Ile Lys Asp Gly Lys Thr Leu
145                 150                 155                 160

Phe Asp Phe Leu Ser Lys Glu Ile Leu Glu Glu Phe Val Ser Glu Val
                165                 170                 175

His Asp Tyr Gly Leu Lys Cys Ala Leu Ala Gly Thr Ile Lys Lys Asp
                180                 185                 190

His Ile Pro Ile Leu Lys Glu Ile Gly Thr Asp Ile Val Gly Val Arg
                195                 200                 205

Gly Ala Ala Cys Lys Gly Gly Asp Arg Asn Lys Gly Arg Ile Asp Arg
210                 215                 220

Asn Leu Val Arg Glu Leu Lys Glu Leu Cys
225                 230

<210> SEQ ID NO 5
<211> LENGTH: 235
<212> TYPE: PRT
<213> ORGANISM: Methanothermococcus okinawensis MfnB 5

<400> SEQUENCE: 5

Met Ile Leu Leu Val Ser Pro Lys Asp Val Asn Glu Ala Ile Glu Thr
1               5                   10                  15

Ile Lys Gly Gly Ala Asp Ile Val Asp Val Lys Asn Pro Pro Glu Gly
                20                  25                  30

Ser Leu Gly Ala Asn Phe Pro Trp Ile Ile Lys Glu Ile Arg Glu Ile
            35                  40                  45

Thr Pro Lys Asn Leu Phe Val Ser Ala Ala Ile Gly Asp Val Pro Tyr
        50                  55                  60

Lys Pro Gly Thr Val Ala Leu Ala Ala Leu Gly Ala Ala Met Ser Gly
65                  70                  75                  80

Ala Asp Tyr Ile Lys Val Gly Leu Tyr Gly Thr Lys Ser Tyr Asn Glu
                85                  90                  95

Ala Val Asp Leu Met Glu Lys Val Val Lys Ala Val Lys Gly Val Asp
            100                 105                 110

Glu Asn Lys Ile Val Val Ala Ala Gly Tyr Ala Asp Ala His Arg Val
            115                 120                 125

Gly Ala Val Glu Pro Leu Ile Val Pro Lys Ile Ala Arg Asp Ala Gly
130                 135                 140

Cys Asp Val Ala Met Leu Asp Thr Ala Val Lys Asp Gly Lys Thr Leu
145                 150                 155                 160

Phe Asp His Leu Asn Glu Lys Ile Leu Ala Glu Phe Val Glu Glu Thr
                165                 170                 175

His Ser Tyr Gly Leu Lys Cys Ala Leu Ala Gly Ser Ile Lys Lys Glu
                180                 185                 190

Glu Ile Pro Ile Leu Lys Asp Ile Asn Cys Asp Ile Val Gly Val Arg
                195                 200                 205
```

Gly Ala Ala Cys Thr Lys Gly Asp Arg Asn Asn Gly Thr Ile Lys Ser
210                 215                 220

Glu Leu Val Lys Glu Leu Ser Lys Leu Cys Lys
225                 230                 235

<210> SEQ ID NO 6
<211> LENGTH: 239
<212> TYPE: PRT
<213> ORGANISM: Methanococcales archaeon HHB MfnB 6

<400> SEQUENCE: 6

Met Arg Ile Leu Ile Ser Pro Lys Asp Ile Glu Glu Ala Lys Glu Ala
1               5                   10                  15

Ile Glu Gly Gly Ala Asp Ile Ile Asp Val Lys Asn Pro Leu Glu Gly
                20                  25                  30

Ser Leu Gly Ala Asn Phe Pro Trp Val Ile Arg Glu Ile Arg Asn Ile
            35                  40                  45

Thr Pro Lys Asp Arg Leu Val Ser Ala Thr Val Gly Asp Val Pro Tyr
        50                  55                  60

Lys Pro Gly Thr Val Ala Leu Ala Ala Val Gly Ala Ala Ile Ser Gly
65                  70                  75                  80

Ala Asp Tyr Ile Lys Val Gly Leu Tyr Gly Thr Lys Ser Tyr Arg Glu
                85                  90                  95

Ala Val Asp Val Met Asn Lys Val Val Lys Ala Val Lys Glu Ile Asp
            100                 105                 110

Glu Asn Lys Ile Val Val Ala Ala Gly Tyr Ala Asp Ala Tyr Arg Val
        115                 120                 125

Gly Ala Val Asp Pro Leu Ile Ile Pro Lys Val Ala Arg Asp Ser Gly
130                 135                 140

Cys Asp Val Ala Met Leu Asp Thr Ala Val Lys Asp Gly Lys Arg Leu
145                 150                 155                 160

Phe Asp His Leu Asn Arg Glu Leu Ile Ser Glu Phe Val Glu Glu Val
                165                 170                 175

His Asn Tyr Gly Leu Glu Cys Ala Leu Ala Gly Ser Ile Arg Lys Glu
            180                 185                 190

Asp Ile Pro Val Leu Lys Glu Ile Gly Cys Asp Ile Val Gly Ile Arg
        195                 200                 205

Gly Ala Ala Cys Thr Lys Gly Asp Arg Asn Asn Gly Lys Ile Lys Lys
210                 215                 220

Glu Leu Val Glu Glu Leu Val Lys Leu Cys Lys Asn Gly Asp Lys
225                 230                 235

<210> SEQ ID NO 7
<211> LENGTH: 237
<212> TYPE: PRT
<213> ORGANISM: Methanobrevibacter smithii MfnB 7

<400> SEQUENCE: 7

Met Leu Leu Leu Ile Ser Pro Ile Asn His Glu Glu Ala Leu Glu Ser
1               5                   10                  15

Ile Lys Gly Gly Ala Asp Ile Val Asp Val Lys Asn Pro Lys Glu Gly
                20                  25                  30

Ser Leu Gly Ala Asn Phe Pro Trp Val Ile Arg Asp Ile Arg Glu Ile
            35                  40                  45

Thr Pro Glu Asp Lys Leu Val Ser Ala Thr Leu Gly Asp Val Pro Tyr
        50                  55                  60

Lys Pro Gly Thr Val Ser Leu Ala Ala Met Gly Ala His Val Ser Gly
65                  70                  75                  80

Ala Asp Tyr Ile Lys Val Gly Leu Tyr Gly Thr Lys Asp Tyr Asp Glu
                85                  90                  95

Ala Val Glu Val Met Glu Asn Val Ala Lys Thr Ile Lys Asp Val Asp
            100                 105                 110

Asn Asp Thr Ile Val Val Ala Ala Gly Tyr Ala Asp Ala His Arg Val
        115                 120                 125

Gly Ala Val Asp Pro Met Glu Ile Pro Lys Val Ala Lys Asp Ala Gly
    130                 135                 140

Cys Asp Leu Ala Met Leu Asp Thr Ala Val Lys Asp Gly His Thr Leu
145                 150                 155                 160

Phe Asp Tyr Leu Ser Ile Glu Asp Leu Glu Lys Phe Val Asn Glu Ala
                165                 170                 175

His Ser Tyr Gly Leu Lys Thr Ala Leu Ala Gly Ser Val Lys Lys Glu
            180                 185                 190

Gln Leu Lys Pro Leu Asn Asp Ile Gly Cys Asp Val Val Gly Ile Arg
        195                 200                 205

Gly Ala Ala Cys Val Gly Gly Asp Arg Asn Thr Gly Lys Ile His His
    210                 215                 220

Ser Ala Val Ala Glu Leu Lys Glu Leu Cys Asp Ser Phe
225                 230                 235

<210> SEQ ID NO 8
<211> LENGTH: 234
<212> TYPE: PRT
<213> ORGANISM: Methanobacterium sp. PtaB.Bin024 MfnB 8

<400> SEQUENCE: 8

Met Leu Leu Leu Ile Ser Pro Ile Asn Thr Gln Glu Ala Arg Glu Ala
1               5                   10                  15

Ile Asp Gly Gly Ala Asp Ile Val Asp Val Lys Asn Pro Lys Glu Gly
            20                  25                  30

Ser Leu Gly Ala Asn Phe Pro Trp Val Ile Arg Asn Ile Arg Glu Ile
        35                  40                  45

Thr Pro Lys Asn Met Lys Val Ser Ala Thr Leu Gly Asp Val Pro Tyr
50                  55                  60

Lys Pro Gly Thr Val Ala Leu Ala Ala Gly Ala Ile Val Ser Gly
65                  70                  75                  80

Ala Asp Tyr Ile Lys Val Gly Leu Tyr Gly Thr Thr Asn Tyr Ser Glu
                85                  90                  95

Ala Leu Glu Val Met Glu Asn Val Val Lys Thr Val Asp Glu Phe Asn
            100                 105                 110

Ser Asp Ala Ile Val Val Ala Ala Gly Tyr Ala Asp Ala His Arg Val
        115                 120                 125

Gly Ala Val Asp Pro Met Glu Ile Pro Lys Ile Ala Ala Asp Ser Gly
    130                 135                 140

Ser Asp Leu Ala Met Val Asp Thr Ala Val Lys Asp Gly Lys Thr Leu
145                 150                 155                 160

Phe Asp Phe Met Asn Glu Glu Thr Leu Ser Gln Phe Thr Glu Gln Thr
                165                 170                 175

His Glu Tyr Gly Leu Lys Ser Ala Leu Ala Gly Ser Val Thr Glu Glu
            180                 185                 190

Gln Leu Pro Ile Leu Ala Glu Leu Gly Cys Asp Val Val Gly Ile Arg
        195                 200                 205

Gly Ala Ala Cys Ile Gly Gly Asp Arg Asn Ser Gly Ser Ile His His
            210                 215                 220

Glu Ala Val Ala Arg Leu Lys Gln Ile Val
225                 230

<210> SEQ ID NO 9
<211> LENGTH: 237
<212> TYPE: PRT
<213> ORGANISM: Methanopyrus sp. KOL6 MfnB 9

<400> SEQUENCE: 9

Met Arg Pro Arg Leu Leu Val Ser Pro Val Asn Arg Asp Glu Ala Leu
1               5                   10                  15

Glu Ala Val Glu Gly Gly Ala His Ile Ile Asp Val Lys Asn Pro Glu
                20                  25                  30

Glu Gly Ser Leu Gly Ala Asn Phe Pro Trp Val Ile Arg Glu Ile Met
            35                  40                  45

Glu Val Val Pro Glu Asp Arg Glu Val Ser Ala Thr Val Gly Asp Val
        50                  55                  60

Pro Tyr Lys Pro Gly Thr Val Ala Gln Ala Val Leu Gly Val Ala Ala
65                  70                  75                  80

Val Gly Val Asp Tyr Ala Lys Val Gly Leu Tyr Gly Thr Lys Thr Glu
                85                  90                  95

Glu Glu Ala Leu Glu Val Met Arg Ala Cys Ser Arg Ala Val Arg Glu
            100                 105                 110

Phe Gly Tyr Asp Thr Arg Val Val Ala Ala Gly Tyr Ala Asp Ala His
        115                 120                 125

Arg Val Asp Ser Ile Asp Pro Met Ser Val Pro Glu Val Ala Ala Glu
130                 135                 140

Ala Glu Cys Asp Val Ala Met Val Asp Thr Ala Val Lys Asp Gly Lys
145                 150                 155                 160

Arg Leu Phe Asp Phe Leu Arg Glu Glu Val Gly Glu Phe Val Asp
                165                 170                 175

Leu Ala His Glu His Gly Leu Val Ala Leu Ala Gly Ser Leu Arg
            180                 185                 190

His Glu Asp Met Pro Ile Val Arg Asp Leu Gly Ala Asp Ile Val Gly
        195                 200                 205

Ile Arg Gly Ala Ala Cys Glu Arg Gly Asp Arg Asn Arg Gly Ala Ile
            210                 215                 220

Arg Ser His Leu Val Arg Lys Leu Ala Glu Ala Leu Ala
225                 230                 235

<210> SEQ ID NO 10
<211> LENGTH: 234
<212> TYPE: PRT
<213> ORGANISM: Candidatus Argoarchaeum ethanivorans MfnB 10

<400> SEQUENCE: 10

Met Thr Met Lys Leu Leu Val Ser Pro Ile Ser Val Glu Glu Ala Arg
1               5                   10                  15

Ile Ala Leu Asp Gly Gly Ala Asp Ile Ile Asp Val Lys Asn Pro Lys
                20                  25                  30

Glu Gly Ser Leu Gly Ala Asn Phe Pro Asp Val Ile Gln Ser Val Lys
            35                  40                  45

Arg Val Ile Thr Lys Pro Met Ser Val Ala Ile Gly Asp Phe Asn Tyr
        50                  55                  60

```
Lys Pro Gly Thr Ala Ser Leu Ala Ala Leu Gly Ala Ser Val Ala Gly
 65                  70                  75                  80

Ala Asp Tyr Ile Lys Ile Gly Leu Phe Asp Val Gln Thr Arg Glu Gln
                 85                  90                  95

Ala Ser Glu Met Thr Glu Arg Val Thr Lys Ala Val Lys Gln Tyr Asp
            100                 105                 110

Ser Lys Lys Val Val Ile Cys Gly Tyr Ser Asp Tyr Asn Arg Ile
        115                 120                 125

Asn Ser Ile Ser Pro Phe Glu Leu Pro Gly Ile Val Ser Asp Ala Gly
        130                 135                 140

Ala Asp Val Val Met Met Asp Thr Gly Val Lys Asp Gly Arg Ser Thr
145                 150                 155                 160

Leu Glu Phe Leu Asn Leu Glu Lys Leu Glu Ser Phe Ile Gly Ser Ala
                165                 170                 175

His Gln Tyr Gly Leu Leu Ala Ala Ile Ala Gly Ser Leu Thr Phe Glu
            180                 185                 190

Asp Ile Glu Ala Leu Lys Glu Val Ala Pro Asp Ile Ile Gly Val Arg
            195                 200                 205

Gly Cys Val Cys Gly Gly Asp Arg Asn Ser Ser Ile Lys Leu Glu Leu
            210                 215                 220

Val Arg Glu Leu Lys Glu Arg Ile His His
225                 230
```

<210> SEQ ID NO 11
<211> LENGTH: 237
<212> TYPE: PRT
<213> ORGANISM: Methanobacterium congolense MfnB 11

<400> SEQUENCE: 11

```
Met Leu Leu Leu Ile Ser Pro Ile Asn Thr Glu Glu Ala Arg Glu Ala
 1               5                  10                  15

Ile Glu Gly Gly Ala Asp Ile Val Asp Val Lys Asn Pro Lys Glu Gly
                 20                  25                  30

Ser Leu Gly Ala Asn Phe Pro Trp Val Ile Lys Ser Ile Ser Glu Leu
            35                  40                  45

Thr Pro Glu Gly Met Tyr Val Ser Ala Thr Leu Gly Asp Val Pro Tyr
 50                  55                  60

Lys Pro Gly Thr Val Ser Leu Ala Ala Ala Gly Ala Val Val Ser Gly
 65                  70                  75                  80

Ala Asp Tyr Ile Lys Val Gly Leu Tyr Gly Thr Lys Asn Tyr Glu Glu
                 85                  90                  95

Ala Leu Glu Val Met Lys Asn Val Val Lys Thr Val Lys Asp Phe Asn
            100                 105                 110

Glu Asp Ala Val Val Val Ala Ala Gly Tyr Ala Asp Ala His Arg Val
            115                 120                 125

Gly Ala Val Asp Pro Met Glu Ile Pro Arg Val Ala Asp Ala Gly
        130                 135                 140

Ala Asp Leu Ala Met Val Asp Thr Ala Val Lys Asp Gly Lys Thr Leu
145                 150                 155                 160

Phe Asp Phe Met Asp Glu Asp Thr Leu Thr Lys Phe Asn Asn Thr Ile
                165                 170                 175

His Asp Tyr Gly Leu Lys Ser Ala Leu Ala Gly Ser Val Lys Lys Glu
            180                 185                 190

Gln Leu Glu Met Leu Tyr Asn Ile Gly Cys Asp Val Val Gly Ile Arg
```

```
            195                 200                 205
Gly Ala Ala Cys Val Gly Gly Asp Arg Asn Thr Gly Lys Ile His Arg
    210                 215                 220

Ser Ala Val Gly Glu Leu Lys Lys Met Ile Glu Asn Phe
225                 230                 235

<210> SEQ ID NO 12
<211> LENGTH: 238
<212> TYPE: PRT
<213> ORGANISM: Methanobrevibacter arboriphilus MfnB 12

<400> SEQUENCE: 12

Met Leu Leu Ile Ser Pro Ile Asn Asn Glu Glu Ala Leu Glu Ser
1               5                   10                  15

Ile Glu Gly Gly Ala Asp Ile Val Asp Val Lys Asn Pro Lys Glu Gly
                20                  25                  30

Ser Leu Gly Ala Asn Phe Pro Trp Val Ile Ser Glu Ile Arg Lys Met
            35                  40                  45

Thr Pro Asp Asp Met Leu Val Ser Ala Thr Leu Gly Asp Val Pro Tyr
        50                  55                  60

Lys Pro Gly Thr Val Ser Leu Ala Ala Met Gly Ala Leu Thr Ser Gly
65                  70                  75                  80

Ala Asp Tyr Ile Lys Val Gly Leu Tyr Gly Thr Ser Asn Tyr Asp Glu
                85                  90                  95

Ala Leu Glu Val Met Thr Asn Val Val Lys Thr Val Lys Ser Asn Asn
            100                 105                 110

Pro Asn Ala Thr Val Val Ala Ser Gly Tyr Gly Asp Ala His Arg Val
        115                 120                 125

Gly Ala Val Ser Pro Trp Asp Ile Pro Lys Val Ala Lys Glu Ser Gly
    130                 135                 140

Ser Asp Leu Ala Met Leu Asp Thr Ala Val Leu Asp Gly Lys Thr Leu
145                 150                 155                 160

Phe Asp Tyr Leu Asn Ile Asp Asp Leu Lys Lys Phe Val Glu Glu Thr
                165                 170                 175

His Ser Tyr Gly Leu Lys Ser Ala Leu Ala Gly Ser Val Lys Lys Glu
            180                 185                 190

Gln Leu Lys Pro Leu Tyr Asp Ile Gly Cys Asp Val Val Gly Val Arg
        195                 200                 205

Gly Ala Ala Cys Thr Gly Gly Asp Arg Asn Asn Gly Lys Ile Ser Arg
    210                 215                 220

Thr Ala Val Ala Glu Leu Lys Glu Leu Val Asn Ser Phe Asp
225                 230                 235

<210> SEQ ID NO 13
<211> LENGTH: 236
<212> TYPE: PRT
<213> ORGANISM: Methanococcus maripaludis MfnB 13

<400> SEQUENCE: 13

Met Ile Leu Leu Val Ser Pro Lys Asp Val Ala Glu Ala His Glu Ala
1               5                   10                  15

Ile Glu Gly Gly Ala Asp Ile Ile Asp Val Lys Asn Pro Glu Gly
                20                  25                  30

Ser Leu Gly Ala Asn Phe Pro Trp Val Ile Lys Glu Thr Arg Glu Ala
            35                  40                  45

Thr Pro Glu Gly Met Leu Val Ser Ala Ala Ile Gly Asp Val Pro Tyr
```

```
            50                  55                  60
Lys Pro Gly Thr Val Thr Leu Ala Ala Leu Gly Ala Ala Ile Ser Gly
 65                  70                  75                  80

Ala Asp Tyr Ile Lys Val Gly Leu Tyr Gly Thr Arg Ser Tyr Gln Glu
                 85                  90                  95

Ala Leu Asp Val Met Lys Asn Val Thr Lys Ala Val Lys Asp Ser Gly
                100                 105                 110

Glu Asn Lys Ile Val Ala Ala Gly Tyr Ala Asp Ala Tyr Arg Val
                115                 120                 125

Gly Gly Val Asp Pro Leu Ile Ile Pro Arg Val Ala Arg Asp Ala Gly
                130                 135                 140

Cys Asp Val Ala Met Leu Asp Thr Ala Val Lys Asp Gly Lys Thr Leu
145                 150                 155                 160

Phe Asp His Met Ser Ile Glu Leu Leu Lys Glu Phe Val Glu Glu Thr
                165                 170                 175

His Lys Tyr Gly Met Lys Cys Ala Leu Ala Gly Ser Ile Lys Ile Glu
                180                 185                 190

Glu Ile Pro Met Leu Lys Glu Ile Asn Cys Asp Ile Val Gly Val Arg
                195                 200                 205

Gly Ala Ala Cys Thr Lys Gly Asp Arg Asn Glu Gly Arg Ile Gln Lys
                210                 215                 220

Asp Leu Val Lys Glu Ile Val Lys Val Cys Arg Gln
225                 230                 235

<210> SEQ ID NO 14
<211> LENGTH: 236
<212> TYPE: PRT
<213> ORGANISM: Methanococcus vannielii MfnB 14

<400> SEQUENCE: 14

Met Ile Leu Leu Val Ser Pro Lys Asp Val Ala Glu Ala Tyr Glu Ala
  1               5                  10                  15

Ile Asn Gly Gly Ala Asp Ile Ile Asp Val Lys Asn Pro Pro Glu Gly
                 20                  25                  30

Ser Leu Gly Ala Asn Phe Pro Trp Val Ile Lys Glu Ile Arg Ser Ala
                 35                  40                  45

Thr Pro Asn Gly Met Leu Val Ser Ala Ala Ile Gly Asp Val His Tyr
                 50                  55                  60

Lys Pro Gly Thr Val Thr Leu Ala Ala Leu Gly Ala Thr Ile Ser Gly
 65                  70                  75                  80

Ala Asp Tyr Ile Lys Ile Gly Leu Tyr Gly Thr Arg Ser Tyr Gln Glu
                 85                  90                  95

Ala Val Asp Val Met Lys Asn Val Ser Asn Ala Val Lys Ser Glu Asp
                100                 105                 110

Pro Lys Lys Ile Val Ala Ala Gly Tyr Ala Asp Ala Tyr Arg Val
                115                 120                 125

Gly Ala Val Asp Pro Leu Ile Ile Pro Lys Ile Ala Arg Asp Ser Gly
                130                 135                 140

Cys Asp Val Ala Met Leu Asp Thr Ala Val Lys Asp Gly Lys Thr Leu
145                 150                 155                 160

Phe Asp His Leu Ser Ile Asp Leu Leu Lys Glu Phe Val Glu Glu Thr
                165                 170                 175

His Lys Tyr Gly Met Lys Cys Ala Leu Ala Gly Ser Ile Lys Lys Glu
                180                 185                 190
```

```
Glu Ile Pro Met Leu Lys Glu Ile Gly Cys Asp Ile Gly Ile Arg
            195                 200                 205

Gly Ala Ala Cys Thr Lys Gly Asp Arg Asn Glu Gly Lys Ile Gln Lys
    210                 215                 220

Asp Leu Val Lys Glu Ile Val Lys Ile Cys Lys Glu
225                 230                 235

<210> SEQ ID NO 15
<211> LENGTH: 234
<212> TYPE: PRT
<213> ORGANISM: Methanosarcina acetivorans MfnB 15

<400> SEQUENCE: 15

Met Lys Leu Leu Val Ser Pro Ile Asn Arg Glu Glu Ala Ile Ile Ala
1               5                   10                  15

Ser Leu Gly Gly Ala Asp Ile Val Asp Val Lys Asn Pro Lys Glu Gly
            20                  25                  30

Ser Leu Gly Ala Asn Phe Pro Trp Val Ile Arg Asp Val Lys Glu Val
        35                  40                  45

Val Asn Gly Arg Gln Pro Ile Ser Ala Thr Ile Gly Asp Phe Asn Tyr
50                  55                  60

Lys Pro Gly Thr Ala Ser Leu Ala Ala Leu Gly Ala Ala Val Ala Gly
65                  70                  75                  80

Ala Asp Tyr Ile Lys Val Gly Leu Tyr Asp Ile Gln Thr Glu Ala Gln
                85                  90                  95

Ala Leu Glu Leu Leu Thr Lys Ile Thr Leu Ala Val Lys Asp Tyr Asp
            100                 105                 110

Pro Ser Lys Lys Val Val Ala Ser Gly Tyr Ser Asp Tyr Lys Arg Ile
        115                 120                 125

Asn Ser Ile Ser Pro Leu Leu Leu Pro Ala Val Ala Glu Ala Gly
130                 135                 140

Val Asp Val Val Met Val Asp Thr Gly Ile Lys Asp Gly Lys Ser Thr
145                 150                 155                 160

Phe Glu Phe Met Asp Glu Gln Glu Leu Lys Glu Phe Thr Asp Leu Ala
                165                 170                 175

His Glu His Gly Leu Glu Asn Ala Ile Ala Gly Ser Leu Lys Phe Glu
            180                 185                 190

Asp Leu Pro Val Leu Glu Arg Ile Gly Pro Asp Ile Ile Gly Val Arg
        195                 200                 205

Gly Met Val Cys Gly Asp Arg Arg Thr Ala Ile Arg Gln Glu Leu
    210                 215                 220

Val Glu Lys Leu Val Ala Glu Cys Gln Ile
225                 230

<210> SEQ ID NO 16
<211> LENGTH: 234
<212> TYPE: PRT
<213> ORGANISM: Methanosarcina barkeri MfnB 16

<400> SEQUENCE: 16

Met Lys Leu Leu Ile Ser Pro Ile Asn Lys Glu Glu Ala Ile Ile Ala
1               5                   10                  15

Ser Arg Gly Gly Ala Asp Ile Val Asp Val Lys Asn Pro Lys Glu Gly
            20                  25                  30

Ser Leu Gly Ala Asn Phe Pro Trp Val Ile Arg Asp Val Lys Gly Ala
        35                  40                  45
```

Val Asn Gly Arg Gln Pro Ile Ser Ala Thr Ile Gly Asp Phe Asn Tyr
 50                  55                  60

Lys Pro Gly Thr Ala Ser Leu Ala Ala Phe Gly Ala Ala Val Ala Gly
 65                  70                  75                  80

Ala Asp Tyr Ile Lys Val Gly Leu Tyr Asp Ile Gln Thr Glu Asp Gln
                 85                  90                  95

Ala Leu Glu Leu Ile Thr Lys Ile Thr Gln Ala Val Lys Asp Tyr Asp
            100                 105                 110

Ser Thr Lys Lys Val Val Ala Ser Gly Tyr Ser Asp Tyr Lys Arg Ile
        115                 120                 125

Asn Ser Ile Ser Pro Leu Leu Leu Pro Ser Ile Ala Ala Lys Ala Gly
130                 135                 140

Ala Asp Val Val Met Val Asp Thr Gly Ile Lys Asp Gly Lys Ser Thr
145                 150                 155                 160

Phe Glu Phe Met Asp Glu Glu Leu Lys Lys Phe Thr Gly Leu Ala
                165                 170                 175

His Glu Cys Gly Leu Glu Asn Ala Ile Ala Gly Ser Leu Lys Phe Glu
            180                 185                 190

Asp Leu Pro Val Leu Glu Arg Ile Gly Pro Asp Ile Ile Gly Val Arg
        195                 200                 205

Gly Met Val Cys Gly Gly Asp Arg Thr Asn Ser Ile Arg Gln Glu Leu
210                 215                 220

Val Glu Lys Leu Val Ala Glu Cys Gln Ala
225                 230

<210> SEQ ID NO 17
<211> LENGTH: 236
<212> TYPE: PRT
<213> ORGANISM: Methylorubrum extorquens MfnB 17

<400> SEQUENCE: 17

Met Ser Asp Ile Val Ser Ile Ser Ser Ala Arg Pro Arg Leu Leu Val
  1               5                  10                  15

Ser Val Arg Gly Pro Asp Glu Ala Leu Thr Ala Leu Arg Ala Gly Ala
             20                  25                  30

Asp Leu Ile Asp Ala Lys Asp Pro Glu Arg Gly Ala Leu Gly Ala Leu
         35                  40                  45

Pro Pro Glu Thr Val Arg Ala Ile Val Ala Gly Val Gly Gly Arg Ala
 50                  55                  60

Val Thr Ser Ala Val Ala Gly Asp Gly Thr Gly Arg Glu Ile Ala Ala
 65                  70                  75                  80

Ala Ile Ala Thr Ile Ala Ala Thr Gly Val Asp Phe Lys Ile Ala
                 85                  90                  95

Val Gly Gly Ala Asp Asp Ala Ala Leu Ala Glu Ala Ala Gln Ala
            100                 105                 110

Pro Gly Arg Val Ile Gly Val Leu Phe Ala Glu Asp Val Ala Glu
        115                 120                 125

Asp Gly Pro Ala Arg Leu Ala Ala Gly Phe Val Gly Ala Met Ile
130                 135                 140

Asp Thr Arg Gly Lys Ser Gly Thr Thr Leu Thr Ser Leu Met Ala Ala
145                 150                 155                 160

Pro Gln Leu Ala Ala Phe Val Ala Gly Cys Arg Thr His Gly Leu Met
                165                 170                 175

Ser Gly Leu Ala Gly Ser Leu Gly Leu Gly Asp Ile Pro Val Leu Ala
            180                 185                 190

```
Arg Leu Asp Pro Asp Tyr Leu Gly Phe Arg Gly Gly Leu Cys Arg Ala
        195                 200                 205

Ser Asp Arg Arg Gln Ala Leu Asp Gly Ala Arg Val Ala Gln Ala Val
210                 215                 220

Glu Ala Met Arg Ala Gly Pro Arg Ala Asp Ala Ala
225                 230                 235
```

<210> SEQ ID NO 18
<211> LENGTH: 242
<212> TYPE: PRT
<213> ORGANISM: Methylobacterium sp. MfnB 18

<400> SEQUENCE: 18

```
Met Thr Arg Pro Glu Pro His Leu Ser Val Arg Ala Ala Pro Arg Leu
1               5                   10                  15

Leu Val Ser Val Arg Asp Ala Ala Glu Ala Glu Val Ala Arg Ala Ala
            20                  25                  30

Gly Ala Asp Leu Val Asp Ala Lys Asp Pro Ala Arg Gly Ala Leu Gly
        35                  40                  45

Ala Leu Asp Pro Ala Leu Val Arg Ala Met Val Ala Arg Ile Gly Asp
50                  55                  60

Arg Ala Thr Thr Ser Ala Val Ala Gly Glu Pro Arg Glu Ala Gly Asp
65                  70                  75                  80

Leu Val Ala Lys Val Ala Ala Met Ala Ala Thr Gly Val Asp Tyr Val
                85                  90                  95

Lys Val Ala Leu Pro Pro Gly Leu Arg Ser Gly Arg Asp Gly Leu Arg
            100                 105                 110

Glu Ala Ala Asp Ala Ala Arg Gly Arg Leu Ile Ala Val Leu Phe Ala
        115                 120                 125

Glu Asp Gly Leu Asp Leu Ala Val Leu Pro Thr Leu Ala Asp Ala Gly
130                 135                 140

Phe Val Gly Ala Met Ile Asp Thr Asn Thr Lys Asp Gly Arg Arg Leu
145                 150                 155                 160

Thr Asp Arg Ile Ala Val Pro Ala Leu Ser Ala Phe Thr Ala Ala Cys
                165                 170                 175

Arg Ala Glu Gly Leu Val Ser Gly Leu Ala Gly Ser Leu Ala Leu Ala
            180                 185                 190

Asp Ile Pro Ala Leu Ser Asp Leu Gly Ala Gly Tyr Leu Gly Phe Arg
        195                 200                 205

Gly Gly Leu Cys Arg Gly Gly Asp Arg Arg Gly Asp Leu Asp Pro Ala
210                 215                 220

Arg Ile Ala Glu Ala Ala Arg Leu Leu Arg Ala Gly Gly Arg Arg Asp
225                 230                 235                 240

Ala Ala
```

<210> SEQ ID NO 19
<211> LENGTH: 234
<212> TYPE: PRT
<213> ORGANISM: Methanosarcina mazei MfnB 19

<400> SEQUENCE: 19

```
Met Lys Leu Leu Val Ser Pro Ile Asn Ser Glu Glu Ala Ile Ile Ala
1               5                   10                  15

Ser Ile Gly Gly Ala Asp Ile Val Asp Val Lys Asn Pro Lys Glu Gly
            20                  25                  30
```

```
Ser Leu Gly Ala Asn Phe Pro Trp Val Ile Arg Glu Val Lys Ala Val
        35                  40                  45

Val Asn Gly Arg Gln Pro Ile Ser Ala Thr Ile Gly Asp Phe Asn Tyr
 50                  55                  60

Lys Pro Gly Thr Ala Ala Leu Ala Ala Leu Gly Ala Ala Val Ala Gly
65                   70                  75                  80

Ala Asp Tyr Ile Lys Val Gly Leu Tyr Asp Ile Gln Thr Glu Ser Gln
                85                  90                  95

Ala Leu Glu Leu Leu Thr Lys Ile Thr Arg Ala Val Lys Asp Tyr Asn
               100                 105                 110

Pro Leu Lys Lys Val Val Ala Ser Gly Tyr Ser Asp Tyr Lys Arg Ile
               115                 120                 125

Asn Ser Ile Ser Pro Leu Leu Leu Pro Ala Val Ala Ala Glu Ala Gly
130                 135                 140

Val Asp Val Val Met Val Asp Thr Gly Val Lys Asp Gly Lys Ser Thr
145                 150                 155                 160

Phe Glu Phe Met Asp Glu Lys Glu Leu Lys Glu Phe Thr Asp Leu Ala
                165                 170                 175

His Ser Tyr Gly Leu Glu Asn Ala Ile Ala Gly Ser Leu Lys Phe Glu
               180                 185                 190

Asp Ile Pro Leu Leu Glu Arg Ile Gly Pro Asp Ile Ile Gly Val Arg
               195                 200                 205

Gly Met Val Cys Gly Gly Asp Arg Ser Thr Ser Ile Arg Gln Glu Leu
               210                 215                 220

Val Glu Lys Leu Val Ala Glu Cys Gln Ala
225                 230

<210> SEQ ID NO 20
<211> LENGTH: 238
<212> TYPE: PRT
<213> ORGANISM: Methyloversatilis universalis MfnB 20

<400> SEQUENCE: 20

Met Ile Arg Met Leu Ala Ser Val Arg Asn Leu Asp Glu Ala Arg Ile
1               5                   10                  15

Val Leu Glu Ala Gly Val Asp Leu Ile Asp Leu Lys Gln Pro Ala Asp
                20                  25                  30

Gly Ala Leu Gly Ala Leu Pro Ala Glu Val Ile Arg Glu Val Val Asp
        35                  40                  45

Phe Val Ala Gly Arg Thr Leu Thr Ser Ala Thr Ala Gly Asn Val Glu
 50                  55                  60

Pro Asp Ala Gln Ala Val Gln Ser Ala Met Ala Arg Ile Ala Ala Thr
65                   70                  75                  80

Gly Val Asp Tyr Val Lys Ala Gly Leu Phe Pro Gly Asn Trp Gln Gln
                85                  90                  95

Gly Gly Arg Asp Tyr Ala Ala Val Arg Ala Cys Leu Arg Gly Leu Thr
               100                 105                 110

Pro Leu Ala Gly Ala Arg Arg Ile Ala Val Met Phe Ala Asp Leu Ser
               115                 120                 125

Pro Pro Leu Ala Leu Val Asp Ala Val Ala Asp Ala Gly Phe Asp Gly
               130                 135                 140

Val Met Val Asp Thr Ala Leu Lys Thr Gly His Ser Leu Pro Asp Val
145                 150                 155                 160

Ala Ser Thr Glu Trp Leu Ser Gly Phe Val Glu Arg Ala Arg Ala Arg
                165                 170                 175
```

Gly Leu Leu Cys Gly Leu Ala Gly Ser Leu Arg Val Thr His Ile Pro
            180                 185                 190

Ala Leu Ala Gln Arg Cys Pro Asp Tyr Leu Gly Phe Arg Gly Ala Leu
            195                 200                 205

Cys Ala Gly Gln Ala Arg Ala Gln Ala Leu Asp Ala Arg Ala Val Leu
210                 215                 220

Ala Val Arg Glu Ala Leu Glu Lys Val Gln Arg Leu Ala Ala
225                 230                 235

<210> SEQ ID NO 21
<211> LENGTH: 234
<212> TYPE: PRT
<213> ORGANISM: Nitrosococcus watsonii MfnB 21

<400> SEQUENCE: 21

Met Ser Cys Trp Leu Ala Ser Val Arg Asn Leu Glu Glu Ile Ser Cys
1               5                   10                  15

Leu Leu Ala Glu Gly Pro Asp Ile Ile Asp Phe Lys Glu Pro Lys Glu
            20                  25                  30

Gly Val Leu Gly Ala Leu Pro Leu Glu Thr Val Arg Glu Ala Val Ala
            35                  40                  45

Leu Ile Gly Arg Arg Cys Gln Thr Ser Ala Ala Ile Gly Asp Phe Pro
    50                  55                  60

Val Asp Ser Pro Gln Ile Tyr Gln Arg Val Leu Glu Met Ala Ala Thr
65                  70                  75                  80

Gly Val Asp Tyr Val Lys Ile Gly Leu Pro Ser Asn Ile Gln Gln Ala
                85                  90                  95

Ala Ala Cys Leu Leu Ser Leu Arg Pro Leu Ala Asp Gln Gly Val Ser
            100                 105                 110

Met Val Gly Val Ile Phe Ala Asp Lys Arg Pro Asp Phe Ser Trp Thr
            115                 120                 125

Tyr Leu Ile Gly Gln Ala Gly Phe Lys Gly Ile Met Leu Asp Thr Ala
    130                 135                 140

Ile Lys Asp Asp Phe Gly Leu Leu Ser His Leu Ser Leu Ser Glu Leu
145                 150                 155                 160

Asn Asn Phe Val Lys Leu Ala Arg Ser Val Arg Leu Ile Ser Gly Leu
                165                 170                 175

Ala Gly Ser Leu Ser Ile Gln Asp Ile Pro Lys Leu Leu Pro Leu Arg
            180                 185                 190

Ala Asp Tyr Leu Gly Phe Arg Ser Ala Leu Cys Val Ala Ala Arg Asn
            195                 200                 205

Arg Cys Ser Arg Leu Asp Pro Lys Ala Val Leu Leu Ile Lys Gln Ala
    210                 215                 220

Met Arg Glu Asn Leu Arg Ile Phe Glu Ile
225                 230

<210> SEQ ID NO 22
<211> LENGTH: 256
<212> TYPE: PRT
<213> ORGANISM: Streptomyces cattleya NRRL 8057 MfnB22

<400> SEQUENCE: 22

Met Lys Glu Pro Thr Leu Leu Leu Ile Ser Pro Asp Ser Val Glu
1               5                   10                  15

Glu Ala Leu Asp Cys Ala Lys Ala Ala Glu His Leu Asp Ile Val Asp
            20                  25                  30

```
Val Lys Lys Pro Asp Glu Gly Ser Leu Gly Ala Asn Tyr Pro Trp Val
         35                  40                  45

Ile Arg Glu Ile Arg Asp Ala Ile Pro Ala Asp Lys Pro Val Ser Ala
 50                  55                  60

Thr Val Gly Asp Val Pro Tyr Lys Pro Gly Thr Val Ala Gln Ala Ala
 65                  70                  75                  80

Leu Gly Ala Val Val Ser Gly Ala Thr Tyr Ile Lys Val Gly Leu Tyr
                 85                  90                  95

Gly Cys Thr Thr Pro Asp Gln Val Val Glu Val Met Arg Gly Val Val
            100                 105                 110

Arg Ala Val Lys Asp His Arg Pro Asp Ala Leu Val Ala Ser Gly
            115                 120                 125

Tyr Ala Asp Ala His Arg Ile Gly Cys Val Asn Pro Leu Ala Ile Pro
 130                 135                 140

Gly Val Ala Gln Arg Ser Gly Cys Asp Ala Ala Met Leu Asp Thr Ala
145                 150                 155                 160

Val Lys Asp Gly Thr Arg Leu Phe Asp His Val Pro Pro Asp Val Cys
                165                 170                 175

Gly Glu Phe Val Arg Leu Ala His Glu Gly Gly Leu Leu Ala Ala Leu
            180                 185                 190

Ala Gly Ser Val Lys Ala Glu Asp Leu Gly Ala Leu Thr Arg Ile Gly
            195                 200                 205

Thr Asp Ile Val Gly Val Arg Gly Ala Val Cys Glu Gly Gly Asp Arg
210                 215                 220

Asn Ala Gly Arg Ile Gln Pro His Leu Val Ala Ala Phe Arg Ala Glu
225                 230                 235                 240

Met Asp Arg His Ala Arg Glu His Ala Ala Val Val Thr Pro Thr Gly
                245                 250                 255

<210> SEQ ID NO 23
<211> LENGTH: 250
<212> TYPE: PRT
<213> ORGANISM: Streptomyces coelicolor MfnB 23

<400> SEQUENCE: 23

Met Leu Leu Leu Ile Ser Pro Asp Gly Val Asp Glu Ala Leu Asp Cys
1               5                   10                  15

Ala Lys Ala Ala Glu His Leu Asp Ile Val Asp Val Lys Lys Pro Asp
                20                  25                  30

Glu Gly Ser Leu Gly Ala Asn Tyr Pro Trp Val Ile Arg Glu Ile Arg
            35                  40                  45

Ala Ala Val Pro Ala Asp Lys Pro Val Ser Ala Thr Val Gly Asp Val
 50                  55                  60

Pro Tyr Lys Pro Gly Thr Val Ala Gln Ala Ala Leu Gly Ala Val
 65                  70                  75                  80

Ser Gly Ala Thr Tyr Ile Lys Val Gly Leu Tyr Gly Cys Ala Thr Pro
                85                  90                  95

Glu Gln Ala Val Glu Val Met Arg Gly Val Val Arg Ala Val Lys Asp
            100                 105                 110

His Arg Ala Asp Ala Phe Val Val Ala Ser Gly Tyr Ala Asp Ala His
            115                 120                 125

Arg Ile Gly Cys Val Asn Pro Leu Ser Leu Pro Asp Ile Ala Arg Arg
 130                 135                 140

Ser Gly Ser Asp Ala Ala Met Leu Asp Thr Ala Ile Lys Asp Gly Thr
```

```
145                 150                 155                 160
Arg Leu Phe Asp His Val Pro Pro Asp Val Cys Ala Glu Phe Val Arg
                165                 170                 175

Arg Ala His Asp Cys Gly Leu Leu Ala Ala Leu Ala Gly Ser Val Arg
                180                 185                 190

Ser Gly Asp Leu Gly Glu Leu Ala Arg Ile Gln Thr Asp Ile Val Gly
                195                 200                 205

Val Arg Gly Ala Val Cys Glu Gly Gly Asp Arg Thr Thr Gly Arg Ile
210                 215                 220

Arg Pro His Leu Val Ala Ala Phe Arg Ala Glu Met Asp Arg His Val
225                 230                 235                 240

Arg Glu His Ala Ala Ala Ala Gln Ser
                245                 250

<210> SEQ ID NO 24
<211> LENGTH: 253
<212> TYPE: PRT
<213> ORGANISM: Streptomyces EFF88969 MfnB 24

<400> SEQUENCE: 24

Met Leu Leu Ile Ser Pro Asp Ser Val Glu Glu Ala Leu Glu Cys Ala
1               5                   10                  15

Lys Ala Ala Gln His Leu Asp Ile Val Asp Val Lys Lys Pro Asp Glu
                20                  25                  30

Gly Ser Leu Gly Ala Asn His Pro Trp Val Ile Arg Ala Val Arg Asp
                35                  40                  45

Ala Val Pro Ala Asp Lys Pro Val Ser Ala Thr Val Gly Asp Val Pro
        50                  55                  60

Tyr Lys Pro Gly Thr Val Ala Gln Ala Ala Leu Gly Ala Thr Val Ser
65                  70                  75                  80

Gly Ala Thr Tyr Ile Lys Val Gly Leu Tyr Gly Cys Thr Thr Pro Asp
                85                  90                  95

Gln Ala Val Glu Val Met Arg Gly Val Val Arg Ala Val Lys Asp Phe
                100                 105                 110

Arg Pro Asp Ala Leu Val Val Ala Ser Gly Tyr Ala Asp Ala His Arg
                115                 120                 125

Ile Gly Cys Val Asn Pro Leu Ala Leu Pro Asp Ile Ala Arg Arg Ser
        130                 135                 140

Gly Ser Asp Gly Ala Met Leu Asp Thr Ala Val Lys Asp Gly Thr Arg
145                 150                 155                 160

Leu Phe Asp His Thr Pro Pro Gln Val Cys Ala Glu Phe Val Arg Leu
                165                 170                 175

Ala His Glu Ala Gly Leu Leu Ala Ala Leu Ala Gly Ser Val Lys Ala
                180                 185                 190

Gly Asp Leu Ala Glu Leu Ala Gly Met Gly Thr Asp Ile Val Gly Val
                195                 200                 205

Arg Gly Ala Val Cys Glu Gly Gly Asp Arg Asn Ala Gly Arg Ile Arg
        210                 215                 220

Pro Glu Leu Val Ala Ala Phe Arg Ala Glu Met Asp Arg Cys Val Gln
225                 230                 235                 240

Gln His Gly Gly Gln Gly Ala Ala Val Ala Ala Ala Ser
                245                 250

<210> SEQ ID NO 25
<211> LENGTH: 250
```

<212> TYPE: PRT
<213> ORGANISM: Streptomyces griseus MfnB 25

<400> SEQUENCE: 25

```
Met Leu Leu Leu Ile Ser Pro Asp Gly Val Glu Glu Leu Ala Cys
1               5                   10                  15

Ala Thr Ala Ala Glu His Leu Asp Ile Val Asp Val Lys Lys Pro Asp
                20                  25                  30

Glu Gly Ser Leu Gly Ala Asn Phe Pro Trp Val Ile Arg Glu Ile Arg
            35                  40                  45

Ala Ala Val Pro Ala Asp Lys Pro Val Ser Ala Thr Val Gly Asp Val
    50                  55                  60

Pro Tyr Lys Pro Gly Thr Val Ala Gln Ala Ala Leu Gly Ala Ala Val
65                  70                  75                  80

Ser Gly Ala Thr Tyr Ile Lys Val Gly Leu Tyr Gly Cys Ala Thr Pro
                85                  90                  95

Asp Gln Ala Ile Asp Val Met Arg Gly Val Val Arg Ala Val Lys Asp
                100                 105                 110

Phe Arg Ala Asp Ala Phe Val Val Ala Ser Gly Tyr Ala Asp Ala His
            115                 120                 125

Arg Ile Gly Cys Val Asn Pro Leu Ala Leu Pro Asp Ile Ala Arg Arg
    130                 135                 140

Ala Gly Ala Asp Ala Ala Met Leu Asp Thr Ala Ile Lys Asp Gly Thr
145                 150                 155                 160

Arg Leu Phe Asp His Val Pro Pro Glu Gly Cys Ala Glu Phe Val Arg
                165                 170                 175

Leu Ala His Glu Ala Gly Leu Leu Ala Leu Ala Gly Ser Val Lys
            180                 185                 190

Ala Ala Asp Leu Ala Thr Leu Thr Arg Ile Gly Thr Asp Ile Val Gly
    195                 200                 205

Val Arg Gly Ala Val Cys Glu Gly Gly Asp Arg Asp Ala Gly Arg Ile
210                 215                 220

Gln Pro Arg Leu Val Ala Ala Phe Arg Ala Glu Met Asp Arg His Ala
225                 230                 235                 240

Arg Ala Phe Ala Ala Ala Pro Ala Ala Ser
                245                 250
```

<210> SEQ ID NO 26
<211> LENGTH: 251
<212> TYPE: PRT
<213> ORGANISM: Streptomyces sp. DH-12 MfnB 26

<400> SEQUENCE: 26

```
Met Leu Leu Leu Ile Ser Pro Asp Gly Val Glu Glu Leu Asp Cys
1               5                   10                  15

Ala Lys Ala Ala Glu His Leu Asp Ile Val Asp Val Lys Lys Pro Asp
                20                  25                  30

Glu Gly Ser Leu Gly Ala Asn Phe Pro Trp Val Ile Arg Glu Ile Arg
            35                  40                  45

Glu Ala Val Pro Ala Asp Lys Pro Val Ser Ala Thr Val Gly Asp Val
    50                  55                  60

Pro Tyr Lys Pro Gly Thr Val Ala Gln Ala Ala Leu Gly Ala Val Val
65                  70                  75                  80

Ser Gly Ala Thr Tyr Ile Lys Val Gly Leu Tyr Gly Cys Thr Thr Pro
                85                  90                  95
```

```
Asp Gln Gly Ile Asp Val Met Arg Ala Val Arg Ala Val Lys Glu
            100                 105                 110

His Asn Pro Asp Ala Leu Val Val Ala Ser Gly Tyr Ala Asp Ala His
            115                 120                 125

Arg Ile Gly Cys Val Asn Pro Leu Ala Val Pro Asp Ile Ala Ala Arg
        130                 135                 140

Ser Gly Ala Asp Ala Ala Met Leu Asp Thr Ala Val Lys Asp Gly Thr
145                 150                 155                 160

Arg Leu Phe Asp His Val Pro Pro Asp Val Cys Ala Glu Phe Val Arg
                165                 170                 175

Leu Ala His Ala Ser Gly Arg Leu Ala Ala Leu Ala Gly Ser Val Arg
            180                 185                 190

Gln Asp Asp Leu Gly Glu Leu Thr Arg Ile Gly Thr Asp Ile Val Gly
            195                 200                 205

Val Arg Gly Ala Val Cys Glu Gly Gly Asp Arg Asn Ala Gly Arg Ile
        210                 215                 220

Gln Pro His Leu Val Ala Ala Phe Arg Ala Glu Met Asp Arg Tyr Asp
225                 230                 235                 240

Arg Glu Arg Thr Ala Gly Leu Pro Ala Ala Arg
                245                 250

<210> SEQ ID NO 27
<211> LENGTH: 251
<212> TYPE: PRT
<213> ORGANISM: Streptomyces venezuelae MfnB 27

<400> SEQUENCE: 27

Met Leu Leu Leu Ile Ser Pro Asp Ser Val Glu Glu Ala Leu Asp Cys
1               5                   10                  15

Val Lys Ala Ala Glu His Leu Asp Ile Val Asp Val Lys Lys Pro Asp
            20                  25                  30

Glu Gly Ser Leu Gly Ala Asn Phe Pro Trp Val Ile Arg Glu Ile Arg
        35                  40                  45

Asp Ala Val Pro Ala Asp Lys Pro Val Ser Ala Thr Val Gly Asp Val
    50                  55                  60

Pro Tyr Lys Pro Gly Thr Val Ala Gln Ala Ala Leu Gly Ala Val Val
65                  70                  75                  80

Ser Gly Ala Thr Tyr Ile Lys Val Gly Leu Tyr Gly Cys Thr Thr Pro
                85                  90                  95

Glu Gln Gly Ile Glu Val Met Arg Ala Val Arg Ala Val Lys Asp
            100                 105                 110

His Arg Pro Asp Ala Leu Val Val Ala Ser Gly Tyr Ala Asp Ala His
            115                 120                 125

Arg Val Gly Cys Val Asn Pro Leu Ala Val Pro Asp Ile Ala Ala Arg
        130                 135                 140

Ser Gly Ala Asp Ala Ala Met Leu Asp Thr Ala Ile Lys Asp Gly Thr
145                 150                 155                 160

Arg Leu Phe Asp His Val Pro Pro Asp Ala Cys Ala Glu Phe Val Arg
                165                 170                 175

Arg Ala His Ala Ser Gly Leu Leu Ala Ala Leu Ala Gly Ser Ile Thr
            180                 185                 190

Gln Ala Asp Leu Gly Pro Leu Thr Arg Met Gly Thr Asp Ile Val Gly
            195                 200                 205

Val Arg Gly Ala Val Cys Ala Gly Gly Asp Arg Asn Ala Gly Arg Ile
        210                 215                 220
```

```
Gln Pro His Leu Ile Thr Ala Phe Arg Ala Glu Met Asp Arg Gln Gly
225                 230                 235                 240

Arg Glu Tyr Ala Val Gly Ile Pro Ala Ala Asn
            245                 250

<210> SEQ ID NO 28
<211> LENGTH: 265
<212> TYPE: PRT
<213> ORGANISM: Streptomyces coelicolor PH1

<400> SEQUENCE: 28

Met Met Pro Glu Pro Pro Arg Glu Arg Arg Thr Ala Ala Asn Arg Ser
1               5                   10                  15

Pro Ala Ile Arg Pro Ile Ala Phe Phe Asp Val Asp Glu Thr Leu Ile
            20                  25                  30

Thr Ala Lys Ser Met Leu Asp Phe Ala Arg Gln Ala Pro His Ser Leu
        35                  40                  45

Arg Asp Asp Ile Thr Ala Gln Ala Ser Gly Gln Arg His Ser Ala Asp
    50                  55                  60

Ala Asp Leu Thr Ala Met Arg Arg Gly Ala Ser Arg Val Glu Met
65                  70                  75                  80

Asn Arg Val Tyr Tyr Arg Arg Tyr Ala Gly Val Ser Leu Ala Arg Leu
                85                  90                  95

Gln Glu Ala Gly Arg Asp Trp Tyr His Ala Tyr Arg Thr Arg Pro Asp
            100                 105                 110

Gly Tyr Val Arg Ala Gly Leu Ala Ala Leu Ala Arg His Arg Arg Ala
        115                 120                 125

Gly His Thr Ile Val Leu Ile Ser Gly Ser Ala Arg Pro Leu Leu Thr
    130                 135                 140

Pro Leu Ala Gln Asp Leu Gly Ala Asp Arg Ile Leu Cys Thr Glu Gln
145                 150                 155                 160

Phe Ala Asp Ala Gln Gly Val Leu Thr Gly Glu Val Asn Arg Pro Met
                165                 170                 175

Ile Gly Glu Ala Lys Ala Glu Ala Val Thr Glu Val Met Ala Lys Arg
            180                 185                 190

Gly Val Val Pro Ala Asp Cys Phe Ala Tyr Gly Asp His Glu Ser Asp
        195                 200                 205

Phe Gly Met Leu Gln Ala Val Gly Asn Pro Val Val Gly Thr Asp
    210                 215                 220

Leu Val Leu Val Arg His Ala Gln Gly Ser Asn Trp Pro Val Leu Pro
225                 230                 235                 240

Ala Asp Ala Gly Pro Arg Cys Ala Cys Ala Arg Arg Pro Gly Pro Leu
                245                 250                 255

Gly His Asp Asp Pro Ser Ala Ile Gly
            260                 265

<210> SEQ ID NO 29
<211> LENGTH: 265
<212> TYPE: PRT
<213> ORGANISM: Streptomyces sp. E5N91 PH2

<400> SEQUENCE: 29

Met Met Pro Glu Pro Pro Arg Glu Arg Arg Thr Ala Ala Asn Arg Ser
1               5                   10                  15

Pro Ala Ile Arg Pro Ile Ala Phe Phe Asp Val Asp Glu Thr Leu Ile
            20                  25                  30
```

```
Thr Ala Lys Ser Met Leu Asp Phe Ala Arg Gln Ala Pro His Ser Leu
         35                  40                  45

Arg Asp Asp Ile Thr Ala Gln Ala Ser Gly Gln Arg His Ser Ala Asp
 50                  55                  60

Ala Asp Leu Thr Ala Met Arg Arg Gly Ala Ser Arg Val Glu Met
 65                  70                  75                  80

Asn Arg Val Tyr Tyr Arg Arg Tyr Ala Gly Val Ser Leu Ala Arg Leu
                 85                  90                  95

Gln Glu Ala Gly Arg Asp Trp Tyr His Ala Tyr Arg Thr Arg Pro Asp
                100                 105                 110

Gly Tyr Val Arg Ala Gly Leu Ala Leu Ala Arg His Arg Arg Ala
             115                 120                 125

Gly His Thr Ile Val Leu Ile Ser Gly Ser Ala Arg Pro Leu Leu Thr
         130                 135                 140

Pro Leu Ala Gln Asp Leu Gly Ala Asp Arg Ile Leu Cys Thr Glu Gln
145                 150                 155                 160

Phe Ala Asp Ala Gln Gly Val Leu Thr Gly Glu Val Asp Arg Pro Met
                 165                 170                 175

Ile Gly Glu Ala Lys Ala Glu Ala Val Thr Glu Val Met Ala Lys Arg
             180                 185                 190

Gly Val Val Ser Ala Asp Cys Phe Ala Tyr Gly Asp His Glu Ser Asp
             195                 200                 205

Phe Gly Met Leu Gln Ala Val Gly Asn Pro Val Val Gly Thr Asp
     210                 215                 220

Leu Val Leu Val Arg His Ala Gln Ala Ser Asn Trp Pro Val Leu Pro
225                 230                 235                 240

Ala Asp Ala Gly Pro Arg Cys Ala Cys Ala Arg Arg Pro Gly Pro Leu
                 245                 250                 255

Gly His Asp Asp Pro Ser Ala Ile Gly
             260                 265

<210> SEQ ID NO 30
<211> LENGTH: 279
<212> TYPE: PRT
<213> ORGANISM: Streptomyces sp. NRRL S-31 PH3

<400> SEQUENCE: 30

Met Ser Ala Leu Arg His Glu Arg Arg Ala Ala Val Ser Arg Pro Val
 1               5                  10                  15

Val Ile Arg His Ile Ala Phe Phe Asp Val Asp Glu Thr Leu Ile Thr
                 20                  25                  30

Ala Lys Ser Leu Leu Asp Phe Ala Gln Arg Val Pro His Gly Leu Trp
             35                  40                  45

Glu Asp Glu Thr Gly Gln Pro Ile Glu Arg Leu Arg Ser Gly Glu Ile
 50                  55                  60

Asp Leu Ala Ala Leu Gln Arg Ser Gly Ala Ser Arg Ala Glu Met Asn
 65                  70                  75                  80

Arg Ala Tyr Tyr Arg Arg Tyr Ala Gly Val Pro Leu Glu Arg Leu Gln
                 85                  90                  95

Lys Ala Gly Arg Asp Trp Tyr His Ala Tyr Arg Met Arg Pro Asp Gly
                100                 105                 110

Tyr Ile Thr Ala Gly Leu Ala Ala Leu Ala Arg His Arg Arg Ala Gly
             115                 120                 125

His Met Ile Val Leu Ile Ser Gly Ser Ala Arg Pro Leu Leu Thr Pro
```

```
                130                 135                 140
Leu Ser Glu Asp Leu Gly Ala Asp Arg Ile Leu Cys Thr Glu Gln Leu
145                 150                 155                 160

Asp Asp Ala Gln Gly Val Leu Thr Gly Glu Val Ala His Pro Met Val
                165                 170                 175

Gly Glu Ala Lys Ala Glu Ala Val Thr Glu Val Met Ala Gln Leu Arg
                180                 185                 190

Val Pro Thr Thr Asp Cys Phe Ala Tyr Gly Asp His Gly Ser Asp Leu
                195                 200                 205

Asp Met Leu Gln Ala Val Gly Ser Pro Val Val Gly Thr Asp Pro
210                 215                 220

Val Leu Ala Arg His Ala Gln Ala Ser Asn Trp Pro Met Leu Pro Ala
225                 230                 235                 240

Asp Ala Gly Pro Arg Ile Ala Arg Ala Gln His His Asp Thr Ser Ala
                245                 250                 255

Gln Tyr Gly Pro Gln Val Ile Ala Leu Ala Ser Gly Arg Gly Ala Ala
                260                 265                 270

Pro Arg Arg Gln Glu Arg Trp
        275

<210> SEQ ID NO 31
<211> LENGTH: 244
<212> TYPE: PRT
<213> ORGANISM: Streptomyces aureus PH4

<400> SEQUENCE: 31

Met Asn Ala Ser Ile Ala Pro Ala Ala Phe Phe Asp Val Asp Glu Thr
1               5                   10                  15

Leu Val Asn Thr Lys Ser Met Phe His Phe Leu Arg Phe Trp Met Ala
                20                  25                  30

Arg Gln Gly Asp Asp Gly Ser Gly His Glu Ala Val Met Ala Gly Val
                35                  40                  45

Arg Arg Ala Ala Ala Ser Gly Val His Arg Ser Glu Ile Asn Arg Ala
            50                  55                  60

Tyr Tyr Arg Arg Phe Ala Gly Val Pro Tyr Ala Ala Leu Leu Glu Ala
65              70                  75                  80

Gly Arg Asp Trp Trp Gln Glu Tyr Arg Arg Gly Ser Asp Ala Val Val
                85                  90                  95

Val Pro Ala Trp Ala Ala Ala Thr Arg His Arg Lys Ala Gly His Leu
                100                 105                 110

Val Val Leu Val Ser Gly Ser Phe Arg Gly Cys Leu Glu Pro Leu Ala
            115                 120                 125

Gln Asp Leu Gly Ala His Arg Ile Leu Cys Ser Glu Pro Leu Val Asp
130                 135                 140

Thr Asp Gly Arg Leu Thr Gly Glu Val Val Arg Pro Met Ile Gly Ser
145                 150                 155                 160

Val Lys Ala Asp Ala Val Arg Glu Thr Val Ala Glu Leu Gly Leu Thr
                165                 170                 175

Ala Ala Asp Cys Ser Cys Tyr Gly Asp His Ser Ser Asp Leu Asp Met
            180                 185                 190

Leu Gly Ala Val Gly Asn Pro Val Val Val Gly Gly Asp Arg Val Leu
                195                 200                 205

Leu Glu His Ala Gln Arg Leu Asp Trp Pro Val Leu Pro Ala Thr Pro
210                 215                 220
```

```
Gly His Leu Pro Ser Pro Asp Ala Ser Pro Arg Leu Leu Thr Ala
225                 230                 235                 240

Ala Glu Arg Arg
```

<210> SEQ ID NO 32
<211> LENGTH: 237
<212> TYPE: PRT
<213> ORGANISM: Saccharothrix syringae PH5

<400> SEQUENCE: 32

```
Met Ser Thr Pro Pro Ala Val Ala Phe Phe Asp Val Asp Glu Thr Val
1               5                   10                  15

Ile Lys Val Lys Ser Met Phe Glu Phe Leu Arg His Trp Met Thr Ala
            20                  25                  30

Gln Gly Asp Asp Gly Ser Ala Tyr Glu Ser Phe Met Ala Gly Val Arg
        35                  40                  45

Glu Leu Ala Asp Ala Gly Val Pro Arg Ala Glu Val Asn Arg His Tyr
    50                  55                  60

Tyr Arg Arg Tyr Ala Gly Ala Ser Ala Ala Asp Val Arg Ala Ala Gly
65                  70                  75                  80

Glu Asp Trp Tyr Ala Ser Tyr Arg Arg Pro Asp Gly Phe Leu Thr
                85                  90                  95

Ala Thr Val Ala Ala Val Ala Ala His Arg Ala Gly Asn Arg Val
            100                 105                 110

Val Leu Val Ser Gly Ser Phe Leu Pro Val Leu Gly Pro Leu Met Ala
        115                 120                 125

Asp Val Gly Ala Asp Glu Ala Leu Cys Gly Asp Pro Glu Val Gly Pro
130                 135                 140

Asp Gly Arg Tyr Thr Gly Ala Ile Ala Val Pro Met Ile Gly Glu Asn
145                 150                 155                 160

Lys Thr Ala Ala Val Arg Ala Arg Met Ala Glu Leu Gly Val Asp Pro
                165                 170                 175

Ala Asp Cys Tyr Ala Tyr Gly Asp His Gln Ser Asp Leu Gly Met Leu
            180                 185                 190

Glu Ala Val Gly Asn Pro Val Val Val Gly Glu Asp Pro Val Leu Val
        195                 200                 205

Gly Lys Ala Glu Ala Gly Gly Trp Arg Arg Leu Pro Ala Thr Thr Gly
    210                 215                 220

Pro Leu Gly Val Pro Pro Arg Val Leu Ser Val Val Glu
225                 230                 235
```

<210> SEQ ID NO 33
<211> LENGTH: 248
<212> TYPE: PRT
<213> ORGANISM: Rhodococcus sp. MTM3W5.2 PH6

<400> SEQUENCE: 33

```
Met Thr His Thr Gly Ser Arg Pro Val Gln Val Ala Phe Phe Asp Val
1               5                   10                  15

Asp Glu Thr Leu Ile Thr Val Lys Ser Met Phe Ala Phe Leu Glu His
            20                  25                  30

Trp Leu Arg Glu Arg Gly Asp Asp Gly Ser Glu Tyr Ser Arg Leu Leu
        35                  40                  45

Ala Ala Leu Arg Arg Ala Ser Asp Glu Gly Ala Pro Arg Glu Glu Val
    50                  55                  60

Asn Arg Ser Tyr Tyr Arg Thr Phe Arg Gly Val Pro Leu Val Glu Leu
```

```
                    65                  70                  75                  80
Glu Glu Ser Gly Arg Arg Trp Tyr Arg Glu Phe Glu Ser Thr Ala Ala
                    85                  90                  95

Pro Tyr Tyr Ala Asp Thr Leu Ala Ala Leu Arg Asp His Arg Asp Ala
                100                 105                 110

Gly Ala Ala Ile Val Leu Leu Ser Gly Ser Phe Ala Pro Ala Leu Gly
                115                 120                 125

Pro Ile Gly Glu Ala Val Cys Ala Asp Arg Ile Val Ala Ser Arg Pro
130                 135                 140

Val Thr Asp Gly His Gly Val Leu Thr Gly Glu Val Glu Arg Pro Met
145                 150                 155                 160

Ile Gly Lys Ala Lys Ala Glu Ala Val Thr Ser Val Leu Glu Glu Leu
                165                 170                 175

Gly Ile Asp Thr Gly Asn Ser Tyr Gly Tyr Gly Asp His Asp Ser Asp
                180                 185                 190

Leu Ala Phe Leu Glu Ala Val Gly His Pro Gly Leu Arg Gly Ser Asp
                195                 200                 205

Pro Val Leu Arg Ala His Ala Ala Arg Asn Arg Trp Arg Val Leu Gly
                210                 215                 220

Ser Ala Thr Thr Gly Leu Ala Gly Ala Val Pro Leu Leu Ala Ala Thr
225                 230                 235                 240

Ser Thr Gly Gln Arg Gly Leu Arg
                245

<210> SEQ ID NO 34
<211> LENGTH: 250
<212> TYPE: PRT
<213> ORGANISM: Rhodococcus sp. UNC363MFTsu5.1 PH7

<400> SEQUENCE: 34

Met Thr Gly Thr Gly Pro Arg Pro Gly Gln Val Ala Phe Phe Asp Val
1                   5                  10                  15

Asp Glu Thr Leu Ile Thr Val Lys Ser Met Phe Ala Phe Leu Glu His
                20                  25                  30

Trp Leu Trp Glu Arg Gly Asp Asp Gly Ser Glu Tyr Ala Arg Leu Leu
            35                  40                  45

Gly Ala Leu Arg Arg Gln Ser Asp Glu Gly Ala Pro Arg Glu Glu Val
        50                  55                  60

Asn Arg Ser Tyr Tyr Arg Thr Phe Arg Gly Val Pro Leu Val Glu Leu
65                  70                  75                  80

Glu Glu Ser Gly Arg Arg Trp Tyr Arg Glu Phe Glu Ser Thr Asn Ala
                85                  90                  95

Pro Tyr Tyr Ala Ala Thr Leu Ala Ala Leu His Ala His Arg Glu Ala
                100                 105                 110

Gly Ala Ala Ile Val Leu Leu Ser Gly Ser Phe Ala Pro Ala Leu Val
                115                 120                 125

Pro Ile Gly Glu Ala Val Gly Ala Asp Arg Ile Val Ala Ser Arg Pro
                130                 135                 140

Val Thr Asp Gln Gly Gly Val Leu Thr Gly Glu Val Glu Arg Pro Met
145                 150                 155                 160

Ile Gly Gln Ala Lys Ala Glu Ala Val Thr Ser Val Gln Ala Glu Leu
                165                 170                 175

Gly Val Asp Ala Glu Asn Ser Tyr Gly Tyr Gly Asp His Glu Ser Asp
                180                 185                 190
```

Leu Ala Phe Leu Glu Ala Val Gly His Pro Gly Leu Arg Gly Asp Asp
            195                 200                 205

Gln Val Leu Leu Ala Arg Ala Ala Arg Asp Arg Trp Arg Ser Leu Gly
    210                 215                 220

Ser Glu Thr Thr Gly Leu Ala Gly Ala Gly Pro Leu Ala Gly Ser Ala
225                 230                 235                 240

Ser Ala Gly Leu Ala Gln Arg Gly Ile Leu
                245                 250

<210> SEQ ID NO 35
<211> LENGTH: 217
<212> TYPE: PRT
<213> ORGANISM: Buttiauxella warmboldiae PH8

<400> SEQUENCE: 35

Met His Thr Ser Ala Ala Phe Phe Asp Val Asp Glu Thr Leu Ile Thr
1               5                   10                  15

Val Lys Ser Met Phe Asp Phe Tyr Asp Phe Trp Cys Arg Glu Asn Asn
            20                  25                  30

Glu Tyr Asp Lys Leu Gln Arg Tyr Met Thr Asp Phe Arg Ser Ala Val
        35                  40                  45

Lys Asn Gly Thr Pro Arg Glu Gln Leu Asn Arg Glu Tyr Tyr Arg Gln
50                  55                  60

Phe Ala Gly Val Asn Tyr Lys Asp Leu Glu Glu Ala Gly Lys Asn Trp
65                  70                  75                  80

Phe Arg Gly Lys Lys Leu Asp Ser Glu Leu Phe Ile Ser Ser Ala Val
                85                  90                  95

Ala Ala Leu Lys Lys His Gln Ala Asn Asn Met Phe Ile Val Phe Ile
            100                 105                 110

Ser Gly Ser Met His Pro Val Leu Ser Pro Val Ala Asn Tyr Leu Gly
        115                 120                 125

Val Thr Asp Ile Leu Cys Thr Pro Leu Glu Leu Thr Gly Glu Gly Ile
    130                 135                 140

Ile Thr Gly Glu Ile Gly Thr Pro Gln Thr Ile Gly Ile Gly Lys Lys
145                 150                 155                 160

Glu Ala Leu Ile Asn Phe Cys Ser Gln Lys Lys Ile Ser Ala Ala Asp
                165                 170                 175

Cys Tyr Ala Tyr Gly Asp Asp Leu Ser Asp Ile Pro Met Leu Glu Ser
            180                 185                 190

Val Gly Tyr Pro Val Cys Val Gly Lys Tyr Thr Glu Leu Ala Arg His
        195                 200                 205

Ala Ile Asn Gln Arg Trp Pro Val Ile
    210                 215

<210> SEQ ID NO 36
<211> LENGTH: 219
<212> TYPE: PRT
<213> ORGANISM: Chania multitudinisentens PH9

<400> SEQUENCE: 36

Met Arg Gln Thr Ala Phe Tyr Asp Val Asp Asp Thr Leu Ile Asn Ile
1               5                   10                  15

Lys Ser Met Phe Asp Phe Phe Gln Phe Trp Ala Ser Glu Asn Gly Leu
            20                  25                  30

Ile Ser Gln Gln Glu Gln Phe Asp Ser Gln Phe Ser Val Leu Ala Arg
        35                  40                  45

```
Lys Met Ser Ser Arg Glu Glu Leu Asn Arg Ala Tyr Tyr Arg Phe Phe
    50                  55                  60

Lys Gly Val Pro Leu Leu Lys Ile Glu Gln Cys Ala Glu Arg Trp Phe
65                  70                  75                  80

Lys Asn Ser Phe Ser Asn Thr Glu Ile Phe Ile Ser Tyr Thr Leu Lys
                    85                  90                  95

Ser Ile Leu Ala His Arg Val Leu Gly His Asn Ile Val Leu Val Ser
                100                 105                 110

Gly Ser Met Thr Pro Leu Leu Lys Pro Ile Ala Gln Leu Leu Gly Ile
            115                 120                 125

Thr Asp Ile Leu Cys Thr Lys Leu Ala Thr Asp Gln Ser Gly Val Val
130                 135                 140

Thr Gly Glu Ile Leu Glu Thr Gln Thr Ile Gly Glu Gly Lys Ala Ile
145                 150                 155                 160

Val Ile Arg Gln Tyr Ala Leu Glu Asn Asp Ile Asn Leu Ser Ala Cys
                165                 170                 175

Phe Ala Tyr Gly Asp Asp Val Ser Asp Ile Pro Met Leu Ala Cys Val
            180                 185                 190

Gly His Pro Ile Cys Ile Gly Glu Gly Thr Ala Leu Ser His Tyr Ala
        195                 200                 205

Ser Asn Asn Asn Trp Pro Ile Val Arg Val Glu
210                 215

<210> SEQ ID NO 37
<211> LENGTH: 222
<212> TYPE: PRT
<213> ORGANISM: Methylosinus sporium PH10

<400> SEQUENCE: 37

Met Met Glu His Arg Ser Phe Ala Phe Phe Asp Val Asp Glu Thr Leu
1               5                   10                  15

Ile Ser Ile Lys Ser Met Phe Asp Phe Phe Pro Phe Trp Cys Lys Trp
                20                  25                  30

Ile Gly Ala Ala Pro Glu Ala Tyr Ser Arg Phe Glu Thr Glu Ile Ala
            35                  40                  45

Ser Ala Ile Ala Arg His Ala Thr Arg Glu Glu Leu Asn Arg Leu Tyr
    50                  55                  60

Tyr Arg Ser Phe Arg Gly Ala Gln Leu Pro Val Leu Glu Ala Ala Gly
65                  70                  75                  80

Ala Ala Trp Phe Leu Gln Arg Phe Gly Arg Ser Pro Pro Tyr Arg Lys
                85                  90                  95

His Val Val Ala Arg Leu Glu Lys His Arg Gln Glu Gly Val Val Pro
                100                 105                 110

Val Leu Val Ser Gly Ser Met Arg Pro Leu Leu Arg Pro Ile Ala Arg
            115                 120                 125

Glu Leu Gln Ala Glu His Cys Leu Cys Thr Gln Leu Val Val Asp Glu
130                 135                 140

Ser Gly Arg Leu Thr Gly Glu Ile Gly Ser Pro Gln Thr Ile Gly Glu
145                 150                 155                 160

Gly Lys Ala Glu Ala Ile Arg Ala Phe Leu Arg Glu Gln Gly Gly Arg
                165                 170                 175

Pro Ala Asp Cys Leu Ala Tyr Gly Asp Asp Ile Ser Asp Leu Ala Met
            180                 185                 190

Leu Glu Leu Val Gly Ala Pro Val Val Val Gly Ala Gln Pro Asp Leu
        195                 200                 205
```

-continued

Leu Ser Ile Cys Arg Gln Arg Asp Trp Pro Tyr Leu Pro Leu
    210                 215                 220

<210> SEQ ID NO 38
<211> LENGTH: 216
<212> TYPE: PRT
<213> ORGANISM: Klebsiella oxytoca PH11

<400> SEQUENCE: 38

Met Gln Gln Ala Ala Ala Phe Phe Asp Val Asp Glu Thr Leu Ile Asn
1               5                   10                  15

Ile Lys Ser Met Phe Asp Phe Asp Phe Trp Cys Lys Glu Asn Asn
            20                  25                  30

Glu Pro Ile Lys Leu His Lys Tyr Met Ala Asn Phe Gln Ser Glu Val
            35                  40                  45

Lys Lys Gly Ile Pro Arg Glu His Leu Asn Arg Glu Tyr Tyr Arg Gln
        50                  55                  60

Phe Ala Gly Ile Ser Tyr Lys Ala Leu Glu Glu Ala Gly Glu Lys Trp
65                  70                  75                  80

Phe Arg Phe Lys Leu Asn Ser Glu Leu Phe Ile Gly Ser Ala Val Ser
                85                  90                  95

Ala Leu Lys Lys His Gln Ala Glu Asn Met Asp Ile Val Phe Ile Ser
            100                 105                 110

Gly Ser Met Leu Pro Val Leu Ser Pro Val Ala Arg Tyr Leu Gly Val
        115                 120                 125

Lys Asp Ile Leu Cys Thr Pro Leu Lys Phe Thr Ala Ala Gly Glu Met
130                 135                 140

Thr Gly Glu Ile Gly Tyr Pro Gln Thr Ile Gly Asp Gly Lys Lys Asp
145                 150                 155                 160

Ala Leu Leu Gln Phe Cys Glu Gln Arg Asn Ile Asn Pro Ser Asp Cys
                165                 170                 175

Tyr Ala Tyr Gly Asp Asp Leu Ser Asp Ile Pro Met Leu Ala Ser Thr
            180                 185                 190

Gly His Pro Val Cys Val Gly Lys His Ser Ala Leu Ala Arg His Ala
        195                 200                 205

Ile Thr His Arg Trp Gln Val Ile
    210                 215

<210> SEQ ID NO 39
<211> LENGTH: 223
<212> TYPE: PRT
<213> ORGANISM: Serratia PH12

<400> SEQUENCE: 39

Met Thr Ser Ala Ala Ala Phe Phe Asp Val Asp Glu Thr Leu Ile Lys
1               5                   10                  15

Met Lys Ser Met Phe His Phe Tyr His Tyr Trp Ser Asn Val Arg Gly
            20                  25                  30

Asn Gln Lys Ala Tyr Glu Glu Phe Ile Lys Arg Phe Gln Gln Ala Val
            35                  40                  45

Ala Glu Gly Val Pro Arg Glu Val Leu Asn Arg Met Tyr Tyr Arg Gln
        50                  55                  60

Phe Ser Gly Ile Asp Ile Asp Asp Val Tyr Gln Val Ala Glu Asp Trp
65                  70                  75                  80

Phe His Lys Tyr Leu His Glu Lys Glu Ala Tyr Ile Ala Ser Ala Val
                85                  90                  95

```
Asp Arg Phe Gln Arg His Lys Ile Ser Gly His Leu Thr Val Phe Ile
                100                 105                 110

Ser Gly Ser Met Leu Pro Leu Leu Lys Pro Leu Gly Gln Arg Leu Gly
            115                 120                 125

Ala Asp Ala Ile Leu Cys Thr Gln Leu Leu Asp Ala Lys Gly Lys
130                 135                 140

Leu Thr Gly Glu Ile Gly Glu Pro Gln Thr Ile Gly Gln Gly Lys Gln
145                 150                 155                 160

Arg Ala Leu Leu Ser Phe Ser Gln Ser His His Ile Asp Leu Ala Lys
                165                 170                 175

Ser Phe Ala Tyr Gly Asp Asp Leu Ser Asp Ile Pro Met Leu Ala Ala
            180                 185                 190

Thr Gly Asn Pro Val Cys Val Gly Glu His Ser Asn Leu Ala Glu Tyr
            195                 200                 205

Ala Arg Arg Asn Asn Trp Asn Met Leu Ala Glu Asn Ala Thr Asn
            210                 215                 220

<210> SEQ ID NO 40
<211> LENGTH: 317
<212> TYPE: PRT
<213> ORGANISM: Saccharomyces cerevisiae ycr015c PH13

<400> SEQUENCE: 40

Met Lys Thr Ile Ile Ile Ser Asp Phe Asp Glu Thr Ile Thr Arg Val
1               5                   10                  15

Asp Thr Ile Cys Thr Ile Ala Lys Leu Pro Tyr Leu Leu Asn Pro Arg
            20                  25                  30

Leu Lys Pro Glu Trp Gly His Phe Thr Lys Thr Tyr Met Asp Gly Tyr
        35                  40                  45

His Lys Tyr Lys Tyr Asn Gly Thr Arg Ser Leu Pro Leu Leu Ser Ser
    50                  55                  60

Gly Val Pro Thr Ile Ile Ser Gln Ser Asn Phe Asn Lys Leu Phe Ala
65                  70                  75                  80

Asp Glu Leu Lys Tyr Gln Asn His Asn Arg Val Val Glu Leu Asn Ser
                85                  90                  95

Val Asn Glu Ile Thr Lys Gln Gln Ile Phe Lys Ser Ile Ser Leu Asp
            100                 105                 110

Gln Met Lys Thr Phe Ala Arg Asp Gln Asn His Glu Asp Cys Leu Leu
        115                 120                 125

Arg Asp Gly Phe Lys Thr Phe Cys Ser Ser Val Val Lys Asn Phe Glu
130                 135                 140

Ser Asp Phe Tyr Val Leu Ser Ile Asn Trp Ser Lys Glu Phe Ile His
145                 150                 155                 160

Glu Val Ile Gly Asp Arg Arg Leu Lys Asn Ser His Ile Phe Cys Asn
                165                 170                 175

Asp Leu Lys Lys Val Ser Asp Lys Cys Ser Gln Ser Tyr Asn Gly Glu
            180                 185                 190

Phe Asp Cys Arg Leu Leu Thr Gly Ser Asp Lys Val Lys Ile Leu Gly
        195                 200                 205

Glu Ile Leu Asp Lys Ile Asp Ser Gly Cys Asn Lys Glu Gly Asn Ser
    210                 215                 220

Cys Ser Tyr Trp Tyr Ile Gly Asp Ser Glu Thr Asp Leu Leu Ser Ile
225                 230                 235                 240

Leu His Pro Ser Thr Asn Gly Val Leu Leu Ile Asn Pro Gln Glu Asn
```

```
                    245                 250                 255
Pro Ser Lys Phe Ile Lys Ile Thr Glu Lys Ile Ile Gly Ile Pro Lys
            260                 265                 270

Asp Lys Ile Ser Ser Phe Glu Ala Asp Asn Gly Pro Ala Trp Leu Gln
        275                 280                 285

Phe Cys Glu Lys Glu Gly Lys Gly Ala Tyr Leu Val Lys Ser Trp
    290                 295                 300

Asp Ser Leu Lys Asp Leu Ile Met Gln Val Thr Lys Met
305                 310                 315

<210> SEQ ID NO 41
<211> LENGTH: 312
<212> TYPE: PRT
<213> ORGANISM: Saccharomyces cerevisiae ydl236w PH14

<400> SEQUENCE: 41

Met Thr Ala Gln Gln Gly Val Pro Ile Lys Ile Thr Asn Lys Glu Ile
1               5                   10                  15

Ala Gln Glu Phe Leu Asp Lys Tyr Asp Thr Phe Leu Phe Asp Cys Asp
            20                  25                  30

Gly Val Leu Trp Leu Gly Ser Gln Ala Leu Pro Tyr Thr Leu Glu Ile
        35                  40                  45

Leu Asn Leu Leu Lys Gln Leu Gly Lys Gln Leu Ile Phe Val Thr Asn
    50                  55                  60

Asn Ser Thr Lys Ser Arg Leu Ala Tyr Thr Lys Lys Phe Ala Ser Phe
65                  70                  75                  80

Gly Ile Asp Val Lys Glu Glu Gln Ile Phe Thr Ser Gly Tyr Ala Ser
                85                  90                  95

Ala Val Tyr Ile Arg Asp Phe Leu Lys Leu Gln Pro Gly Lys Asp Lys
            100                 105                 110

Val Trp Val Phe Gly Glu Ser Gly Ile Gly Glu Glu Leu Lys Leu Met
        115                 120                 125

Gly Tyr Glu Ser Leu Gly Gly Ala Asp Ser Arg Leu Asp Thr Pro Phe
    130                 135                 140

Asp Ala Ala Lys Ser Pro Phe Leu Val Asn Gly Leu Asp Lys Asp Val
145                 150                 155                 160

Ser Cys Val Ile Ala Gly Leu Asp Thr Lys Val Asn Tyr His Arg Leu
                165                 170                 175

Ala Val Thr Leu Gln Tyr Leu Gln Lys Asp Ser Val His Phe Val Gly
            180                 185                 190

Thr Asn Val Asp Ser Thr Phe Pro Gln Lys Gly Tyr Thr Phe Pro Gly
        195                 200                 205

Ala Gly Ser Met Ile Glu Ser Leu Ala Phe Ser Ser Asn Arg Arg Pro
    210                 215                 220

Ser Tyr Cys Gly Lys Pro Asn Gln Asn Met Leu Asn Ser Ile Ile Ser
225                 230                 235                 240

Ala Phe Asn Leu Asp Arg Ser Lys Cys Cys Met Val Gly Asp Arg Leu
                245                 250                 255

Asn Thr Asp Met Lys Phe Gly Val Glu Gly Gly Leu Gly Gly Thr Leu
            260                 265                 270

Leu Val Leu Ser Gly Ile Glu Thr Glu Glu Arg Ala Leu Lys Ile Ser
        275                 280                 285

His Asp Tyr Pro Arg Pro Lys Phe Tyr Ile Asp Lys Leu Gly Asp Ile
    290                 295                 300
```

Tyr Thr Leu Thr Asn Asn Glu Leu
305                 310

<210> SEQ ID NO 42
<211> LENGTH: 321
<212> TYPE: PRT
<213> ORGANISM: Saccharomyces cerevisiae ydl236w PH15

<400> SEQUENCE: 42

Met Thr Ile Ala Lys Asp Tyr Arg Thr Ile Tyr Arg Asn Gln Ile Lys
1               5                   10                  15

Lys Gln Ile Arg Leu Asn Gln Glu His Leu Gln Ser Leu Thr His Leu
            20                  25                  30

Gly Ser Gln Ile Asn Phe Glu Val Asp Pro Lys Leu Pro Asp Pro
        35                  40                  45

Asp Pro Ala Arg Lys Val Phe Phe Asp Ile Asp Asn Thr Leu Tyr
    50                  55                  60

Arg Lys Ser Thr Lys Val Gln Leu Leu Met Gln Gln Ser Leu Ser Asn
65                  70                  75                  80

Phe Phe Lys Tyr Glu Leu Gly Phe Asp Asp Glu Ala Glu Arg Leu
                85                  90                  95

Ile Glu Ser Tyr Tyr Gln Glu Tyr Gly Leu Ser Val Lys Gly Leu Ile
                100                 105                 110

Lys Asn Lys Gln Ile Asp Asp Val Leu Gln Tyr Asn Thr Phe Ile Asp
            115                 120                 125

Asp Ser Leu Pro Leu Gln Asp Tyr Leu Lys Pro Asp Trp Lys Leu Arg
        130                 135                 140

Glu Leu Leu Ile Asn Leu Lys Lys Lys Leu Gly Lys Phe Asp Lys
145                 150                 155                 160

Leu Trp Leu Phe Thr Asn Ser Tyr Lys Asn His Ala Ile Arg Cys Val
                165                 170                 175

Lys Ile Leu Gly Ile Ala Asp Leu Phe Asp Gly Ile Thr Tyr Cys His
            180                 185                 190

Tyr Asp Arg Pro Ile Glu Glu Glu Phe Ile Cys Lys Pro Asp Pro Lys
        195                 200                 205

Phe Phe Glu Thr Ala Lys Leu Gln Ser Gly Leu Ser Ser Phe Ala Asn
    210                 215                 220

Ala Trp Phe Ile Asp Asp Asn Glu Ser Asn Val Arg Ser Ala Leu Ser
225                 230                 235                 240

Met Gly Met Gly His Val Ile His Leu Ile Glu Asp Tyr Gln Tyr Glu
                245                 250                 255

Ser Glu Asn Ile Val Thr Lys Asp His Lys Asn Lys Gln Gln Phe Ser
            260                 265                 270

Ile Leu Lys Asp Ile Leu Glu Ile Pro Leu Ile Met Asp Val Glu Val
        275                 280                 285

Tyr Arg Pro Ser Ser Ile Ala Ile Lys Glu Met Glu Glu Leu Glu Glu
    290                 295                 300

Glu Gly Glu Ala Val Asn Trp Ser Asn Gln Gln Ile Asn Val Gln Ser
305                 310                 315                 320

Ser

<210> SEQ ID NO 43
<211> LENGTH: 250
<212> TYPE: PRT
<213> ORGANISM: Saccharomyces cerevisiae yer062c PH16

<400> SEQUENCE: 43

```
Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
            115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
    195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250
```

<210> SEQ ID NO 44
<211> LENGTH: 254
<212> TYPE: PRT
<213> ORGANISM: Saccharomyces cerevisiae yfl045c PH17

<400> SEQUENCE: 44

```
Met Ser Ile Ala Glu Phe Ala Tyr Lys Glu Lys Pro Glu Thr Leu Val
1               5                   10                  15

Leu Phe Asp Val Asp Gly Thr Leu Thr Pro Ala Arg Leu Thr Val Ser
            20                  25                  30

Glu Glu Val Arg Lys Thr Leu Ala Lys Leu Arg Asn Lys Cys Cys Ile
        35                  40                  45

Gly Phe Val Gly Gly Ser Asp Leu Ser Lys Gln Leu Glu Gln Leu Gly
    50                  55                  60

Pro Asn Val Leu Asp Glu Phe Asp Tyr Ser Phe Ser Glu Asn Gly Leu
65                  70                  75                  80

Thr Ala Tyr Arg Leu Gly Lys Glu Leu Ala Ser Gln Ser Phe Ile Asn
                85                  90                  95

Trp Leu Gly Glu Glu Lys Tyr Asn Lys Leu Ala Val Phe Ile Leu Arg
            100                 105                 110
```

```
Tyr Leu Ser Glu Ile Asp Leu Pro Lys Arg Arg Gly Thr Phe Leu Glu
            115                 120                 125

Phe Arg Asn Gly Met Ile Asn Val Ser Pro Ile Gly Arg Asn Ala Ser
        130                 135                 140

Thr Glu Glu Arg Asn Glu Phe Glu Arg Tyr Asp Lys Glu His Gln Ile
145                 150                 155                 160

Arg Ala Lys Phe Val Glu Ala Leu Lys Lys Glu Phe Pro Asp Tyr Gly
                165                 170                 175

Leu Thr Phe Ser Ile Gly Gly Gln Ile Ser Phe Asp Val Phe Pro Ala
            180                 185                 190

Gly Trp Asp Lys Thr Tyr Cys Leu Gln His Val Glu Lys Asp Gly Phe
        195                 200                 205

Lys Glu Ile His Phe Phe Gly Asp Lys Thr Met Val Gly Gly Asn Asp
    210                 215                 220

Tyr Glu Ile Phe Val Asp Glu Arg Thr Ile Gly His Ser Val Gln Ser
225                 230                 235                 240

Pro Asp Asp Thr Val Lys Ile Leu Thr Glu Leu Phe Asn Leu
                245                 250

<210> SEQ ID NO 45
<211> LENGTH: 280
<212> TYPE: PRT
<213> ORGANISM: Saccharomyces cerevisiae ygl224c PH18

<400> SEQUENCE: 45

Met Thr Val Glu Tyr Thr Ala Ser Asp Leu Ala Thr Tyr Gln Asn Glu
1               5                   10                  15

Val Asn Glu Gln Ile Ala Lys Asn Lys Ala His Leu Glu Ser Leu Thr
            20                  25                  30

His Pro Gly Ser Lys Val Thr Phe Pro Ile Asp Gln Asp Ile Ser Ala
        35                  40                  45

Thr Pro Gln Asn Pro Asn Leu Lys Val Phe Phe Asp Ile Asp Asn
    50                  55                  60

Cys Leu Tyr Lys Ser Ser Thr Arg Ile His Asp Leu Met Gln Gln Ser
65                  70                  75                  80

Ile Leu Arg Phe Phe Gln Thr His Leu Lys Leu Ser Pro Glu Asp Ala
                85                  90                  95

His Val Leu Asn Asn Ser Tyr Tyr Lys Glu Tyr Gly Leu Ala Ile Arg
            100                 105                 110

Gly Leu Val Met Phe His Lys Val Asn Ala Leu Glu Tyr Asn Arg Leu
        115                 120                 125

Val Asp Asp Ser Leu Pro Leu Gln Asp Ile Leu Lys Pro Asp Ile Pro
    130                 135                 140

Leu Arg Asn Met Leu Leu Arg Leu Arg Gln Ser Gly Lys Ile Asp Lys
145                 150                 155                 160

Leu Trp Leu Phe Thr Asn Ala Tyr Lys Asn His Ala Ile Arg Cys Leu
                165                 170                 175

Arg Leu Leu Gly Ile Ala Asp Leu Phe Asp Gly Leu Thr Tyr Cys Asp
            180                 185                 190

Tyr Ser Arg Thr Asp Thr Leu Val Cys Lys Pro His Val Lys Ala Phe
        195                 200                 205

Glu Lys Ala Met Lys Glu Ser Gly Leu Ala Arg Tyr Glu Asn Ala Tyr
    210                 215                 220

Phe Ile Asp Asp Ser Gly Lys Asn Ile Glu Thr Gly Ile Lys Leu Gly
225                 230                 235                 240
```

```
Met Lys Thr Cys Ile His Leu Val Glu Asn Glu Val Asn Glu Ile Leu
                245                 250                 255

Gly Gln Thr Pro Glu Gly Ala Ile Val Ile Ser Asp Ile Leu Glu Leu
            260                 265                 270

Pro His Val Val Ser Asp Leu Phe
        275                 280

<210> SEQ ID NO 46
<211> LENGTH: 246
<212> TYPE: PRT
<213> ORGANISM: Saccharomyces cerevisiae yhr043c PH19

<400> SEQUENCE: 46

Met Pro Gln Phe Ser Val Asp Leu Cys Leu Phe Asp Leu Asp Gly Thr
1               5                   10                  15

Ile Val Ser Thr Thr Ala Ala Glu Ser Ala Trp Lys Lys Leu Cys
                20                  25                  30

Arg Gln His Gly Val Asp Pro Val Glu Leu Phe Lys His Ser His Gly
            35                  40                  45

Ala Arg Ser Gln Glu Met Met Lys Lys Phe Pro Lys Leu Asp Asn
    50                  55                  60

Thr Asp Asn Lys Gly Val Leu Ala Leu Glu Lys Asp Met Ala Asp Asn
65                  70                  75                  80

Tyr Leu Asp Thr Val Ser Leu Ile Pro Gly Ala Glu Asn Leu Leu Leu
                85                  90                  95

Ser Leu Asp Val Asp Thr Glu Thr Gln Lys Lys Leu Pro Glu Arg Lys
            100                 105                 110

Trp Ala Ile Val Thr Ser Gly Ser Pro Tyr Leu Ala Phe Ser Trp Phe
        115                 120                 125

Glu Thr Ile Leu Lys Asn Val Gly Lys Pro Lys Val Phe Ile Thr Gly
    130                 135                 140

Phe Asp Val Lys Asn Gly Lys Pro Asp Pro Glu Gly Tyr Ser Arg Ala
145                 150                 155                 160

Arg Asp Leu Leu Arg Gln Asp Leu Gln Leu Thr Gly Lys Gln Asp Leu
                165                 170                 175

Lys Tyr Val Val Phe Glu Asp Ala Pro Val Gly Ile Lys Ala Gly Lys
            180                 185                 190

Ala Met Gly Ala Ile Thr Val Gly Ile Thr Ser Ser Tyr Asp Lys Ser
        195                 200                 205

Val Leu Phe Asp Ala Gly Ala Asp Tyr Val Val Cys Asp Leu Thr Gln
    210                 215                 220

Val Ser Val Val Lys Asn Asn Glu Asn Gly Ile Val Ile Gln Val Asn
225                 230                 235                 240

Asn Pro Leu Thr Arg Asp
                245

<210> SEQ ID NO 47
<211> LENGTH: 246
<212> TYPE: PRT
<213> ORGANISM: Saccharomyces cerevisiae yhr044c PH20

<400> SEQUENCE: 47

Met Ala Glu Phe Ser Ala Asp Leu Cys Leu Phe Asp Leu Asp Gly Thr
1               5                   10                  15

Ile Val Ser Thr Thr Val Ala Ala Glu Lys Ala Trp Thr Lys Leu Cys
                20                  25                  30
```

```
Tyr Glu Tyr Gly Val Asp Pro Ser Glu Leu Phe Lys His Ser His Gly
        35                  40                  45

Ala Arg Thr Gln Glu Val Leu Arg Arg Phe Phe Pro Lys Leu Asp Asp
 50                  55                  60

Thr Asp Asn Lys Gly Val Leu Ala Leu Glu Lys Asp Ile Ala His Ser
 65                  70                  75                  80

Tyr Leu Asp Thr Val Ser Leu Ile Pro Gly Ala Glu Asn Leu Leu Leu
                 85                  90                  95

Ser Leu Asp Val Asp Thr Glu Thr Gln Lys Lys Leu Pro Glu Arg Lys
                100                 105                 110

Trp Ala Ile Val Thr Ser Gly Ser Pro Tyr Leu Ala Phe Ser Trp Phe
            115                 120                 125

Glu Thr Ile Leu Lys Asn Val Gly Lys Pro Lys Val Phe Ile Thr Gly
130                 135                 140

Phe Asp Val Lys Asn Gly Lys Pro Asp Pro Glu Gly Tyr Ser Arg Ala
145                 150                 155                 160

Arg Asp Leu Leu Arg Gln Asp Leu Gln Leu Thr Gly Lys Gln Asp Leu
                165                 170                 175

Lys Tyr Val Val Phe Glu Asp Ala Pro Val Gly Ile Lys Ala Gly Lys
            180                 185                 190

Ala Met Gly Ala Ile Thr Val Gly Ile Thr Ser Ser Tyr Asp Lys Ser
        195                 200                 205

Val Leu Phe Asp Ala Gly Ala Asp Tyr Val Val Cys Asp Leu Thr Gln
210                 215                 220

Val Ser Val Lys Asn Asn Glu Asn Gly Ile Val Ile Gln Val Asn
225                 230                 235                 240

Asn Pro Leu Thr Arg Ala
                245

<210> SEQ ID NO 48
<211> LENGTH: 250
<212> TYPE: PRT
<213> ORGANISM: Saccharomyces cerevisiae yil053w PH21

<400> SEQUENCE: 48

Met Pro Leu Thr Thr Lys Pro Leu Ser Leu Lys Ile Asn Ala Ala Leu
1               5                   10                  15

Phe Asp Val Asp Gly Thr Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile His Ile Ser His Gly Trp Arg Thr Tyr Asp Ala Ile Ala Lys
 50                  55                  60

Phe Ala Pro Asp Phe Ala Asp Glu Glu Tyr Val Asn Lys Leu Glu Gly
 65                  70                  75                  80

Glu Ile Pro Glu Lys Tyr Gly Glu His Ser Ile Glu Val Pro Gly Ala
                 85                  90                  95

Val Lys Leu Cys Asn Ala Leu Asn Ala Leu Pro Lys Glu Lys Trp Ala
                100                 105                 110

Val Ala Thr Ser Gly Thr Arg Asp Met Ala Lys Lys Trp Phe Asp Ile
            115                 120                 125

Leu Lys Ile Lys Arg Pro Glu Tyr Phe Ile Thr Ala Asn Asp Val Lys
130                 135                 140

Gln Gly Lys Pro His Pro Glu Pro Tyr Leu Lys Gly Arg Asn Gly Leu
```

```
145                 150                 155                 160
Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 49
<211> LENGTH: 352
<212> TYPE: PRT
<213> ORGANISM: Saccharomyces cerevisiae ykr070w PH22

<400> SEQUENCE: 49

Met Ile Gly Lys Arg Phe Phe Gln Thr Thr Ser Lys Lys Ile Ala Phe
1               5                   10                  15

Ala Phe Asp Ile Asp Gly Val Leu Phe Arg Gly Lys Lys Pro Ile Ala
            20                  25                  30

Gly Ala Ser Asp Ala Leu Lys Leu Leu Asn Arg Asn Lys Ile Pro Tyr
        35                  40                  45

Ile Leu Leu Thr Asn Gly Gly Gly Phe Ser Glu Arg Ala Arg Thr Glu
    50                  55                  60

Phe Ile Ser Ser Lys Leu Asp Val Asp Val Ser Pro Leu Gln Ile Ile
65                  70                  75                  80

Gln Ser His Thr Pro Tyr Lys Ser Leu Val Asn Lys Tyr Ser Arg Ile
                85                  90                  95

Leu Ala Val Gly Thr Pro Ser Val Arg Gly Val Ala Glu Gly Tyr Gly
            100                 105                 110

Phe Gln Asp Val Val His Gln Thr Asp Ile Val Arg Tyr Asn Arg Asp
        115                 120                 125

Ile Ala Pro Phe Ser Gly Leu Ser Asp Glu Gln Val Met Glu Tyr Ser
    130                 135                 140

Arg Asp Ile Pro Asp Leu Thr Thr Lys Lys Phe Asp Ala Val Leu Val
145                 150                 155                 160

Phe Asn Asp Pro His Asp Trp Ala Ala Asp Ile Gln Ile Ile Ser Asp
                165                 170                 175

Ala Ile Asn Ser Glu Asn Gly Met Leu Asn Thr Leu Arg Asn Glu Lys
            180                 185                 190

Ser Gly Lys Pro Ser Ile Pro Ile Tyr Phe Ser Asn Gln Asp Leu Leu
        195                 200                 205

Trp Ala Asn Pro Tyr Lys Leu Asn Arg Phe Gly Gln Gly Ala Phe Arg
    210                 215                 220

Leu Leu Val Arg Arg Leu Tyr Leu Glu Leu Asn Gly Glu Pro Leu Gln
225                 230                 235                 240

Asp Tyr Thr Leu Gly Lys Pro Thr Lys Leu Thr Tyr Asp Phe Ala His
                245                 250                 255

His Val Leu Ile Asp Trp Glu Lys Arg Leu Ser Gly Lys Ile Gly Gln
            260                 265                 270
```

```
Ser Val Lys Gln Lys Leu Pro Leu Gly Thr Lys Pro Ser Thr Ser
            275                 280                 285

Pro Phe His Ala Val Phe Met Val Gly Asp Asn Pro Ala Ser Asp Ile
290                 295                 300

Ile Gly Ala Gln Asn Tyr Gly Trp Asn Ser Cys Leu Val Lys Thr Gly
305                 310                 315                 320

Val Tyr Asn Glu Gly Asp Asp Leu Lys Glu Cys Lys Pro Thr Leu Ile
            325                 330                 335

Val Asn Asp Val Phe Asp Ala Val Thr Lys Thr Leu Glu Lys Tyr Ala
            340                 345                 350

<210> SEQ ID NO 50
<211> LENGTH: 241
<212> TYPE: PRT
<213> ORGANISM: Saccharomyces cerevisiae ynl010w PH23

<400> SEQUENCE: 50

Met Val Lys Ala Val Ile Phe Thr Asp Phe Asp Gly Thr Val Thr Leu
1               5                   10                  15

Glu Asp Ser Asn Asp Tyr Leu Thr Asp Thr Leu Gly Phe Gly Lys Glu
            20                  25                  30

Lys Arg Leu Lys Val Phe Glu Gly Val Leu Asp Asp Thr Lys Ser Phe
        35                  40                  45

Arg Gln Gly Phe Met Glu Met Leu Glu Ser Ile His Thr Pro Phe Pro
50                  55                  60

Glu Cys Ile Lys Ile Leu Glu Lys Lys Ile Arg Leu Asp Pro Gly Phe
65                  70                  75                  80

Lys Asp Thr Phe Glu Trp Ala Gln Glu Asn Asp Val Pro Val Ile Val
                85                  90                  95

Val Ser Ser Gly Met Lys Pro Ile Ile Lys Val Leu Leu Thr Arg Leu
            100                 105                 110

Val Gly Gln Glu Ser Ile His Lys Ile Asp Ile Val Ser Asn Glu Val
        115                 120                 125

Glu Ile Asp Ala His Asp Gln Trp Lys Ile Ile Tyr Lys Asp Glu Ser
130                 135                 140

Pro Phe Gly His Asp Lys Ser Arg Ser Ile Asp Ala Tyr Lys Lys Lys
145                 150                 155                 160

Phe Glu Ser Thr Leu Lys Ala Gly Glu Gln Arg Pro Val Tyr Phe Tyr
                165                 170                 175

Cys Gly Asp Gly Val Ser Asp Leu Ser Ala Ala Lys Glu Cys Asp Leu
            180                 185                 190

Leu Phe Ala Lys Arg Gly Lys Asp Leu Val Thr Tyr Cys Lys Lys Gln
        195                 200                 205

Asn Val Pro Phe His Glu Phe Asp Thr Phe Lys Asp Ile Leu Ala Ser
    210                 215                 220

Met Lys Gln Val Leu Ala Gly Glu Lys Thr Val Ala Glu Leu Met Glu
225                 230                 235                 240

Asn

<210> SEQ ID NO 51
<211> LENGTH: 218
<212> TYPE: PRT
<213> ORGANISM: Saccharomyces cerevisiae yor131c PH24

<400> SEQUENCE: 51

Met Thr Lys Leu Gln Gly Leu Gln Gly Leu Lys His Ile Lys Ala Val
```

```
1               5                   10                  15
Val Phe Asp Met Asp Gly Thr Leu Cys Leu Pro Gln Pro Trp Met Phe
            20                  25                  30

Pro Ala Met Arg Asn Ala Ile Gly Leu Glu Asp Lys Ser Ile Asp Ile
            35                  40                  45

Leu His Phe Ile Asp Thr Leu Pro Thr Glu Lys Glu Lys Lys Glu Ala
    50                  55                  60

His Asp Arg Ile Glu Leu Val Glu Ala Lys Ala Met Lys Glu Met Gln
65                  70                  75                  80

Pro Gln Pro Gly Leu Val Asp Ile Met Arg Tyr Leu Thr Lys Asn Gly
                85                  90                  95

Ile Ser Lys Asn Ile Cys Thr Arg Asn Val Gly Ala Pro Val Glu Thr
            100                 105                 110

Phe Val Lys Arg Phe Ile Pro Ser Glu Leu Ser Arg Phe Asp Tyr Ile
            115                 120                 125

Val Thr Arg Glu Phe Arg Pro Thr Lys Pro Gln Pro Asp Pro Leu Leu
        130                 135                 140

His Ile Ala Ser Lys Leu Asn Ile Arg Pro Leu Glu Met Ile Met Val
145                 150                 155                 160

Gly Asp Ser Phe Asp Asp Met Lys Ser Gly Arg Ser Ala Gly Cys Phe
                165                 170                 175

Thr Val Leu Leu Lys Asn His Val Asn Gly His Leu Leu Leu Glu His
            180                 185                 190

Lys Glu Leu Val Asp Val Ser Val Glu Asp Leu Ser Glu Ile Ile Glu
        195                 200                 205

Leu Ile Gln Asn Met Asn Lys Glu Ser Phe
    210                 215

<210> SEQ ID NO 52
<211> LENGTH: 450
<212> TYPE: PRT
<213> ORGANISM: Saccharomyces cerevisiae yor155c PH25

<400> SEQUENCE: 52

Met Ser Ser Arg Tyr Arg Val Glu Tyr His Leu Lys Ser His Arg Lys
1               5                   10                  15

Asp Glu Phe Ile Asp Trp Val Lys Gly Leu Leu Ala Ser Pro Phe Val
            20                  25                  30

Leu His Ala Val Ser His Glu Gly Asp Tyr Asn Asp Asp Leu Ala Thr
            35                  40                  45

Thr Gln Arg Val Arg Ser Gln Tyr Ala Asp Ile Phe Lys Asp Ile Glu
    50                  55                  60

Gly Leu Ile Lys Asp Lys Ile Glu Phe Asp Ser Arg Asn Met Ser Gln
65                  70                  75                  80

Asp Glu Ile Glu Asp Gly Ala Ser Ser Gln Ser Leu Asn Ile Leu Gly
                85                  90                  95

Gln Ser Arg Leu Asn Leu Leu Val Pro Ser Ile Gly Thr Phe Phe Thr
            100                 105                 110

Glu Leu Pro Leu Glu Gln Ala Phe Leu Trp Glu Asp Ser Gln Arg Ala
            115                 120                 125

Ile Ser Ala Arg Arg Met Val Ala Pro Ser Phe Asn Asp Ile Arg His
        130                 135                 140

Ile Leu Asn Thr Ala Gln Ile Phe His Phe Lys Lys Gln Glu Asn Leu
145                 150                 155                 160
```

```
His Asn Gly Lys Val Leu Arg Leu Val Thr Phe Asp Gly Asp Val Thr
                165                 170                 175

Leu Tyr Glu Asp Gly Gly Ser Leu Val Tyr Thr Asn Pro Val Ile Pro
            180                 185                 190

Tyr Ile Leu Lys Leu Leu Arg Cys Gly Ile Asn Val Gly Ile Val Thr
        195                 200                 205

Ala Ala Gly Tyr Asp Glu Ala Gly Thr Tyr Glu Asn Arg Leu Lys Gly
210                 215                 220

Leu Ile Val Ala Leu His Asp Ser Thr Asp Ile Pro Val Ser Gln Lys
225                 230                 235                 240

Gln Asn Leu Thr Ile Met Gly Gly Glu Ser Ser Tyr Leu Phe Arg Tyr
                245                 250                 255

Tyr Glu Asp Pro Glu Glu Asp Asn Phe Gly Phe Arg Gln Ile Asp Lys
            260                 265                 270

Glu Glu Trp Leu Leu Pro Arg Met Lys Ala Trp Ser Leu Glu Asp Val
        275                 280                 285

Glu Lys Thr Leu Asp Phe Ala Glu Arg Thr Leu Asn Arg Leu Arg Lys
290                 295                 300

Arg Leu Asn Leu Pro Ser Glu Ile Ser Ile Arg Lys Val Arg Ala
305                 310                 315                 320

Val Gly Ile Val Pro Gly Glu Arg Tyr Asp Glu Ala Ser Lys Arg Gln
                325                 330                 335

Val Pro Val Lys Leu Asp Arg Glu Gln Leu Glu Ile Val Leu Thr
            340                 345                 350

Leu Gln Asn Thr Leu Glu Ser Phe Ala Pro Ser Arg Arg Ile Gln Phe
        355                 360                 365

Ser Cys Phe Asp Gly Gly Ser Asp Val Trp Cys Asp Ile Gly Gly Lys
370                 375                 380

Asp Leu Gly Val Arg Ser Leu Gln Gln Phe Tyr Asn Pro Glu Ser Pro
385                 390                 395                 400

Ile Gln Pro Ser Glu Thr Leu His Val Gly Asp Gln Phe Ala Pro Val
                405                 410                 415

Gly Ser Ala Asn Asp Phe Lys Ala Arg Leu Ala Gly Cys Thr Leu Trp
            420                 425                 430

Ile Ala Ser Pro Gln Glu Thr Val Asn Tyr Leu His Arg Leu Leu Glu
        435                 440                 445

Thr Asp
450

<210> SEQ ID NO 53
<211> LENGTH: 222
<212> TYPE: PRT
<213> ORGANISM: Escherichia coli YniC PH26

<400> SEQUENCE: 53

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45

Thr Leu Gly Leu Arg Ile Asp Met Val Val Asp Leu Trp Tyr Ala Arg
    50                  55                  60

Gln Pro Trp Asn Gly Pro Ser Arg Gln Glu Val Val Glu Arg Val Ile
65                  70                  75                  80
```

Ala Arg Ala Ile Ser Leu Val Glu Glu Thr Arg Pro Leu Leu Pro Gly
            85                  90                  95

Val Arg Glu Ala Val Ala Leu Cys Lys Glu Gln Gly Leu Leu Val Gly
            100                 105                 110

Leu Ala Ser Ala Ser Pro Leu His Met Leu Glu Lys Val Leu Thr Met
            115                 120                 125

Phe Asp Leu Arg Asp Ser Phe Asp Ala Leu Ala Ser Ala Glu Lys Leu
130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
            165                 170                 175

Gly Met Ile Ala Ser Lys Ala Ala Arg Met Arg Ser Ile Val Val Pro
            180                 185                 190

Ala Pro Glu Ala Gln Asn Asp Pro Arg Phe Val Leu Ala Asn Val Lys
            195                 200                 205

Leu Ser Ser Leu Thr Glu Leu Thr Ala Lys Asp Leu Leu Gly
210                 215                 220

<210> SEQ ID NO 54
<211> LENGTH: 216
<212> TYPE: PRT
<213> ORGANISM: Escherichia coli YfbT PH27

<400> SEQUENCE: 54

Met Arg Cys Lys Gly Phe Leu Phe Asp Leu Asp Gly Thr Leu Val Asp
1               5                   10                  15

Ser Leu Pro Ala Val Glu Arg Ala Trp Ser Asn Trp Ala Arg Arg His
            20                  25                  30

Gly Leu Ala Pro Glu Glu Val Leu Ala Phe Ile His Gly Lys Gln Ala
            35                  40                  45

Ile Thr Ser Leu Arg His Phe Met Ala Gly Lys Ser Glu Ala Asp Ile
50                  55                  60

Ala Ala Glu Phe Thr Arg Leu Glu His Ile Glu Ala Thr Glu Thr Glu
65                  70                  75                  80

Gly Ile Thr Ala Leu Pro Gly Ala Ile Ala Leu Ser His Leu Asn
            85                  90                  95

Lys Ala Gly Ile Pro Trp Ala Ile Val Thr Ser Gly Ser Met Pro Val
            100                 105                 110

Ala Arg Ala Arg His Lys Ile Ala Gly Leu Pro Ala Pro Glu Val Phe
            115                 120                 125

Val Thr Ala Glu Arg Val Lys Arg Gly Lys Pro Glu Pro Asp Ala Tyr
130                 135                 140

Leu Leu Gly Ala Gln Leu Leu Gly Leu Ala Pro Gln Glu Cys Val Val
145                 150                 155                 160

Val Glu Asp Ala Pro Ala Gly Val Leu Ser Gly Leu Ala Ala Gly Cys
            165                 170                 175

His Val Ile Ala Val Asn Ala Pro Ala Asp Thr Pro Arg Leu Asn Glu
            180                 185                 190

Val Asp Leu Val Leu His Ser Leu Glu Gln Ile Thr Val Thr Lys Gln
            195                 200                 205

Pro Asn Gly Asp Val Ile Ile Gln
210                 215

```
<210> SEQ ID NO 55
<211> LENGTH: 222
<212> TYPE: PRT
<213> ORGANISM: Escherichia coli YieH PH28

<400> SEQUENCE: 55
```

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45

Thr Leu Gly Leu Arg Ile Asp Met Val Val Asp Leu Trp Tyr Ala Arg
    50                  55                  60

Gln Pro Trp Asn Gly Pro Ser Arg Gln Glu Val Val Glu Arg Val Ile
65                  70                  75                  80

Ala Arg Ala Ile Ser Leu Val Glu Glu Thr Arg Pro Leu Leu Pro Gly
                85                  90                  95

Val Arg Glu Ala Val Ala Leu Cys Lys Glu Gln Gly Leu Leu Val Gly
            100                 105                 110

Leu Ala Ser Ala Ser Pro Leu His Met Leu Glu Lys Val Leu Thr Met
        115                 120                 125

Phe Asp Leu Arg Asp Ser Phe Asp Ala Leu Ala Ser Ala Glu Lys Leu
    130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
                165                 170                 175

Gly Met Ile Ala Ser Lys Ala Ala Arg Met Arg Ser Ile Val Val Pro
            180                 185                 190

Ala Pro Glu Ala Gln Asn Asp Pro Arg Phe Val Leu Ala Asp Val Lys
        195                 200                 205

Leu Ser Ser Leu Thr Glu Leu Thr Ala Lys Asp Leu Leu Gly
    210                 215                 220

```
<210> SEQ ID NO 56
<211> LENGTH: 199
<212> TYPE: PRT
<213> ORGANISM: Escherichia coli YihX PH29

<400> SEQUENCE: 56
```

Met Leu Tyr Ile Phe Asp Leu Gly Asn Val Ile Val Asp Ile Asp Phe
1               5                   10                  15

Asn Arg Val Leu Gly Ala Trp Ser Asp Leu Thr Arg Ile Pro Leu Ala
            20                  25                  30

Ser Leu Lys Lys Ser Phe His Met Gly Glu Ala Phe His Gln His Glu
        35                  40                  45

Arg Gly Glu Ile Ser Asp Glu Ala Phe Ala Glu Ala Leu Cys His Glu
    50                  55                  60

Met Ala Leu Pro Leu Ser Tyr Glu Gln Phe Ser His Gly Trp Gln Ala
65                  70                  75                  80

Val Phe Val Ala Leu Arg Pro Glu Val Ile Ala Ile Met His Lys Leu
                85                  90                  95

Arg Glu Gln Gly His Arg Val Val Leu Ser Asn Thr Asn Arg Leu
            100                 105                 110

His Thr Thr Phe Trp Pro Glu Glu Tyr Pro Glu Ile Arg Asp Ala Ala

```
               115                 120                 125
Asp His Ile Tyr Leu Ser Gln Asp Leu Gly Met Arg Lys Pro Glu Ala
    130                 135                 140

Arg Ile Tyr Gln His Val Leu Gln Ala Glu Gly Phe Ser Pro Ser Asp
145                 150                 155                 160

Thr Val Phe Phe Asp Asp Asn Ala Asp Asn Ile Glu Gly Ala Asn Gln
                165                 170                 175

Leu Gly Ile Thr Ser Ile Leu Val Lys Asp Lys Thr Thr Ile Pro Asp
            180                 185                 190

Tyr Phe Ala Lys Val Leu Cys
            195

<210> SEQ ID NO 57
<211> LENGTH: 253
<212> TYPE: PRT
<213> ORGANISM: Escherichia coli YjjG PH31

<400> SEQUENCE: 57

Met Arg Ile Leu Leu Ser Asn Asp Asp Gly Val His Ala Pro Gly Ile
1               5                   10                  15

Gln Thr Leu Ala Lys Ala Leu Arg Glu Phe Ala Asp Val Gln Val Val
            20                  25                  30

Ala Pro Asp Arg Asn Arg Ser Gly Ala Ser Asn Ser Leu Thr Leu Glu
        35                  40                  45

Ser Ser Leu Arg Thr Phe Thr Phe Glu Asn Gly Asp Ile Ala Val Gln
    50                  55                  60

Met Gly Thr Pro Thr Asp Cys Val Tyr Leu Gly Val Asn Ala Leu Met
65                  70                  75                  80

Arg Pro Arg Pro Asp Ile Val Val Ser Gly Ile Asn Ala Gly Pro Asn
                85                  90                  95

Leu Gly Asp Asp Val Ile Tyr Ser Gly Thr Val Ala Ala Ala Met Glu
            100                 105                 110

Gly Arg His Leu Gly Phe Pro Ala Leu Ala Val Ser Leu Asp Gly His
        115                 120                 125

Lys His Tyr Asp Thr Ala Ala Ala Val Thr Cys Ser Ile Leu Arg Ala
    130                 135                 140

Leu Cys Lys Glu Pro Leu Arg Thr Gly Arg Ile Leu Asn Ile Asn Val
145                 150                 155                 160

Pro Asp Leu Pro Leu Asp Gln Ile Lys Gly Ile Arg Val Thr Arg Cys
                165                 170                 175

Gly Thr Arg His Pro Ala Asp Gln Val Ile Pro Gln Gln Asp Pro Arg
            180                 185                 190

Gly Asn Thr Leu Tyr Trp Ile Gly Pro Pro Gly Gly Lys Cys Asp Ala
        195                 200                 205

Gly Pro Gly Thr Asp Phe Ala Ala Val Asp Glu Gly Tyr Val Ser Ile
    210                 215                 220

Thr Pro Leu His Val Asp Leu Thr Ala His Ser Ala Gln Asp Val Val
225                 230                 235                 240

Ser Asp Trp Leu Asn Ser Val Gly Val Gly Thr Gln Trp
                245                 250

<210> SEQ ID NO 58
<211> LENGTH: 188
<212> TYPE: PRT
<213> ORGANISM: Escherichia coli YqaB PH32
```

-continued

<400> SEQUENCE: 58

```
Met Tyr Glu Arg Tyr Ala Gly Leu Ile Phe Asp Met Asp Gly Thr Ile
1               5                   10                  15

Leu Asp Thr Glu Pro Thr His Arg Lys Ala Trp Arg Glu Val Leu Gly
            20                  25                  30

His Tyr Gly Leu Gln Tyr Asp Ile Gln Ala Met Ile Ala Leu Asn Gly
        35                  40                  45

Ser Pro Thr Trp Arg Ile Ala Gln Ala Ile Ile Glu Leu Asn Gln Ala
    50                  55                  60

Asp Leu Asp Pro His Ala Leu Ala Arg Glu Lys Thr Glu Ala Val Arg
65                  70                  75                  80

Ser Met Leu Leu Asp Ser Val Glu Pro Leu Pro Leu Val Asp Val Val
                85                  90                  95

Lys Ser Trp His Gly Arg Arg Pro Met Ala Val Gly Thr Gly Ser Glu
            100                 105                 110

Ser Ala Ile Ala Glu Ala Leu Leu Ala His Leu Gly Leu Arg His Tyr
        115                 120                 125

Phe Asp Ala Val Val Ala Ala Asp His Val Lys His His Lys Pro Ala
    130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
                165                 170                 175

Ala Ala Gly Met Asp Ala Val Asp Val Arg Leu Leu
            180                 185
```

<210> SEQ ID NO 59
<211> LENGTH: 238
<212> TYPE: PRT
<213> ORGANISM: Escherichia coli YigB PH33

<400> SEQUENCE: 59

```
Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Glu Ala Ser Ala
                85                  90                  95

Gly Ala His Ala Ala Met Ile Asn Phe Ala Lys Trp Arg Ser Arg Ile
            100                 105                 110

Asp Val Pro Gln Gln Thr His Asp Thr Leu Lys Gln Leu Ala Lys Lys
        115                 120                 125

Trp Pro Leu Val Ala Ile Thr Asn Gly Asn Ala Gln Pro Glu Leu Phe
    130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175
```

```
Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Arg
        195                 200                 205

Pro Glu Asn Gly Asp Leu Met Gln Thr Trp Asp Ser Arg Leu Leu Pro
210                 215                 220

His Leu Glu Ile Ser Arg Leu Ala Ser Leu Thr Ser Leu Ile
225                 230                 235

<210> SEQ ID NO 60
<211> LENGTH: 222
<212> TYPE: PRT
<213> ORGANISM: Escherichia coli YrfG PH34

<400> SEQUENCE: 60

Met His Ile Asn Ile Ala Trp Gln Asp Val Thr Val Leu Leu Asp
1               5                   10                  15

Met Asp Gly Thr Leu Leu Asp Leu Ala Phe Asp Asn Tyr Phe Trp Gln
            20                  25                  30

Lys Leu Val Pro Glu Thr Trp Gly Ala Lys Asn Gly Val Thr Pro Gln
        35                  40                  45

Glu Ala Met Glu Tyr Met Arg Gln Gln Tyr His Asp Val Gln His Thr
50                  55                  60

Leu Asn Trp Tyr Cys Leu Asp Tyr Trp Ser Glu Gln Leu Gly Leu Asp
65                  70                  75                  80

Ile Cys Ala Met Thr Thr Glu Met Gly Pro Arg Ala Val Leu Arg Glu
                85                  90                  95

Asp Thr Ile Pro Phe Leu Glu Ala Leu Lys Ala Ser Gly Lys Gln Arg
            100                 105                 110

Ile Leu Leu Thr Asn Ala His Pro His Asn Leu Ala Val Lys Leu Glu
        115                 120                 125

His Thr Gly Leu Asp Ala His Leu Asp Leu Leu Leu Ser Thr His Thr
130                 135                 140

Phe Gly Tyr Pro Lys Glu Asp Gln Arg Leu Trp His Ala Val Ala Glu
145                 150                 155                 160

Ala Thr Gly Leu Lys Ala Glu Arg Thr Leu Phe Ile Asp Asp Ser Glu
                165                 170                 175

Ala Ile Leu Asp Ala Ala Ala Gln Phe Gly Ile Arg Tyr Cys Leu Gly
            180                 185                 190

Val Thr Asn Pro Asp Ser Gly Ile Ala Glu Lys Gln Tyr Gln Arg His
        195                 200                 205

Pro Ser Leu Asn Asp Tyr Arg Arg Leu Ile Pro Ser Leu Met
210                 215                 220

<210> SEQ ID NO 61
<211> LENGTH: 222
<212> TYPE: PRT
<213> ORGANISM: Escherichia coli Gph PH35

<400> SEQUENCE: 61

Met Ser Thr Pro Arg Gln Ile Leu Ala Ala Ile Phe Asp Met Asp Gly
1               5                   10                  15

Leu Leu Ile Asp Ser Glu Pro Leu Trp Asp Arg Ala Glu Leu Asp Val
            20                  25                  30

Met Ala Ser Leu Gly Val Asp Ile Ser Arg Arg Asn Glu Leu Pro Asp
        35                  40                  45
```

Thr Leu Gly Leu Arg Ile Asp Met Val Val Asp Leu Trp Tyr Ala Arg
 50                  55                  60

Gln Pro Trp Asn Gly Pro Ser Arg Gln Glu Val Val Glu Arg Val Ile
 65                  70                  75                  80

Ala Arg Ala Ile Ser Leu Val Glu Glu Thr Arg Pro Leu Leu Pro Gly
                 85                  90                  95

Val Arg Glu Ala Val Ala Leu Cys Lys Glu Gln Gly Leu Leu Val Gly
            100                 105                 110

Leu Ala Ser Ala Ser Pro Leu His Met Leu Glu Lys Val Leu Thr Met
            115                 120                 125

Phe Asp Leu Arg Asp Ser Phe Asp Ala Leu Ala Ser Ala Glu Lys Leu
130                 135                 140

Pro Tyr Ser Lys Pro His Pro Gln Val Tyr Leu Asp Cys Ala Ala Lys
145                 150                 155                 160

Leu Gly Val Asp Pro Leu Thr Cys Val Ala Leu Glu Asp Ser Val Asn
                165                 170                 175

Gly Met Ile Ala Ser Lys Ala Ala Arg Met Arg Ser Ile Val Val Pro
            180                 185                 190

Ala Pro Glu Ala Gln Asn Asp Pro Arg Phe Val Leu Ala Asp Val Lys
            195                 200                 205

Leu Ser Ser Leu Thr Glu Leu Thr Ala Lys Asp Leu Leu Gly
210                 215                 220

<210> SEQ ID NO 62
<211> LENGTH: 271
<212> TYPE: PRT
<213> ORGANISM: Escherichia coli YbiV PH36

<400> SEQUENCE: 62

Met Ser Val Lys Val Ile Val Thr Asp Met Asp Gly Thr Phe Leu Asn
 1               5                  10                  15

Asp Ala Lys Thr Tyr Asn Gln Pro Arg Phe Met Ala Gln Tyr Gln Glu
             20                  25                  30

Leu Lys Lys Arg Gly Ile Lys Phe Val Val Ala Ser Gly Asn Gln Tyr
         35                  40                  45

Tyr Gln Leu Ile Ser Phe Phe Pro Glu Leu Lys Asp Glu Ile Ser Phe
 50                  55                  60

Val Ala Glu Asn Gly Ala Leu Val Tyr Glu His Gly Lys Gln Leu Phe
 65                  70                  75                  80

His Gly Glu Leu Thr Arg His Glu Ser Arg Ile Val Ile Gly Glu Leu
                 85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
            115                 120                 125

His Tyr His Arg Leu Lys Pro Val Lys Asp Tyr Gln Glu Ile Asp Asp
130                 135                 140

Val Leu Phe Lys Phe Ser Leu Asn Leu Pro Asp Glu Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Ile Pro Gly Leu His Lys
            180                 185                 190

Ala Asn Gly Ile Ser Arg Leu Leu Lys Arg Trp Asp Leu Ser Pro Gln
            195                 200                 205

Asn Val Val Ala Ile Gly Asp Ser Gly Asn Asp Ala Glu Met Leu Lys
            210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270

<210> SEQ ID NO 63
<211> LENGTH: 270
<212> TYPE: PRT
<213> ORGANISM: Escherichia coli YidA PH37

<400> SEQUENCE: 63

Met Ala Ile Lys Leu Ile Ala Ile Asp Met Asp Gly Thr Leu Leu Leu
1               5                   10                  15

Pro Asp His Thr Ile Ser Pro Ala Val Lys Asn Ala Ile Ala Ala Ala
            20                  25                  30

Arg Ala Arg Gly Val Asn Val Val Leu Thr Thr Gly Arg Pro Tyr Ala
        35                  40                  45

Gly Val His Asn Tyr Leu Lys Glu Leu His Met Glu Gln Pro Gly Asp
    50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
                245                 250                 255

Glu Asp Gly Val Ala Phe Ala Ile Glu Lys Tyr Val Leu Asn
            260                 265                 270

<210> SEQ ID NO 64
<211> LENGTH: 272
<212> TYPE: PRT
<213> ORGANISM: Escherichia coli YbhA PH38

<400> SEQUENCE: 64

```
Met Thr Thr Arg Val Ile Ala Leu Asp Leu Asp Gly Thr Leu Leu Thr
1               5                   10                  15

Pro Lys Lys Thr Leu Leu Pro Ser Ser Ile Glu Ala Leu Ala Arg Ala
            20                  25                  30

Arg Glu Ala Gly Tyr Arg Leu Ile Ile Val Thr Gly Arg His His Val
        35                  40                  45

Ala Ile His Pro Phe Tyr Gln Ala Leu Ala Leu Asp Thr Pro Ala Ile
    50                  55                  60

Cys Cys Asn Gly Thr Tyr Leu Tyr Asp Tyr His Ala Lys Thr Val Leu
65                  70                  75                  80

Glu Ala Asp Pro Met Pro Val Asn Lys Ala Leu Gln Leu Ile Glu Met
                85                  90                  95

Leu Asn Glu His His Ile His Gly Leu Met Tyr Val Asp Asp Ala Met
            100                 105                 110

Val Tyr Glu His Pro Thr Gly His Val Ile Arg Thr Ser Asn Trp Ala
        115                 120                 125

Gln Thr Leu Pro Pro Glu Gln Arg Pro Thr Phe Thr Gln Val Ala Ser
    130                 135                 140

Leu Ala Glu Thr Ala Gln Gln Val Asn Ala Val Trp Lys Phe Ala Leu
145                 150                 155                 160

Thr His Asp Asp Leu Pro Gln Leu Gln His Phe Gly Lys His Val Glu
                165                 170                 175

His Glu Leu Gly Leu Glu Cys Glu Trp Ser Trp His Asp Gln Val Asp
            180                 185                 190

Ile Ala Arg Gly Gly Asn Ser Lys Gly Lys Arg Leu Thr Lys Trp Val
        195                 200                 205

Glu Ala Gln Gly Trp Ser Met Glu Asn Val Val Ala Phe Gly Asp Asn
210                 215                 220

Phe Asn Asp Ile Ser Met Leu Glu Ala Ala Gly Thr Gly Val Ala Met
225                 230                 235                 240

Gly Asn Ala Asp Asp Ala Val Lys Ala Arg Ala Asn Ile Val Ile Gly
                245                 250                 255

Asp Asn Thr Thr Asp Ser Ile Ala Gln Phe Ile Tyr Ser His Leu Ile
            260                 265                 270

<210> SEQ ID NO 65
<211> LENGTH: 238
<212> TYPE: PRT
<213> ORGANISM: Escherichia coli YbjI PH39

<400> SEQUENCE: 65

Met Arg Phe Tyr Arg Pro Leu Gly Arg Ile Ser Ala Leu Thr Phe Asp
1               5                   10                  15

Leu Asp Asp Thr Leu Tyr Asp Asn Arg Pro Val Ile Leu Arg Thr Glu
            20                  25                  30

Arg Glu Ala Leu Thr Phe Val Gln Asn Tyr His Pro Ala Leu Arg Ser
        35                  40                  45

Phe Gln Asn Glu Asp Leu Gln Arg Leu Arg Gln Ala Val Arg Glu Ala
    50                  55                  60

Glu Pro Glu Ile Tyr His Asp Val Thr Arg Trp Arg Phe Arg Ser Ile
65                  70                  75                  80

Glu Gln Ala Met Leu Asp Ala Gly Leu Ser Ala Glu Glu Ala Ser Ala
                85                  90                  95

Gly Ala His Ala Ala Met Ile Asn Phe Ala Lys Trp Arg Ser Arg Ile
```

```
            100                 105                 110
Asp Val Pro Gln Gln Thr His Asp Thr Leu Lys Gln Leu Ala Lys Lys
        115                 120                 125

Trp Pro Leu Val Ala Ile Thr Asn Gly Asn Ala Gln Pro Glu Leu Phe
130                 135                 140

Gly Leu Gly Asp Tyr Phe Glu Phe Val Leu Arg Ala Gly Pro His Gly
145                 150                 155                 160

Arg Ser Lys Pro Phe Ser Asp Met Tyr Phe Leu Ala Ala Glu Lys Leu
                165                 170                 175

Asn Val Pro Ile Gly Glu Ile Leu His Val Gly Asp Asp Leu Thr Thr
            180                 185                 190

Asp Val Gly Gly Ala Ile Arg Ser Gly Met Gln Ala Cys Trp Ile Arg
        195                 200                 205

Pro Glu Asn Gly Asp Leu Met Gln Thr Trp Asp Ser Arg Leu Leu Pro
210                 215                 220

His Leu Glu Ile Ser Arg Leu Ala Ser Leu Thr Ser Leu Ile
225                 230                 235

<210> SEQ ID NO 66
<211> LENGTH: 266
<212> TYPE: PRT
<213> ORGANISM: Escherichia coli YigL PH40

<400> SEQUENCE: 66

Met Tyr Gln Val Val Ala Ser Asp Leu Asp Gly Thr Leu Leu Ser Pro
1               5                   10                  15

Asp His Thr Leu Ser Pro Tyr Ala Lys Glu Thr Leu Lys Leu Leu Thr
            20                  25                  30

Ala Arg Gly Ile Asn Phe Val Phe Ala Thr Gly Arg His His Val Asp
        35                  40                  45

Val Gly Gln Ile Arg Asp Asn Leu Glu Ile Lys Ser Tyr Met Ile Thr
    50                  55                  60

Ser Asn Gly Ala Arg Val His Asp Leu Asp Gly Asn Leu Ile Phe Ala
65                  70                  75                  80

His Asn Leu Asp Arg Asp Ile Ala Ser Asp Leu Phe Gly Val Val Asn
                85                  90                  95

Asp Asn Pro Asp Ile Ile Thr Asn Val Tyr Arg Asp Asp Glu Trp Phe
            100                 105                 110

Met Asn Arg His Arg Pro Glu Glu Met Arg Phe Phe Lys Glu Ala Val
        115                 120                 125

Phe Gln Tyr Ala Leu Tyr Glu Pro Gly Leu Leu Glu Pro Glu Gly Val
130                 135                 140

Ser Lys Val Phe Phe Thr Cys Asp Ser His Glu Gln Leu Leu Pro Leu
145                 150                 155                 160

Glu Gln Ala Ile Asn Ala Arg Trp Gly Asp Arg Val Asn Val Ser Phe
                165                 170                 175

Ser Thr Leu Thr Cys Leu Glu Val Met Ala Gly Val Ser Lys Gly
            180                 185                 190

His Ala Leu Glu Ala Val Ala Lys Lys Leu Gly Tyr Ser Leu Lys Asp
        195                 200                 205

Cys Ile Ala Phe Gly Asp Gly Met Asn Asp Ala Glu Met Leu Ser Met
    210                 215                 220

Ala Gly Lys Gly Cys Ile Met Gly Ser Ala His Gln Arg Leu Lys Asp
225                 230                 235                 240
```

Leu His Pro Glu Leu Glu Val Ile Gly Thr Asn Ala Asp Asp Ala Val
            245                 250                 255

Pro His Tyr Leu Arg Lys Leu Tyr Leu Ser
            260                 265

<210> SEQ ID NO 67
<211> LENGTH: 266
<212> TYPE: PRT
<213> ORGANISM: Escherichia coli OtsB PH41

<400> SEQUENCE: 67

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
            100                 105                 110

Val Ile Ala Gln Tyr Pro Gly Ala Glu Leu Glu Ala Lys Gly Met Ala
        115                 120                 125

Phe Ala Leu His Tyr Arg Gln Ala Pro Gln His Glu Asp Ala Leu Met
    130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
            260                 265

<210> SEQ ID NO 68
<211> LENGTH: 191
<212> TYPE: PRT
<213> ORGANISM: Escherichia coli YaeD PH42

<400> SEQUENCE: 68

Met Ala Lys Ser Val Pro Ala Ile Phe Leu Asp Arg Asp Gly Thr Ile
1               5                   10                  15

Asn Val Asp His Gly Tyr Val His Glu Ile Asp Asn Phe Glu Phe Ile
            20                  25                  30

-continued

Asp Gly Val Ile Asp Ala Met Arg Glu Leu Lys Lys Met Gly Phe Ala
            35                  40                  45

Leu Val Val Val Thr Asn Gln Ser Gly Ile Ala Arg Gly Lys Phe Thr
 50                  55                  60

Glu Ala Gln Phe Glu Thr Leu Thr Glu Trp Met Asp Trp Ser Leu Ala
 65                  70                  75                  80

Asp Arg Asp Val Asp Leu Asp Gly Ile Tyr Tyr Cys Pro His His Pro
                 85                  90                  95

Gln Gly Ser Val Glu Glu Phe Arg Gln Val Cys Asp Cys Arg Lys Pro
                100                 105                 110

His Pro Gly Met Leu Leu Ser Ala Arg Asp Tyr Leu His Ile Asp Met
             115                 120                 125

Ala Ala Ser Tyr Met Val Gly Asp Lys Leu Glu Asp Met Gln Ala Ala
130                 135                 140

Val Ala Ala Asn Val Gly Thr Lys Val Leu Val Arg Thr Gly Lys Pro
145                 150                 155                 160

Ile Thr Pro Glu Ala Glu Asn Ala Ala Asp Trp Val Leu Asn Ser Leu
                165                 170                 175

Ala Asp Leu Pro Gln Ala Ile Lys Lys Gln Gln Lys Pro Ala Gln
            180                 185                 190

<210> SEQ ID NO 69
<211> LENGTH: 385
<212> TYPE: PRT
<213> ORGANISM: Zymomonas mobilis DH1

<400> SEQUENCE: 69

Met Leu Asn Phe Asp Tyr Tyr Asn Pro Thr His Ile Val Phe Gly Lys
 1               5                  10                  15

Gly Arg Ile Ala Gln Leu Asp Thr Leu Leu Ser Lys Asp Ala Arg Val
             20                  25                  30

Leu Val Leu Tyr Gly Gly Ser Ser Ala Gln Lys Thr Gly Thr Leu Asp
         35                  40                  45

Glu Val Arg Lys Ala Leu Gly Asp Arg Thr Tyr Phe Glu Phe Gly Gly
 50                  55                  60

Ile Glu Pro Asn Pro Ser Tyr Glu Thr Leu Met Lys Ala Val Glu Gln
 65                  70                  75                  80

Val Lys Gln Glu Lys Val Asp Phe Leu Leu Ala Val Gly Gly Gly Ser
             85                  90                  95

Val Ile Asp Gly Thr Lys Phe Val Ala Ala Val Pro Tyr Glu Gly
            100                 105                 110

Glu Pro Trp Glu Ile Leu Glu Thr Asp Gly Lys Lys Ile Lys Glu Ala
         115                 120                 125

Leu Pro Val Gly Thr Val Leu Thr Leu Pro Ala Thr Gly Ser Glu Met
130                 135                 140

Asn Arg Asn Ser Val Val Thr Arg Lys Ser Ile Lys Ser Lys Arg Gly
145                 150                 155                 160

Phe His Asn Asp His Val Phe Pro Val Phe Ser Ile Leu Asp Pro Thr
                165                 170                 175

Lys Val Tyr Thr Leu Pro Pro Arg Gln Leu Ala Asn Gly Val Val Asp
            180                 185                 190

Ser Phe Ile His Ile Thr Glu Gln Tyr Leu Thr Tyr Pro Val Asp Gly
         195                 200                 205

Met Val Gln Asp Glu Phe Ala Glu Gly Leu Leu Arg Thr Leu Ile Lys
210                 215                 220

```
Ile Gly Pro Glu Leu Leu Lys Asp Gln Lys Asn Tyr Asp Leu Ala Ala
225                 230                 235                 240

Asn Phe Met Trp Thr Ala Thr Leu Ala Leu Asn Gly Leu Ile Gly Ala
            245                 250                 255

Gly Val Pro Gln Asp Trp Ala Thr His Met Val Gly His Glu Leu Thr
            260                 265                 270

Ala Ala Phe Gly Ile Asp His Gly Arg Thr Leu Ala Ile Ile Leu Pro
            275                 280                 285

Ser Leu Leu Gln Asn Gln Arg Glu Ala Lys Lys Gly Lys Leu Leu Gln
            290                 295                 300

Tyr Ala Lys Asn Val Trp His Ile Asp Gln Gly Ser Asp Asp Glu Arg
305                 310                 315                 320

Ile Asp Ala Ala Ile Glu Lys Thr Arg His Phe Phe Glu Ser Leu Gly
            325                 330                 335

Ile Pro Thr His Leu Lys Asp Tyr Asp Val Gly Glu Glu Ser Ile Asp
            340                 345                 350

Met Leu Val Lys Glu Leu Glu Ala His Gly Met Ser Gln Leu Gly Glu
            355                 360                 365

His Lys Ala Ile Thr Pro Glu Val Ser Arg Ala Ile Leu Leu Ala Ser
            370                 375                 380

Leu
385

<210> SEQ ID NO 70
<211> LENGTH: 385
<212> TYPE: PRT
<213> ORGANISM: Zymomonas mobilis subsp. pomaceae ATCC 29192 DH2

<400> SEQUENCE: 70

Met Leu Asn Phe Asp Tyr Tyr Asn Pro Thr His Ile Ala Phe Gly Lys
1               5                   10                  15

Asp Ser Ile Ala Lys Leu Asp Thr Leu Ile Pro Gln Asp Ala Cys Val
            20                  25                  30

Met Val Leu Tyr Gly Gly Ser Ser Ala Lys Lys Thr Gly Thr Leu Asp
            35                  40                  45

Glu Val Lys Thr Ala Leu Gly Ser Arg Lys Ile His Glu Phe Gly Gly
    50                  55                  60

Ile Glu Pro Asn Pro Ser Tyr Glu Thr Leu Met Gln Ala Val Glu Gln
65                  70                  75                  80

Val Lys Lys Glu Lys Ile Asp Phe Leu Leu Ala Val Gly Gly Gly Ser
            85                  90                  95

Val Ile Asp Gly Thr Lys Phe Val Ala Ala Val Pro Tyr Glu Gly
            100                 105                 110

Glu Pro Trp Glu Ile Leu Glu Thr Asp Gly Lys Lys Ile Lys Lys Ala
            115                 120                 125

Leu Pro Leu Gly Thr Val Leu Thr Leu Pro Ala Thr Gly Ser Glu Met
            130                 135                 140

Asn Pro Asn Ser Val Val Thr Arg Lys Ser Ile Lys Ala Lys Arg Ala
145                 150                 155                 160

Phe His Asn Lys Ile Val Phe Pro Leu Phe Ser Ile Leu Asp Pro Thr
            165                 170                 175

Lys Val Tyr Thr Leu Pro Pro Arg Gln Ile Ala Asn Gly Ile Val Asp
            180                 185                 190

Ser Phe Val His Ile Thr Glu Gln Tyr Leu Thr Tyr Pro Val Glu Gly
```

```
            195                 200                 205
Met Val Gln Asp Glu Phe Ala Glu Gly Leu Leu Arg Ile Leu Ile Asn
210                 215                 220

Ile Gly Pro Lys Leu Leu Lys Asp Gln Lys Asn Tyr Asp Leu Ala Ala
225                 230                 235                 240

Asn Phe Met Trp Thr Ala Thr Leu Ala Leu Asn Gly Leu Ile Gly Ala
                245                 250                 255

Gly Val Pro Gln Asp Trp Ala Thr His Met Ile Gly His Glu Ile Thr
                260                 265                 270

Ala Ala Phe Gly Val Asp His Gly Arg Thr Leu Ala Ile Ile Leu Pro
            275                 280                 285

Ser Leu Leu Gln Asn Gln Arg Gln Val Lys Asp Lys Leu Leu Gln
290                 295                 300

Tyr Ala Lys Asn Val Trp His Ile Glu Ser Gly Ser Glu Lys Glu Arg
305                 310                 315                 320

Ile Asp Ala Val Ile Ala Lys Thr Arg Ser Phe Phe Glu Glu Met Gly
                325                 330                 335

Ile Pro Thr His Leu Ser Asp Tyr Asn Ile Gly Lys Glu Ser Ile Asp
                340                 345                 350

Met Leu Ile His Glu Leu Glu Ala His Gly Met Thr Lys Leu Gly Glu
            355                 360                 365

His Asn Ala Ile Thr Pro Asp Val Ser Arg Ala Ile Leu Ile Ala Ser
370                 375                 380

Leu
385

<210> SEQ ID NO 71
<211> LENGTH: 385
<212> TYPE: PRT
<213> ORGANISM: Shewanella baltica DH3

<400> SEQUENCE: 71

Met Leu Asn Phe Asn Tyr Tyr Asn Pro Thr Arg Ile Arg Phe Gly Lys
1               5                   10                  15

Asp Thr Ile Ala Glu Ile Asp Thr Leu Val Pro Ser Asp Ala Lys Val
                20                  25                  30

Met Ile Leu Phe Gly Gly Ser Ser Ala Arg Lys Thr Gly Thr Leu Asp
            35                  40                  45

Glu Val Lys Gln Ser Leu Gly Asn Arg Phe Ile Val Glu Phe Asp Gly
50                  55                  60

Ile Glu Pro Asn Pro Thr Tyr Glu Thr Leu Met Lys Ala Val Ala Gln
65                  70                  75                  80

Val Arg Glu Gln Lys Ile Asp Phe Leu Leu Ala Val Gly Gly Gly Ser
                85                  90                  95

Val Ile Asp Gly Thr Lys Phe Val Ala Ala Ala Val Phe Glu Gly
            100                 105                 110

Glu Pro Trp Asp Ile Leu Thr Ser Trp Gly Ala Lys Val Thr Gln Ala
        115                 120                 125

Met Pro Phe Gly Ser Val Leu Thr Leu Pro Ala Thr Gly Ser Glu Met
130                 135                 140

Asn Asn Ala Ser Val Val Thr Arg Lys Ser Leu Gln Ala Lys Leu Pro
145                 150                 155                 160

Phe Arg Asn Asp Leu Val Tyr Pro Gln Phe Ser Ile Leu Asp Pro Thr
                165                 170                 175
```

Lys Thr Phe Thr Leu Pro Glu Arg Gln Val Ala Asn Gly Val Val Asp
            180                 185                 190

Ala Phe Val His Ile Thr Glu Gln Tyr Leu Thr Tyr Pro Val Asn Ala
        195                 200                 205

Ala Val Gln Asp Arg Phe Ala Glu Gly Leu Leu Gln Thr Leu Ile Glu
    210                 215                 220

Leu Gly Pro Gln Val Leu Ala Gln Pro Glu Asp Tyr Asp Ile Arg Ala
225                 230                 235                 240

Asn Leu Met Trp Val Ala Thr Met Ala Leu Asn Gly Thr Ile Gly Val
                245                 250                 255

Gly Val Pro His Asp Trp Ala Thr His Met Ile Gly His Glu Leu Thr
            260                 265                 270

Ala Leu Tyr Asp Ile Asp His Ala Arg Thr Leu Ala Ile Val Leu Pro
        275                 280                 285

Ala Leu Leu Gln Cys Thr Lys Glu Ala Lys Arg Glu Lys Leu Leu Gln
    290                 295                 300

Tyr Ala Asp Arg Val Trp His Ile Asn Thr Gly Thr Asp Asp Glu Arg
305                 310                 315                 320

Ile Asp Ala Ala Ile Ala Lys Thr Lys Ala Phe Phe Glu Ala Met Gly
                325                 330                 335

Ile Pro Thr His Leu Ser Ala Tyr Asp Leu Asp Ala Ser His Val Asp
            340                 345                 350

Thr Leu Val Lys Gln Leu Glu Leu His Gly Met Val Ala Leu Gly Glu
        355                 360                 365

His Gly Asn Ile Asn Pro Ala Met Ser Arg Asp Ile Leu Thr Leu Ala
    370                 375                 380

Leu
385

<210> SEQ ID NO 72
<211> LENGTH: 385
<212> TYPE: PRT
<213> ORGANISM: Burkholderia pseudomallei DH4

<400> SEQUENCE: 72

Met Leu Asn Phe Asp Phe Tyr Asn Pro Thr Arg Ile Val Phe Gly Glu
1               5                   10                  15

Lys Thr Ala Ala Arg Leu Asn Asp Leu Leu Pro Ala Ala Ala Arg Val
            20                  25                  30

Leu Val Leu Tyr Gly Gly Glu Ser Ala Arg Ser Asn Gly Thr Leu Asp
        35                  40                  45

Glu Val Arg Ala Ala Leu Gly Ala Arg Asp Val Arg Glu Phe Gly Gly
    50                  55                  60

Ile Glu Pro Asn Pro Ala Tyr Glu Thr Leu Met Arg Ala Val Glu Leu
65                  70                  75                  80

Ala Arg Arg Glu Arg Val Asp Phe Leu Leu Ala Val Gly Gly Gly Ser
                85                  90                  95

Val Ile Asp Gly Thr Lys Phe Val Ala Ala Val Pro Phe Glu Gly
            100                 105                 110

Asp Pro Trp Thr Ile Leu Glu Thr His Gly Ala Asn Val Ala Ala Ala
        115                 120                 125

Leu Pro Phe Gly Cys Val Leu Thr Leu Pro Ala Thr Gly Ser Glu Met
    130                 135                 140

Asn Asn Gly Ala Val Leu Thr Arg Arg Ala Thr Arg Ala Lys Leu Ala
145                 150                 155                 160

```
Phe Arg His Pro Leu Val Phe Pro Thr Phe Ser Ile Leu Asp Pro Thr
            165                 170                 175

Lys Thr Tyr Thr Leu Pro Pro Arg Gln Val Ala Asn Gly Val Val Asp
            180                 185                 190

Ala Phe Thr His Ile Val Glu Gln Tyr Leu Thr Tyr Pro Ala Asp Gly
            195                 200                 205

Leu Ala Gln Asp Arg Phe Ala Glu Gly Leu Leu Gln Thr Leu Ile Glu
            210                 215                 220

Ile Gly Pro Lys Ala Leu Ala Glu Pro Arg Asp Tyr Ala Thr Arg Ala
225                 230                 235                 240

Asn Leu Met Trp Val Ala Thr Leu Ala Leu Asn Gly Leu Ile Gly Ala
            245                 250                 255

Gly Val Pro Gln Asp Arg Ala Thr His Met Val Gly His Glu Leu Thr
            260                 265                 270

Ala Arg Tyr Asp Ile Asp His Ala Arg Thr Leu Ala Val Val Leu Pro
            275                 280                 285

Ser Met Leu Asp Val Arg Arg Asp Ala Lys Arg Ala Lys Leu Leu Gln
            290                 295                 300

Tyr Ala Ala Arg Val Trp Asn Ile Val Asp Gly Pro Glu Asp Ala Arg
305                 310                 315                 320

Ile Asp Ala Ala Ile Ala Arg Thr Arg Ala Phe Phe Glu Ser Leu Gly
            325                 330                 335

Val Lys Thr Arg Leu Ala Asp Tyr Gly Val Gly Ala Asp Ala Ile Asp
            340                 345                 350

Gly Leu Ile Ala Gln Leu Glu Ala His Gly Met Thr Arg Leu Gly Glu
            355                 360                 365

Arg Lys Asp Val Thr Leu Asp Val Ser Arg Arg Val Leu Glu Ala Ser
            370                 375                 380

Leu
385

<210> SEQ ID NO 73
<211> LENGTH: 348
<212> TYPE: PRT
<213> ORGANISM: Saccharomyces cerevisiae DH5

<400> SEQUENCE: 73

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Thr Lys Leu Pro Leu Val
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
            85                  90                  95

Ser Cys Met Ala Cys Glu Tyr Cys Glu Leu Gly Asn Glu Pro Asn Cys
            100                 105                 110

Pro His Ala Asp Ser Ser Gly Tyr Thr His Asp Gly Ser Phe Gln Gln
            115                 120                 125

Tyr Ala Thr Ala Asp Ala Val Gln Ala Ala His Ile Pro Gln Gly Thr
```

```
            130                 135                 140
Asp Leu Ala Glu Val Ala Pro Val Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
            195                 200                 205

Glu Leu Phe Arg Ser Ile Gly Gly Glu Val Phe Ile Asp Phe Thr Lys
            210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
            275                 280                 285

Ile Ser Ile Val Gly Ser Cys Val Gly Asn Arg Ala Asp Thr Arg Glu
            290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 74
<211> LENGTH: 360
<212> TYPE: PRT
<213> ORGANISM: Saccharomyces cerevisiae DH6

<400> SEQUENCE: 74

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
            35                  40                  45

Asp Ile His Cys Ala Ala Gly His Trp Gly Asn Met Lys Met Pro Leu
        50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
            115                 120                 125

Tyr Val Ser Gln Gly Gly Tyr Ala Asn Tyr Val Arg Val His Glu His
        130                 135                 140

Phe Val Val Pro Ile Pro Glu Asn Ile Pro Ser His Leu Ala Ala Pro
145                 150                 155                 160
```

Leu Leu Cys Gly Gly Leu Thr Val Tyr Ser Pro Leu Val Arg Asn Gly
            165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
            195                 200                 205

Ile Ser Arg Ser Ser Arg Lys Arg Glu Asp Ala Met Lys Met Gly Ala
            210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
            245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
            275                 280                 285

Tyr Gly Leu Lys Ala Val Ser Ile Ser Tyr Ser Ala Leu Gly Ser Ile
            290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
            325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
            355                 360

<210> SEQ ID NO 75
<211> LENGTH: 526
<212> TYPE: PRT
<213> ORGANISM: Pseudomonas putida DH7

<400> SEQUENCE: 75

Met Ser Ile Glu His Arg Leu Asn His Ile Ala Gly Gln Leu Ser Gly
1               5                   10                  15

Asn Gly Glu Val Leu Leu Asn Ser Val Asp Ala His Thr Gly Glu Pro
            20                  25                  30

Leu Pro Tyr Ala Phe His Gln Ala Thr Ser Asp Glu Val Asp Ala Ala
            35                  40                  45

Val Gln Ala Ala Glu Ala Ala Tyr Pro Ala Tyr Arg Ser Thr Ser Pro
        50                  55                  60

Ala Gln Arg Ala Ala Phe Leu Asp Ala Ile Ala Asn Glu Leu Asp Ala
65                  70                  75                  80

Leu Gly Asp Asp Phe Val Gln His Val Met Arg Glu Thr Ala Leu Pro
            85                  90                  95

Glu Ala Arg Ile Arg Gly Glu Arg Ala Arg Thr Ser Asn Gln Leu Arg
            100                 105                 110

Leu Phe Ala Asp Val Val Arg Arg Gly Asp Phe Leu Gly Ala Arg Ile
            115                 120                 125

Asp Arg Ala Gln Pro Glu Arg Thr Pro Leu Pro Arg Pro Asp Leu Arg
            130                 135                 140

Gln Tyr Arg Ile Gly Val Gly Pro Val Ala Val Phe Gly Ala Ser Asn
145                 150                 155                 160

Phe Pro Leu Ala Phe Ser Thr Ala Gly Gly Asp Thr Ala Ser Ala Leu
            165                 170                 175

Ala Ala Gly Cys Pro Val Val Phe Lys Ala His Ser Gly His Met Leu
            180                 185                 190

Thr Ala Ala His Val Ala Ala Ile Asp Arg Ala Val Ala Gly Ser
        195                 200                 205

Gly Met Pro Ala Gly Val Phe Asn Met Ile Tyr Gly Ala Gly Val Gly
    210                 215                 220

Glu Val Leu Val Lys His Pro Ala Ile Gln Ala Val Gly Phe Thr Gly
225                 230                 235                 240

Ser Leu Arg Gly Gly Arg Ala Leu Cys Asp Met Ala Ala Arg Pro
            245                 250                 255

Gln Pro Ile Pro Val Phe Ala Glu Met Ser Ser Ile Asn Pro Val Ile
            260                 265                 270

Val Leu Pro Gln Ala Leu Gln Ala Arg Gly Glu Gln Val Ala Gly Glu
        275                 280                 285

Leu Ala Ala Ser Val Val Leu Gly Cys Gly Gln Phe Cys Thr Asn Pro
        290                 295                 300

Gly Leu Val Val Gly Ile Lys Ser Pro Gln Phe Glu Arg Phe Val His
305                 310                 315                 320

Thr Leu Val Ala Arg Met Ala Asp Gln Ala Pro Gln Thr Met Leu Asn
            325                 330                 335

Ala Gly Thr Leu Arg Ser Tyr Gln Ser Gly Val Gln His Leu Leu Ala
        340                 345                 350

His Pro Gly Ile Gln His Leu Ala Gly Gln Pro Gln Ala Gly Lys Gln
            355                 360                 365

Ala Gln Pro Gln Leu Phe Lys Ala Asp Val Ser Leu Leu Asp Ser
        370                 375                 380

Asp Pro Leu Leu Gln Glu Glu Val Phe Gly Pro Thr Thr Val Val Val
385                 390                 395                 400

Glu Val Ala Asp Ala Gln Gln Leu Ala Glu Ala Leu Arg His Leu Gln
            405                 410                 415

Gly Gln Leu Thr Ala Thr Leu Ile Ala Glu Pro Asp Asp Leu Arg Ala
        420                 425                 430

Phe Ala Ala Leu Val Pro Leu Leu Glu Arg Lys Ala Gly Arg Leu Leu
        435                 440                 445

Leu Asn Gly Tyr Pro Thr Gly Val Glu Val Ser Asp Ala Met Val His
    450                 455                 460

Gly Gly Pro Tyr Pro Ala Thr Ser Asp Ala Arg Gly Thr Ser Val Gly
465                 470                 475                 480

Thr Leu Ala Ile Asp Arg Phe Leu Arg Pro Val Cys Phe Gln Asn Tyr
            485                 490                 495

Pro Asp Ala Leu Leu Pro Glu Ala Leu Lys Ser Ala Asn Pro Leu Gly
            500                 505                 510

Ile Ala Arg Leu Val Asp Gly Val Ala Ser Arg Gly Ala Val
            515                 520                 525

<210> SEQ ID NO 76
<211> LENGTH: 526
<212> TYPE: PRT
<213> ORGANISM: Pseudomonas putida DH8

<400> SEQUENCE: 76

Met Ser Ile Glu His Arg Leu Asn His Ile Ala Gly Gln Leu Ser Gly
1               5                   10                  15

Asn Gly Asp Val Leu Leu Asn Ser Val Asp Ala His Thr Gly Glu Pro

-continued

```
                20                  25                  30
Leu Pro Tyr Ala Phe His Gln Ala Thr Gly Asp Glu Val Glu Ala Ala
                35                  40                  45

Val Gln Ala Ala Asp Ala Ala Tyr Pro Ala Tyr Arg Ser Thr Ser Pro
 50                  55                  60

Ala Gln Arg Ala Ala Phe Leu Asp Ala Ile Ala Asn Glu Leu Asp Ala
 65                  70                  75                  80

Leu Gly Asp Asp Phe Ile Gln His Val Met Arg Glu Thr Ala Leu Pro
                85                  90                  95

Glu Ala Arg Ile Arg Gly Glu Arg Ser Arg Thr Ser Asn Gln Leu Arg
                100                 105                 110

Leu Phe Ala Glu Val Val Arg Arg Gly Asp Phe Tyr Ala Ala Arg Ile
                115                 120                 125

Asp Arg Ala Leu Pro Gln Arg Thr Pro Leu Pro Arg Pro Asp Leu Arg
130                 135                 140

Gln Tyr Arg Ile Gly Val Gly Pro Val Ala Val Phe Gly Ala Ser Asn
145                 150                 155                 160

Phe Pro Leu Ala Phe Ser Thr Ala Gly Gly Asp Thr Ala Ser Ala Leu
                165                 170                 175

Ala Ala Gly Cys Pro Val Val Phe Lys Ala His Ser Gly His Met Leu
                180                 185                 190

Thr Ala Ala His Val Ala Gly Ala Ile Asp Arg Ala Val Ala Thr Ser
                195                 200                 205

Gly Met Pro Ala Gly Val Phe Asn Leu Ile Tyr Gly Ala Gly Val Gly
                210                 215                 220

Glu Ala Leu Val Lys His Pro Ala Ile Gln Ala Val Gly Phe Thr Gly
225                 230                 235                 240

Ser Leu Arg Gly Gly Arg Ala Leu Cys Asp Met Ala Ala Ala Arg Pro
                245                 250                 255

Gln Pro Ile Pro Val Phe Ala Glu Met Ser Ser Ile Asn Pro Val Ile
                260                 265                 270

Val Leu Pro Gln Ala Leu Gln Ala Arg Gly Glu Gln Val Ala Gly Glu
                275                 280                 285

Leu Ala Ala Ser Val Val Met Gly Cys Gly Gln Phe Cys Thr Asn Pro
290                 295                 300

Gly Leu Val Val Gly Ile Gln Ser Pro Gln Phe Glu His Phe Val Gln
305                 310                 315                 320

Thr Leu Val Ala Arg Met Ala Asp Gln Gly Pro Gln Thr Met Leu Asn
                325                 330                 335

Ala Gly Thr Leu Arg Ser Tyr Gln Asn Gly Val Gln His Leu Leu Ala
                340                 345                 350

His Pro Gly Ile Gln His Leu Ala Gly Gln Pro His Thr Gly Asn Gln
                355                 360                 365

Ala Gln Pro Gln Leu Phe Lys Ala Asp Val Ser Leu Leu Leu Asn Gly
                370                 375                 380

Asp Pro Leu Leu Gln Glu Glu Val Phe Gly Pro Thr Thr Val Val Val
385                 390                 395                 400

Glu Val Ala Asp Ala Glu Gln Leu Ala Glu Ala Leu Arg His Leu Gln
                405                 410                 415

Gly Gln Leu Thr Ala Thr Leu Ile Ala Glu Pro Asp Asp Leu Arg Ala
                420                 425                 430

Phe Ala Ser Leu Val Pro Leu Leu Glu Arg Lys Ala Gly Arg Leu Leu
                435                 440                 445
```

Leu Asn Gly Tyr Pro Thr Gly Val Glu Val Ser Asp Ala Met Val His
            450                 455                 460

Gly Gly Pro Tyr Pro Ala Thr Ser Asp Ala Arg Gly Thr Ser Val Gly
465                 470                 475                 480

Thr Leu Ala Ile Asp Arg Phe Leu Arg Pro Val Cys Phe Gln Asn Tyr
                485                 490                 495

Pro Asp Ala Leu Leu Pro Asp Ala Leu Lys Asn Ala Asn Pro Leu Gly
            500                 505                 510

Ile Ala Arg Leu Leu Asp Gly Val Asn Ser Arg Asp Ala Val
            515                 520                 525

<210> SEQ ID NO 77
<211> LENGTH: 526
<212> TYPE: PRT
<213> ORGANISM: Pseudomonas sp. NBRC 111139 DH9

<400> SEQUENCE: 77

Met Ser Ile Glu His Arg Leu Asn His Ile Ala Gly Gln Leu Ser Gly
1               5                   10                  15

His Gly Asp Val Leu Leu His Ser Leu Asp Ala His Thr Gly Glu Ala
            20                  25                  30

Leu Pro Tyr Ala Phe His Gln Ala Thr Gly Asp Glu Val Glu Ala Ala
        35                  40                  45

Ala Gln Ala Ala Glu Val Ala Tyr Pro Ser Tyr Arg Ser Thr Arg Pro
    50                  55                  60

Asp Gln Arg Ala Ala Phe Leu Asp Ala Ile Ala Ser Glu Leu Asp Ala
65                  70                  75                  80

Leu Gly Asp Asp Phe Ile Gln Asp Val Met Arg Glu Thr Ala Leu Pro
                85                  90                  95

Glu Ala Arg Ile Arg Gly Glu Arg Ser Arg Thr Ser Asn Gln Leu Arg
            100                 105                 110

Leu Phe Ala Glu Val Val Arg Arg Gly Asp Phe Tyr Ala Ala Arg Ile
        115                 120                 125

Asp Arg Ala Leu Pro Gln Arg Thr Pro Leu Pro Arg Pro Asp Leu Arg
130                 135                 140

Gln Tyr Arg Ile Gly Val Gly Pro Val Ala Val Phe Gly Ala Ser Asn
145                 150                 155                 160

Phe Pro Leu Ala Phe Ser Thr Ala Gly Gly Asp Thr Ala Ser Ala Leu
                165                 170                 175

Ala Ala Gly Cys Pro Val Val Phe Lys Ala His Ser Gly His Met Leu
            180                 185                 190

Thr Ala Ala His Val Ala Ala Ile Asp Arg Ala Val Thr Gly Ser
        195                 200                 205

Gly Met Pro Ala Gly Val Phe Asn Met Ile Tyr Gly Ala Gly Val Gly
    210                 215                 220

Glu Ala Leu Val Lys His Pro Ala Ile Gln Ala Val Gly Phe Thr Gly
225                 230                 235                 240

Ser Leu Arg Gly Gly Arg Ala Leu Cys Asp Met Ala Ala Ala Arg Pro
                245                 250                 255

Gln Pro Ile Pro Val Phe Ala Glu Met Ser Ser Ile Asn Pro Val Ile
            260                 265                 270

Val Leu Pro Gln Ala Leu Gln Ala Arg Gly Glu Gln Val Ala Thr Glu
        275                 280                 285

Leu Ala Ala Ser Val Val Leu Gly Cys Gly Gln Phe Cys Thr Asn Pro

Gly Leu Val Val Gly Ile Arg Ser Pro His Phe Glu His Phe Leu Gln
            290                 295                 300
305                                 310                 315                 320

Thr Leu Val Ala Arg Met Ala Asp Gln Gly Pro Gln Thr Met Leu Asn
                    325                 330                 335

Ala Gly Thr Leu Arg Ser Tyr Gln Asn Ala Val Gln His Leu Leu Ala
                340                 345                 350

His Pro Gly Ile Gln His Leu Ala Gly Gln Pro Gln Thr Gly Asn Gln
            355                 360                 365

Ala Gln Pro Gln Leu Phe Lys Ala Asp Val Ser Leu Leu Leu Asn Gly
        370                 375                 380

Asp Pro Leu Leu Gln Glu Glu Val Phe Gly Pro Cys Thr Val Val Val
385                 390                 395                 400

Glu Val Ala Asp Ala Gln Gln Leu Ala Glu Ala Leu Arg His Leu Gln
                    405                 410                 415

Gly Gln Leu Thr Ala Thr Leu Ile Ala Glu Pro Asp Asp Leu Arg Ala
                420                 425                 430

Phe Ala Ser Leu Val Pro Leu Leu Glu Arg Lys Ala Gly Arg Leu Leu
        435                 440                 445

Leu Asn Gly Tyr Pro Thr Gly Val Glu Val Ser Asp Ala Met Val His
    450                 455                 460

Gly Gly Pro Tyr Pro Ala Thr Ser Asp Ala Arg Gly Thr Ser Val Gly
465                 470                 475                 480

Thr Leu Ala Ile Asp Arg Phe Leu Arg Pro Val Cys Phe Gln Asn Tyr
                485                 490                 495

Pro Asp Ala Leu Leu Pro Asp Ala Leu Lys Asn Ala Asn Pro Leu Gly
            500                 505                 510

Ile Ala Arg Leu Leu Glu Gly Val Ser Ser Arg Glu Ala Val
        515                 520                 525

<210> SEQ ID NO 78
<211> LENGTH: 525
<212> TYPE: PRT
<213> ORGANISM: Pseudomonas sp. JUb52 DH10

<400> SEQUENCE: 78

Met Gln Ile Gln Gly Lys Asn Tyr Ile Gly Gly Ala Arg Ser Gly Glu
1               5                   10                  15

Gly Glu Val Arg Val Tyr Ser Ile Asp Ala Thr Thr Gly Glu Lys Leu
                20                  25                  30

Pro Tyr Glu Phe Phe Gln Ala Ser Thr Ala Glu Val Asp Ala Ala Ala
            35                  40                  45

Arg Ala Ala Glu Gln Ala Ala Pro Leu Tyr Arg Lys Leu Ser Ala Glu
        50                  55                  60

Gln Arg Ala Thr Phe Leu Asp Ala Ile Ala Asp Glu Leu Asp Ala Leu
65                  70                  75                  80

Gly Asp Asp Phe Val Gln Leu Val Cys Gln Glu Thr Ala Leu Pro Ala
                85                  90                  95

Gly Arg Ile Gln Gly Glu Arg Gly Arg Thr Ser Gly Gln Met Arg Leu
            100                 105                 110

Phe Ala Lys Val Leu Arg Arg Gly Asp Phe His Gly Ala Arg Ile Asp
        115                 120                 125

Thr Ala Leu Pro Glu Arg Lys Pro Leu Pro Arg Pro Asp Leu Arg Gln
    130                 135                 140

Tyr Arg Ile Gly Leu Gly Pro Val Ala Val Phe Gly Ala Ser Asn Phe
145                 150                 155                 160

Pro Leu Ala Phe Ser Thr Ala Gly Gly Asp Thr Ala Ala Ala Leu Ala
            165                 170                 175

Ala Gly Cys Pro Val Val Phe Lys Ala His Ser Gly His Met Val Thr
        180                 185                 190

Ala Glu Tyr Val Ala Asp Ala Ile Ile Arg Ala Ala Glu Lys Thr Gly
    195                 200                 205

Met Pro Lys Gly Val Phe Asn Met Ile Tyr Gly Gly Val Gly Glu
210                 215                 220

Gln Leu Val Lys His Pro Ala Ile Gln Ala Val Gly Phe Thr Gly Ser
225                 230                 235                 240

Leu Arg Gly Gly Arg Ala Leu Cys Asp Met Ala Ala Ala Arg Pro Gln
            245                 250                 255

Pro Ile Pro Val Phe Ala Glu Met Ser Ser Ile Asn Pro Val Val Val
        260                 265                 270

Leu Pro Glu Ala Leu Lys Ala Arg Gly Asp Ala Ile Thr Gly Glu Leu
    275                 280                 285

Ala Ala Ser Val Val Leu Gly Cys Gly Gln Phe Cys Thr Asn Pro Gly
290                 295                 300

Leu Val Ile Gly Leu Arg Ser Pro Glu Phe Ser Thr Phe Leu Glu Gly
305                 310                 315                 320

Leu Ala Ala Ala Met Asn Glu Gln Ala Pro Gln Thr Met Leu Asn Pro
            325                 330                 335

Gly Thr Leu Lys Ser Tyr Glu Lys Gly Val Ala Leu Leu Ala His
        340                 345                 350

Ser Gly Val Gln His Leu Ala Gly Ala Asn Gln Glu Gly Asn Gln Ala
    355                 360                 365

Arg Pro Gln Leu Phe Lys Ala Asp Val Ser Leu Leu Leu Glu Asn Asp
370                 375                 380

Glu Leu Leu Gln Glu Glu Val Phe Gly Pro Thr Thr Val Val Val Glu
385                 390                 395                 400

Val Ala Asp Glu Ala Gln Leu His Gln Ala Leu Gln Gly Leu His Gly
            405                 410                 415

Gln Leu Thr Ala Thr Leu Leu Ala Glu Pro Ala Asp Leu Gln Arg Phe
        420                 425                 430

Glu Ala Ile Ile Gly Leu Leu Glu Gln Lys Ala Gly Arg Leu Leu Leu
    435                 440                 445

Asn Gly Tyr Pro Thr Gly Val Glu Val Cys Asp Ala Met Val His Gly
450                 455                 460

Gly Pro Tyr Pro Ala Thr Ser Asp Ala Arg Gly Thr Ser Val Gly Thr
465                 470                 475                 480

Leu Ala Ile Asp Arg Phe Leu Arg Pro Val Cys Tyr Gln Asn Tyr Pro
            485                 490                 495

Asp Ala Phe Leu Pro Glu Ala Leu Gln Asn Ala Asn Pro Leu Gly Ile
        500                 505                 510

Gln Arg Leu Val Asn Gly Glu Asn Thr Lys Ala Ala Ile
    515                 520                 525

<210> SEQ ID NO 79
<211> LENGTH: 523
<212> TYPE: PRT
<213> ORGANISM: Pseudomonas citronellolis DH11

<400> SEQUENCE: 79

```
Met Phe Gly His Asn Phe Ile Gly Gly Ala Arg Thr Ala Gln Gly Asn
1               5                   10                  15

Leu Thr Leu Gln Ser Leu Asp Ala Gly Thr Glu Ala Leu Pro Tyr
            20                  25                  30

Ser Phe His Gln Ala Thr Pro Glu Glu Val Asp Ala Ala Leu Ala
            35                  40                  45

Ala Glu Ala Ala Phe Pro Ala Tyr Arg Ala Leu Pro Asp Ala Arg Arg
50                  55                  60

Ala Glu Phe Leu Asp Ala Ile Ala Ala Glu Leu Asp Ala Leu Gly Glu
65                  70                  75                  80

Asp Phe Ile Ala Ile Val Cys Arg Glu Thr Ala Leu Pro Ala Ala Arg
                85                  90                  95

Ile Gln Gly Glu Arg Ala Arg Thr Ser Asn Gln Leu Arg Leu Phe Ala
                100                 105                 110

Gln Val Leu Arg Arg Gly Asp Tyr His Gly Ala Arg Ile Asp Arg Ala
            115                 120                 125

Leu Pro Glu Arg Gln Pro Leu Pro Arg Pro Asp Leu Arg Gln Cys Arg
            130                 135                 140

Ile Gly Val Gly Pro Val Ala Val Phe Gly Ala Ser Asn Phe Pro Leu
145                 150                 155                 160

Ala Phe Ser Thr Ala Gly Gly Asp Thr Ala Ala Leu Ala Ala Gly
                165                 170                 175

Cys Pro Val Val Phe Lys Ala His Ser Gly His Met Ala Thr Ala Glu
                180                 185                 190

His Val Ala Ser Ala Ile Val Arg Ala Ala Gln Ala Thr Gly Met Pro
            195                 200                 205

Ala Gly Val Phe Asn Met Ile Tyr Gly Gly Gly Val Gly Glu Arg Leu
            210                 215                 220

Val Lys His Pro Ala Ile Gln Ala Val Gly Phe Thr Gly Ser Leu Lys
225                 230                 235                 240

Gly Gly Arg Ala Leu Cys Asp Leu Ala Ala Ala Arg Pro Gln Pro Ile
                245                 250                 255

Pro Val Phe Ala Glu Met Ser Ser Ile Asn Pro Val Leu Ala Leu Pro
                260                 265                 270

Ala Ala Leu Ala Ala Arg Gly Glu Gln Val Ala Ala Asp Leu Ala Ala
                275                 280                 285

Ser Val Val Leu Gly Cys Gly Gln Phe Cys Thr Asn Pro Gly Met Val
            290                 295                 300

Ile Gly Ile Ala Ser Ala Glu Phe Ser Ala Phe Val Ala Ser Leu Thr
305                 310                 315                 320

Gly Arg Met Ala Asp Gln Pro Ala Gln Thr Met Leu Asn Ala Gly Thr
                325                 330                 335

Leu Lys Ser Tyr Glu Arg Gly Ile Ala Ala Leu His Ala His Pro Gly
            340                 345                 350

Ile Arg His Leu Ala Gly Gln Pro Gln Lys Gly Arg Gln Ala Leu Pro
            355                 360                 365

Gln Leu Phe Gln Ala Asp Ala Arg Leu Leu Ile Glu Gly Asp Glu Leu
            370                 375                 380

Leu Gln Glu Glu Val Phe Gly Pro Val Thr Val Val Glu Val Ala
385                 390                 395                 400

Asp Ala Ala Glu Leu Gln Arg Ala Leu Gln Gly Leu Arg Gly Gln Leu
                405                 410                 415
```

```
Thr Ala Thr Leu Ile Ala Glu Pro Glu Asp Leu Ser Cys Phe Ala Ala
            420                 425                 430

Leu Val Pro Leu Leu Glu Arg Lys Ala Gly Arg Leu Leu Leu Asn Gly
        435                 440                 445

Tyr Pro Thr Gly Val Glu Val Cys Asp Ala Met Val His Gly Gly Pro
        450                 455                 460

Tyr Pro Ala Thr Ser Asp Ala Arg Gly Thr Ser Val Gly Thr Leu Ala
465                 470                 475                 480

Ile Asp Arg Phe Leu Arg Pro Val Cys Tyr Gln Asn Tyr Pro Asp Ala
                485                 490                 495

Leu Leu Pro Pro Ala Leu Lys Asp Ala Asn Pro Leu Gly Ile Ala Arg
            500                 505                 510

Leu Val Asp Gly Val Ala Ser Arg Glu Pro Leu
            515                 520

<210> SEQ ID NO 80
<211> LENGTH: 531
<212> TYPE: PRT
<213> ORGANISM: Methylovorus sp HmfH1

<400> SEQUENCE: 80

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
        35                  40                  45

Glu Ile His Asp Gly Leu Arg Pro Trp Leu Pro Arg Leu Ser Gly Asp
    50                  55                  60

Lys Phe Phe Trp Pro Asn Leu Thr Ile His Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Val Ser Asn Arg Gly Leu Pro Arg
            100                 105                 110

Asp Tyr Asp Glu Trp Gln Ala Leu Gly Ala Asp Gly Trp Asp Trp Gln
        115                 120                 125

Gly Val Leu Pro Tyr Phe Ile Lys Thr Glu Arg Asp Ala Asp Tyr Gly
        130                 135                 140

Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
                165                 170                 175

Glu Ala Ala Gly Leu Pro Asn Ile His Asp Gln Asn Ala Arg Phe Asp
            180                 185                 190

Asp Gly Tyr Phe Pro Pro Ala Phe Thr Leu Lys Gly Glu Glu Arg Phe
        195                 200                 205

Ser Ala Ala Arg Gly Tyr Leu Asp Ala Ser Val Arg Val Arg Pro Asn
    210                 215                 220

Leu Ser Leu Trp Thr Glu Ser Arg Val Leu Lys Leu Leu Thr Thr Gly
225                 230                 235                 240

Asn Ala Ile Thr Gly Val Ser Val Leu Arg Gly Arg Glu Thr Leu Gln
                245                 250                 255

Val Gln Ala Arg Glu Val Ile Leu Thr Ala Gly Ala Leu Gln Ser Pro
            260                 265                 270
```

Ala Ile Leu Leu Arg Thr Gly Ile Gly Pro Ala Ala Asp Leu His Ala
            275                 280                 285

Leu Gly Ile Pro Val Leu Ala Asp Arg Pro Gly Val Gly Arg Asn Leu
        290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
                325                 330                 335

Ile Arg Ala Ser Ser Gly Val Asp Pro Ala Thr Pro Ser Asp Leu Phe
            340                 345                 350

Leu His Ile Gly Ala Asp Pro Val Ser Gly Leu Ala Ser Ala Val Phe
        355                 360                 365

Trp Val Asn Lys Pro Ser Ser Thr Gly Trp Leu Lys Leu Lys Asp Ala
        370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Thr His Tyr
                405                 410                 415

Phe Ala Ala Pro Ser Leu Ala Lys Tyr Gly Leu Ala Leu Ala Leu Ser
            420                 425                 430

Arg Phe Ala Ala Pro Gln Pro Gly Gly Pro Leu Leu Asn Asp Leu Leu
        435                 440                 445

Gln Asp Glu Ala Ala Leu Glu Arg Tyr Leu Arg Thr Asn Val Gly Gly
        450                 455                 460

Val Trp His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                485                 490                 495

Arg Val Ala Asp Ala Ser Ile Met Pro Thr Val Pro Thr Ala Asn Thr
            500                 505                 510

Asn Leu Pro Thr Leu Met Leu Ala Glu Lys Ile Ala Asp Ala Ile Leu
        515                 520                 525

Thr Gln Ala
    530

<210> SEQ ID NO 81
<211> LENGTH: 579
<212> TYPE: PRT
<213> ORGANISM: Cupriavidus basilensis HmfH2

<400> SEQUENCE: 81

Met Asp Thr Pro Arg Glu Arg Phe Asp Tyr Val Ile Val Gly Gly Gly
1               5                   10                  15

Ser Ala Gly Cys Val Leu Ala Asn Arg Leu Ser Gln Asp Pro Ala Ile
            20                  25                  30

Arg Val Ala Leu Ile Glu Ala Gly Val Asp Thr Pro Asp Ala Val
        35                  40                  45

Pro Ala Glu Ile Leu Asp Ser Tyr Pro Met Pro Leu Phe Phe Gly Asp
    50                  55                  60

Arg Tyr Ile Trp Pro Ser Leu Gln Ala Arg Val Ala Gly Gly Arg
65                  70                  75                  80

Ser Lys Val Tyr Glu Gln Gly Arg Val Met Gly Gly Ser Ser Ile
                85                  90                  95

Asn Val Gln Ala Ala Asn Arg Gly Leu Pro Arg Asp Tyr Asp Glu Trp

-continued

```
            100                 105                 110
Ala Ala Ser Gly Ala Ser Gly Trp Ser Trp Gln Asp Val Leu Pro Tyr
            115                 120                 125
Phe Arg His Leu Glu Arg Asp Val Asp Tyr Gly Asn Ser Pro Leu His
            130                 135                 140
Gly Ser His Gly Pro Val Pro Ile Arg Arg Ile Leu Pro Gln Ala Trp
145                 150                 155                 160
Pro Pro Phe Cys Thr Glu Phe Ala His Ala Met Gly Arg Ser Gly Leu
                165                 170                 175
Ser Ala Leu Ala Asp Gln Asn Ala Glu Phe Gly Asp Gly Trp Phe Pro
            180                 185                 190
Ala Ala Phe Ser Asn Leu Asp Asp Lys Arg Val Ser Thr Ala Ile Ala
            195                 200                 205
Tyr Leu Asp Ala Asp Thr Arg Arg Ala Asn Leu Arg Ile Tyr Ala
            210                 215                 220
Glu Thr Thr Val Arg Lys Leu Val Val Ser Gly Arg Glu Ala Arg Gly
225                 230                 235                 240
Val Ile Ala Met Arg Ala Asp Gly Ser Arg Leu Ala Leu Asp Ala Gly
                245                 250                 255
Glu Val Ile Val Ser Ala Gly Ala Leu Gln Ser Pro Ala Ile Leu Met
                260                 265                 270
Arg Ala Gly Ile Gly Asp Ala Gly Ala Leu Gln Ala Leu Gly Ile Glu
            275                 280                 285
Val Val Ala Asp Arg Pro Gly Val Gly Arg Asn Leu Gln Asp His Pro
            290                 295                 300
Ala Leu Thr Phe Cys Gln Phe Leu Ala Pro Gln Tyr Arg Met Pro Leu
305                 310                 315                 320
Ser Arg Arg Arg Ala Ser Met Thr Ala Ala Arg Phe Ser Ser Gly Val
                325                 330                 335
Pro Gly Gly Glu Ala Ser Asp Met Tyr Leu Ser Ser Ser Thr Arg Ala
            340                 345                 350
Gly Trp His Ala Leu Gly Asn Arg Leu Gly Leu Phe Phe Leu Trp Cys
            355                 360                 365
Asn Arg Pro Phe Ser Arg Gly Gln Val Ser Leu Ala Gly Ala Gln Pro
            370                 375                 380
Asp Val Pro Pro Met Val Glu Leu Asn Leu Leu Asp Asp Glu Arg Asp
385                 390                 395                 400
Leu Arg Arg Met Val Ala Gly Val Arg Lys Leu Val Gln Ile Val Gly
                405                 410                 415
Ala Ser Ala Leu His Gln His Pro Gly Asp Phe Phe Pro Ala Thr Phe
            420                 425                 430
Ser Pro Arg Val Lys Ala Leu Ser Arg Val Ser Arg Gly Asn Val Leu
            435                 440                 445
Leu Thr Glu Leu Leu Gly Ala Val Leu Asp Val Ser Gly Pro Leu Arg
            450                 455                 460
Arg Ser Leu Ile Ala Arg Phe Val Thr Gly Gly Ala Asn Leu Ala Ser
465                 470                 475                 480
Leu Leu Thr Asp Glu Ser Ala Leu Glu Gly Phe Val Arg Gln Ser Val
                485                 490                 495
Phe Gly Val Trp His Ala Ser Gly Thr Cys Arg Met Gly Ala His Ala
                500                 505                 510
Asp Arg Ser Ala Val Thr Asp Ala Ala Gly Arg Val His Asp Val Gly
            515                 520                 525
```

```
Arg Leu Arg Val Ile Asp Ala Ser Leu Met Pro Arg Leu Pro Thr Ala
        530                 535                 540

Asn Thr Asn Ile Pro Thr Ile Met Leu Ala Glu Lys Ile Ala Asp Thr
545                 550                 555                 560

Met Gln Ala Glu Arg Arg Ala Val Arg Pro Ala Ser Ser Glu Val Ala
                565                 570                 575

His Pro Ser

<210> SEQ ID NO 82
<211> LENGTH: 579
<212> TYPE: PRT
<213> ORGANISM: Cupriavidus necator HmfH3

<400> SEQUENCE: 82

Met Asp Thr Pro Arg Glu Arg Phe Asp Tyr Val Ile Val Gly Gly Gly
1               5                   10                  15

Ser Ala Gly Cys Val Leu Ala Asn Arg Leu Ser Gln Asp Pro Ala Ile
                20                  25                  30

Arg Val Ala Leu Ile Glu Gly Gly Val Asp Thr Pro Pro Asp Ala Val
            35                  40                  45

Pro Val Glu Ile Leu Asp Ser Tyr Pro Met Pro Leu Phe Phe Gly Asp
        50                  55                  60

Arg Tyr Ile Trp Pro Ser Leu Gln Ala Arg Ala Val Gly Gly Arg
65                  70                  75                  80

Ser Lys Val Tyr Glu Gln Gly Arg Val Met Gly Gly Ser Ser Ile
                85                  90                  95

Asn Val Gln Ala Ala Asn Arg Gly Leu Pro Arg Asp Tyr Asp Glu Trp
                100                 105                 110

Ala Ala Ser Gly Ala Pro Gly Trp Ser Trp Gln Asp Val Leu Pro Tyr
            115                 120                 125

Phe Arg Asn Leu Glu Arg Asp Val Asp Tyr Gly Asn Ser Pro Leu His
        130                 135                 140

Gly Ser His Gly Pro Val Pro Ile Arg Arg Ile Leu Pro Gln Ala Trp
145                 150                 155                 160

Pro Pro Phe Cys Thr Glu Phe Ala His Ala Met Gly Leu Ser Gly Leu
                165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
        195                 200                 205

Tyr Leu Asp Ala Asp Thr Arg Arg Ala Asn Leu Arg Ile Tyr Ala
    210                 215                 220

Glu Thr Thr Val Arg Lys Leu Val Ser Gly Arg Glu Ala Arg Gly
225                 230                 235                 240

Val Ile Ala Ile Arg Ala Asp Gly Ser Arg Leu Ala Leu Asp Ala Gly
                245                 250                 255

Glu Val Ile Val Ser Ala Gly Ala Leu Gln Ser Pro Ala Ile Leu Met
            260                 265                 270

Arg Ala Gly Ile Gly Asp Ala Gly Ala Leu Gln Ala Leu Gly Ile Glu
        275                 280                 285

Val Val Ala Asp Arg Pro Gly Val Gly Arg Asn Leu Gln Asp His Pro
    290                 295                 300

Ala Leu Thr Phe Cys Gln Phe Leu Ala Pro Gln Tyr Arg Met Pro Leu
305                 310                 315                 320
```

```
Ser Arg Arg Arg Ala Ser Met Thr Ala Ala Arg Phe Ser Ser Gly Val
                325                 330                 335

Pro Gly Gly Glu Ala Ser Asp Met Tyr Leu Ser Ser Thr Arg Ala
            340                 345                 350

Gly Trp His Ala Leu Gly Asn Arg Leu Gly Leu Phe Phe Leu Trp Cys
            355                 360                 365

Asn Arg Pro Phe Ser Arg Gly Gln Val Ser Leu Ala Gly Ala Gln Pro
            370                 375                 380

Asp Val Pro Pro Met Val Glu Leu Asn Leu Leu Asp Asp Glu Arg Asp
385                 390                 395                 400

Leu Arg Arg Met Val Ala Gly Val Arg Lys Leu Val Gln Ile Val Gly
                405                 410                 415

Ala Ser Ala Leu His Gln His Pro Gly Asp Phe Phe Pro Ala Thr Phe
                420                 425                 430

Ser Pro Arg Val Lys Ala Leu Ser Arg Leu Ser Arg Gly Asn Ala Leu
            435                 440                 445

Leu Thr Glu Leu Leu Gly Ala Leu Leu Asp Val Ser Gly Pro Leu Arg
            450                 455                 460

Arg Ser Leu Ile Ala Arg Phe Val Thr Gly Gly Ala Asn Leu Ala Ser
465                 470                 475                 480

Leu Leu Val Glu Glu Ser Ala Leu Glu Gly Phe Val Arg Gln Ser Val
                485                 490                 495

Phe Gly Val Trp His Ala Ser Gly Thr Cys Arg Met Gly Ala His Ala
            500                 505                 510

Asp Arg Ser Ala Val Thr Asp Ala Gly Arg Val His Asp Val Gly
            515                 520                 525

Arg Leu Arg Val Val Asp Ala Ser Leu Met Pro Arg Leu Pro Thr Ala
            530                 535                 540

Asn Thr Asn Ile Pro Thr Ile Met Leu Ala Glu Lys Ile Ala Asp Thr
545                 550                 555                 560

Met Gln Ala Glu Arg Arg Ala Val Arg Leu Ala Ser Ser Glu Val Ala
                565                 570                 575

His Gln Ser

<210> SEQ ID NO 83
<211> LENGTH: 579
<212> TYPE: PRT
<213> ORGANISM: Cupriavidus pinatubonensis HmfH4

<400> SEQUENCE: 83

Met Gly Thr Pro Arg Asp Arg Phe Asp Tyr Val Ile Val Gly Gly Gly
1               5                   10                  15

Ser Ala Gly Cys Val Leu Ala Asn Arg Leu Ser Arg Asp Pro Gly Ile
                20                  25                  30

Arg Val Ala Leu Ile Glu Gly Gly Val Asp Thr Pro Pro Gly Ala Val
            35                  40                  45

Pro Ala Glu Ile Leu Asp Ser Tyr Pro Met Pro Leu Phe Phe Gly Asp
        50                  55                  60

Arg Tyr Leu Trp Pro Ser Leu Gln Ala Arg Ala Val Ala Gly Gly Arg
65                  70                  75                  80

Ala Arg Leu Tyr Glu Gln Gly Arg Val Met Gly Gly Gly Ser Ser Ile
                85                  90                  95

Asn Val Gln Ala Ala Asn Arg Gly Leu Pro Arg Asp Tyr Asp Glu Trp
            100                 105                 110
```

```
Ala Ala Ser Gly Ala Pro Gly Trp Ser Trp Gln Glu Val Leu Pro Tyr
        115                 120                 125

Phe Arg Lys Leu Glu Arg Asp Val Asp Phe Ala Ser Ser Pro Met His
        130                 135                 140

Gly Ser Asp Gly Pro Val Pro Ile Arg Arg Ile Leu Pro Pro Ala Trp
145                 150                 155                 160

Pro Pro Phe Cys Thr Ala Phe Ala Gln Ala Met Gly Arg Ser Gly Leu
                165                 170                 175

Ser Ala Leu Asp Asp Gln Asn Ala Glu Phe Gly Asp Gly Trp Phe Pro
            180                 185                 190

Ala Ala Phe Ser Asn Leu Asp Gly Lys Arg Val Ser Thr Ala Ile Ala
            195                 200                 205

Tyr Leu Asp Ala Asn Thr Arg Lys Arg Thr Asn Leu Arg Ile Phe Ala
210                 215                 220

Glu Thr Thr Val Lys Glu Leu Val Val Ser Gly Arg Glu Ala Arg Gly
225                 230                 235                 240

Val Ile Ala Val Arg Ala Asp Gly Ala Arg Leu Ala Leu Glu Ala Ala
                245                 250                 255

Glu Val Ile Val Ser Ala Gly Ala Leu Gln Ser Pro Ala Ile Leu Met
            260                 265                 270

Arg Ala Gly Ile Gly Asp Ala Ala Leu Gln Ala Leu Gly Ile Glu
            275                 280                 285

Val Val Ala Asp Arg Pro Gly Val Gly Arg Asn Leu Gln Asp His Pro
290                 295                 300

Ala Leu Thr Phe Cys Gln Phe Leu Ala Pro Glu Tyr Arg Met Pro Leu
305                 310                 315                 320

Ala Arg Arg Arg Ser Ser Met Thr Ala Ala Arg Phe Ser Ser Glu Val
                325                 330                 335

Pro Gly Gly Glu Ala Ser Asp Met Tyr Leu Ser Ser Ser Thr Arg Ala
            340                 345                 350

Gly Trp His Ala Leu Gly Asn Arg Leu Gly Leu Phe Phe Leu Trp Cys
            355                 360                 365

Asn Arg Pro Phe Ser Arg Gly Gln Val Ser Leu Ala Gly Ala Gln Pro
370                 375                 380

Glu Val Ser Pro Leu Val Glu Leu Asn Leu Leu Asp Asp Glu Arg Asp
385                 390                 395                 400

Leu Arg Arg Met Val Ala Gly Val Arg Leu Val Arg Ile Val Gly
                405                 410                 415

Ala Ser Ala Leu His Gln His Pro Asp Asp Phe Pro Ala Ile Phe
            420                 425                 430

Ser Pro Arg Val Lys Ala Met Ser Arg Val Ser Pro Gly Asn Ala Leu
            435                 440                 445

Leu Thr Ala Leu Leu Gly Ala Leu Leu Asp Val Ser Gly Pro Leu Arg
450                 455                 460

Arg Ser Leu Ile Ala Arg Phe Val Thr Gly Gly Ala Asn Leu Ala Ser
465                 470                 475                 480

Leu Leu Ala Asp Glu Ser Ala Leu Glu Gly Phe Val Arg Gln Ser Val
                485                 490                 495

Phe Gly Val Trp His Ala Ser Gly Thr Cys Arg Met Gly Ala His Ala
            500                 505                 510

Asp Arg Ser Ala Val Thr Asp Thr Gly Arg Val His Asp Val Gly
            515                 520                 525
```

Arg Leu Arg Val Val Asp Ala Ser Leu Met Pro Arg Leu Pro Thr Ala
            530                 535                 540

Asn Thr Asn Ile Pro Thr Ile Met Leu Ala Glu Lys Ile Ala Asp Ala
545                 550                 555                 560

Met Leu Ala Glu Arg Arg Ala Thr Arg Arg Ala Leu Ser Glu Val Ala
                565                 570                 575

Asp Pro Gly

<210> SEQ ID NO 84
<211> LENGTH: 591
<212> TYPE: PRT
<213> ORGANISM: Pandoraea sp. B-6 HmfH5

<400> SEQUENCE: 84

Met Pro Arg Gly His Ala His Arg Arg Ile Arg Arg His Ser Val Gln
1               5                   10                  15

Asn Val Arg Glu Arg Phe Asp Tyr Val Ile Gly Gly Gly Ser Ala
                20                  25                  30

Gly Cys Val Leu Ala His Arg Leu Ser Ala Asn Arg Glu Leu Arg Val
                35                  40                  45

Ala Leu Ile Glu Ala Gly Ser Asp Thr Pro Pro Gly Ala Ile Pro Ala
50                  55                  60

Glu Ile Leu Asp Ser Tyr Pro Met Pro Val Phe Cys Gly Asp Arg Tyr
65                  70                  75                  80

Ile Trp Pro Glu Leu Lys Ala Lys Ala Thr Ala Ala Ser Pro Leu Lys
                85                  90                  95

Val Tyr Glu Gln Gly Lys Val Met Gly Gly Ser Ser Ile Asn Val
                100                 105                 110

Gln Ala Ala Asn Arg Gly Leu Pro Arg Asp Tyr Asp Asp Trp Ala Glu
                115                 120                 125

Gln Gly Ala Ser Gly Trp Ala Trp Lys Asp Val Leu Pro Tyr Phe Arg
130                 135                 140

Lys Leu Glu Arg Asp Ala Asp Tyr Gly Gly Ser Ala Leu His Gly Ala
145                 150                 155                 160

Asp Gly Pro Val Ala Ile Arg Arg Ile Lys Pro Asp Ala Trp Pro Arg
                165                 170                 175

Phe Cys His Ala Phe Ala Glu Gly Leu Gln Arg Asn Gly Leu Pro Met
                180                 185                 190

Leu Glu Asp Gln Asn Ala Glu Phe Gly Asp Gly Met Phe Pro Ala Ala
                195                 200                 205

Phe Ser Asn Leu Asp Asp Lys Arg Val Ser Thr Ala Val Ala Tyr Leu
210                 215                 220

Asp Ala Ala Thr Arg Ala Arg Thr Asn Leu Arg Ile Tyr Ser Asn Thr
225                 230                 235                 240

Thr Val Glu Arg Leu Ile Val Thr Gly Gln Arg Ala His Gly Val Val
                245                 250                 255

Ala Met Ser Ala Gly Gly Glu Arg Gln Ile Asp Ala Ala Glu Val
                260                 265                 270

Ile Val Ser Ala Gly Ala Leu Gln Ser Pro Ala Leu Leu Leu Arg Ala
                275                 280                 285

Gly Ile Gly Ala Gly Ser Glu Leu Gln Ala Leu Gly Ile Pro Val Val
                290                 295                 300

Ala Asp Arg Pro Gly Val Gly Arg Asn Leu Gln Asp His Pro Ser Leu
305                 310                 315                 320

-continued

```
Thr Phe Cys His Phe Leu Asp Pro Glu Phe Arg Met Pro Leu Ser Arg
            325                 330                 335

Arg Arg Ala Ser Met Thr Ala Ala Arg Phe Ser Ser Gly Leu Asp Gly
        340                 345                 350

Cys Asp Asn Ala Asp Met Tyr Leu Ser Ser Ala Thr Arg Ala Ala Trp
        355                 360                 365

His Ala Leu Gly Asn Arg Leu Gly Leu Phe Phe Leu Trp Cys Asn Arg
    370                 375                 380

Pro Phe Ser Arg Gly Arg Val Gln Leu Thr Ser Ala Asp Pro Phe Thr
385                 390                 395                 400

Pro Pro Arg Val Asp Leu Asn Leu Leu Asp Asp Glu Arg Asp Ala Arg
                405                 410                 415

Arg Met Ala Ile Gly Val Arg Val Ala Gln Ile Val Gln Gln Thr
            420                 425                 430

Ala Leu His Arg His Pro Asp Asp Phe Phe Pro Ala Ala Phe Ser Pro
        435                 440                 445

Arg Val Lys Ala Leu Ser Arg Phe Ser Ala Gly Asn Ala Ala Leu Thr
    450                 455                 460

Lys Val Leu Gly Leu Ala Leu Asp Thr Pro Ala Pro Leu Arg Arg Trp
465                 470                 475                 480

Ile Ile Asp Thr Phe Val Thr Gly Gly Ile Arg Met Ser Ala Leu Leu
                485                 490                 495

Ala Asp Asp Lys Glu Leu Asp Ala Phe Ile Arg Lys Tyr Val Phe Gly
            500                 505                 510

Val Trp His Ala Ser Gly Thr Cys Arg Met Gly Pro Ala Ser Asp Arg
        515                 520                 525

Met Ala Val Thr Asn Gln Glu Gly Leu Val His Asp Val Ala Asn Leu
    530                 535                 540

Arg Val Val Asp Ala Ser Leu Met Pro Lys Leu Pro Ser Ala Asn Thr
545                 550                 555                 560

Asn Ile Pro Thr Ile Met Met Ala Glu Lys Ile Ala Asp Ala Ile Leu
                565                 570                 575

Ala Arg Arg Lys Ala Pro Pro Gly Val Leu Val Ser Ser Glu Ala
            580                 585                 590

<210> SEQ ID NO 85
<211> LENGTH: 531
<212> TYPE: PRT
<213> ORGANISM: Methylovorus sp HmfH6

<400> SEQUENCE: 85

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
        35                  40                  45

Glu Ile His Asp Gly Leu Arg Pro Trp Leu Pro Arg Leu Ser Gly Asp
    50                  55                  60

Lys Phe Phe Trp Pro Asn Leu Thr Ile His Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Val Ser Asn Arg Gly Leu Pro Arg
            100                 105                 110
```

```
Asp Tyr Asp Glu Trp Gln Ala Leu Gly Ala Asp Gly Trp Asp Trp Gln
        115                 120                 125

Gly Val Leu Pro Tyr Phe Ile Lys Thr Glu Arg Asp Ala Asp Tyr Gly
        130                 135                 140

Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
                165                 170                 175

Glu Ala Ala Gly Leu Pro Asn Ile His Asp Gln Asn Ala Arg Phe Asp
            180                 185                 190

Asp Gly Tyr Phe Pro Pro Ala Phe Thr Leu Lys Gly Glu Glu Arg Phe
        195                 200                 205

Ser Ala Ala Arg Gly Tyr Leu Asp Ala Ser Val Arg Val Arg Pro Asn
    210                 215                 220

Leu Ser Leu Trp Thr Glu Ser Arg Val Leu Lys Leu Thr Thr Gly
225                 230                 235                 240

Asn Ala Ile Thr Gly Val Ser Val Leu Arg Gly Arg Glu Thr Leu Gln
                245                 250                 255

Val Gln Ala Arg Glu Val Ile Leu Thr Ala Gly Ala Leu Gln Ser Pro
            260                 265                 270

Ala Ile Leu Leu Arg Thr Gly Ile Gly Pro Ala Ala Asp Leu His Ala
        275                 280                 285

Leu Gly Ile Pro Val Leu Ala Asp Arg Pro Gly Val Gly Arg Asn Leu
        290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
                325                 330                 335

Ile Arg Ala Ser Ser Gly Val Asp Pro Ala Thr Pro Ser Asp Leu Phe
            340                 345                 350

Leu His Ile Gly Ala Asp Pro Val Ser Gly Leu Ala Ser Ala Arg Phe
        355                 360                 365

Trp Val Asn Lys Pro Ser Ser Thr Gly Trp Leu Lys Leu Lys Asp Ala
        370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Thr His Tyr
                405                 410                 415

Phe Ala Ala Pro Ser Leu Ala Lys Tyr Gly Leu Ala Leu Ala Leu Ser
            420                 425                 430

Arg Phe Ala Ala Pro Gln Pro Gly Pro Leu Leu Asn Asp Leu Leu
        435                 440                 445

Gln Asp Glu Ala Ala Leu Glu Arg Tyr Leu Arg Thr Asn Val Gly Gly
450                 455                 460

Val Phe His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                485                 490                 495

Arg Val Ala Asp Ala Ser Ile Met Pro Thr Val Pro Thr Ala Asn Thr
            500                 505                 510

Asn Leu Pro Thr Leu Met Leu Ala Glu Lys Ile Ala Asp Ala Ile Leu
        515                 520                 525
```

Thr Gln Ala
    530

<210> SEQ ID NO 86
<211> LENGTH: 531
<212> TYPE: PRT
<213> ORGANISM: Methylovorus sp MUT HmfH7

<400> SEQUENCE: 86

Met Thr Asp Thr Ile Phe Asp Tyr Val Ile Val Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
            35                  40                  45

Glu Ile His Asp Gly Leu Arg Pro Trp Leu Pro Arg Leu Ser Gly Asp
    50                  55                  60

Lys Phe Phe Trp Pro Asn Leu Thr Val Tyr Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Val Ser Asn Arg Gly Leu Pro Arg
            100                 105                 110

Asp Tyr Asp Glu Trp Gln Ala Leu Gly Ala Asp Gly Trp Asp Trp Gln
            115                 120                 125

Gly Val Leu Pro Tyr Phe Ile Lys Thr Glu Arg Asp Ala Asp Tyr Gly
            130                 135                 140

Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
                165                 170                 175

Glu Ala Ala Gly Leu Pro Asn Ile His Asp Gln Asn Ala Arg Phe Asp
            180                 185                 190

Asp Gly Tyr Phe Pro Pro Ala Phe Thr Leu Lys Gly Glu Glu Arg Phe
            195                 200                 205

Ser Ala Ala Arg Gly Tyr Leu Asp Ala Ser Val Arg Val Arg Pro Asn
    210                 215                 220

Leu Ser Leu Trp Thr Glu Ser Arg Val Leu Lys Leu Leu Thr Thr Gly
225                 230                 235                 240

Asn Ala Ile Thr Gly Val Ser Val Leu Arg Gly Arg Glu Thr Leu Gln
                245                 250                 255

Val Gln Ala Arg Glu Val Ile Leu Thr Ala Gly Ala Leu Gln Ser Pro
            260                 265                 270

Ala Ile Leu Leu Arg Thr Gly Ile Gly Pro Ala Ala Asp Leu His Ala
            275                 280                 285

Leu Gly Ile Pro Val Leu Ala Asp Arg Pro Gly Val Gly Arg Asn Leu
            290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
                325                 330                 335

Ile Arg Ala Ser Ser Gly Val Asp Pro Ala Thr Pro Ser Asp Leu Phe
            340                 345                 350

Leu His Ile His Ala Asp Pro Val Ser Gly Leu Ala Ser Ala Arg Phe
            355                 360                 365

-continued

Trp Val Asn Lys Pro Ser Ser Thr Gly Trp Leu Lys Leu Lys Asp Ala
    370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Lys His Tyr
                405                 410                 415

Phe Ala Tyr Pro Ser Leu Ala Lys Tyr Gly Leu Ala Leu Ala Leu Ser
            420                 425                 430

Arg Phe Glu Ala Pro Gln Pro Gly Gly Pro Leu Leu Asn Asp Leu Leu
        435                 440                 445

Gln Asp Glu Ala Ala Leu Glu Arg Tyr Leu Arg Thr Asn Val Gly Gly
    450                 455                 460

Val Phe His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                485                 490                 495

Arg Val Ala Asp Ala Ser Ile Met Pro Thr Val Pro Thr Ala Asn Thr
            500                 505                 510

Asn Leu Pro Thr Leu Met Leu Ala Glu Lys Ile Ala Asp Ala Ile Leu
        515                 520                 525

Thr Gln Ala
    530

<210> SEQ ID NO 87
<211> LENGTH: 385
<212> TYPE: PRT
<213> ORGANISM: Zymomonas mobilis DH1

<400> SEQUENCE: 87

Met Leu Asn Phe Asp Tyr Tyr Asn Pro Thr His Ile Val Phe Gly Lys
1               5                   10                  15

Gly Arg Ile Ala Gln Leu Asp Thr Leu Leu Ser Lys Asp Ala Arg Val
            20                  25                  30

Leu Val Leu Tyr Gly Gly Ser Ser Ala Gln Lys Thr Gly Thr Leu Asp
        35                  40                  45

Glu Val Arg Lys Ala Leu Gly Asp Arg Thr Tyr Phe Glu Phe Gly Gly
    50                  55                  60

Ile Glu Pro Asn Pro Ser Tyr Glu Thr Leu Met Lys Ala Val Glu Gln
65                  70                  75                  80

Val Lys Gln Glu Lys Val Asp Phe Leu Leu Ala Val Gly Gly Gly Ser
                85                  90                  95

Val Ile Asp Gly Thr Lys Phe Val Ala Ala Val Pro Tyr Glu Gly
            100                 105                 110

Glu Pro Trp Glu Ile Leu Glu Thr Asp Gly Lys Lys Ile Lys Glu Ala
        115                 120                 125

Leu Pro Val Gly Thr Val Leu Thr Leu Pro Ala Thr Gly Ser Glu Met
    130                 135                 140

Asn Arg Asn Ser Val Val Thr Arg Lys Ser Ile Lys Ser Lys Arg Gly
145                 150                 155                 160

Phe His Asn Asp His Val Phe Pro Val Phe Ser Ile Leu Asp Pro Thr
                165                 170                 175

Lys Val Tyr Thr Leu Pro Pro Arg Gln Leu Ala Asn Gly Val Val Asp
            180                 185                 190

Ser Phe Ile His Ile Thr Glu Gln Tyr Leu Thr Tyr Pro Val Asp Gly

```
            195                 200                 205
Met Val Gln Asp Glu Phe Ala Glu Gly Leu Leu Arg Thr Leu Ile Lys
    210                 215                 220

Ile Gly Pro Glu Leu Leu Lys Asp Gln Lys Asn Tyr Asp Leu Ala Ala
225                 230                 235                 240

Asn Phe Met Trp Thr Ala Thr Leu Ala Leu Asn Gly Leu Ile Gly Ala
                245                 250                 255

Gly Val Pro Gln Asp Trp Ala Thr His Met Val Gly His Glu Leu Thr
                260                 265                 270

Ala Ala Phe Gly Ile Asp His Gly Arg Thr Leu Ala Ile Ile Leu Pro
                275                 280                 285

Ser Leu Leu Gln Asn Gln Arg Glu Ala Lys Lys Gly Lys Leu Leu Gln
    290                 295                 300

Tyr Ala Lys Asn Val Trp His Ile Asp Gln Gly Ser Asp Asp Glu Arg
305                 310                 315                 320

Ile Asp Ala Ala Ile Glu Lys Thr Arg His Phe Phe Glu Ser Leu Gly
                325                 330                 335

Ile Pro Thr His Leu Lys Asp Tyr Asp Val Gly Glu Glu Ser Ile Asp
                340                 345                 350

Met Leu Val Lys Glu Leu Glu Ala His Gly Met Ser Gln Leu Gly Glu
                355                 360                 365

His Lys Ala Ile Thr Pro Glu Val Ser Arg Ala Ile Leu Leu Ala Ser
370                 375                 380

Leu
385

<210> SEQ ID NO 88
<211> LENGTH: 385
<212> TYPE: PRT
<213> ORGANISM: Zymomonas mobilis subsp. pomaceae ATCC 29192 DH2

<400> SEQUENCE: 88

Met Leu Asn Phe Asp Tyr Tyr Asn Pro Thr His Ile Ala Phe Gly Lys
1               5                   10                  15

Asp Ser Ile Ala Lys Leu Asp Thr Leu Ile Pro Gln Asp Ala Cys Val
                20                  25                  30

Met Val Leu Tyr Gly Gly Ser Ser Ala Lys Lys Thr Gly Thr Leu Asp
            35                  40                  45

Glu Val Lys Thr Ala Leu Gly Ser Arg Lys Ile His Glu Phe Gly Gly
        50                  55                  60

Ile Glu Pro Asn Pro Ser Tyr Glu Thr Leu Met Gln Ala Val Glu Gln
65                  70                  75                  80

Val Lys Lys Glu Lys Ile Asp Phe Leu Leu Ala Val Gly Gly Gly Ser
                85                  90                  95

Val Ile Asp Gly Thr Lys Phe Val Ala Ala Val Pro Tyr Glu Gly
            100                 105                 110

Glu Pro Trp Glu Ile Leu Glu Thr Asp Gly Lys Lys Ile Lys Lys Ala
        115                 120                 125

Leu Pro Leu Gly Thr Val Leu Thr Leu Pro Ala Thr Gly Ser Glu Met
    130                 135                 140

Asn Pro Asn Ser Val Val Thr Arg Lys Ser Ile Lys Ala Lys Arg Ala
145                 150                 155                 160

Phe His Asn Lys Ile Val Phe Pro Leu Phe Ser Ile Leu Asp Pro Thr
                165                 170                 175
```

```
Lys Val Tyr Thr Leu Pro Pro Arg Gln Ile Ala Asn Gly Ile Val Asp
            180                 185                 190

Ser Phe Val His Ile Thr Glu Gln Tyr Leu Thr Tyr Pro Val Glu Gly
        195                 200                 205

Met Val Gln Asp Glu Phe Ala Glu Gly Leu Leu Arg Ile Leu Ile Asn
    210                 215                 220

Ile Gly Pro Lys Leu Leu Lys Asp Gln Lys Asn Tyr Asp Leu Ala Ala
225                 230                 235                 240

Asn Phe Met Trp Thr Ala Thr Leu Ala Leu Asn Gly Leu Ile Gly Ala
                245                 250                 255

Gly Val Pro Gln Asp Trp Ala Thr His Met Ile Gly His Glu Ile Thr
            260                 265                 270

Ala Ala Phe Gly Val Asp His Gly Arg Thr Leu Ala Ile Ile Leu Pro
        275                 280                 285

Ser Leu Leu Gln Asn Gln Arg Gln Val Lys Lys Asp Lys Leu Leu Gln
    290                 295                 300

Tyr Ala Lys Asn Val Trp His Ile Glu Ser Gly Ser Glu Lys Glu Arg
305                 310                 315                 320

Ile Asp Ala Val Ile Ala Lys Thr Arg Ser Phe Phe Glu Glu Met Gly
                325                 330                 335

Ile Pro Thr His Leu Ser Asp Tyr Asn Ile Gly Lys Glu Ser Ile Asp
            340                 345                 350

Met Leu Ile His Glu Leu Glu Ala His Gly Met Thr Lys Leu Gly Glu
        355                 360                 365

His Asn Ala Ile Thr Pro Asp Val Ser Arg Ala Ile Leu Ile Ala Ser
370                 375                 380

Leu
385

<210> SEQ ID NO 89
<211> LENGTH: 385
<212> TYPE: PRT
<213> ORGANISM: Shewanella baltica DH3

<400> SEQUENCE: 89

Met Leu Asn Phe Asn Tyr Tyr Asn Pro Thr Arg Ile Arg Phe Gly Lys
1               5                   10                  15

Asp Thr Ile Ala Glu Ile Asp Thr Leu Val Pro Ser Asp Ala Lys Val
            20                  25                  30

Met Ile Leu Phe Gly Gly Ser Ser Ala Arg Lys Thr Gly Thr Leu Asp
        35                  40                  45

Glu Val Lys Gln Ser Leu Gly Asn Arg Phe Ile Val Glu Phe Asp Gly
    50                  55                  60

Ile Glu Pro Asn Pro Thr Tyr Glu Thr Leu Met Lys Ala Val Ala Gln
65                  70                  75                  80

Val Arg Glu Gln Lys Ile Asp Phe Leu Leu Ala Val Gly Gly Gly Ser
                85                  90                  95

Val Ile Asp Gly Thr Lys Phe Val Ala Ala Ala Val Phe Glu Gly
            100                 105                 110

Glu Pro Trp Asp Ile Leu Thr Ser Trp Gly Ala Lys Val Thr Gln Ala
        115                 120                 125

Met Pro Phe Gly Ser Val Leu Thr Leu Pro Ala Thr Gly Ser Glu Met
    130                 135                 140

Asn Asn Ala Ser Val Val Thr Arg Lys Ser Leu Gln Ala Lys Leu Pro
145                 150                 155                 160
```

Phe Arg Asn Asp Leu Val Tyr Pro Gln Phe Ser Ile Leu Asp Pro Thr
                165                 170                 175

Lys Thr Phe Thr Leu Pro Glu Arg Gln Val Ala Asn Gly Val Val Asp
            180                 185                 190

Ala Phe Val His Ile Thr Glu Gln Tyr Leu Thr Tyr Pro Val Asn Ala
        195                 200                 205

Ala Val Gln Asp Arg Phe Ala Glu Gly Leu Leu Gln Thr Leu Ile Glu
    210                 215                 220

Leu Gly Pro Gln Val Leu Ala Gln Pro Glu Asp Tyr Asp Ile Arg Ala
225                 230                 235                 240

Asn Leu Met Trp Val Ala Thr Met Ala Leu Asn Gly Thr Ile Gly Val
                245                 250                 255

Gly Val Pro His Asp Trp Ala Thr His Met Ile Gly His Glu Leu Thr
            260                 265                 270

Ala Leu Tyr Asp Ile Asp His Ala Arg Thr Leu Ala Ile Val Leu Pro
        275                 280                 285

Ala Leu Leu Gln Cys Thr Lys Glu Ala Lys Arg Glu Lys Leu Leu Gln
    290                 295                 300

Tyr Ala Asp Arg Val Trp His Ile Asn Thr Gly Thr Asp Asp Glu Arg
305                 310                 315                 320

Ile Asp Ala Ala Ile Ala Lys Thr Lys Ala Phe Phe Glu Ala Met Gly
                325                 330                 335

Ile Pro Thr His Leu Ser Ala Tyr Asp Leu Asp Ala Ser His Val Asp
            340                 345                 350

Thr Leu Val Lys Gln Leu Glu Leu His Gly Met Val Ala Leu Gly Glu
        355                 360                 365

His Gly Asn Ile Asn Pro Ala Met Ser Arg Asp Ile Leu Thr Leu Ala
    370                 375                 380

Leu
385

<210> SEQ ID NO 90
<211> LENGTH: 385
<212> TYPE: PRT
<213> ORGANISM: Burkholderia pseudomallei DH4

<400> SEQUENCE: 90

Met Leu Asn Phe Asp Phe Tyr Asn Pro Thr Arg Ile Val Phe Gly Glu
1               5                   10                  15

Lys Thr Ala Ala Arg Leu Asn Asp Leu Leu Pro Ala Ala Arg Val
            20                  25                  30

Leu Val Leu Tyr Gly Gly Glu Ser Ala Arg Ser Asn Gly Thr Leu Asp
        35                  40                  45

Glu Val Arg Ala Ala Leu Gly Ala Arg Asp Val Arg Glu Phe Gly Gly
    50                  55                  60

Ile Glu Pro Asn Pro Ala Tyr Glu Thr Leu Met Arg Ala Val Glu Leu
65                  70                  75                  80

Ala Arg Arg Glu Arg Val Asp Phe Leu Leu Ala Val Gly Gly Gly Ser
                85                  90                  95

Val Ile Asp Gly Thr Lys Phe Val Ala Ala Val Pro Phe Glu Gly
            100                 105                 110

Asp Pro Trp Thr Ile Leu Glu Thr His Gly Ala Asn Val Ala Ala Ala
        115                 120                 125

Leu Pro Phe Gly Cys Val Leu Thr Leu Pro Ala Thr Gly Ser Glu Met

```
            130                 135                 140
Asn Asn Gly Ala Val Leu Thr Arg Arg Ala Thr Arg Ala Lys Leu Ala
145                 150                 155                 160

Phe Arg His Pro Leu Val Phe Pro Thr Phe Ser Ile Leu Asp Pro Thr
                    165                 170                 175

Lys Thr Tyr Thr Leu Pro Pro Arg Gln Val Ala Asn Gly Val Val Asp
                180                 185                 190

Ala Phe Thr His Ile Val Glu Gln Tyr Leu Thr Tyr Pro Ala Asp Gly
            195                 200                 205

Leu Ala Gln Asp Arg Phe Ala Glu Gly Leu Leu Gln Thr Leu Ile Glu
        210                 215                 220

Ile Gly Pro Lys Ala Leu Ala Glu Pro Arg Asp Tyr Ala Thr Arg Ala
225                 230                 235                 240

Asn Leu Met Trp Val Ala Thr Leu Ala Leu Asn Gly Leu Ile Gly Ala
                245                 250                 255

Gly Val Pro Gln Asp Arg Ala Thr His Met Val Gly His Glu Leu Thr
                260                 265                 270

Ala Arg Tyr Asp Ile Asp His Ala Arg Thr Leu Ala Val Val Leu Pro
            275                 280                 285

Ser Met Leu Asp Val Arg Arg Asp Ala Lys Arg Ala Lys Leu Leu Gln
        290                 295                 300

Tyr Ala Ala Arg Val Trp Asn Ile Val Asp Gly Pro Glu Asp Ala Arg
305                 310                 315                 320

Ile Asp Ala Ala Ile Ala Arg Thr Arg Ala Phe Phe Glu Ser Leu Gly
                325                 330                 335

Val Lys Thr Arg Leu Ala Asp Tyr Gly Val Gly Ala Asp Ala Ile Asp
                340                 345                 350

Gly Leu Ile Ala Gln Leu Glu Ala His Gly Met Thr Arg Leu Gly Glu
            355                 360                 365

Arg Lys Asp Val Thr Leu Asp Val Ser Arg Arg Val Leu Glu Ala Ser
        370                 375                 380

Leu
385

<210> SEQ ID NO 91
<211> LENGTH: 348
<212> TYPE: PRT
<213> ORGANISM: Saccharomyces cerevisiae DH5

<400> SEQUENCE: 91

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Thr Lys Leu Pro Leu Val
        50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Pro Asn Cys
            100                 105                 110
```

```
Pro His Ala Asp Ser Ser Gly Tyr Thr His Asp Gly Ser Phe Gln Gln
            115                 120                 125

Tyr Ala Thr Ala Asp Ala Val Gln Ala Ala His Ile Pro Gln Gly Thr
130                 135                 140

Asp Leu Ala Glu Val Ala Pro Val Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Cys Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 92
<211> LENGTH: 360
<212> TYPE: PRT
<213> ORGANISM: Saccharomyces cerevisiae DH6

<400> SEQUENCE: 92

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140
```

```
Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
        210             215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

METHOD FOR THE IN VIVO SYNTHESIS OF 4-HYDROXYMETHYLFURFURAL AND DERIVATIVES THEREOF

CROSS-REFERENCE TO RELATED APPLICATIONS

This application is a continuation of U.S. application Ser. No. 16/806,728, filed Mar. 2, 2020, entitled "METHOD FOR THE IN VIVO SYNTHESIS OF 4-HYDROXYM-ETHYLFURFURAL AND DERIVATIVES THEREOF", which claims priority to U.S. Provisional Application No. 62/812,904 filed Mar. 1, 2019, entitled "METHOD FOR THE IN VIVO SYNTHESIS OF 4-HYDROXYMETHYL-FURFURAL AND DERIVATIVES THEREOF", the entire disclosures of which are incorporated by reference herein.

FIELD OF THE INVENTION

This application relates to recombinant microorganisms for the biosynthesis of one or more of 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA and methods of producing the recombinant microorganisms. The application also relates to methods of producing one or more of 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA with enzymatic catalysts in the absence of microorganisms or substantially free of microorganisms. The application further relates to methods of producing a polymer and a plasticizer agent from one or more of 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. The application further relates to compositions comprising one or more of these compounds and/or the recombinant microorganisms.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 127125-5014-US-01_Sequence_Listing_ST25.txt. The text file is about 241 KB, was created on Jan. 29, 2021, and is being submitted electronically via EFS-Web.

BACKGROUND 2,5-Furandicarboxylic acid (2,5-FDCA) has gained much attention due to its potential of substituting terephthalic acid in the synthesis of polyesters, specially polyethylene terephthalate (PET) (Sousa, Andreia F., et al. "Biobased polyesters and other polymers from 2, 5-furandicarboxylic acid: a tribute to furan excellency." Polymer chemistry 6.33 (2015): 5961-5983). Substituting terephthalic acid to its furan analogue 2,5-FDCA in PET can lead to 2,5-furandicarboxylate (2,5-PEF) and this polymer has several advantages when compared to PET. In one aspect, 2,5-PEF has better thermal, barrier and mechanical properties when compared to its counterpart (PEP Report 294). Furthermore, as it is known that ethylene glycol could be produced from renewable resources, then 2,5-PEF could be 100% renewable as opposed to the semi renewable PET.

Despite all the aforementioned advantages of 2,5-FDCA in comparison to terephthalic acid, 2,5-FDCA production cost is still a current limitation in expanding the monomer usage. Existing technologies are not cost-competitive when compared to terephthalic acid. One of the possible reasons for this is related to the several sequential industrial steps required. One issue that could help reduce 2,5-FDCA production costs is finding a direct fermentation route from sugar to the desired molecule, but such a route has never been reported.

The present disclosure a direct fermentation pathway for 2,4-FDCA, an isomer of 2,5-FDCA. To our knowledge, besides the present disclosure, there is no described direct fermentation routes for any of FDCA isomers.

Significantly, the disclosed 2,4-FDCA molecule possesses unique properties compared to the well-studied 2,5-FDCA. Catalytically polymerizing 2,4-FDCA with a diol yields a polymer composed of 2,4-FDCA with valuable properties. In one study, Thiyagarajan and collaborators (2014) compare polyesters made of 2,4-FDCA, 3,4-FDCA, 2,5-FDCA and terephthalic acid and concluded that 2,4-FDCA and 3,4-FDCA polyesters can be made in sufficient molecular weights by industrially applicable methods (Thiyagarajan, Shanmugam, et al. "Biobased furandicarboxylic acids (FDCAs): effects of isomeric substitution on polyester synthesis and properties." Green Chemistry 16.4 (2014): 1957-1966). In another study, Thiyagarajan and colleagues concluded that structural analysis of 2,4-FDCA and 2,5-FDCA reveal that 2,4-FDCA possesses more linear characteristics resembling terephthalic acid than does 2,5-FDCA. These features make 2,4-FDCA an interesting monomer for synthetic polyesters (Thiyagarajan et al. "Concurrent formation of furan-2,5- and furan-2,4-dicarboxylic acid: unexpected aspects of the Henkel reaction" RSC Advances 3 (2013): 15678-15686). Further, these materials have properties unlike 2,5-FDCA polyesters (Bourdet et al. "Molecular Mobility in Amorphous Biobased Poly (ethylene 2, 5-furandicarboxylate) and Poly (ethylene 2, 4-furandicarboxylate)." Macromolecules 51.5 (2018): 1937-1945).

In certain cases, 2,4-FDCA polymers have been reported to have superior properties to those possessed by 2,5-FDCA polymers. Cui and collaborators (2016) report that the bond-angle between the double carboxyl groups linking with the central ring is a key factor that influences the stability of nematic liquid crystal molecules such as those utilized in LCD TVs, notebook computers, and other display elements (Cui, Min-Shu, et al. "Production of 4-hydroxymethylfurfural from derivatives of biomass-derived glycerol for chemicals and polymers." ACS Sustainable Chemistry & Engineering 4.3 (2016): 1707-1714). The first discovered liquid crystal, terephthalic acid diester molecules has a bond-angle between two carboxyl groups of 180°. In comparison, 2,5-furan dicarboxylic acid has a bond-angle between two carboxyl groups of 137°. Significantly, 2,4-furan dicarboxylic acid has a bond-angle between two carboxyl groups of 160° making it more suitable for synthesis of nematic liquid crystal molecules.

Despite these potential applications of 2,4-FDCA polymers, the production cost of 2,4-FDCA is also a current bottleneck in expanding this monomer applications (Cui M S, et al. (2016) Production of 4-Hydroxymethylfurfural from Derivatives of Biomass-Derived Glycerol for Chemicals and Polymers. ACS Sustainable Chem. Eng. 4(3):1707-1714 and WO2011003300A1). Previous synthesis of 2,4-substituted furans, including 2,4-FDCA, required multiple synthetic steps and therefore 2,4-FDCA-derived polymers are cost-prohibitive by currently available methodologies and industrial techniques.

The present disclosure provides, for the first time, a direct fermentation route to 2,4-FDCA in a recombinant microorganism. The novel direct fermentation of 2,4-FDCA from a glyceraldehyde-3-phosphate (G3P) from a carbon feedstock such as glucose, xylose, glycerol, or from any CO2 derived/capture technology will enable the production of novel polymers and materials with commercial applicability on an industrial scale. The present disclosure further provides, for the first time, direct fermentation routes for the production of one or more of 4-HMF, 2,4-furandimethanol, furan-2,4-dicarbaldehyde, 4-(hydroxymethyl)furoic acid, 2-formylfuran-4-carboxylate, and 4-formylfuran-2-carboxylate in a recombinant microorganism. The present disclosure also demonstrate, for the first time, that endogenous phosphatases from yeast and E. coli are able to dephosphorylate (5-formylfuran-3-yl)methyl phosphate to 4-HMF and that enzymes (oxidases, dehydrogenase and/or peroxigenase) are capable to oxidize the 4-HMF to 2,4 FDCA (directly or through the production of intermediates). While some of the enzymes candidates here deployed have been characterized as having activity on a 5-HMF isomer substrate, and intermediates, their activity against 4-HMF (and its intermediates) has nto been characterized. These novel direct fermentation routes will enable the production of 2,4-substituted furans with commercial applicability. See Deng et al. (2013. Linked Strategy for the Production of Fuels via Formose Reaction. *Scientific Reports,* 3:1244) for exemplary applications of 4-HMF as a precursor to biofuels. See Zeng et al. (2013. Bio-based Furan Polymers with Self-Healing Ability. *Macromolecules,* 46.5:1794-1802) for exemplary applications of 2,4-furandimethanol in polymers with advanced properties.

SUMMARY OF THE DISCLOSURE

In certain cases, 2,4-FDCA polymers have been reported to have superior properties to those possessed by 2,5-FDCA polymers. Cui and collaborators (2016) report that the bond-angle between the double carboxyl groups linking with the central ring is a key factor that influences the stability of nematic liquid crystal molecules such as those utilized in LCD TVs, notebook computers, and other display elements (Cui, Min-Shu, et al. "Production of 4-hydroxymethylfurfural from derivatives of biomass-derived glycerol for chemicals and polymers." ACS Sustainable Chemistry & Engineering 4.3 (2016): 1707-1714). The first discovered liquid crystal, terephthalic acid diester molecules has a bond-angle between two carboxyl groups of 180°. In comparison, 2,5-furan dicarboxylic acid has a bond-angle between two carboxyl groups of 137°. Significantly, 2,4-furan dicarboxylic acid has a bond-angle between two carboxyl groups of 160° making it more suitable for synthesis of nematic liquid crystal molecules.

The disclosure provides a method of producing 2,4-furandicarboxylic acid (2,4-FDCA) by enzymatically converting glyceraldehyde 3-phosphate (G3P) to 2,4-furandicarboxylic acid (2,4-FDCA), the method comprising: (a) providing G3P in the presence of a methyl phosphate synthase that catalyzes the conversion of G3P to (5-formylfuran-3-yl)methyl phosphate; (b) providing the (5-formylfuran-3-yl)methyl phosphate from (a) a phosphatase that catalyzes the conversion of the (5-formylfuran-3-yl)methyl phosphate to 4-hydroxymethylfurfural (4-HMF); (c) providing the 4-HMF from (b) to a dehydrogenase and/or an oxidase that catalyzes independently or in synergy the oxidation of 4-HMF from (b) to 2,4 FDCA, directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some embodiments, the 2,4-FDCA is produced from furan-2,4-dicarbaldehyde, and/or-(hydroxymethyl)furoic acid intermediates, wherein: (a) a dehydrogenase, an oxidase, or a peroxigenase catalyzes the conversion of the 4-HMF to furan-2,4-dicarbaldehyde, and/or 4-(hydroxymethyl)furoic acid; and/or (b) a dehydrogenase, an oxidase, or a peroxigenase catalyzes the conversion of the furan-2,4-dicarbaldehyde from (a) to 4-formylfuran-2-carboxylate; and/or (c) a dehydrogenase, an oxidase, or a peroxigenase catalyzes the conversion of the 4-(hydroxymethyl)furoic acid from (a) to 4-formylfuran-2-carboxylate; and/or (d) a dehydrogenase, an oxidase, or a peroxigenase catalyzes the conversion of the furan-2,4-dicarbaldehyde from (a) to 2-formylfuran-4-carboxylate; and or (e) a dehydrogenase, an oxidase, or a peroxigenase catalyzes the conversion of the the 4-formylfuran-2-carboxylate from (b) and/or (c) or the 2-formylfuran-4-carboxylate from (d) to 2,4-FDCA.

In some embodiments, the methyl phosphate synthase from (a) is classified as EC number 4.2.3.153. In some embodiments, the methyl phosphate synthase is (5-formylfuran-3-yl)methyl phosphate synthase. In some embodiments, the (5-formylfuran-3-yl)methyl phosphate synthase is selected from MfnB1, MfnB7, and MfnB14.

In some embodiments, the (5-formylfuran-3-yl)methyl phosphate synthase comprises an amino acid sequence comprising SEQ ID NO: 1, SEQ ID NO: 7, or SEQ ID NO: 14. In some embodiments, the phosphatase from (b) is classified as EC number 3.1.3. In some embodiments, the phosphatase is classified as a haloacid dehalogenase. In some embodiments, the phosphatase is endogenous to the host.

In some embodiments, the phosphatase enzyme endogenous to the host is overexpressed. In some embodiments, wherein the phosphatase is a 4-HMF phosphatase.

In some embodiments, the 4-HMF phosphatase is derived from *Streptomyces coelicolor, Saccharomyces cerevisiae,* or *Escherichia coli.*

In some embodiments, the 4-HMF phosphatase is encoded by an amino acid sequence comprising SEQ ID NO: 28, any one of SEQ ID NOs 40-52, or any one of SEQ ID NOs 53-68.

In some embodiments, the dehydrogenase from (c) is classified as EC number 1.1.1. or EC number 1.2.1. In some embodiments, the dehydrogenase is an alcohol dehydrogenase or an aldehyde dehydrogenase. In some embodiments, the oxidase from (c) is classified as EC number 1.1.3. In some embodiments, the oxidase is 5-hydroxymethylfurfural oxidase. In some embodiments, the dehydrogenase is classified as EC number 1.2.1. or EC number 1.1.1. In some embodiments, the dehydrogenase is an aldehyde dehydrogenase or and alcohol dehydrogenase.

In some embodiments, the oxidase is classified as EC number 1.1.3. In some embodiments, the oxidase is 5-hydroxymethylfurfural oxidase. In some embodiments, the oxidase is a 4-HMF oxidase. In some embodiments, the 4-HMF oxidase is selected from HmfH6 and HmfH7. In some embodiments, the 4-HMF oxidase comprises an amino acid sequence comprising SEQ ID NO: 85 or SEQ ID NO: 86.

In some embodiments, the dehydrogenase is classified as EC number 1.2.1. In some embodiments, the dehydrogenase is an aldehyde dehydrogenase.

The disclosure provides a recombinant microorganism capable of producing 2,4-furandicarboxylic acid (2,4-FDCA) from a feedstock comprising a carbon source, wherein the recombinant microorganism expresses the following: (a) endogenous and/or exogenous nucleic acid molecules capable of converting a carbon source to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) at least one endogenous or exogenous nucleic acid molecule encoding a peroxigenase, dehydrogenase, or a oxidase that catalyzes independently or in synergy the oxidation of 4-HMF from (c) to 2,4 FDCA, directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some embodiments, the carbon source comprises a hexose, a pentose, glycerol, CO2, sucroses and/or combinations thereof. In some embodiments, the methyl phosphate synthase from (a) is classified as EC number 4.2.3.153. In some embodiments, wherein the synthase is (5-formylfuran-3-yl)methyl phosphate synthase.

In some embodiments, the phosphatase from (c) is classified as EC number 3.1.3. In some embodiments, the phosphatase is classified as haloacid dehalogenase. In some embodiments, the phosphatase is endogenous to the host. In some embodiments, phosphatase enzyme endogenous to the host is overexpressed.

In some embodiments, the oxidase from (d) is classified as EC number 1.1.3. In some embodiments, the oxidase from (d) is a 5-hydroxymethylfurfural oxidase.

In some embodiments, the dehydrogenase from (d) is classified as EC number 1.1.1. or EC number 1.2.1. In some embodiments, the dehydrogenase is an alcohol dehydrogenase or an aldehyde dehydrogenase.

In some embodiments, the 2,4-FDCA is produced from furan-2,4-dicarbaldehyde, and/or -(hydroxymethyl)furoic acid intermediates, wherein: (a) a dehydrogenase, an oxidase, or a peroxigenase catalyzes the conversion of the 4-HMF from (c) to furan-2,4-dicarbaldehyde, and/or 4-(hydroxymethyl)furoic acid; and/or (b) a dehydrogenase, an oxidase, or a peroxigenase catalyzes the conversion of the furan-2,4-dicarbaldehyde from (a) to 4-formylfuran-2-carboxylate; and/or (c) a dehydrogenase, an oxidase, or a peroxigenase catalyzes the conversion of the 4-(hydroxymethyl)furoic acid from (b) to 4-formylfuran-2-carboxylate; and/or (d) a dehydrogenase, an oxidase, or a peroxigenase catalyzes the conversion of the furan-2,4-dicarbaldehyde from (c) to 2-formylfuran-4-carboxylate; and/or (e) a dehydrogenase, an oxidase, or a peroxigenase catalyzes the conversion of the 4-formylfuran-2-carboxylate from (b) and/or (c) or the 2-formylfuran-4-carboxylate from (d) to 2,4-FDCA.

In some embodiments, the dehydrogenase from (a), (b), (c), (d) and/or (e) is classified as EC number 1.2.1. or EC number 1.1.1 In some embodiments, the dehydrogenase is an aldehyde dehydrogenase or an alcohol dehydrogenase. In some embodiments, the oxidase from (a), (b), (c), (d) and/or (e) is classified as EC number 1.1.3. In some embodiments, the oxidase is 5-(hydroxymethyl)furfural oxidase.

In some embodiments, the one or more recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Corynebacterium glutamicum*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Candida krusei*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Issatchenkia orientalis*, *Sporomusa termitida*, *Moorella glycerini*, *Eubacterium aggregans*, *Treponema azotonutricium*, *Pichia kudriavzevii*, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and *Terrisporobacter glycolicus*.

In some embodiments, the one or more recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Corynebacterium glutamicum*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Candida krusei*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Issatchenkia orientalis*, *Sporomusa termitida*, *Moorella glycerini*, *Eubacterium aggregans*, *Treponema azotonutricium*, *Pichia kudriavzevii*, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and *Terrisporobacter glycolicus*.

The disclosure provides a method of producing 2,4-FDCA using a recombinant microorganism of claim 27, the method comprising cultivating the recombinant microorganism in a culture medium containing a feedstock providing a carbon source until the 2,4-FDCA is produced.

The disclosure provides a method of producing a recombinant microorganism capable of producing 2,4-FDCA from a feedstock comprising a carbon source, the method comprising introducing into and/or overexpressing in the recombinant microorganism the following: (a) endogenous and/or exogenous nucleic acid molecules capable of converting glycerol or a monosaccharide to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) at least one endogenous or exogenous nucleic acid molecule encoding a peroxigenase, dehydrogenase, or a oxidase that catalyzes independently or in synergy the oxidation of 4-HMF from (c) to 2,4 FDCA, directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some embodiments, the carbon source comprises a hexose, a pentose, glycerol, CO2, sucroses and/or combinations thereof. In some embodiments, the methyl phosphate synthase from (a) is classified as EC number 4.2.3.153. In some embodiments, the synthase is (5-formylfuran-3-yl) methyl phosphate synthase. In some embodiments, the phosphatase from (c) is classified as EC number 3.1.3. In some embodiments, the phosphatase is classified as haloacid dehalogenase. In some embodiments, the phosphatase is endogenous to the host. In some embodiments, the phosphatase enzyme endogenous to the host is overexpressed.

In some embodiments, the dehydrogenase from (d) is classified as EC number 1.1.1. or EC number 1.2.1. In some embodiments, the dehydrogenase is an alcohol dehydrogenase or an aldehyde dehydrogenase. In some embodiments, the oxidase from (d) is classified as EC number 1.1.3. In some embodiments, the oxidase is (5-(hydroxymethyl)furfural oxidase.

In some embodiments, the 2,4-FDCA is produced from furan-2,4-dicarbaldehyde, and/or -(hydroxymethyl)furoic acid intermediates, wherein: (a) a dehydrogenase, an oxidase, or a peroxigenase catalyzes the conversion of the 4-HMF to furan-2,4-dicarbaldehyde, and/or 4-(hydroxymethyl)furoic acid; and/or (b) a dehydrogenase, an oxidase, or a peroxigenase catalyzes the conversion of the furan-2,4-dicarbaldehyde from (a) to 4-formylfuran-2-carboxylate; and/or (c) a dehydrogenase, an oxidase, or a peroxigenase catalyzes the conversion of the 4-(hydroxymethyl)furoic acid from (a) to 4-formylfuran-2-carboxylate; and/or (d) a dehydrogenase, an oxidase, or a peroxigenase catalyzes the conversion of the furan-2,4-dicarbaldehyde from (a) to 2-formylfuran-4-carboxylate; and/or (e) a dehydrogenase, an oxidase, or a peroxigenase catalyzes the conversion of the the 4-formylfuran-2-carboxylate from (b) and/or (c) or the 2-formylfuran-4-carboxylate from (d) to 2,4-FDCA.

In some embodiments, the dehydrogenase from (a), (b), (c), (d) and/or (e) is classified as EC number 1.2.1. or EC number 1.1.1 In some embodiments, the dehydrogenase is an aldehyde dehydrogenase or an alcohol dehydrogenase. In some embodiments, the oxidase from (a), (b), (c), (d) and/or (e) is classified as EC number 1.1.3. In some embodiments, the oxidase is 5-(hydroxymethyl)furfural oxidase.

The disclosure provides a 2,4-FDCA produced according to the methods of the disclosure.

The disclosure provides a 2,4-FDCA produced according to the microorganisms of the disclosure.

The disclosure provides a polymer produced from the 2,4-FDCA of embodiments of the disclosure. In some embodiments, the polymer from 2,4-FDCA is formed in a non-biological process.

The disclosure provides a recombinant microorganism capable of producing 4-hydroxymethylfurfural (4-HIVIF) from a feedstock comprising an exogenous carbon source, wherein the recombinant microorganism expresses the following: (a) endogenous and/or exogenous nucleic acid molecules capable of converting the carbon source to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; and (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF).

In some embodiments, the methyl phosphate synthase from (a) is classified as EC number 4.2.3.153. In some embodiments, the synthase is (5-formylfuran-3-yl)methyl phosphate synthase. In some embodiments, the phosphatase from (c) is classified as EC number 3.1.3. In some embodiments, the phosphatase is classified as haloacid dehalogenase. In some embodiments, the phosphatase is endogenous to the host. In some embodiments, the phosphatase enzyme endogenous to the host is overexpressed.

The disclosure provides a recombinant microorganism capable of producing 2,4-furandicarboxylic acid (2,4-FDCA) from a feedstock comprising a carbon source, wherein the recombinant microorganism expresses one or more of the following: (a) endogenous and/or exogenous nucleic acid molecules capable of converting glycerol or a monosaccharide to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) at least one endogenous or exogenous nucleic acid molecule encoding a dehydrogenases and/or an oxidase that catalyzes independently or in synergy the oxidation of 4-HMF from (b) to 2,4 FDCA, directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some aspects, the disclosure is generally drawn to a method of producing 2,4-furandicarboxylic acid (2,4-FDCA) by enzymatically converting glyceraldehyde 3-phosphate (G3P) to 2,4-furandicarboxylic acid (2,4-FDCA) in a recombinant microorganism, by enzymatic catalysts in the absence of microorganisms, the method comprising: (a) providing G3P in the presence of a methyl phosphate synthase or any enzyme able to catalyzes the conversion of G3P to (5-formylfuran-3-yl)methyl phosphate; (b) providing the (5-formylfuran-3-yl)methyl phosphate from (a) to a phosphatase or any enzyme able to catalyze the conversion of the (5-formylfuran-3-yl)methyl phosphate to 4-hydroxymethylfurfural (4-HMF); (c) providing the 4-HMF from (b) to oxidases, dehydrogenase or peroxigenase able to catalyze independently or in synergy the oxidation of 4-HMF to 2,4 FDCA, directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In this sense, step C could be performed by providing the 4-HMF from (b) to a dehydrogenase or an oxidase or that catalyzes the conversion of the 4-HMF to: (i) furan-2,4-dicarbaldehyde, and/or (ii) 4-(hydroxymethyl)furoic acid; (d) providing the: (i) furan-2,4-dicarbaldehyde from (c)(i) to a dehydrogenase, an oxidase, or a peroxigenase that catalyzes the conversion of the furan-2,4-dicarbaldehyde to 4-formylfuran-2-carboxylate; (ii) 4-(hydroxymethyl)furoic acid from (c)(ii) to a dehydrogenase, an oxidase, or a peroxigenase that catalyzes the conversion of the 4-(hydroxymethyl)furoic acid to 4-formylfuran-2-carboxylate; and/or (iii) furan-2,4-dicarbaldehyde from I(i) to a dehydrogenase, an oxidase, or a peroxigenase that catalyzes the conversion of the furan-2,4-dicarbaldehyde to 2-formylfuran-4-carboxylate; and (e) providing the 4-formylfuran-2-carboxylate from (d)(i) and/or (d)(ii) or the 2-formylfuran- 4-carboxylate from (d)(iii) to a dehydrogenase or an oxidase that catalyzes the conversion of the 4-formylfuran-2-carboxylate from (d)(i) and/or (d)(ii) or the 2-formylfuran-4-carboxylate from (d)(iii) to 2,4-FDCA.

In some aspects, the methyl phosphate synthase from (a) is classified as EC number 4.2.3.153. In some aspects, the synthase is (5-formylfuran-3-yl)methyl phosphate synthase.

In some aspects, the phosphatase from (b) is a Phosphoric monoester hydrolase classified as EC number 3.1.3. In some aspects, the phosphatase is classified as haloacid dehalogenase (Koonin et al. J. Mol. Biol. 244(1). 1994). In some aspects, the phosphatase of reaction b is endogenous to the host (Offley et al. Curr. Gen. 65. 2019). In some aspects, the phosphatase enzyme endogenous to the host is overexpressed. In some cases a heterologous phosphatase able to perform the desired reaction is used and is selected from an alkaline phosphatase, acid phosphatase, fructose-bisphosphatase, sugar-phosphatase, or sugar-terminal-phosphatase.

In some aspects, the dehydrogenase from (c) is classified as EC number 1.1.1. when oxidizing an alcohol to a carbonyl or EC number 1.2.1. when oxidizing a carbonyl to an acid. In some aspects, the dehydrogenase is an alcohol dehydrogenase or an aldehyde dehydrogenase.

In some aspects, the oxidase from (c) is classified as EC number 1.1.3. In some aspects, the oxidase is 5-(hydroxymethylfurfural oxidase. In some aspects the 5-hydroxymethylfurfural oxidase convert the 4-hydroxymethylfurfural (4-HMF) into 2,4 FDCA in a three-step reaction.

In some aspects, the disclosure is generally drawn to a recombinant microorganism capable of producing 2,4-furandicarboxylic acid (2,4-FDCA) from a feedstock comprising a carbon source, wherein the recombinant microorganism expresses the following: (a) endogenous and/or exogenous nucleic acid molecules capable of converting a carbon source to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) at least one endogenous or exogenous nucleic acid molecule encoding a peroxigenase, dehydrogenase, or a oxidase that catalyzes the conversion of 4-HMF from (c) to 2,4 FDCA directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some aspects, 2,4-furandicarboxylic acid (2,4-FDCA) can be produced by providing the 4-HMF from (c) to a dehydrogenase or an oxidase or peroxidase that catalyzes the conversion of the 4-HMF to: (i) furan-2,4-dicarbaldehyde, and/or (ii) 4-(hydroxymethyl)furoic acid; (d) providing the: (i) furan-2,4-dicarbaldehyde from (c)(i) to a dehydrogenase, an oxidase, or a peroxigenase that catalyzes the conversion of the furan-2,4-dicarbaldehyde to 4-formylfuran-2-carboxylate; (ii) 4-(hydroxymethyl)furoic acid from (c)(ii) to a dehydrogenase, an oxidase, or a peroxigenase that catalyzes the conversion of the 4-(hydroxymethyl)furoic acid to 4-formylfuran-2-carboxylate; and/or (iii) furan-2,4-dicarbaldehyde from I(i) to a dehydrogenase, an oxidase, or a peroxigenase that catalyzes the conversion of the furan-2,4-dicarbaldehyde to 2-formylfuran-4-carboxylate; and (e) providing the 4-formylfuran-2-carboxylate from (d)(i) and/or (d)(ii) or the 2-formylfuran-4-carboxylate from (d)(iii) to a dehydrogenase or an oxidase that catalyzes the conversion of the 4-formylfuran-2-carboxylate from (d)(i) and/or (d)(ii) or the 2-formylfuran-4-carboxylate from (d)(iii) to 2,4-FDCA.

In some aspects, the host microorganism is genetically modified to improve G3P availability to the (5-formylfuran-3-yl)methyl phosphate synthase that catalyzes the conversion of G3P to (5-formylfuran-3-yl)methyl phosphate. Different metabolic engineering strategies can be performed to achieve varied levels of gene expression through modification of regulation of transcription (Alper et al. PNAS 102 (36). 2005), mRNA stability and translation (Ferreira et al. PNAS 110(28). 2013) (Salis et al. Nat. Biotech. 27. 2009), protein stability (Cameron et al. Nat. Biotech. 32. 2014) or genes substitution for a less or more efficient orthologue.

In some aspects, the carbon source comprises a hexose, a pentose, glycerol, $CO_2$, sucroses and/or combinations thereof.

In some aspects, the methyl phosphate synthase from (b) is classified as EC number 4.2.3.153. In some aspects, the synthase is (5-formylfuran-3-yl)methyl phosphate synthase (Table 1).

In some aspects, the phosphatase from (c) is a Phosphoric monoester hydrolases classified as EC number 3.1.3 In some aspects, the phosphatase is classified as haloacid dehalogenase (Koonin et al. J. Mol. Biol. 244(1). 1994). In some aspects, the phosphatase of reaction c is endogenous to the host (Offley et al. Curr. Gen. 65. 2019). In some aspects, the phosphatase enzyme endogenous to the host is overexpressed. In some cases, a heterologous phosphatase able to perform the desired reaction is used and is selected from an alkaline phosphatase, acid phosphatase, fructose-bisphosphatase, sugar-phosphatase, or sugar-terminal-phosphatase.

In some aspects, the oxidase from (d) is classified as EC number 1.1.3. In some aspects, the oxidase is 5-hydroxymethylfurfural oxidase. In some aspects the 5-hydroxymethylfurfural oxidase convert the 4-hydroxymethylfurfural (4-HMF) into 2,4 FDCA in a three-step reaction.

In some aspects, the dehydrogenase from (d) is classified as EC number 1.1.1. when oxidizing an alcohol to a carbonyl or EC number 1.2.1. when oxidizing an carbonyl to acid. In some aspects, the dehydrogenase is an alcohol dehydrogenase or an aldehyde dehydrogenase.

In some aspects, the dehydrogenase from (e) is classified as EC number 1.2.1. or EC number 1.1.1 In some aspects, the dehydrogenase is an aldehyde dehydrogenase or an alcohol dehydrogenase. In some aspects, the oxidase from (e) is classified as EC number 1.1.3. In some aspects, the oxidase is (5-(hydroxymethyl)furfuraloxidase. In some aspects, the dehydrogenase from (f) is classified as EC number 1.2.1. In some aspects, the dehydrogenase is an aldehyde dehydrogenase. In some aspects, the oxidase from (f) is classified as EC number 1.1.3. In some aspects, the oxidase is (5-(hydroxymethyl)furfural oxidase.

In some aspects, the one or more recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Ther-*

*moacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus sp., Corynebacterium sp., Yarrowia lipolytica, Scheffersomyces stipitis,* and *Terrisporobacter glycolicus.*

In some aspects, the disclosure is generally drawn to a method of producing 2,4-FDCA using a recombinant microorganism of the disclosure, the method comprising cultivating the recombinant microorganism in a culture medium containing a feedstock providing a carbon source until the 2,4-FDCA is produced.

In some aspects, the disclosure is generally drawn to a method of producing a recombinant microorganism capable of producing 2,4-FDCA from a feedstock comprising a carbon source, the method comprising introducing into and/or overexpressing in the recombinant microorganism the following: (a) endogenous and/or exogenous nucleic acid molecules capable of converting glycerol or a monosaccharide to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) at least one endogenous or exogenous nucleic acid molecule encoding a peroxigenase, dehydrogenase, or an oxidase that catalyzes the conversion of 4-HMF from (c) to: (i) furan-2,4-dicarbaldehyde and/or (ii) 4-(hydroxymethyl) furoic acid; (e) at least one endogenous or exogenous nucleic acid molecule encoding a peroxigenase, dehydrogenase, or a oxidase that catalyzes the conversion of: (i) furan-2,4-dicarbaldehyde from (d)(i) to 4-formylfuran-2-carboxylate and/or (ii) 4-(hydroxymethyl)furoic acid from (d)(ii) to 4-formylfuran-2-carboxylate; and/or (iii) furan-2,4-dicarbaldehyde from (c)(i) to 2-formylfuran-4-carboxylate; and (f) at least one endogenous or exogenous nucleic acid molecule encoding a peroxigenase, dehydrogenase, or an oxidase that catalyzes the conversion of 4-formylfuran-2-carboxylate from (e)(i) and (e)(ii) or 2-formylfuran-4-carboxylate from (e)(iii) to 2,4-FDCA.

In some aspects, the carbon source comprises a hexose, a pentose, glycerol, and/or combinations thereof. In some aspects, the methyl phosphate synthase from (b) is classified as EC number 4.2.3.153. In some aspects, the synthase is (5-formylfuran-3-yl)methyl phosphate synthase. In some aspects, the phosphatase from (c) is a Phosphoric monoester hydrolase classified as EC number 3.1.3. In some aspects, the phosphatase is classified as haloacid dehalogenase (Koonin et al. J. Mol. Biol. 244(1). 1994). In some aspects, the phosphatase of reaction c is endogenous to the host (Offley et al. Curr. Gen. 65. 2019). In some aspects, the phosphatase enzyme endogenous to the host is overexpressed. In some cases, a heterologous phosphatase able to perform the desired reaction is used and is selected from an alkaline phosphatase, acid phosphatase, fructose-bisphosphatase, sugar-phosphatase, or sugar-terminal-phosphatase.

In some aspects, the dehydrogenase from (d) is classified as EC number 1.1.1. when oxidizing an alcohol to a carbonyl or EC number 1.2.1. when oxidizing a carbonyl to an acid. In some aspects, the dehydrogenase is an alcohol dehydrogenase or an aldehyde dehydrogenase.

In some aspects, the oxidase from (d) is classified as EC number 1.1.3. In some aspects, the oxidase is 5-(hydroxymethylfurfural oxidase. In some aspects the 5-hydroxymethylfurfural oxidase convert the 4-hydroxymethylfurfural (4-HMF) into 2,4 FDCA in a three-step reaction.

In some aspects, the oxidase from (e) is classified as EC number 1.1.3. In some aspects, the oxidase is (5-(hydroxymethyl)furfural oxidase. In some aspects, the dehydrogenase from (f) is classified as EC number 1.2.1. In some aspects, the dehydrogenase is aldehyde dehydrogenase. In some aspects, the oxidase from (f) is classified as EC number 1.1.3. In some aspects, the oxidase is (5-(hydroxymethyl) furfural oxidase.

In some aspects, the disclosure is drawn to a method of producing a polymer from 2,4-FDCA produced by the microorganism wherein the 2,4-FDCA and a diol are catalytically polymerized in a non-biological process. In some aspects the 2,4-FDCA is part of a plasticizer agent composition and where the plasticizer agent is part of a plasticized polymer composition.

In some aspects, the disclosure is generally drawn to a recombinant microorganism capable of producing 4-hydroxymethylfurfural (4-HMF) from a feedstock comprising an exogenous carbon source, wherein the recombinant microorganism expresses the following: (a) endogenous and/or exogenous nucleic acid molecules capable of converting the carbon source to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; and (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF).

In some aspects, the phosphatase is classified as haloacid dehalogenase (Koonin et al. J. Mol. Biol. 244(1). 1994). In some aspects, the phosphatase of reaction b is endogenous to the host (Offley et al. Curr. Gen. 65. 2019). In some aspects, the phosphatase enzyme endogenous to the host is overexpressed. In some cases, a heterologous phosphatase able to perform the desired reaction is used and is selected from an alkaline phosphatase, acid phosphatase, fructose-bisphosphatase, sugar-phosphatase, or sugar-terminal-phosphatase.

In some aspects, the disclosure is generally drawn to a recombinant microorganism capable of producing 2,4-furandicarboxylic acid (2,4-FDCA) from a feedstock comprising a carbon source, wherein the recombinant microorganism expresses one or more of the following: (a) endogenous and/or exogenous nucleic acid molecules capable of converting glycerol or a monosaccharide to glyceraldehyde 3-phosphate (G3P); (b) at least one endogenous or exogenous nucleic acid molecule encoding a (5-formylfuran-3-yl)methyl phosphate synthase that catalyzes the conversion of G3P from (a) to (5-formylfuran-3-yl)methyl phosphate; (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); (d) that catalyzes the conversion of 4-HMF from (c) to 2,4 FDCA directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In some aspects, 2,4-furandicarboxylic acid (2,4-FDCA) can be produced by providing the 4-HMF from (c) to at least one endogenous or exogenous nucleic acid molecule encoding a peroxigenase, dehydrogenase, or an oxidase that catalyzes the conversion of 4-HMF from (c) to: (i) furan-2, 4-dicarbaldehyde and/or (ii) 4-(hydroxymethyl)furoic acid; (e) at least one endogenous or exogenous nucleic acid molecule encoding a peroxigenase, dehydrogenase, or an oxidase that catalyzes the conversion of: (i) furan-2,4-dicarbaldehyde from (d)(i) to 4-formylfuran-2-carboxylate and/or (ii) 4-(hydroxymethyl)furoic acid from (d)(ii) to 4-formylfuran-2-carboxylate; and (f) at least one endogenous or exogenous nucleic acid molecule encoding a peroxigenase, dehydrogenase, or an oxidase that catalyzes the conversion of 4-formylfuran-2-carboxylate from (e) to 2,4-FDCA.

DETAILED DESCRIPTION

Definitions

Figure 1:
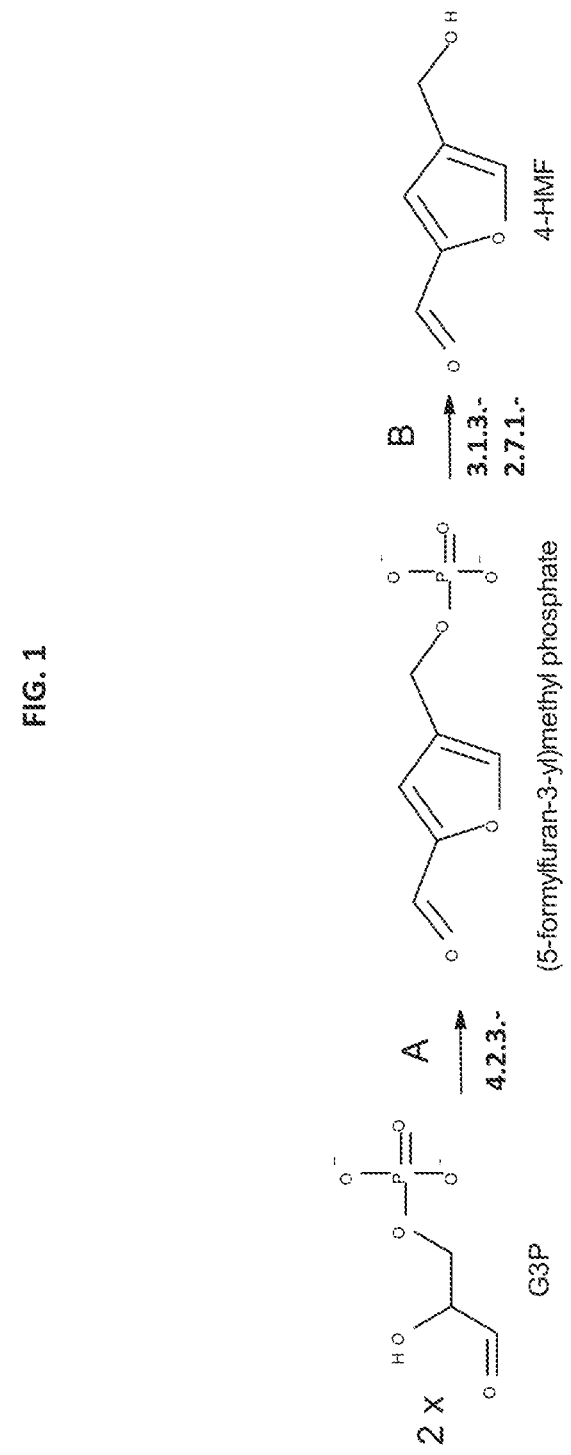
FIG. 1 is a schematic overview of the biosynthetic pathway utilized by recombinant microorganisms of the disclosure for the novel conversion of G3P to 4-HMF. The numbers below the enzymatic reaction rows indicate the 3-digit EC number for the corresponding enzymes.

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. It is understood that the terms "recombinant microorganism" and "recombinant host cell" refer not only to the particular recombinant microorganism but to the progeny or potential progeny of such a microorganism.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "decreasing" or "reducing" the level of expression of a gene or an enzyme activity refers to the partial or complete suppression of the expression of a gene or enzyme activity. This suppression of expression or activity can be either an inhibition of the expression of the gene, a deletion of all or part of the promoter region necessary for the gene expression, a deletion in the coding region of the gene, or the replacement of the wild-type promoter by a weaker natural or synthetic promoter. For example, a gene may be completely deleted and may be replaced by a selection marker gene that facilitates the identification, isolation and purification of the strains according to the present disclosure. Alternatively, endogenous genes may be knocked out or deleted to favor the new metabolic pathway. In yet another embodiment, the expression of the gene may be decreased or reduced by using a weak promoter or by introducing certain mutations.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

The term "yield potential" or as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balance" refers to the overall amount of redox cofactors in a given set of reactions. When there is a shortage of redox cofactors, the redox balance is negative and the yield of such pathway would not be realistic since there is a need to burn feedstock to fulfill the cofactor demand. When there is a surplus of redox cofactors, the redox balance is said to be positive and the yield of such pathway is lower than the maximum yield (Dugar et al. "Relative potential of biosynthetic pathways for biofuels and bio-based products" Nature biotechnology 29.12 (2011): 1074). In addition, when the pathway produces the same amount of redox cofactors as it consumes, the redox balance is zero and one can refer to this pathway as "redox balanced." Designing metabolic pathways and engineering an organism such that the redox cofactors are balanced or close to being balanced usually results in a more efficient, higher yield production of the desired compounds when compared to an unbalanced pathway. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. The term redox state is often used to describe the balance of NAD+/NADH and NADP+/NADPH of natural or non-natural metabolic pathways in a biological system such as a microbial cell. The redox state is reflected in the balance of several sets of metabolites (e.g., lactate and pyruvate, beta-hydroxybutyrate, and acetoacetate), whose interconversion is dependent on these ratios. In one embodiment, an external source of hydrogen or electrons, combined or not with the use of hydrogenase enzymes able to convert hydrogen to NAD(P)H, may be beneficial to increase product yield in metabolic pathways with negative redox balance, i.e., when there is a shortage in redox cofactors, such as NAD(P)H.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The term "biologically pure culture" or "substantially pure culture" refers to a culture of a bacterial species described herein containing no other bacterial species in quantities sufficient to interfere with the replication of the culture or be detected by normal bacteriological techniques.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "catalytically polymerized" as used herein refers to polymerization process wherein monomers of the disclosure are polymerized in a non-biological or non-in vivo context.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, stored, or transferred, which does not detrimentally effect the microbe.

As used herein, the term "productivity" refers to the total amount of bioproduct, such as (2,4-FDCA), produced per hour.

As used herein, the term "biosynthesis products" refers to any one or more of the following products contemplated herein: 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA.

Recombinant Microorganisms

In one embodiment, the present disclosure provides a recombinant microorganism capable of producing any one or more of the biosynthetic products contemplated herein. In one embodiment, a recombinant microorganism produces a 4-HMF. In one embodiment, a recombinant microorganism produces a 2,4,furandimethanol. In one embodiment, a recombinant microorganism produces a furan-2,4-dicarbaldehyde. In one embodiment, a recombinant microorganism produces a 4-(hydroxymethyl)furoic acid. In one embodiment, a recombinant microorganism produces a 2-formylfuran-4-carboxylate. In one embodiment, a recombinant microorganism produces a 4-formylfuran-2-carboxylate. In one embodiment, a recombinant microorganism produces a 2,4-FDCA.

In one embodiment, a recombinant microorganism produces any six of the biosynthetic products. In one embodiment, a recombinant microorganism produces any five of the biosynthetic products. In one embodiment, a recombinant microorganism produces any four of the biosynthetic products. In one embodiment, a recombinant microorganism produces any three of the biosynthetic products.

In one embodiment, the carbon source is converted to glyceraldehyde 3-phosphate (G3P). G3P is a common natural intermediary metabolite. In some embodiments, it can be produced from glucose via the glycolysis pathway or from xylose (like from the pentose phosphate pathway but not limited) or from glycerol. In some embodiments, G3P can be derived from CO2 capture technologies. In one embodiment, the recombinant microorganism capable of producing any one or more of the biosynthetic products utilizing a carbon source that comprises a hexose, a pentose, glycerol, or from CO2 capture technologies. In certain embodiments, the carbon source is glycerol.

In one embodiment, the recombinant microorganism comprises the novel capacity to convert G3P to any one or more of the biosynthetic products via several enzymatically-catalyzed successive steps.

In one embodiment, the host microorganism is genetically modified to improve G3P availability to the (5-formylfuran-3-yl)methyl phosphate synthase that catalyzes the conversion of G3P to (5-formylfuran-3-yl)methyl phosphate.

In one embodiment, the recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis*, *Methylovorus* sp., *Cupriavidus* sp., *Methanocaldococcus* sp. and *Terrisporobacter glycolicus*.

4-HMF

In one embodiment, the present disclosure comprises converting one or more carbon sources to glyceraldehyde 3-phosphate (G3P); converting G3P to (5-formylfuran-3-yl)methyl phosphate (Step A); converting (5-formylfuran-3-yl)methyl phosphate to 4-hydroxymethylfurfural (4-HMF) (Step B).

In one embodiment, the recombinant microorganism of any one of the embodiments disclosed herein comprises an endogenous and/or exogenous nucleic acid molecules capable of converting a carbon source to glyceraldehyde 3-phosphate (G3P). In one embodiment, glycerol is converted to glycerol-3-phopshate by at least one endogenous or exogenous nucleic acid molecule encoding a glycerol kinase. In one embodiment, glycerol-3-phosphate is converted to dihydroxyacetone phosphate (DHAP) by at least one endogenous or exogenous nucleic acid molecule encoding a glycerol-3-phosphate dehydrogenase. In one embodiment, glycerol is converted to dihydroxyacetone by at least one endogenous or exogenous nucleic acid molecule encoding a glycerol dehydrogenase. In one embodiment, dihydroxyacetone is converted to dihydroxyacetone phosphate (DHAP) by at least one endogenous or exogenous nucleic acid molecule encoding a dihydroxyacetone kinase. In one embodiment, DHAP is converted to G3P by at least one endogenous or exogenous nucleic acid molecule encoding a triose phosphate isomerase. See Zhang et al. (2010. Applied and Environmental Microbiology, 76.8:2397-2401) for exemplary, but non-limiting, glycerol assimilation pathways contemplated herein.

In one embodiment, the recombinant microorganism of any one of the embodiments of disclosed herein comprises at least one endogenous or exogenous nucleic acid molecule encoding a (5-formylfuran-3-yl)methyl phosphate synthase that catalyzes the conversion of G3P to (5-formylfuran-3-yl)methyl phosphate. In one embodiment, the (5-formylfuran-3-yl)methyl phosphate synthase is classified as EC number 4.2.3.153. In some embodiments the EC 4.2.3.153 (5-formylfuran-3-yl)methyl phosphate synthase can be derived from the gene mfnB. In some embodiments, mfnB can be derived from *Methanocaldococcus jannaschii*. In some embodiments, the (5-formylfuran-3-yl)methyl phosphate synthase can be derived from enzyme candidates listed at Table 1. In some embodiments the (5-formylfuran-3-yl) methyl phosphate synthase is encoded by an amino acid sequence listed in Table 1. In some embodiments, the (5-formylfuran-3-yl)methyl phosphate synthase is homologous or similar to the enzymes listed at Table 1. In some embodiments, an (5-formylfuran-3-yl)methyl phosphate synthase enzyme is evolved or engineered to improve its catalytic efficiency, markedly kcat.

TABLE 1

(5-formylfuran-3-yl)methyl phosphate synthases enzymes

| Name | Organism | Sequence |
|---|---|---|
| MfnB 1 | *Methanocaldococcus jannaschii* | MILLVSPIDVEEAKEAIAGGADIIDVKNPKEGSLGANFPWMIKAIREVT<br>PKDLLVSATVGDVPYKPGTISLAAVGAAISGADYIKVGLYGVKNYYQAV<br>ELMKNVVRAVKDIDENKIVVAAGYADAYRVGAVEPLIVPKIARDAGCDV<br>AMLDTAIKDGKTLFDFQSKEILAEFVDEAHSYGLKCALAGSIKKEHIPI<br>LKEIGTDIVGVRGAACKGGDRNNGRIDRELVKELKELCK (SEQ ID NO: 1) |
| MfnB 2 | *Methanocaldococcus fervens* | MILLVSPIDVEEAKEAIAGGADIIDVKNPKEGSLGANFPWMIKAIREVT<br>PKELLVSATVGDVPFKPGTISLAAVGAAISGADYIKVGLYGVKNYYEGV<br>ELMKNVVRAVKDIDENKIVVAAGYADAHRVGAVEPLIIPKIARDAGCDV<br>AMLDTAVKDGKTLFDFQSKEILEEFVQESHDYGLKCALAGSIKKEHIPI<br>LKEIGTDIVGVRGAVCKGGDRNNGRIDRELVRELKELCK (SEQ ID NO: 2) |
| MfnB 3 | *Methanocaldococcus vulcanius* | MILLVSPIDVDEAREAIAGGADIIDVKNPKEGSLGANFPWMIKAIREIT<br>PKELLVSATVGDVPYKPGTVSLASVGAAMSGADYIKVGLYGVKNYYEAV<br>ELMKNVVRAVKDVDENKIVVAAGYADAHRVGAVDPLIIPKIARDADCDV<br>AMLDTAIKDGKTLFDFQSKEILEEFVEETHSYGLKCALAGSIKKEHIPI<br>LKEIGTDIVGVRGAVCKGGDRNKGRIDRNLVKELKELV (SEQ ID NO: 3) |
| MfnB 4 | *Methanocaldococcus infernus* | MLLLVSPIDVEEAKEAIEGGADIIDVKNPKEGSLGANFPWVIREVRKIT<br>PKSLLVSATVGDVPYKPGTVSLAALGAGMSGADYIKVGLYGVKNYNQAV<br>ELMKSVVKAVKDFDDNKIVVAAGYADAYRVGAVDPLVIPKIARDSGADV<br>AMLDTAIKDGKTLFDFLSKEILEEFVSEVHDYGLKCALAGTIKKDHIPI<br>LKEIGTDIVGVRGAACKGGDRNKGRIDRNLVRELKELC (SEQ ID NO: 4) |
| MfnB 5 | *Methanothermococcus okinawensis* | MILLVSPKDVNEAIETIKGGADIVDVKNPPEGSLGANFPWIIKEIREIT<br>PKNLFVSAAIGDVPYKPGIVALAALGAAMSGADYIKVGLYGIKSYNEAV<br>DLMEKVVKAVKGVDENKIVVAAGYADAHRVGAVEPLIVPKIARDAGCDV<br>AMLDTAVKDGKTLFDHLNEKILAEFVEETHSYGLKCALAGSIKKEEIPI<br>LKDINCDIVGVRGAACTKGDRNNGTIKSELVKELSKLCK (SEQ ID NO: 5) |
| MfnB 6 | *Methanococcales archaeon HHB* | MRILISPKDIEEAKEAIEGGADIIDVKNPLEGSLGANFPWVIREIRNIT<br>PKDRLVSATVGDVPYKPGIVALAAVGAAISGADYIKVGLYGIKSYREAV<br>DVMNKVVKAVKEIDENKIVVAAGYADAYRVGAVDPLIIPKVARDSGCDV<br>AMLDTAVKDGKRLFDHLRELISEFVEEVHNYGLECALAGSIRKEDIPV<br>LKEIGCDIVGIRGAACTKGDRNNGKIKKELVEELVKLCKNGDK (SEQ ID NO: 6) |
| MfnB 7 | *Methanobrevibacter smithii* | MLLLISPINHEEALESIKGGADIVDVKNPKEGSLGANFPWVIRDIREIT<br>PEDKLVSATLGDVPYKPGIVSLAAMGAHVSGADYIKVGLYGTKDYDEAV<br>EVMENVAKTIKDVDNDTIVVAAGYADAHRVGAVDPMEIPKVAKDAGCDL<br>AMLDTAVKDGHTLFDYLSIEDLEKFVNEAHSYGLKTALAGSVKKEQLKP<br>LNDIGCDVVGIRGAACVGGDRNTGKIHHSAVAELKELCDSF (SEQ ID NO: 7) |
| MfnB 8 | *Methanobacterium sp. PtaB.Bin024* | MLLLISPINTQEAREAIDGGADIVDVKNPKEGSLGANFPWVIRNIREIT<br>PKNMKVSATLGDVPYKPGIVALAAAGAIVSGADYIKVGLYGTTNYSEAL<br>EVMENVVKIVDEENSDAIVVAAGYADAHRVGAVDPMEIPKIAADSGSDL<br>AMVDTAVKDGKILFDFMNEETLSQFTEQTHEYGLKSALAGSVIEEQLPI<br>LAELGCDVVGIRGAACIGGDRNSGSIHHEAVARLKQIV (SEQ ID NO: 8) |
| MfnB 9 | *Methanopyrus sp. KOL6* | MRPRLLVSPVNRDEALEAVEGGAHIIDVKNPEEGSLGANFPWVIREIME<br>VVPEDREVSATVGDVPYKPGTVAQAVLGVAAVGVDYAKVGLYGTKTEEE<br>ALEVMRACSRAVREFGYDIRVVAAGYADAHRVDSIDPMSVPEVAAEAEC<br>DVAMVDTAVKDGKRLFDFLREEEVGEFVDLAHEHGLEVALAGSLRHEDM<br>PIVRDLGADIVGIRGAACERGDRNRGAIRSHLVRKLAEALA (SEQ ID NO: 9) |
| MfnB 10 | *Candidatus Argoarchaeum ethanivorans* | MTMKLLVSPISVEEARIALDGGADIIDVKNPKEGSLGANFPDVIQSVKR<br>VITKPMSVAIGDFNYKPGTASLAALGASVAGADYIKIGLFDVQTREQAS<br>EMTERVTKAVKQYDSKKKVVICGYSDYNRINSISPFELPGIVSDAGADV<br>VMMDTGVKDGRSTLEFLNLEKLESFIGSAHQYGLLAAIAGSLTFEDIEA<br>LKEVAPDIIGVRGCVCGGDRNSSIKLELVRELKERIHH (SEQ ID NO: 10) |
| MfnB 11 | *Methanobacterium congolense* | MLLLISPINTEEAREAIEGGADIVDVKNPKEGSLGANFPWVIKSISELT<br>PEGMYVSATLGDVPYKPGIVSLAAAGAVVSGADYIKVGLYGTKNYEEAL<br>EVMKNVVKTVKDFNEDAVVVAAGYADAHRVGAVDPMEIPRVAADAGADL<br>AMVDTAVKDGKILFDFMDEDTLIKFNNTIHDYGLKSALAGSVKKEQLEM<br>LYNIGCDVVGIRGAACVGGDRNTGKIHRSAVGELKKMIENF (SEQ ID NO: 11) |

TABLE 1-continued (5-formylfuran-3-yl)methyl phosphate synthases enzymes

| Name | Organism | Sequence |
|---|---|---|
| MfnB12 | Methanobrevibacter arboriphilus | MLLLISPINNEEALESIEGGADIVDVKNPKEGSLGANFPWVISEIRKMT PDDMLVSATLGDVPYKPGIVSLAAMGALTSGADYIKVGLYGISNYDEAL EVMINVVKIVKSNNPNATVVASGYGDAHRVGAVSPWDIPKVAKESGSDL AMLDTAVKDGKTLFDYLNIDDLKKFVEETHSYGLKSALAGSVKKEQLKP LYDIGCDVVGVRGAACTGGDRNNGKISRTAVAELKELVNSFD (SEQ ID NO: 12) |
| MfnB 13 | Methanococcus marrpaludis | MILLVSPKDVAEAHEAIEGGADIIDVKNPPEGSLGANFPWVIKETREAT PEGMLVSAAIGDVPYKPGIVTLAALGAAISGADYIKVGLYGIRSYQEAL DVMKNVTKAVKDSGENKIVVAAGYADAYRVGGVDPLIIPRVARDAGCDV AMLDTAVKDGKTLFDHMSIELLKEFVEETHKYGMKCALAGSIKIEEIPM LKEINCDIVGVRGAACTKGDRNEGRIQKDLVKEIVKVCRQ (SEQ ID NO: 13) |
| MfnB 14 | Methanococcus vannielii | MILLVSPKDVAEAYEAINGGADIIDVKNPPEGSLGANFPWVIKEIRSAT PNGMLVSAAIGDVHYKPGIVTLAALGATISGADYIKIGLYGIRSYQEAV DVMKNVSNAVKSEDPKKIVVAAGYADAYRVGAVDPLIIPKIARDSGCDV AMLDTAVKDGKTLFDHLSIDLLKEFVEETHKYGMKCALAGSIKKEEIPM LKEIGCDIVGIRGAACTKGDRNEGKIQKDLVKEIVKICKE (SEQ ID NO: 14) |
| MfnB 15 | Methanosarcina acetivorans | MKLLVSPINREEAIIASLGGADIVDVKNPKEGSLGANFPWVIRDVKEVV NGRQPISATIGDFNYKPGTASLAALGAAVAGADYIKVGLYDIQTEAQAL ELLTKITLAVKDYDPSKKVVASGYSDYKRINSISPLLLPAVAAEAGVDV VMVDTGIKDGKSTFEFMDEQELKEFTDLAHEHGLENAIAGSLKFEDLPV LERIGPDIIGVRGMVCGGDRRTAIRQELVEKLVAECQI (SEQ ID NO: 15) |
| MfnB 16 | Methanosarcina barkeri | MKLLISPINKEEAIIASRGGADIVDVKNPKEGSLGANFPWVIRDVKGAV NGRQPISATIGDFNYKPGTASLAAFGAAMAGADYIKVGLYDIQTEDQAL ELITKITQAVKDYDSTKKVVASGYSDYKRINSISPLLLPSIAAKAGADV VMVDTGIKDGKSTFEFMDEEELKKFTGLAHECGLENAIAGSLKFEDLPV LERIGPDIIGVRGMVCGGDRTNSIRQELVEKLVAECQA (SEQ ID NO: 16) |
| MfnB 17 | Methylorubrum extorquens | MSDIVSISSARPRLLVSVRGPDEALTALRAGADLIDAKDPERGALGALP PETVRAIVAGVGGRAVISAVAGDGIGREIAAAIATIAATGVDFIKIAVG GADDAALAEAAAQAPGRVIGVLFAEDDVAEDGPARLAAAGFVGAMIDTR GKSGTILTSLMAAPQLAAFVAGCRTHGLMSGLAGSLGLGDIPVLARLDP DYLGFRGGLCRASDRRQALDGARVAQAVEAMRAGPRADAA (SEQ ID NO: 17) |
| MfnB 18 | Methylobacterium sp. | MTRPEPHLSVRAAPRLLVSVRDAAEAEVARAAGADLVDAKDPARGALGA LDPALVRAMVARIGDRATTSAVAGEPREAGDLVAKVAAMAATGVDYVKV ALPPGLRSGRDGLREAADAARGRLIAVLFAEDGLDLAVLFPTLADAGFVG AMIDINTKDGRRLTDRIAVPALSAFTAACRAEGLVSGLAGSLALADIPA LSDLGAGYLGFRGGLCRGGDRRGDLDPARIAEAARLLRAGGRRDAA (SEQ ID NO: 18) |
| MfnB 19 | Methanosarcina mazei | MKLLVSPINSEEAIIASIGGADIVDVKNPKEGSLGANFPWVIREVKAVV NGRQPISATIGDFNYKPGTAALAALGAAVAGADYIKVGLYDIQTESQAL ELLTKITRAVKDYNPLKKVVASGYSDYKRINSISPLLLPAVAAEAGVDV VMVDTGVKDGKSTFEFMDEKELKEFTDLAHSYGLENAIAGSLKFEDIPL LERIGPDIIGVRGMVCGGDRSTSIRQELVEKLVAECQA (SEQ ID NO: 19) |
| MfnB 20 | Methyloversatilis universalis | MIRMLASVRNLDEARIVLEAGVDLIDLKQPADGALGALPAEVIREVVDF VAGRILTSATAGNVEPDAQAVQSAMARIAATGVDYVKAGLFPGNWQQGG RDYAAVRACLRGLTPLAGARRIAVMFADLSPPLALVDAVADAGFDGMV DTALKIGHSLPDVASTEWLSGFVERARARGLLCGLAGSLRVIHIPALAQ RCPDYLGFRGALCAGQARAQALDARAVLAVREALEKVQRLAA (SEQ ID NO: 20) |
| MfnB 21 | Nitrosococcus watsonii | MSCWLASVRNLEEISCLLAEGPDIIDFKEPKEGVLGALPLETVREAVAL IGRRCQTSAAIGDFPVDSPQIYQRVLEMAATGVDYVKIGLPSNIQQAAA CLLSLRPLADQGVSMVGVIFADKRPDFSWTYLIGQAGFKGIMLDTAIKD DFGLLSHLSLSELNNFVKLARSVRLISGLAGSLSIQDIPKLLPLRADYL GFRSALCVAARNRCSRLDPKAVLLIKQAMRENLRIFEI (SEQ ID NO: 21) |
| MfnB 22 | Streptomyces cattleya NRRL 8057 | MKEPTLLLLISPDSVEEALDCAKAAEHLDIVDVKKPDEGSLGANYPWVI REIRDAIPADKPVSATVGDVPYKPGTVAQAALGAVVSGATYIKVGLYGC TTPDQVVEVMRGVVRAVKDHRPDALVVASGYADAHRIGCVNPLAIPGVA QRSGCDAAMLDTAVKDGTRLFDHVPPDVCGEFVRLAHEGGLLAALAGSV |

TABLE 1-continued (5-formylfuran-3-yl)methyl phosphate synthases enzymes

| Name | Organism | Sequence |
|---|---|---|
| | | KAEDLGALTRIGTDIVGVRGAVCEGGDRNAGRIQPHLVAAFRAEMDRHA<br>REHAAVVTPTG (SEQ ID NO: 22) |
| MfnB 23 | *Streptomyces coelicolor* | MLLLISPDGVDEALDCAKAAEHLDIVDVKKPDEGSLGANYPWVIREIRA<br>AVPADKPVSATVGDVPYKPGTVAQAALGAAVSGATYIKVGLYGCATPEQ<br>AVEVMRGVVRAVKDHRADAFVVASGYADAHRIGCVNPLSLPDIARRSGS<br>DAAMLDTAIKDGTRLFDHVPPDVCAEFVRRAHDCGLLAALAGSVRSGDL<br>GELARIQTDIVGVRGAVCEGGDRTTGRIRPHLVAAFRAEMDRHVREHAA<br>AAAQS (SEQ ID NO: 23) |
| MfnB 24 | *Streptomyces* EFF88969 | MLLISPDSVEEALECAKAAQHLDIVDVKKPDEGSLGANHPWVIRAVRDA<br>VPADKPVSATVGDVPYKPGIVAQAALGATVSGATYIKVGLYGCTTPDQA<br>VEVMRGVVRAVKDFRPDALVVASGYADAHRIGCVNPLALPDIARRSGSD<br>GAMLDTAVKDGTRLFDHTPPQVCAEFVRLAHEAGLLAALAGSVKAGDLA<br>ELAGMGTDIVGVRGAVCEGGDRNAGRIRPELVAAFRAEMDRCVQQHGGQ<br>GAAVAAAS (SEQ ID NO: 24) |
| MfnB 25 | *Streptomyces griseus* | MLLLISPDGVEEALACATAAEHLDIVDVKKPDEGSLGANFPWVIREIRA<br>AVPADKPVSATVGDVPYKPGTVAQAALGAAVSGATYIKVGLYGCATPDQ<br>AIDVMRGVVRAVKDFRADAFVVASGYADAHRIGCVNPLALPDIARRAGA<br>DAAMLDTAIKDGTRLFDHVPPEGCAEFVRLAHEAGLLAALAGSVKAADL<br>ATLTRIGTDIVGVRGAVCEGGDRDAGRIQPRLVAAFRAEMDRHARAFAA<br>APAAS (SEQ ID NO: 25) |
| MfnB 26 | *Streptomyces* sp. DH-12 | MLLLISPDGVEEALDCAKAAEHLDIVDVKKPDEGSLGANFPWVIREIRE<br>AVPADKPVSATVGDVPYKPGTVAQAALGAVVSGATYIKVGLYGCTTPDQ<br>GIDVMRAVVRAVKEHNPDALVVASGYADAHRIGCVNPLAVPDIAARSGA<br>DAAMLDTAVKDGTRLFDHVPPDVCAEFVRLAHASGRLAALAGSVRQDDL<br>GELTRIGTDIVGVRGAVCEGGDRNAGRIQPHLVAAFRAEMDRYDRERTA<br>GLPAAR (SEQ ID NO: 26) |
| MfnB 27 | *Streptomyces venezuelae* | MLLLISPDSVEEALDCVKAAEHLDIVDVKKPDEGSLGANFPWVIREIRD<br>AVPADKPVSATVGDVPYKPGIVAQAALGAVVSGATYIKVGLYGCTIPEQ<br>GIEVMRAVVRAVKDHRPDALVVASGYADAHRVGCVNPLAVPDIAARSGA<br>DAAMLDTAIKDGTRLFDHVPPDACAEFVRRAHASGLLAALAGSITQADL<br>GPLIRMGIDIVGVRGAVCAGGDRNAGRIQPHLITAFRAEMDRQGREYAV<br>GIPAAN (SEQ ID NO: 27) |

In one embodiment, the recombinant microorganism of any one of the embodiments disclosed herein comprises at least one endogenous or exogenous nucleic acid molecule encoding a phosphatase or a kinase that catalyzes the conversion of (5-formylfuran-3-yl)methyl phosphate to (4-HMF). In one embodiment, the phosphatase is classified as haloacid dehalogenase (Koonin et al. J. Mol. Biol. 244(1). 1994). In some aspects, the phosphatase of reaction b is endogenous to the host (Offley et al. Curr. Gen. 65. 2019). In some aspects, the phosphatase enzyme endogenous to the host is overexpressed. In some cases a heterologous phosphatase able to perform the desired reaction is used and is selected from an alkaline phosphatase, acid phosphatase, fructose-bisphosphatase, sugar-phosphatase, or sugar-terminal-phosphatase. In some embodiments, the phosphatase can be derived from enzyme candidates listed at Table 2. In some embodiments, the phosphatase is homologous or similar to the enzymes listed at Table 2. In some embodiments the 4-HMF phosphatase enzyme is encoded by an amino acid sequence listed in Table 2. In some embodiments, a phosphatase enzyme is evolved or engineered to improve its catalytic efficiency and or specificity for the conversion of (5-formylfuran-3-yl)methyl phosphate to (4-HMF).

TABLE 2

4-HMF phosphatase enzymes

| Name | Organism | Sequence |
|---|---|---|
| PH1 | *Streptomyces coelicolor* | MMPEPPRERRTAANRSPAIRPIAFFDVDETLITAKSMLDFARQAPHSLR<br>DDITAQASGQRHSADADLTAMRRRGASRVEMNRVYYRRYAGVSLARLQE<br>AGRDWYHAYRTRPDGYVRAGLAALARHRRAGHTIVLISGSARPLLTPLA<br>QDLGADRILCTEQFADAQGVLTGEVNRPMIGEAKAEAVTEVMAKRGVVP<br>ADCFAYGDHESDFGMLQAVGNPVVVGTDLVLVRHAQGSNWPVLPADAGP<br>RCACARRPGPLGHDDPSAIG (SEQ ID NO: 28) |
| PH2 | *Streptomyces* sp. E5N91 | MMPEPPRERRTAANRSPAIRPIAFFDVDETLITAKSMLDFARQAPHSLR<br>DDITAQASGQRHSADADLTAMRRRGASRVEMNRVYYRRYAGVSLARLQE<br>AGRDWYHAYRTRPDGYVRAGLAALARHRRAGHTIVLISGSARPLLTPLA<br>QDLGADRILCTEQFADAQGVLTGEVDRPMIGEAKAEAVTEVMAKRGVVS<br>ADCFAYGDHESDFGMLQAVGNPVVVGTDLVLVRHAQASNWPVLPADAGP<br>RCACARRPGPLGHDDPSAIG (SEQ ID NO: 29) |

TABLE 2-continued

4-HMF phosphatase enzymes

| Name | Organism | Sequence |
|---|---|---|
| PH3 | Streptomyces sp. NRRL S-31 | MSALRHERRAAVSRPVVIRHIAFFDVDETLITAKSLLDFAQRVPHGLWE DETGQPIERLRSGEIDLAALQRSGASRAEMNRAYYRRYAGVPLERLQKA GRDWYHAYRMRPDGYITAGLAALARHRRAGHMIVLISGSARPLLTPLSE DLGADRILCTEQLDDAQGVLTGEVAHPMVGEAKAEAVTEVMAQLRVPTT DCFAYGDHGSDLDMLQAVGSPVVVGTDPVLARHAQASNWPMLPADAGPR IARAQHHDTSAQYGPQVIALASGRGAAPRRQERW (SEQ ID NO: 30) |
| PH4 | Streptomyces aureus | MNASIAPAAFFDVDETLVNTKSMEHFLRFWMARQGDDGSGHEAVMAGVR RAAASGVHRSEINRAYYRRFAGVPYAALLEAGRDWWQEYRRGSDAVVVP AWAAATRHRKAGHLVVLVSGSFRGCLEPLAQDLGAHRILCSEPLVDTDG RLTGEVVRPMIGSVKADAVRETVAELGLTAADCSCYGDHSSDLDMLGAV GNPVVVGGDRVLLEHAQRLDWPVLPATPGHLPSPDASPARLLTAAERR (SEQ ID NO: 31) |
| PH5 | Saccharothrix syringae | MSTPPAVAFFDVDETVIKVKSMFEFLRHWMTAQGDDGSAYESFMAGVRE LADAGVPRAEVNRHYYRRYAGASAADVRAAGEDWYASYRRRPDGFLTAT VAAVAAHRAAGNRVVLVSGSFLPVLGPLMADVGADEALCGDPEVGPDGR YTGAIAVPMIGENKTAAVRARMAELGVDPADCYAYGDHQSDLGMLEAVG NPVVVGEDPVLVGKAEAGGWRRLPATTGPLGVPPRVLSVVE (SEQ ID NO: 32) |
| PH6 | Rhodococcus sp. MTM3W5.2 | MTHTGSRPVQVAFFDVDETLITVKSMFAFLEHWLRERGDDGSEYSRLLA ALRRASDEGAPREEVNRSYYRTFRGVPLVELEESGRRWYREFESTAAPY YADTLAALRDHRDAGAAIVLLSGSFAPALGPIGEAVCADRIVASRPVTD GHGVLTGEVERPMIGKAKAEAVTSVLEELGIDTGNSYGYGDHDSDLAFL EAVGHPGLRGSDPVLRAHAARNRWRVLGSATTGLAGAVPLLAATSTGQR GLR (SEQ ID NO: 33) |
| PH7 | Rhodococcus sp. UNC363MFTsu5.1 | MIGTGPRPGQVAFFDVDETLITVKSMFAFLEHWLWERGDDGSEYARLLG ALRRQSDEGAPREEVNRSYYRTFRGVPLVELEESGRRWYREFESTNAPY YAATLAALHAHREAGAAIVLLSGSFAPALVPIGEAVGADRIVASRPVTD QGGVLIGEVERPMIGQAKAEAVISVQAELGVDAENSYGYGDHESDLAFL EAVGHPGLRGDDQVLLARAARDRWRSLGSETTGLAGAGPLAGSASAGLA QRGIL (SEQ ID NO: 34) |
| PH8 | Buttiauxella warmboldiae | MHTSAAFFDVDETLITVKSMFDFYDFWCRENNEYDKLQRYMTDFRSAVK NGTPREQLNREYYRQFAGVNYKDLEEAGKNWERGKKLDSELFISSAVAA LKKHQANNMFIVFISGSMHPVLSPVANYLGVIDILCIPLELTGEGIITG EIGTPQTIGIGKKEALINFCSQKKISAADCYAYGDDLSDIPMLESVGYP VCVGKYTELARHAINQRWPVI (SEQ ID NO: 35) |
| PH9 | Chania multitudinisentens | MRQTAFYDVDDTLINIKSMFDFFQFWASENGLISQQEQFDSQFSVLARK MSSREELNRAYYRFFKGVPLLKIEQCAERWFKNSFSNTEIFISYTLKSI LAHRVLGHNIVLVSGSMTPLLKPIAQLLGITDILCIKLATDQSGVVTGE ILETQTIGEGKAIVIRQYALENDINLSACFAYGDDVSDIPMLACVGHPI CIGEGTALSHYASNNNWPIVRVE (SEQ ID NO: 36) |
| PH10 | Methylosinus sporium | MMEHRSFAFFDVDETLISIKSMFDFFPPFWCKWIGAAPEAYSRFETEIAS AIARHATREELNRLYYRSFRGAQLPVLEAAGAAWFLQRFGSPPYRKHV VARLEKHRQEGVVPVLVSGSMRPLLRPIARELQAEHCLCTQLVVDESGR LIGEIGSPQTIGEGKAEAIRAFLREQGGRPADCLAYGDDISDLAMLELV GAPVVVGAQPDLLSICRQRDWPYLPL (SEQ ID NO: 37) |
| PH11 | Klebsiella oxytoca | MQQAAAFFDVDETLINIKSMFDFFDFWCKENNEPIKLHKYMANFQSEVK KGIPREHLNREYYRQFAGISYKALEEAGEKWERFKLNSELFIGSAVSAL KKHQAENMDIVFISGSMLPVLSPVARYLGVKDILCIPLKFTAAGEMTGE IGYPQTIGDGKKDALLQFCEQRNINPSDCYAYGDDLSDIPMLASIGHPV CVGKHSALARHAITHRWQVI (SEQ ID NO: 38) |
| PH12 | Serratia | MISAAAFFDVDETLIKMKSMEHEYHYWSNVRGNQKAYEEFIKREQQAVA EGVPREVLNRMYYRQFSGIDIDDDVYQVAEDWFHKYLHEKEAYIASAVDR FQRHKISGHLTVFISGSMLPLLKPLGQRLGADAILCTQLLLDAKGKLIG EIGEPQTIGQGKQRALLSFSQSHHIDLAKSFAYGDDLSDIPMLAATGNP VCVGEHSNLAEYARRNNWNMLAENATN (SEQ ID NO: 39) |
| PH13 | Saccharomyces cerevisiae ycr015c | MKTIIISDFDETITRVDTICTIAKLPYLLNPRLKPEWGHFIKTYMDGYH KYKYNGIRSLPLLSSGVPIIISQSNENKLFADELKYQNHRVVELNSVN EITKQQIFKSISLDQMKTFARDQNHEDCLLRDGFKTFCSSVVKNFESDF YVLSINWSKEFIHEVIGDRRLKNSHIFCNDLKKVSDKCSQSYNGEFDCR LLIGSDKVKILGEILDKIDSGCNKEGNSCSYWYIGDSEIDLLSILHPST NGVLLINPQENPSKFIKITEKIIGIPKDKISSFEADNGPAWLQFCEKEG GKGAYLVKSWDSLKDLIMQVTKM (SEQ ID NO: 40) |
| PH14 | Saccharomyces cereyislae yd1236w | MTAQQGVPIKITNKEIAQEFLDKYDTFLFDCDGVLWLGSQALPYTLEIL NLLKQLGKQLIFVTNNSTKSRLAYTKKFASFGIDVKEEQIFTSGYASAV |

TABLE 2-continued

4-HMF phosphatase enzymes

| Name | Organism | Sequence |
|---|---|---|
| | | YIRDFLKLQPGKDKVWVFGESGIGEELKLMGYESLGGADSRLDTPFDAA KSPPFLVNGLDKDVSCVIAGLDTKVNYHRLAVTLQYLQKDSVHFVGINVD STFPQKGYTFPGAGSMIESLAFSSNRRPSYCGKPNQNMLNSIISAFNLD RSKCCMVGDRLNTDMKFGVEGGLGGILLVLSGIETEERALKISHDYPRP KFYIDKLGDIYILTNNEL (SEQ ID NO: 41) |
| PH15 | Saccharomyces cerevisiae ydl236w | MTIAKDYRTIYRNQIKKQIRLNQEHLQSLTHLGSQINFEVDPPKLPDPD RARKVEFFDIDNTLYRKSTKVQLLMQQSLSNEFKYELGEDDDEAERLIE SYYQEYGLSVKGLIKNKQIDDVLQYNTFIDDSLPLQDYLKPDWKLRELL INLKKKKLGKFDKLWLFINSYKNHAIRCVKILGIADLFDGITYCHYDRP IEEEFICKPDPKFFETAKLQSGLSSFANAWFIDDNESNVRSALSMGMGH VIHLIEDYQYESENIVTKDHKNKQQFSILKDILEIPLIMDVEVYRPSSI AIKEMEELEEEGEAYNWSNQQINVQSS (SEQ ID NO: 42) |
| PH16 | Saccharomyces cerevisiae yer062c | MGLITKPLSLKVNAALFDVDGIIIISQPAIAAFWRDEGKDKPYFDAEHV IQVSHGWRTFDAIAKFAPDFANEEYVNKLEAEIPVKYGEKSIEVPGAVK LCNALNALPKEKWAVATSGTRDMAQKWFEHLGIRRPKYFITANDVKQGK PHPEPYLKGRNGLGYPINEQDPSKSKVVVFEDAPAGIAAGKAAGCKIIG IATTFDLDFLKEKGCDIIVKNHESIRVGGYNAETDEVEFIFDDYLYAKD DLLKW (SEQ ID NO: 43) |
| PH17 | Saccharomyces cerevisiae yfl045c | MSIAEFAYKEKPETLVLFDVDGILTPARLIVSEEVRKTLAKLRNKCCIG FVGGSDLSKQLEQLGPNVLDEFDYSFSENGLTAYRLGKELASQSFINWL GEEKYNKLAVFILRYLSEIDLPKRRGTFLEFRNGMINVSPIGRNASTEE RNEFERYDKEHQIRAKFVEALKKEFPDYGLIFSIGGQISFDVFPAGWDK TYCLQHVEKDGFKEIHFFGDKTMVGGNDYEIFVDERTIGHSVQSPDDTV KILTELFNL (SEQ ID NO: 44) |
| PH18 | Saccharomyces cerevisiae ygl224c | MTVEYTASDLATYQNEVNEQIAKNKAHLESLTHPGSKVTFPIDQDISAT PQNPNLKVFFFDIDNCLYKSSTRIHDLMQQSILRFFQTHLKLSPEDAHV LNNSYYKEYGLAIRGLVMPHKVNALEYNRLVDDSLPLQDILKPDIPLRN MLLRLRQSGKIDKLWLFTNAYKNHAIRCLRLLGIADLFDGLTYCDYSRT DILVCKPHVKAFEKAMKESGLARYENAYFIDDSGKNIETGIKLGMKTCI HLVENEVNEILGQTPEGAIVISDILELPHVVSDLF (SEQ ID NO: 45) |
| PH19 | Saccharomyces cerevisiae yhr043c | MPQFSVDLCLFDLDGTIVSITTAAESAWKKLCRQHGVDPVELFKHSHGA RSQEMMKKFFPKLDNIDNKGVLALEKDMADNYLDTVSLIPGAENLLLSL DVDTETQKKLPERKWAIVISGSPYLAFSWFETILKNVGKPKVFITGFDV KNGKPDPEGYSRARDLLRQDLQLIGKQDLKYVVFEDAPVGIKAGKAMGA ITVGITSSYDKSVLFDAGADYVVCDLIQVSVVKNNENGIVIQVNNPLIR D (SEQ ID NO: 46) |
| PH20 | Saccharomyces cerevisiae yhr044c | MAEFSADLCLFDLDGTIVSTIVAAEKAWTKLCYEYGVDPSELFKHSHGA RTQEVLRRFFPKLDDIDNKGVLALEKDIAHSYLDTVSLIPGAENLLLSL DVDTETQKKLPERKWAIVISGSPYLAFSWFETILKNVGKPKVFITGFDV KNGKPDPEGYSRARDLLRQDLQLIGKQDLKYVVFEDAPVGIKAGKAMGA ITVGITSSYDKSVLFDAGADYVVCDLIQVSVVKNNENGIVIQVNNPLIR A (SEQ ID NO: 47) |
| PH21 | Saccharomyces cerevisiae yil053w | MPLITKPLSLKINAALFDVDGIIIISQPAIAAFWRDFGKDKPYFDAEHV IHISHGWRTYDAIAKFAPDFADEEYVNKLEGEIPEKYGEHSIEVPGAVK LCNALNALPKEKWAVATSGTRDMAKKWFDILKIKRPEYFITANDVKQGK PHPEPYLKGRNGLGFPINEQDPSKSKVVVFEDAPAGIAAGKAAGCKIVG IATTFDLDFLKEKGCDIIVKNHESIRVGEYNAETDEVELIFDDYLYAKD DLLKW (SEQ ID NO: 48) |
| PH22 | Saccharomyces cerevisiae ykr070w | MIGKRFFQTTSKKIAFAFDIDGVLFRGKKPIAGASDALKLLNRNKIPYI LLINGGGESERARTEFISSKLDVDVSPLQIIQSHIPYKSLVNKYSRILA VGTPSVRGVAEGYGFQDVVHQTDIVRYNRDIAPFSGLSDEQVMEYSRDI PDLTIKKFDAVLVFNDPHDWAADIQIISDAINSENGMLNTLRNEKSGKP SIPIYFSNQDLLWANPYKLNRFGQGAFRLLVRRLYLELNGEPLQDYTLG KPTKLTYDFAHHVLIDWEKRLSGKIGQGSVKQKLPLLGTKPSTSPFHAVF MVGDNPASDIIGAQNYGWNSCLVKIGVYNEGDDLKECKPILIVNDVFDA VTKTLEKYA (SEQ ID NO: 49) |
| PH23 | Saccharomyces cerevisiae ynl010w | MVKAVIFTDEDGIVTLEDSNDYLIDTLGEGKEKRLKVFEGVLDDIKSFR QGFMEMLESIHTPFPECIKILEKKIRLDPGFKDIFEWAQENDVPVIVVS SGMKPIIKVLLTRLVGQESIHKIDIVSNEVEIDAHDQWKIIYKDESPFG HDKSRSIDAYKKKFESTLKAGEQRPVYFYCGDGVSDLSAAKECDLLFAK RGKDLVTYCKKQNVPFHEFDTFKDILASMKQVLAGEKTVAELMEN (SEQ ID NO: 50) |
| PH24 | Saccharomyces cerevisiae yor131c | MTKLQGLQGLKHIKAVVEDMDGILCLPQPWMFPAMRNAIGLEDKSIDIL HFIDTLPTEKEKKEAHDRIELVEAKAMKEMQPQPGLVDIMRYLIKNGIS KNICTRNVGAPVETFVKRFIPSELSRFDYIVTREFRPTKPQPDPLLHIA |

TABLE 2-continued

| | | 4-HMF phosphatase enzymes |
|---|---|---|
| Name | Organism | Sequence |
| | | SKLNIRPLEMIMVGDSFDDMKSGRSAGCFTVLLKNHVNGHLLLEHKELV<br>DVSVEDLSEIIELIQNMNKESF (SEQ ID NO: 51) |
| PH25 | *Saccharomyces cerevisiae* yor155c | MSSRYRVEYHLKSHRKDEFIDWVKGLLASPFVLHAVSHEGDYNDDLATT<br>QRVRSQYADIFKDIEGLIKDKIEFDSRNMSQDEIEDGASSQSLNILGQS<br>RLNLLVPSIGIFFTELPLEQAFLWEDSQRAISARRMVAPSFNDIRHILN<br>TAQIFHFKKQENLHNGKVLRLVTFDGDVTLYEDGGSLVYTNPVIPYILK<br>LLRCGINVGIVTAAGYDEAGTYENRLKGLIVALHDSTDIPVSQKQNLTI<br>MGGESSYLFRYYEDPEEDNFGFRQIDKEEWLLPRMKAWSLEDVEKTLDF<br>AERTLNRLRKRLNLPSEISIIRKVRAVGIVPGERYDEASKRQVPVKLDR<br>EQLEEIVLTLQNTLESFAPSRRIQFSCFDGGSDVWCDIGGKDLGVRSLQ<br>QFYNPESPIQPSETLHVGDQFAPVGSANDFKARLAGCTLWIASPQETVN<br>YLHRLLETD (SEQ ID NO: 52) |
| PH26 | *Escherichia coli* YniC | MSTPRQILAAIFDMDGLLIDSEPLWDRAELDVMASLGVDISRRNELPDT<br>LGLRIDMVVDLWYARQPWNGPSRQEVVERVIARAISLVEETRPLLPGVR<br>EAVALCKEQGLLVGLASASPLHMLEKVLTMFDLRDSFDALASAEKLPYS<br>KPHPQVYLDCAAKLGVDPLTCVALEDSVNGMIASKAARMRSIVVPAPEA<br>QNDPRFVLANVKLSSLTELTAKDLLG (SEQ ID NO: 53) |
| PH27 | *Escherichia coli* YfbT | MRCKGFLFDLDGTLVDSLPAVERAWSNWARRHGLAPEEVLAFIHGKQAI<br>TSLRHFMAGKSEADIAAEFTRLEHIEATETEGITALPGAIALLSHLNKA<br>GIPWAIVISGSMPVARARHKIAGLPAPEVEVTAERVKRGKPEPDAYLLG<br>AQLLGLAPQECVVVEDAPAGVLSGLAAGCHVIAVNAPADTPRLNEVDLV<br>LHSLEQIIVIKQPNGDVIIQ (SEQ ID NO: 54) |
| PH28 | *Escherichia coli* YieH | MSTPRQILAAIFDMDGLLIDSEPLWDRAELDVMASLGVDISRRNELPDT<br>LGLRIDMVVDLWYARQPWNGPSRQEVVERVIARAISLVEETRPLLPGVR<br>EAVALCKEQGLLVGLASASPLHMLEKVLTMFDLRDSFDALASAEKLPYS<br>KPHPQVYLDCAAKLGVDPLTCVALEDSVNGMIASKAARMRSIVVPAPEA<br>QNDPRFVLADVKLSSLTELTAKDLLG (SEQ ID NO: 55) |
| PH29 | *Escherichia coli* YihX | MLYIFDLGNVIVDIDFNRVLGAWSDLTRIPLASLKKSFHMGEAFHQHER<br>GEISDEAFAEALCHEMALPLSYEQFSHGWQAVFVALRPEVIAIMHKLRE<br>QGHRVVVLSNTNRLHTTFWPEEYPEIRDAADHIYLSQDLGMRKPEARIY<br>QHVLQAEGFSPSDIVFFDDNADNIEGANQLGITSILVKDKITIPDYFAK<br>VLC (SEQ ID NO: 56) |
| PH31 | *Escherichia coli* YjjG | MRILLSNDDGVHAPGIQTLAKALREFADVQVVAPDRNRSGASNSLTLES<br>SLRIFTFENGDIAVQMGIPTDCVYLGVNALMRPRPDIVVSGINAGPNLG<br>DDVIYSGTVAAAMEGRHLGFPALAVSLDGHKHYDTAAAVICSILRALCK<br>EPLRTGRILNINVPDLPLDQIKGIRVIRCGTRHPADQVIPQQDPRGNIL<br>YWIGPPGGKCDAGPGTDFAAVDEGYVSITPLHVDLTAHSAQDVVSDWLN<br>SVGVGTQW (SEQ ID NO: 57) |
| PH32 | *Escherichia coli* YqaB | MYERYAGLIFDMDGTILDTEPTHRKAWREVLGHYGLQYDIQAMIALNGS<br>PTWRIAQAIIELNQADLDPHALAREKTEAVRSMLLDSVEPLPLVDVVKS<br>WHGRRPMAVGTGSESAIAEALLAHLGLRHYFDAVVAADHVKHHKPAPDT<br>FLLCAQRMGVQPTQCVVFEDADFGIQAARAAGMDAVDVRLL (SEQ ID<br>NO: 58) |
| PH33 | *Escherichia coli* YigB | MRFYRPLGRISALTFDLDDTLYDNRPVILRTEREALTFVQNYHPALRSF<br>QNEDLQRLRQAVREAEPEIYHDVTRWRFRSIEQAMLDAGLSAEEASAGA<br>HAAMINFAKWRSRIDVPQQTHDTLKQLAKKWPLVAITNGNAQPELFGLG<br>DYFEFVLRAGPHGRSKPFSDMYFLAAEKLNVPIGEILHVGDDLTTDVGG<br>AIRSGMQACWIRPENGDLMQTWDSRLLPHLEISRLASLTSLI (SEQ<br>ID NO: 59) |
| PH34 | *Escherichia coli* YrfG | MHINIAWQDVDTVLLDMDGILLDLAFDNYFWQKLVPETWGAKNGVIPQE<br>AMEYMRQQYHDVQHTLNWYCLDYWSEQLGLDICAMTTEMGPRAVLREDT<br>IPPFLEALKASGKQRILLTNAHPHNLAVKLEHTGLDAHLDLLLSTHTFGY<br>PKEDQRLWHAVAEATGLKAERTLFIDDSEAILDAAAQFGIRYCLGVINP<br>DSGIAEKQYQRHPSLNDYRRLIPSLM (SEQ ID NO: 60) |
| PH35 | *Escherichia coli* Gph | MSTPRQILAAIFDMDGLLIDSEPLWDRAELDVMASLGVDISRRNELPDT<br>LGLRIDMVVDLWYARQPWNGPSRQEVVERVIARAISLVEETRPLLPGVR<br>EAVALCKEQGLLVGLASASPLHMLEKVLTMFDLRDSFDALASAEKLPYS<br>KPHPQVYLDCAAKLGVDPLTCVALEDSVNGMIASKAARMRSIVVPAPEA<br>QNDPRFVLADVKLSSLTELTAKDLLG (SEQ ID NO: 61) |
| PH36 | *Escherichia coli* YbiV | MSVKVIVTDMDGTFLNDAKTYNQPRFMAQYQELKKRGIKFVVASGNQYY<br>QLISFFPELKDEISFVAENGALVYEHGKQLFHGELTRHESRIVIGELLK<br>DKQLNFVACGLQSAYVSENAPEAFVALMAKHYHRLKPVKDYQEIDDVLF<br>KFSLNLPDEQIPLVIDKLHVALDGIMKPVTSGFGFIDLIIPGLHKANGI<br>SRLLKRWDLSPQNVVAIGDSGNDAEMLKMARYSFAMGNAAENIKQIARY<br>ATDDNNHEGALNVIQAVLDNTSPFNS (SEQ ID NO: 62) |

TABLE 2-continued

4-HMF phosphatase enzymes

| Name | Organism | Sequence |
|------|----------|----------|
| PH37 | *Escherichia coli* YidA | MAIKLIAIDMDGILLLPDHTISPAVKNAIAAARARGVNVVLITGRPYAG VHNYLKELHMEQPGDYCITYNGALVQKAADGSTVAQTALSYDDYRFLEK LSREVGSHFHALDRITLYTANRDISYYTVHESFVATIPLVFCEAEKMDP NTQFLKVMMIDEPAILDQAIARIPQEVKEKYTVLKSAPYFLEILDKRVN KGTGVKSLADVLGIKPEEIMAIGDQENDIAMIEYAGVGVAMDNAIPSVK EVANFVTKSNLEDGVAFAIEKYVLN (SEQ ID NO: 63) |
| PH38 | *Escherichia coli* YbhA | MITRVIALDLDGILLTPKKILLPSSIEALARAREAGYRLIIVTGRHHVA IHPFYQALALDTPAICCNGTYLYDYHAKTVLEADPMPVNKALQLIEMLN EHHIHGLMYVDDAMVYEHPIGHVIRTSNWAQTLPPEQRPTFTQVASLAE TAQQVNAVWKFALTHDDLPQLQHFGKHVEHELGLECEWSWHDQVDIARG GNSKGKRLIKWVEAQGWSMENVVAFGDNENDISMLEAAGIGVAMGNADD AVKARANIVIGDNITDSIAQFIYSHLI (SEQ ID NO: 64) |
| PH39 | *Escherichia coli* YbjI | MRFYRPLGRISALTFDLDDTLYDNRPVILRTEREALTFVQNYHPALRSF QNEDLQRLRQAVREAEPEIYHDVTRWRFRSIEQAMLDAGLSAEEASAGA HAAMINFAKWRSRIDVPQQTHDTLKQLAKKWPLVAITNGNAQPELFGLG DYFEFVLRAGPHGRSKPFSDMYFLAAEKLNVPIGEILHVGDDLTTDVGG AIRSGMQACWIRPENGDLMQTWDSRLLPHLEISRLASLTSLI (SEQ ID NO: 65) |
| PH40 | *Escherichia coli* YigL | MYQVVASDLDGILLSPDHILSPYAKETLKLLTARGINFVFATGRHHVDV GQIRDNLEIKSYMITSNGARVHDLDGNLIFAHNLDRDIASDLFGVVNDN PDIITNVYRDDEWFMNRHRPEEMRFFKEAVFQYALYEPGLLEPEGVSKV FFICDSHEQLLPLEQAINARWGDRVNVSFSTLICLEVMAGGVSKGHALE AVAKKLGYSLKDCIAFGDGMNDAEMLSMAGKGCIMGSAHQRLKDLHPEL EVIGTNADDAVPHYLRKLYLS (SEQ ID NO: 66) |
| PH41 | *Escherichia coli* OtsB | MTEPLIETPELSAKYAWFFDLDGILAEIKPHPDQVVVPDNILQGLQLLA TASDGALALISGRSMVELDALAKPYRFPLAGVHGAERRDINGKTHIVHL PDAIARDISVQLHTVIAQYPGAELEAKGMAFALHYRQAPQHEDALMTLA QRITQIWPQMALQQGKCVVEIKPRGISKGEAIAAFMQEAPFIGRIPVFL GDDLTDESGFAVVNRLGGMSVKIGTGATQASWRLAGVPDVWSWLEMITT ALQQKRENNRSDDYESFSRSI (SEQ ID NO: 67) |
| PH42 | *Escherichia coli* YaeD | MAKSVPAIFLDRDGTINVDHGYVHEIDNFEFIDGVIDAMRELKKMGFAL VVVINQSGIARGKFTEAQFETLIEWMDWSLADRDVDLDGIYYCPHHPQG SVEEFRQVCDCRKPHPGMLLSARDYLHIDMAASYMVGDKLEDMQAAVAA NVGIKVLVRIGKPITPEAENAADWVLNSLADLPQAIKKQQKPAQ (SEQ ID NO: 68) |

Accordingly, in one embodiment, provided herein is a recombinant microorganism that comprises an endogenous and/or exogenous nucleic acid molecules capable of converting a carbon source to glyceraldehyde 3-phosphate (G3P); at least one endogenous or exogenous nucleic acid molecule encoding a (5-formylfuran-3-yl)methyl phosphate synthase that catalyzes the conversion of G3P to (5-formylfuran-3-yl)methyl phosphate; at least one endogenous or exogenous nucleic acid molecule encoding a phosphatase that catalyzes the conversion of (5-formylfuran-3-yl)methyl phosphate to 4-HMF.

2,4-FDCA

In one embodiment, the present disclosure provides a recombinant microorganism capable of producing 2,4-furandicarboxylic acid (2,4-FDCA) from a carbon source. Some embodiments of the present disclosure are presented in FIG. 1, FIG. 2, and FIG. 3, which collectively detail the biosynthetic conversion of a carbon feedstock to 2,4-FDCA.

In one embodiment, the recombinant microorganism comprises the novel capacity to convert G3P to 2,4-FDCA via several enzymatically-catalyzed successive steps described herein. In one embodiment, the present disclosure comprises converting 4-HMF to 2,4 FDCA directly or through the production of intermediates furan-2,4-dicarbaldehyde, 4-(hydroxymethyl)furoic acid, 4-formylfuran-2-carboxylate, 4-formylfuran-2-carboxylate, 2-formylfuran-4-carboxylate.

In one embodiment, the present disclosure comprises converting 4-HMF to furan-2,4-dicarbaldehyde (Step D) and/or 4-(hydroxymethyl)furoic acid (Step E); converting furan-2,4-dicarbaldehyde to 4-formylfuran-2-carboxylate (Step G) and/or 2-formylfuran-4-carboxylate (Step F) and/or converting 4-(hydroxymethyl)furoic acid to 4-formylfuran-2-carboxylate (Step H); converting 4-formylfuran-2-carboxylate to 2,4-FDCA (Step J) and/or converting 2-formylfuran-4-carboxylate to 2,4-FDCA (Step I).

In one embodiment, the dehydrogenase is classified as EC number 1.1.1. when oxidizing an alcohol to a carbonyl group or EC number 1.2.1. when oxidizing an carbonyl to acid. In some aspects, the dehydrogenase is an alcohol dehydrogenase or an aldehyde dehydrogenase.

In some aspects, the oxidase from (c) is classified as EC number 1.1.3. In some aspects, the oxidase is 5-hydroxymethylfurfural oxidase. In some aspects the 5-hydroxymethylfurfural oxidase convert the 4-hydroxymethylfurfural (4-HMF) into 2,4 FDCA in a three-step reaction.

In a further embodiment, the one or more carbon sources may include glycerol or a monosaccharide.

In one embodiment, a microorganism comprises at least one endogenous or exogenous nucleic acid molecule encoding a dehydrogenase, an oxidase, or a peroxygenase that catalyzes the conversion of 4-HMF to furan-2,4-dicarbaldehyde and/or 4-(hydroxymethyl)furoic acid; at least one endogenous or exogenous nucleic acid molecule encoding a dehydrogenase, an oxidase, or a peroxygenase that catalyzes the conversion of furan-2,4-dicarbaldehyde to 4-formylfuran-2-carboxylate and/or 2-formylfuran-4-carboxylate and/or the conversion of 4-(hydroxymethyl)furoic acid to 4-formylfuran-2-carboxylate; at least one endogenous or exogenous nucleic acid molecule encoding a dehydrogenase, an oxidase, or a peroxygenase that catalyzes the conversion of 2-formylfuran-4-carboxylate to 2,4-FDCA and/or 4-formylfuran-2-carboxylate to 2,4-FDCA.

In one embodiment, the recombinant microorganism of any one of the embodiments disclosed herein comprises at least one endogenous or exogenous nucleic acid molecule encoding a dehydrogenase, an oxidase, or a peroxygenase that catalyzes the conversion of 4-HMF to furan-2,4-dicarbaldehyde. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment the dehydrogenases can be derived from enzyme candidates listed at Table 3. In some embodiments, the dehydrogenases are homologous or similar to the enzymes listed at Table 3. In some embodiments the 4-HMF dehydrogenase enzyme is encoded by an amino acid sequence listed in Table 3. In some embodiments, a dehydrogenase is evolved or engineered to improve its catalytic efficiency against its desirable substrate.

TABLE 3

4 HMF Dehydrogenases enzymes

| Name | Organism | Sequence |
|---|---|---|
| DH1 | Zymomonas mobilis | MLNFDYYNPTHIVFGKGRIAQLDILLSKDARVLVLYGGSSAQKTGILDE VRKALGDRTYFEFGGIEPNPSYETLMKAVEQVKQEKVDFLLAVGGGSVI DGIKEVAAAVPYEGEPWEILETDGKKIKEALPVGIVLILPATGSEMNRN SVVIRKSIKSKRGFHNDHVFPVFSILDPIKVYTLPPRQLANGVVDSFIH ITEQYLTYPVDGMVQDEFAEGLLRTLIKIGPELLKDQKNYDLAANFMWT ATLALNGLIGAGVPQDWATHMVGHELTAAFGIDHGRTLAIILPSLLQNQ REAKKGKLLQYAKNVWHIDQGSDDERIDAAIEKTRHFFESLGIPTHLKD YDVGEESIDMLVKELEAHGMSQLGEHKAITPEVSRAILLASL (SEQ ID NO: 69) |
| DH2 | Zymomonas mobilis subsp. pomaceae ATCC 29192 | MLNFDYYNPTHIAFGKDSIAKLDTLIPQDACVMVLYGGSSAKKTGILDE VKTALGSRKIHEFGGIEPNPSYETLMQAVEQVKKEKIDFLLAVGGGSVI DGIKEVAAAVPYEGEPWEILETDGKKIKKALPLGTVLILPATGSEMNPN SVVIRKSIKAKRAFHNKIVFPLFSILDPIKVYTLPPRQIANGIVDSFVH ITEQYLTYPVEGMVQDEFAEGLLRILINIGPKLLKDQKNYDLAANFMWT ATLALNGLIGAGVPQDWATHMIGHEITAAFGVDHGRTLAIILPSLLQNQ RQVKKDKLLQYAKNVWHIESGSEKERIDAVIAKTRSFFEEMGIPTHLSD YNIGKESIDMLIHELEAHGMTKLGEHNAITPDVSRAILIASL (SEQ ID NO: 70) |
| DH3 | Shewanella baltica | MLNFNYYNPTRIRFGKDTIAEIDTLVPSDAKVMILFGGSSARKTGILDE VKQSLGNRFIVEFDGIEPNPTYETLMKAVAQVREQKIDFLLAVGGGSVI DGIKEVAAAAVFEGEPWDILTSWGAKVTQAMPFGSVLILPAIGSEMNNA SVVIRKSLQAKLPFRNDLVYPQFSILDPIKTFTLPERQVANGVVDAFVH ITEQYLTYPVNAAVQDRFAEGLLQTLIELGPQVLAQPEDYDIRANLMWV ATMALNGTIGVGVPHDWATHMIGHELTALYDIDHARTLAIVLPALLQCT KEAKREKLLQYADRVWHINTGIDDERIDAAIAKTKAFFEAMGIPTHLSA YDLDASHVDTLVKQLELHGMVALGEHGNINPAMSRDILTLAL (SEQ ID NO: 71) |
| DH4 | Burkholderia pseudoomallei | MLNFDFYNPTRIVFGEKTAARLNDLLPAAARVLVLYGGESARSNGTLDE VRAALGARDVREFGGIEPNPAYETLMRAVELARRERVDFLLAVGGGSVI DGIKEVAAAVPFEGDPWTILETHGANVAAALPFGCVLILPATGSEMNNG AVLIRRATRAKLAFRHPLVEPTESILDPIKTYTLPPRQVANGVVDAFTH IVEQYLTYPADGLAQDRFAEGLLQTLIEIGPKALAEPRDYATRANLMWV ATLALNGLIGAGVPQDRATHMVGHELTARYDIDHARTLAVVLPSMLDVR RDAKRAKLLQYAARVWNIVDGPEDARIDAAIARTRAFFESLGVKIRLAD YGVGADAIDGLIAQLEAHGMTRLGERKDVILDVSRRVLEASL (SEQ ID NO: 72) |
| DH5 | Saccharomyces cerevisiae | MSIPETQKGVIFYESHGKLEYKDIPVPKPKANELLINVKYSGVCHTDLH AWHGDWPLPTKLPLVGGHEGAGVVVGMGENVKGWKIGDYAGIKWLNGSC MACEYCELGNEPNCPHADSSGYTHDGSFQQYATADAVQAAHIPQGTDLA EVAPVLCAGITVYKALKSANLMAGHWVAISGAAGGLGSLAVQYAKAMGY RVLGIDGGEGKEELFRSIGGEVFIDFIKEKDIVGAVLKAIDGGAHGVIN VSVSEAAIEASTRYVRANGTTVLVGMPAGAKCCSDVFNQVVKSISIVGS CVGNRADTREALDFFARGLVKSPIKVVGLSILPEIYEKMEKGQIVGRYV VDTSK (SEQ ID NO: 73) |
| DH6 | Saccharomyces cerevisiae | MSYPEKFEGIAIQSHEDWKNPKKTKYDPKPFYDHDIDIKIEACGVCGSD IHCAAGHWGNMKMPLVVGHEIVGKVVKLGPKSNSGLKVGQRVGVGAQVF SCLECDRCKNDNEPYCTKFVTTYSQPYEDGYVSQGGYANYVRVHEHFVV PIPENIPSHLAAPLLCGGLTVYSPLVRNGCGPGKKVGIVGLGGIGSMGT LISKAMGAETYVISRSSRKREDAMKMGADHYIATLEEGDWGEKYFDTFD LIVVCASSLTDIDFNIMPKAMKVGGRIVSISIPEQHEMLSLKPYGLKAV |

TABLE 3-continued

4 HMF Dehydrogenases enzymes

| Name | Organism | Sequence |
|---|---|---|
| | | SISYSALGSIKELNQLLKLVSEKDIKIWVETLPVGEAGVHEAFERMEKG DVRYRFTLVGYDKEFSD (SEQ ID NO: 74) |
| DH7 | Pseudomonas putida | MSIEHRLNHIAGQLSGNGEVLLNSVDAHTGEPLPYAFHQATSDEVDAAV QAAEAAYPAYRSTSPAQRAAFLDAIANELDALGDDFVQHVMRETALPEA RIRGERARTSNQLRLFADVVRRGDFLGARIDRAQPERTPLPRPDLRQYR IGVGPVAVFGASNFPLAFSTAGGDTASALAAGCPVVFKAHSGHMLTAAH VAAAIDRAVAGSGMPAGVFNMIYGAGVGEVLVKHPAIQAVGFTGSLRGG RALCDMAAARPQPIPVFAEMSSINPVIVLPQALQARGEQVAGELAASVV LGCGQFCTNPGLVVGIKSPQFERFVHTLVARMADQAPQTMLNAGTLRSY QSGVQHLLAHPGIQHLAGQPQAGKQAQPQLFKADVSLLLDSDPLLQEEV FGPTTVVVEVADAQQLAEALRHLQGQLTATLIAEPDDLRAFAALVPLLE RKAGRLLLNGYPTGVEVSDAMVHGGPYPATSDARGTSVGTLAIDRFLRP VCFQNYPDALLPEALKSANPLGIARLVDGVASRGAV (SEQ ID NO: 75) |
| DH8 | Pseudomonas putida | MSIEHRLNHIAGQLSGNGDVLLNSVDAHTGEPLPYAFHQATGDEVEAAV QAADAAYPAYRSTSPAQRAAFLDAIANELDALGDDFIQHVMRETALPEA RIRGERSRTSNQLRLFAEVVRRGDFYAARIDRALPQRTPLPRPDLRQYR IGVGPVAVFGASNFPLAFSTAGGDTASALAAGCPVVFKAHSGHMLTAAH VAGAIDRAVATSGMPAGVFNLIYGAGVGEALVKHPAIQAVGFTGSLRGG RALCDMAAARPQPIPVFAEMSSINPVIVLPQALQARGEQVAGELAASVV MGCGQFCTNPGLVVGIQSPQFEHFVQTLVARMADQGPQTMLNAGTLRSY QNGVQHLLAHPGIQHLAGQPHTGNQAQPQLFKADVSLLLNGDPLLQEEV FGPTTVVVEVADAEQLAEALRHLQGQLTATLIAEPDDLRAFASLVPLLE RKAGRLLLNGYPTGVEVSDAMVHGGPYPATSDARGTSVGTLAIDRFLRP VCFQNYPDALLPDALKNANPLGIARLLDGVNSRDAV (SEQ ID NO: 76) |
| DH9 | Pseudomonas sp. NBRC 111139 | MSIEHRLNHIAGQLSGHGDVLLHSLDAHTGEALPYAFHQATGDEVEAAA QAAEVAYPSYRSTRPDQRAAFLDAIASELDALGDDFIQDVMRETALPEA RIRGERSRTSNQLRLFAEVVRRGDFYAARIDRALPQRTPLPRPDLRQYR IGVGPVAVFGASNFPLAFSTAGGDTASALAAGCPVVFKAHSGHMLTAAH VAAAIDRAVTGSGMPAGVFNMIYGAGVGEALVKHPAIQAVGFTGSLRGG RALCDMAAARPQPIPVFAEMSSINPVIVLPQALQARGEQVATELAASVV LGCGQFCTNPGLVVGIRSPHFEHFLQTLVARMADQGPQTMLNAGTLRSY QNAVQHLLAHPGIQHLAGQPQTGNQAQPQLFKADVSLLLNGDPLLQEEV FGPCTVVVEVADAQQLAEALRHLQGQLTATLIAEPDDLRAFASLVPLLE RKAGRLLLNGYPTGVEVSDAMVHGGPYPATSDARGTSVGTLAIDRFLRP VCFQNYPDALLPDALKNANPLGIARLLEGVSSREAV (SEQ ID NO: 77) |
| DH10 | Pseudomonas sp. JUb52 | MQIQGKNYIGGARSGEGEVRVYSIDATTGEKLPYEFFQASTAEVDAAAR AAEQAAPLYRKLSAEQRATFLDAIADELDALGDDFVQLVCQETALPAGR IQGERGRTSGQMRLFAKVLRRGDFHGARIDTALPERKPLPRPDLRQYRI GLGPVAVFGASNFPLAFSTAGGDTAAALAAGCPVVFKAHSGHMVTAEYV ADAIIRAAEKTGMPKGVFNMIYGGGVGEQLVKHPAIQAVGFTGSLRGGR ALCDMAAARPQPIPVFAEMSSINPVVVLPEALKARGDAITGELAASVVL GCGQFCTNPGLVIGLRSPEFSTFLEGLAAAMNEQAPQTMLNPGTLKSYE KGVAALLAHSGVQHLAGANQEGNQARPQLFKADVSLLLENDELLQEEVF GPTTVVVEVADEAQLHQALQGLHGQLTATLLAEPADLQRFEAIIGLLEQ KAGRLLLNGYPTGVEVCDAMVHGGPYPATSDARGTSVGTLAIDRFLRPV CYQNYPDAFLPEALQNANPLGIQRLVNGENTKAAI (SEQ ID NO: 78) |
| DH11 | Pseudomonas citronellolis | MFGHNFIGGARTAQGNLTLQSLDAGTGEALPYSFHQATPEEVDAAALAA EAAFPAYRALPDARRAEFLDAIAAELDALGEDFIAIVCRETALPAARIQ GERARTSNQLRLFAQVLRRGDYHGARIDRALPERQPLPRPDLRQCRIGV GPVAVFGASNFPLAFSTAGGDTAAALAAGCPVVFKAHSGHMATAEHVAS AIVRAAQATGMPAGVFNMIYGGGVGERLVKHPAIQAVGFTGSLKGGRAL CDLAAARPQPIPVFAEMSSINPVLALPAALAARGEQVAADLAASVVLGC GQFCTNPGMVIGIASAEFSAFVASLTGRMADQPAQTMLNAGTLKSYERG IAALHAHPGIRHLAGQPQKGRQALPQLFQADARLLIEGDELLQEEVFGP VTVVVEVADAAELQRALQGLRGQLTATLIAEPEDLSCFAALVPLLERKA GRLLLNGYPTGVEVCDAMVHGGPYPATSDARGTSVGTLAIDRFLRPVCY QNYPDALLPPALKDANPLGIARLVDGVASREPL (SEQ ID NO: 79) |

In one embodiment, the oxidase is classified as EC number 1.1.3. In one embodiment, the oxidase EC number 1.1.3 is 5-(hydroxymethylfurfural oxidase (EC number 1.1.3.47). In some embodiments the HMF oxidase can be derived from the gene hmfH. In some embodiments, HMF oxidase can be derived from *Methylovorus* sp. MP688 or *Cupriavidus basilensis*. See Dijkman and Fraaije (2014. Applied Environmental Microbiology, 80.3:1082-1090) and Koopman et al. (2010. PNAS, 107(11):4919-4924). In one embodiment, the HMF oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015). In some embodiments, the HMF oxidase can be derived from enzyme candidates listed at Table 4. In some embodiments, the HMF oxidase is homologous or similar to the enzymes listed at Table 4. In some embodiments the 4-HMF oxidaze enzyme is encoded by an amino acid sequence listed in Table 4. In some embodiments, the HMF oxidase enzyme is evolved or engineered to improve its catalytic efficiency (See Martin et al. Biotechnology for Biofuels. (2018) 11, Article number: 56).

TABLE 4

| | | 4-HMF oxidases enzymes |
|---|---|---|
| Name | Organism | Sequence |
| HmfH1 | *Methylovorus* sp | MTDTIFDYVIVGGGTAGSVLANRLSARPENRVLLIEAGIDTPENNIPPE IHDGLRPWLPRLSGDKFFWPNLTIHRAAEHPGITREPQFYEQGRLLGGG SSVNMVVSNRGLPRDYDEWQALGADGWDWQGVLPYFIKTERDADYGDDP LHGNAGPIPIGRVDSRHWSDFTVAATQALEAAGLPNIHDQNARFDDGYF PPAFTLKGEERFSAARGYLDASVRVRPNLSLWTESRVLKLLTTGNAITG VSVLRGRETLQVQAREVILTAGALQSPAILLRTGIGPAADLHALGIPVL ADRPGVGRNLWEHSSIGVVAPLTEQARADASTGKAGSRHQLGIRASSGV DPATPSDLFLHIGADPVSGLASAVFWVNKPSSTGWLKLKDADPFSYPDV DFNLLSDPRDLGRLKAGLRLITHYFAAPSLAKYGLALALSRFAAPQPGG PLLNDLLQDEAALERYLRTNVGGVWHASGTARIGRADDSQAVVDKAGRV YGVTGLRVADASIMPTVPTANTNLPTLMLAEKIADAILTQA (SEQ ID NO: 80) |
| HmfH2 | *Cupriavidus basilensis* | MDTPRERFDYVIVGGGSAGCVLANRLSQDPAIRVALIEAGVDTPPDAVP AEILDSYPMPLFFGDRYIWPSLQARAVAGGRSKVYEQGRVMGGGSSINV QAANRGLPRDYDEWAASGASGWSWQDVLPYFRHLERDVDYGNSPLHGSH GPVPIRRILPQAWPPFCTEFAHAMGRSGLSALADQNAEFGDGWFPAAFS NLDDKRVSTAIAYLDADTRRRANLRIYAETTVRKLVVSGREARGVIAMR ADGSRLALDAGEVIVSAGALQSPAILMRAGIGDAGALQALGIEVVADRP GVGRNLQDHPALTFCQFLAPQYRMPLSRRASMTAARFSSGVPGGEASD MYLSSSTRAGWHALGNRLGLFFLWCNRPFSRGQVSLAGAQPDVPPMVEL NLLDDERDLRRMVAGVRKLVQIVGASALHQHPGDFFPATFSPRVKALSR VSRGNVLLTELLGAVLDVSGPLRRSLIARFVTGGANLASLLTDESALEG FVRQSVFGVWHASGTCRMGAHADRSAVTDAAGRVHDVGRLRVIDASLMP RLPTANTNIPTIMLAEKIADTMQAERRAVRPASSEVAHPS (SEQ ID NO: 81) |
| HmfH3 | *Cupriavidus necator* | MDTPRERFDYVIVGGGSAGCVLANRLSQDPAIRVALIEGGVDTPPDAVP VEILDSYPMPLFFGDRYIWPSLQARAVAGGRSKVYEQGRVMGGGSSINV QAANRGLPRDYDEWAASGAPGWSWQDVLPYFRNLERDVDYGNSPLHGSH GPVPIRRILPQAWPPFCTEFAHAMGLSGLSALADQNAEFGDGWFPAAFS NLDDKRVSTAIAYLDADIRRRANLRIYAETTVRKLVVSGREARGVIAIR ADGSRLALDAGEVIVSAGALQSPAILMRAGIGDAGALQALGIEVVADRP GVGRNLQDHPALTFCQFLAPQYRMPLSRRRASMTAARFSSGVPGGEASD MYLSSSTRAGWHALGNRLGLFFLWCNRPFSRGQVSLAGAQPDVPPMVEL NLLDDERDLRRMVAGVRKLVQIVGASALHQHPGDFFPATFSPRVKALSR LSRGNALLTELLGALLDVSGPLRRSLIARFVTGGANLASLLVEESALEG FVRQSVFGVWHASGTCRMGAHADRSAVTDAAGRVHDVGRLRVVDASLMP RLPTANTNIPTIMLAEKIADTMQAERRAVRLASSEVAHQS (SEQ ID NO: 82) |
| HmfH4 | *Cupriavidus pinatubonensis* | MGTPRDRFDYVIVGGGSAGCVLANRLSRDPGIRVALIEGGVDTPPGAVP AEILDSYPMPLFFGDRYLWPSLQARAVAGGRARLYEQGRVMGGGSSINV QAANRGLPRDYDEWAASGAPGWSWQEVLPYFRKLERDVDFASSPMHGSD GPVPIRRILPPAWPPFCTAFAQAMGRSGLSALDDQNAEFGDGWFPAAFS NLDGKRVSTAIAYLDANTRKRTNLRIFAETTVKELVVSGREARGVIAVR ADGARLALEAAEVIVSAGALQSPAILMRAGIGDAAALQALGIEVVADRP GVGRNLQDHPALTFCQFLAPEYRMPLARRRSSMTAARFSSEVPGGEASD MYLSSSTRAGWHALGNRLGLFFLWCNRPFSRGQVSLAGAQPEVSPLVEL NLLDDERDLRRMVAGVRRLVRIVGASALHQHPDDFFPAIFSPRVKAMSR VSPGNALLTALLGALLDVSGPLRRSLIARFVTGGANLASLLADESALEG FVRQSVFGVWHASGTCRMGAHADRSAVTDTTGRVHDVGRLRVVDASLMP RLPTANTNIPTIMLAEKIADAMLAERRATRRALSEVADPG (SEQ ID NO: 83) |
| HmfH5 | *Pandoraea* sp. B-6 | MPRGHAHRRIRRHSVQNVRERFDYVIIGGGSAGCVLAHRLSANRELRVA LIEAGSDTPPGAIPAEILDSYPMPVFCGDRYIWPELKAKATAASPLKVY EQGKVMGGGSSINVQAANRGLPRDYDDWAEQGASGWAWKDVLPYFRKLE RDADYGGSALHGADGPVAIRRIKPDAWPRFCHAFAEGLQRNGLPMLEDQ NAEFGDGMFPAAFSNLDDKRVSTAVAYLDAATRARTNLRIYSNTIVERL IVTGQRAHGVVAMSAGGERLQIDAAEVIVSAGALQSPALLLRAGIGAGS ELQALGIPVVADRPGVGRNLQDHPSLTFCHFLDPEFRMPLSRRRASMTA ARFSSGLDGCDNADMYLSSATRAAWHALGNRLGLFFLWCNRPFSRGRVQ LTSADPFTPPRVDLNLLDDERDARRMAIGVRRVAQIVQQTALHRHPDDF FPAAFSPRVKALSRFSAGNAALTKVLGLALDTPAPLRRWIIDTFVTGGI RMSALLADDKELDAFIRKYVEGVWHASGICRMGPASDRMAVINQEGLVH DVANLRVVDASLMPKLPSANTNIPTIMMAEKIADAILARRKAPPGVLVS SEA (SEQ ID NO: 84) |

TABLE 4-continued

4-HMF oxidases enzymes

| Name | Organism | Sequence |
|---|---|---|
| HmfH6 | *Methylovorus* sp | MIDTIFDYVIVGGGTAGSVLANRLSARPENRVLLIEAGIDTPENNIPPE<br>IHDGLRPWLPRLSGDKFFWPNLTIHRAAEHPGITREPQFYEQGRLLGGG<br>SSVNMVVSNRGLPRDYDEWQALGADGWDWQGVLPYFIKTERDADYGDDP<br>LHGNAGPIPIGRVDSRHWSDFTVAATQALEAAGLPNIHDQNARFDDGYF<br>PPAFTLKGEERFSAARGYLDASVRVRPNLSLWIESRVLKLLTIGNAITG<br>VSVLRGRETLQVQAREVILTAGALQSPAILLRTGIGPAADLHALGIPVL<br>ADRPGVGRNLWEHSSIGVVAPLTEQARADASIGKAGSRHQLGIRASSGV<br>DPATPSDLFLHIGADPVSGLASARFWVNKPSSTGWLKLKDADPFSYPDV<br>DFNLLSDPRDLGRLKAGLRLITHYFAAPSLAKYGLALALSRFAAPQPGG<br>PLLNDLLQDEAALERYLRINVGGVFHASGTARIGRADDSQAVVDKAGRV<br>YGVTGLRVADASIMPTVPTANTNLPTLMLAEKIADAILTQA (SEQ ID NO: 85) |
| HmfH7 | *Methylovorus* sp MUT | MIDTIFDYVIVGGGTAGSVLANRLSARPENRVLLIEAGIDTPENNIPPE<br>IHDGLRPWLPRLSGDKFFWPNLTVYRAAEHPGITREPQFYEQGRLLGGG<br>SSVNMVVSNRGLPRDYDEWQALGADGWDWQGVLPYFIKTERDADYGDDP<br>LHGNAGPIP1GRVDSRHWSDFTVAATQALEAAGLPNIHDQNARFDDGYF<br>PPAFTLKGEERFSAARGYLDASVRVRPNLSLWTESRVLKLLTTGNATTG<br>VSVLRGRETLQVQAREVILTAGALQSPAILLRTGIGPAADLHALGIPVL<br>ADRPGVGRNLWEHSSIGVVAPLTEQARADASTGKAGSRHQLGIRASSGV<br>DPATPSDLFLHIHADPVSGLASARFWVNKPSSTGWLKLKDADPFSYPDV<br>DFNLLSDPRDLGRLKAGLRLIKHYFAYPSLAKYGLALALSRFEAPQPGG<br>PLLNDLLQDEAALERYLRTNVGGVFHASGTARIGRADDSQAVVDKAGRV<br>YGVTGLRVADASIMPTVPTANTNLPTLMLAEKIADAILTQA (SEQ ID NO: 86) |

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-HMF to 4-(hydroxymethyl)furoic acid. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 4-formylfuran-2-carboxylate and/or to 2-formylfuran-4-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-(hydroxymethyl)furoic acid to 4-formylfuran-2-carboxylate. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the dehydrogenase EC number 1.1.1 is. In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-formylfuran-2-carboxylate and/or 2-formylfuran-4-carboxylate to 2,4-FDCA. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino) butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In some aspects, 2,4-FDCA is produced enzymatically, in the absence of microbes. In some aspects, 2,4-FDCA is produced enzymatically in one or more vessels. In some aspects, the one or more vessels are substantially free of microbes. In some aspects, the enzymatic production of 2,4-FDCA is performed in the same step-wise fashion as described with in the methods utilizing recombinant microorganisms, but substantially free of microorganisms or in the absence of microorganisms. In some aspects, the enzymes utilized in the enzymatic production of 2,4-FDCA are isolated from microbes, recombinant or otherwise, and provided to their corresponding substrates for the stepwise production of the intermediates utilized to produce 2,4-FDCA. In some aspects, one or more of the steps of the methods are performed in the same vessel. In some aspects, once the desired product is produced as a result of the individual method steps described herein, the product is isolated and purified and then utilized as the substrate in the next step of the method of producing 2,4-FDCA.

2,4-furandimethanol

In one embodiment, the present disclosure provides a recombinant microorganism capable of producing 2,4-furandimethanol from a carbon source. Some embodiments of the present disclosure are presented in FIG. 1, FIG. 2, and FIG. 3, which collectively detail the biosynthetic conversion of a carbon feedstock to 2,4-furandimethanol.

In one embodiment, the bioproduction of 2,4-furandimethanol from 4-HMF is catalyzed by a dehydrogenase encoded by the microorganism. In one embodiment, the dehydrogenase is classified as EC number 1.1.1. In one embodiment, the dehydrogenase EC number 1.1.1 is selected from alcohol dehydrogenase (EC number 1.1.1.1). In one embodiment, the dehydrogenase EC number 1.1.1 is selected from alcohol dehydrogenase (NADP+) (EC number 1.1.1.2). In one embodiment, the dehydrogenase EC number 1.1.1 is selected from D-xylose reductase (EC number 1.1.1.90). In one embodiment, the dehydrogenase EC number 1.1.1 is selected from aryl-alcohol dehydrogenase (EC number 1.1.1.91). In one embodiment the dehydrogenases can be derived from enzyme candidates listed at Table 5. In some embodiments, the dehydrogenases are homologous or similar to the enzymes listed at Table 5. In some embodiments the 4-HMF reductase enzyme is encoded by an amino acid sequence listed in Table 5. In some embodiments, a dehydrogenases is evolved or engineered to improve its catalytic efficiency for 4-HMF reduction to 2,4-furandimethanol.

TABLE 5

| 4-HMF reductase enzymes (4-HMF reduction to 2,4-furandimethanol) | | |
|---|---|---|
| Name | Organism | Sequence |
| DH1 | Zymomonas mobilis | MLNFDYYNPTHIVFGKGRIAQLDILLSKDARVLVLYGGSSAQKTGILDE VRKALGDRTYFEFGGIEPNPSYETLMKAVEQVKQEKVDFLLAVGGGSVI DGIKEVAAAVPYEGEPWEILETDGKKIKEALPVGIVLILPATGSEMNRN SVVIRKSIKSKRGFHNDHVFPVFSILDPIKVYTLPPRQLANGVVDSFIH ITEQYLTYPVDGMVQDEFAEGLLRTLIKIGPELLKDQKNYDLAANFMWT ATLALNGLIGAGVPQDWATHMVGHELTAAFGIDHGRTLAIILPSLLQNQ REAKKGKLLQYAKNVWHIDQGSDDERIDAAIEKTRHFFESLGIPTHLKD YDVGEESIDMLVKELEAHGMSQLGEHKAITPEVSRAILLASL (SEQ ID NO: 87) |
| DH2 | Zymomonas mobilis subsp. pomaceae ATCC 29192 | MLNFDYYNPTHIAFGKDSIAKLDTLIPQDACVMVLYGGSSAKKTGILDE VKTALGSRKIHEFGGIEPNPSYETLMQAVEQVKKEKIDFLLAVGGGSVI DGIKEVAAAVPYEGEPWEILETDGKKIKKALPLGTVLILPATGSEMNPN SVVIRKSIKAKRAFHNKIVFPLFSILDPIKVYTLPPRQIANGIVDSFVH ITEQYLTYPVEGMVQDEFAEGLLRILINIGPKLLKDQKNYDLAANFMWT ATLALNGLIGAGVPQDWATHMIGHEITAAFGVDHGRTLAIILPSLLQNQ RQVKKDKLLQYAKNVWHIESGSEKERIDAVIAKTRSFFEEMGIPTHLSD YNIGKESIDMLIHELEAHGMTKLGEHNAITPDVSRAILIASL (SEQ ID NO: 88) |
| DH3 | Shewanella baltica | MLNFNYYNPTRIRFGKDTIAEIDTLVPSDAKVMILFGGSSARKTGILDE VKQSLGNRFIVEFDGIEPNPTYETLMKAVAQVREQKIDFLLAVGGGSVI DGIKEVAAAAVPFEGEPWDILTSWGAKVTQAMPFGSVLILPAIGSEMNNA SVVIRKSLQAKLPFRNDLVYPQFSILDPIKTFTLPERQVANGVVDAFVH ITEQYLTYPVNAAVQDRFAEGLLQTLIELGPQVLAQPEDYDIRANLMWV ATMALNGTIGVGVPHDWATHMIGHELTALYDIDHARTLAIVLPALLQCT KEAKREKLLQYADRVWHINTGIDDERIDAAIAKTKAFFEAMGIPTHLSA YDLDASHVDTLVKQLELHGMVALGEHGNINPAMSRDILTLAL (SEQ ID NO: 89) |
| DH4 | Burkholderia pseudoomallei | MLNFDFYNPTRIVFGEKTAARLNDLLPAAARVLVLYGGESARSNGTLDE VRAALGARDVREFGGIEPNPAYETLMRAVELARRERVDFLLAVGGGSVI DGIKEVAAAVPFEGDPWTILETHGANVAAALPFGCVLILPATGSEMNNG |

TABLE 5-continued

4-HMF reductase enzymes (4-HMF reduction to 2,4-furandimethanol)

| Name | Organism | Sequence |
|---|---|---|
| | | AVLIRRATRAKLAFRHPLVEPTESILDPIKTYTLPPRQVANGVVDAFTH<br>IVEQYLTYPADGLAQDRFAEGLLQTLIEIGPKALAEPRDYATRANLMWV<br>ATLALNGLIGAGVPQDRATHMVGHELTARYDIDHARTLAVVLPSMLDVR<br>RDAKRAKLLQYAARVWNIVDGPEDARIDAAIARTRAFFESLGVKTRLAD<br>YGVGADAIDGLIAQLEAHGMTRLGERKDVILDVSRRVLEASL (SEQ ID NO: 90) |
| DH5 | Saccharomyces cerevisiae | MSIPETQKGVIFYESHGKLEYKDIPVPKPKANELLINVKYSGVCHTDLH<br>AWHGDWPLPTKLPLVGGHEGAGVVVGMGENVKGWKIGDYAGIKWLNGSC<br>MACEYCELGNEPNCPHADSSGYTHDGSFQQYATADAVQAAHIPQGTDLA<br>EVAPVLCAGITVYKALKSANLMAGHWVAISGAAGGLGSLAVQYAKAMGY<br>RVLGIDGGEGKEELFRSIGGEVFIDFIKEKDIVGAVLKAIDGGAHGVIN<br>VSVSEAAIEASTRYVRANGTTVLVGMPAGAKCCSDVFNQVVKSISIVGS<br>CVGNRADTREALDFFARGLVKSPIKVVGLSTLPEIYEKMEKGQIVGRYV<br>VDTSK (SEQ ID NO: 91) |
| DH6 | Saccharomyces cerevisiae | MSYPEKFEGIAIQSHEDWKNPKKTKYDPKPFYDHDIDIKIEACGVCGSD<br>IHCAAGHWGNMKMPLVVGHEIVGKVVKLGPKSNSGLKVGQRVGVGAQVF<br>SCLECDRCKNDNEPYCTKFVTTYSQPYEDGYVSQGGYANYVRVHEHFVV<br>PIPENIPSHLAAPLLCGGLTVYSPLVRNGCGPGKKVGIVGLGGIGSMGT<br>LISKAMGAETYVISRSSRKREDAMKMGADHYIATLEEGDWGEKYFDTFD<br>LIVVCASSLTDIDFNIMPKAMKVGGRIVSISIPEQHEMLSLKPYGLKAV<br>SISYSALGSIKELNQLLKLVSEKDIKIWVETLPVGEAGVHEAFERMEKG<br>DVRYRFTLVGYDKEFSD (SEQ ID NO: 92) |

In some aspects, 2,4-furandimethanol is produced enzymatically, in the absence of microbes. In some aspects, 2,4-furandimethanol is produced enzymatically in one or more vessels. In some aspects, the one or more vessels are substantially free of microbes. In some aspects, the enzymatic production of 2,4-furandimethanol is performed in the same step-wise fashion as described with in the methods utilizing recombinant microorganisms, but substantially free of microorganisms or in the absence of microorganisms. In some aspects, the enzymes utilized in the enzymatic production of 2,4-furandimethanol are isolated from microbes, recombinant or otherwise, and provided to their corresponding substrates for the stepwise production of the intermediates utilized to produce 2,4-furandimethanol. In some aspects, one or more of the steps of the methods are performed in the same vessel. In some aspects, once the desired product is produced as a result of the individual method steps described herein, the product is isolated and purified and then utilized as the substrate in the next step of the method of producing 2,4-furandimethanol.

Furan-2,4-dicarbaldehyde

In one embodiment, the present disclosure provides a recombinant microorganism capable of producing furan-2,4-dicarbaldehyde from a carbon source. Some embodiments of the present disclosure are presented in FIG. 1, FIG. 2, and FIG. 3, which collectively detail the biosynthetic conversion of a carbon feedstock to furan-2,4-dicarbaldehyde.

Figure 2:
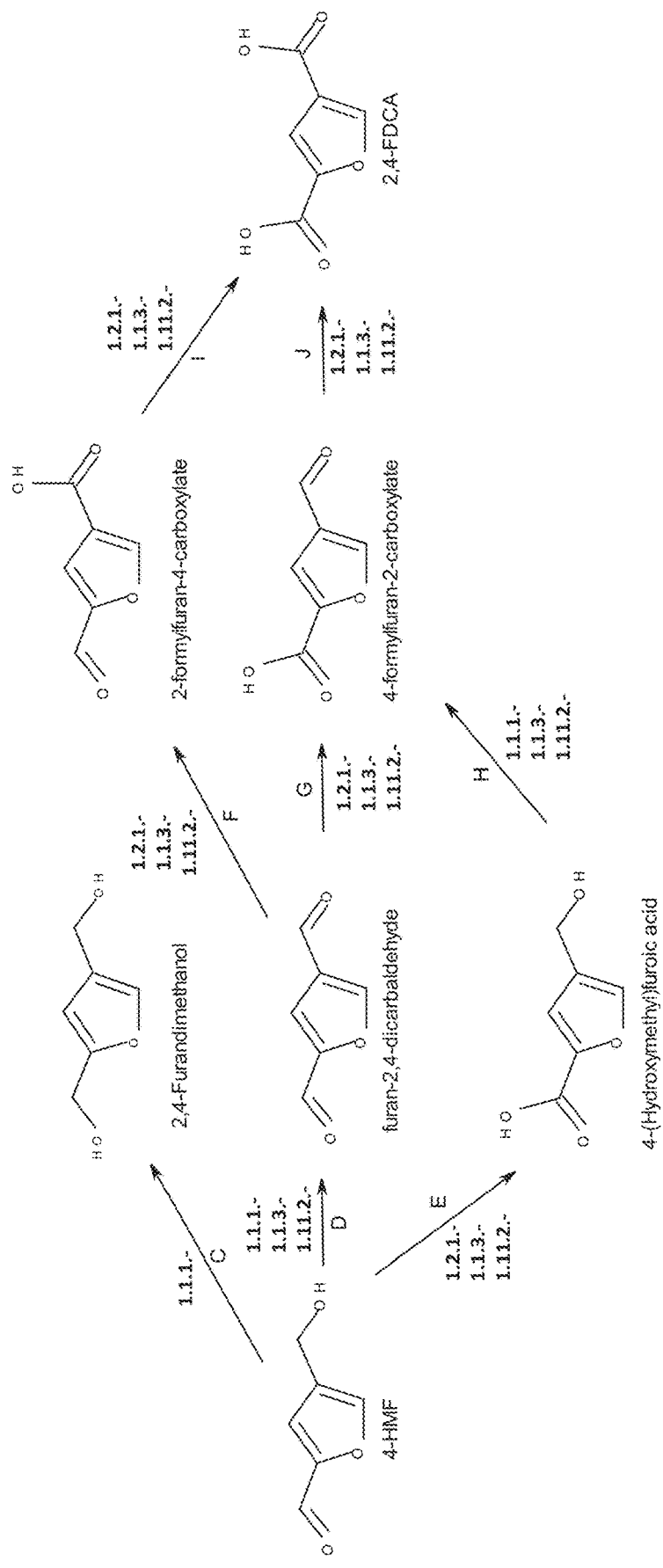
FIG. 2 is a schematic overview of the biosynthetic production of products contemplated, utilizing 4-HMF as a substrate. The products include, but are not limited to, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. The numbers near the enzymatic reaction rows indicate the 3-digit EC number for the corresponding enzymes.
Figure 3:
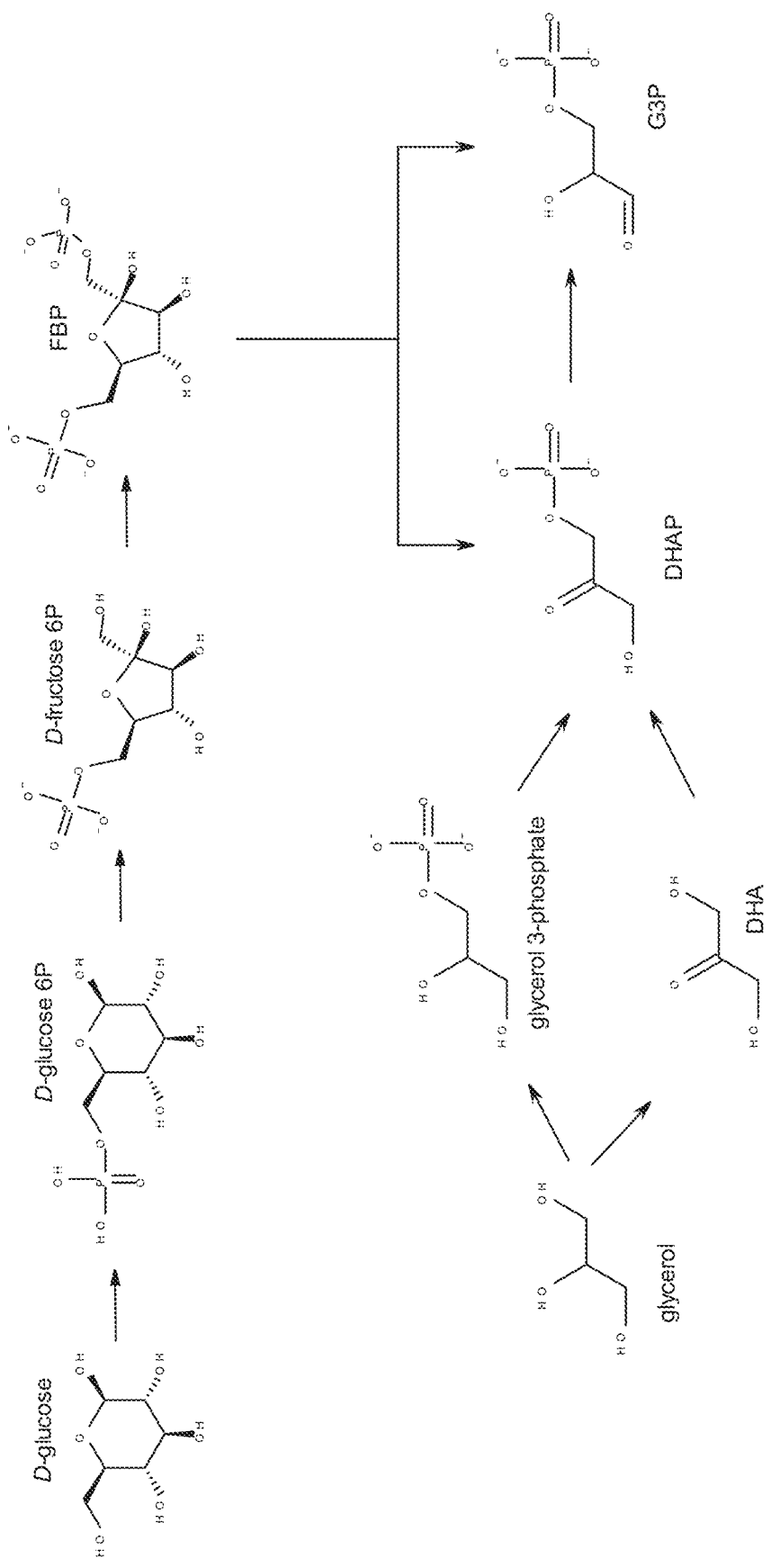
FIG. 3 is a schematic overview of possible biosynthetic pathways for the conversion of a carbon source (in this case glucose or glycerol) to G3P.

In one embodiment, step D in FIG. 2 is a single step reaction utilizing 4-HMF as a substrate. In one embodiment, the bioproduction of furan-2,4-dicarbaldehyde from 4-HMF is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, an oxidase, or a peroxygenase that catalyzes the conversion of 4-HMF to furan-2,4-dicarbaldehyde. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from Methylovorus sp. MP688 or Cupriavidus basilensis. See Dijkman and Fraaije (2014) and Koopman et al. (2010). In one embodiment, the oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015).

In some aspects, furan-2,4-dicarbaldehyde is produced enzymatically, in the absence of microbes. In some aspects, furan-2,4-dicarbaldehyde is produced enzymatically in one or more vessels. In some aspects, the one or more vessels are substantially free of microbes. In some aspects, the enzymatic production of furan-2,4-dicarbaldehyde is performed in the same step-wise fashion as described with in the methods utilizing recombinant microorganisms, but substantially free of microorganisms or in the absence of microorganisms. In some aspects, the enzymes utilized in the enzymatic production of furan-2,4-dicarbaldehyde are isolated from microbes, recombinant or otherwise, and provided to their corresponding substrates for the stepwise production of the intermediates utilized to produce furan-2,4-dicarbaldehyde. In some aspects, one or more of the steps of the methods are performed in the same vessel. In some aspects, once the desired product is produced as a result of the individual method steps described herein, the product is isolated and purified and then utilized as the substrate in the next step of the method of producing furan-2,4-dicarbaldehyde.

4-(hydroxymethyl)furoic acid

In one embodiment, the present disclosure provides a recombinant microorganism capable of producing 4-(hydroxymethyl)furoic acid from a carbon source. Some embodiments of the present disclosure are presented in FIG. 1, FIG. 2, and FIG. 3, which collectively detail the biosynthetic conversion of a carbon feedstock to 4-(hydroxymethyl)furoic acid.

In one embodiment, step E in FIG. 2 is a single step reaction utilizing 4-HMF as a substrate. In one embodiment, the bioproduction of 4-(hydroxymethyl)furoic acid from 4-HMF is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-HMF to 4-(hydroxymethyl)furoic acid. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In some aspects, 4-(hydroxymethyl)furoic acid is produced enzymatically, in the absence of microbes. In some aspects, 4-(hydroxymethyl)furoic acid is produced enzymatically in one or more vessels. In some aspects, the one or more vessels are substantially free of microbes. In some aspects, the enzymatic production of 4-(hydroxymethyl)furoic acid is performed in the same step-wise fashion as described with in the methods utilizing recombinant microorganisms, but substantially free of microorganisms or in the absence of microorganisms. In some aspects, the enzymes utilized in the enzymatic production of 4-(hydroxymethyl)furoic acid are isolated from microbes, recombinant or otherwise, and provided to their corresponding substrates for the stepwise production of the intermediates utilized to produce 4-(hydroxymethyl)furoic acid. In some aspects, one or more of the steps of the methods are performed in the same vessel. In some aspects, once the desired product is produced as a result of the individual method steps described herein, the product is isolated and purified and then utilized as the substrate in the next step of the method of producing 4-(hydroxymethyl)furoic acid.

2-formylfuran-4-carboxylate

In one embodiment, the present disclosure provides a recombinant microorganism capable of producing 2-formylfuran-4-carboxylate from a carbon source. Some embodiments of the present disclosure are presented in FIG. 1, FIG. 2, and FIG. 3, which collectively detail the biosynthetic conversion of a carbon feedstock to 2-formylfuran-4-carboxylate.

In one embodiment, step F in FIG. 2 is a single step reaction utilizing furan-2,4-dicarbaldehyde as a substrate. In one embodiment, the bioproduction of 2-formylfuran-4-carboxylate from furan-2,4-dicarbaldehyde is catalyzed by one or more enzymes represented by EC numbers 1.2.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 2-formylfuran-4-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In some aspects, 2-formylfuran-4-carboxylate is produced enzymatically, in the absence of microbes. In some aspects, 2-formylfuran-4-carboxylate is produced enzymatically in one or more vessels. In some aspects, the one or more vessels are substantially free of microbes. In some aspects, the enzymatic production of 2-formylfuran-4-carboxylate is performed in the same step-wise fashion as described with in the methods utilizing recombinant microorganisms, but substantially free of microorganisms or in the absence of microorganisms. In some aspects, the enzymes utilized in the enzymatic production of 2-formylfuran-4-carboxylate are isolated from microbes, recombinant or otherwise, and provided to their corresponding substrates for the stepwise production of the intermediates utilized to produce 2-formylfuran-4-carboxylate. In some aspects, one or more of the steps of the methods are performed in the same vessel. In some aspects, once the desired product is produced as a result of the individual method steps described herein, the product is isolated and purified and then utilized as the substrate in the next step of the method of producing 2-formylfuran-4-carboxylate.

4-formylfuran-2-carboxylate

In one embodiment, the present disclosure provides a recombinant microorganism capable of producing 4-formylfuran-2-carboxylate from a carbon source. Some embodiments of the present disclosure are presented in FIG. 1, FIG. 2, and FIG. 3, which collectively detail the biosynthetic conversion of a carbon feedstock to 4-formylfuran-2-carboxylate.

In one embodiment, step G in FIG. 2 is a single step reaction utilizing furan-2,4-dicarbaldehyde as a substrate. In one embodiment, the bioproduction of 4-formylfuran-2-carboxylate from furan-2,4-dicarbaldehyde is catalyzed by one or more enzymes represented by EC numbers 1.2.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 4-formylfuran-2-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, step H in FIG. 2 is a single step reaction utilizing 4-(hydroxymethyl)furoic acid as a substrate. In one embodiment, the bioproduction of 4-formylfuran-2-carboxylate from 4-(hydroxymethyl)furoic acid is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-(hydroxymethyl)furoic acid to 4-formylfuran-2-carboxylate. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. See Dijkman and Fraaije (2014) and Koopman et al. (2010). In one embodiment, the oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015).

In some aspects, 4-formylfuran-2-carboxylate is produced enzymatically, in the absence of microbes. In some aspects, 4-formylfuran-2-carboxylate is produced enzymatically in one or more vessels. In some aspects, the one or more vessels are substantially free of microbes. In some aspects, the enzymatic production of 4-formylfuran-2-carboxylate is performed in the same step-wise fashion as described with in the methods utilizing recombinant microorganisms, but substantially free of microorganisms or in the absence of microorganisms. In some aspects, the enzymes utilized in the enzymatic production of 4-formylfuran-2-carboxylate are isolated from microbes, recombinant or otherwise, and provided to their corresponding substrates for the stepwise production of the intermediates utilized to produce 4-formylfuran-2-carboxylate. In some aspects, one or more of the steps of the methods are performed in the same vessel. In some aspects, once the desired product is produced as a result of the individual method steps described herein, the product is isolated and purified and then utilized as the substrate in the next step of the method of producing 4-formylfuran-2-carboxylate.

Generation of Microbial Populations
Genetic Modification

The genetic modification introduced into one or more microbes of the present disclosure may alter or abolish a regulatory sequence of a target gene. In some aspects, the genetic modification introduced into one or more microbes of the present disclosure may introduce a new trait or phenotype into the one or more microbes. One or more regulatory sequences may also be inserted, including heterologous regulatory sequences and regulatory sequences found within a genome of an animal, plant, fungus, yeast, bacteria, or virus corresponding to the microbe into which the genetic variation is introduced. Moreover, regulatory sequences may be selected based on the expression level of a gene in a microbial culture. The genetic variation may be a pre-determined genetic variation that is specifically introduced to a target site. In some aspects the genetic variation is a nucleic acid sequence that is introduced into one or more microbial chromosomes. In some aspects, the genetic variation is a nucleic acid sequence that is introduced into one or more extrachromosomal nucleic acid sequence. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of desired modifications in the microbes.

In some aspects, one or more of the substrates set forth in the production of the 2,4-FDCA monomers and polymers are biosynthesized from a carbon feedstock (e.g., glucose or glycerol).

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling.

Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethyl sulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation.

Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique, the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some aspects, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some aspects, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some aspects, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for assessing conferral of an improved trait.

A CRISPR nuclease may be used as the site-specific nuclease to direct cleavage to a target site. An improved selection of mutated microbes can be obtained by using Cas9 to kill non-mutated cells. Microbes can then be re-isolated from tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Microbes

As described herein, in some aspects, recombinant microorganisms are capable of producing 4-HMF, 2,4-furandimethanol, furan-2,4-dicarbaldehyde, 4-(hydroxymethyl)furoic acid, 2-formylfuran-4-carboxylate, 4-formylfuran-2-carboxylate, or 2,4-FDCA, and any combination thereof.

As described herein, in some aspects, the recombinant microorganisms are prokaryotic microorganism. In some aspects, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, Micrococcus, others) (2) low G+C group (*Bacillus*, Clostridia, *Lactobacillus*, Staphylococci, Streptococci, *Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

In some aspects, the microorganisms of the present disclosure are fungi.

In some aspects, the recombinant microorganism is a eukaryotic microorganism. In some aspectsts, the eukaryotic microorganism is a yeast. In exemplary aspects, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

In some aspects, the recombinant microorganism is a prokaryotic microorganism. In exemplary aspects, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some aspects, microorganism for use in the methods of the present disclosure can be selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula, Myxozyma, Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some aspects, a microbe resulting from the methods described herein may be a species selected from any of the following genera: *Neisseria, Spirillum, Pasteurella, Brucella, Yersinia, Francisella, Haemophilus, Bordetella, Candida, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Actinomyces, Bacillus, Clostridium, Corynebacterium, Erysipelothrix, Lactobacillus, Listeria, Mycobacterium, Myxococcus, Nocardia, Issatchenkia, Staphylococcus, Streptococcus, Streptomyces, Saccharomyces, Pichia*, and *Aspergillus*.

In some aspects, microorganisms for use in the methods of the present disclosure include *Clostridium* sp., *Clostridium ljungdahlii, Clostridium autoethanogenum, Clostridium ragsdalei, Eubacterium limosum, Butyribacterium methylotrophicum, Moorella thermoacetica, Corynebacterium glutamicum, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Candida krusei, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Issatchenkia orientalis, Sporomusa termitida, Moorella glycerini, Eubacterium aggregans, Treponema azotonutricium, Pichia kudriavzevii, Escherichia coli, Saccharomyces cerevisiae, Pseudomonas putida, Bacillus* sp, *Corynebacterium* sp., *Yarrowia lipolytica, Scheffersomyces stipitis*, and *Terrisporobacter glycolicus*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

Culturing of the microorganisms used in the methods of the disclosure may be conducted using any number of processes known in the art for culturing and fermenting substrates using the microorganisms of the present disclosure.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioreactor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. In some aspects, the bioreactor comprises a first, growth reactor in which the microorganisms are cultured, and a second, fermentation reactor, to which fermentation broth from the growth reactor is fed and in which most of the fermentation product is produced. In some aspects, the bioreactor simultaneously accomplishes the culturing of microorganism and the producing the fermentation product from carbon sources such substrates and/or feedstocks provided.

In some aspects, the disclosure is drawn to a method of recovering/isolating a 2,4-FDCA monomer. In some aspects, the disclosure is drawn to a method of recovering/isolating 4-HMF, 2,4-furandimethanol, furan-2,4-dicarbaldehyde, 4-(hydroxymethyl)furoic acid, 2-formylfuran-4-carboxylate, 4-formylfuran-2-carboxylate, or 2,4-FDCA, and any combination thereof. In some aspects, the disclosure is drawn to a method of recovering/isolating a 2,4-furandimethanol, furan-2,4-dicarbaldehyde, 4-(hydroxymethyl)furoic acid, 2-formylfuran-4-carboxylate, and/or 4-formylfuran-2-carboxylate monomer or polymer. In some aspects, the disclosure is drawn to a method of recovering/isolating 4-HMF, 2,4-furandimethanol, furan-2,4-dicarbaldehyde, 4-(hydroxymethyl)furoic acid, 2-formylfuran-4-carboxylate, 4-formylfuran-2-carboxylate, or 2,4-FDCA, and any combination thereof. The recovery/collection/isolation can be by methods known in the art, such as distillation, membrane-based separation gas stripping, precipitation, solvent extraction, and expanded bed adsorption.

Feedstock

In some aspects, the feedstock comprises a carbon source. In some aspects, the carbon source may be selected from sugars, glycerol, alcohols, organic acids, alkanes, fatty acids, lignocellulose, proteins, carbon dioxide, and carbon monoxide. In one aspect, the carbon source is a sugar. In one aspect, the sugar is a monosaccharide. In one aspect, the sugar is a polysaccharide. In one aspect, the sugar is glucose or oligomers of glucose thereof. In one aspect, the oligomers of glucose are selected from fructose, sucrose, starch, cellobiose, maltose, lactose and cellulose. In one aspect, the sugar is a five carbon sugar. In one aspect, the sugar is a six carbon sugar. In some aspects, the feedstock comprises one or more five carbon sugars and/or one or more six carbon sugars. In some aspects, the feedstock comprises one or more of xylose, glucose, arabinose, galactose, maltose, fructose, mannose, sucrose, and/or combinations thereof. In some aspects, the feedstock comprises one or more of xylose and/or glucose. In some aspects, the feedstock comprises one or more of arabinose, galactose, maltose, fructose, mannose, sucrose, and/or combinations thereof.

In some aspects, the microbes utilize one or more five carbon sugars (pentoses) and/or one or more six carbon sugars (hexoses). In some aspects, the microbes utilize one or more of xylose and/or glucose. In some aspects, the microbes utilize one or more of arabinose, galactose, maltose, fructose, mannose, sucrose, and/or combinations thereof. In some aspects, the microbes utilize one or more of xylose, glucose, arabinose, galactose, maltose, fructose, mannose, sucrose, and/or combinations thereof.

In some aspects, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some aspects, pentoses may be selected from D-xylose, D-ribose, D-arabinose, D-lyxose, D-xylulose, D-ribulose, and other pentoses known in the art. In some aspects, the hexoses and pentoses may be selected from the levorotary or dextrorotary enantiomer of any of the hexoses and pentoses disclosed herein.

Microbial Compositions

In some aspects, the microbes of the disclosure are combined into microbial compositions.

In some aspects, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim milk powder; sweet whey powder; maltodextrin; lactose; inulin; dextrose; and products of vegetable origin such as cereal meals, tree bark meal, wood meal, and nutshell meal.

In some aspects, the microbial compositions of the present disclosure are liquid. In further aspects, the liquid comprises a solvent that may include water or an alcohol or a saline or carbohydrate solution. In some aspects, the microbial compositions of the present disclosure include binders such as polymers, carboxymethylcellulose, starch, polyvinyl alcohol, and the like.

In some aspects, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In further aspect, microbial compositions comprise polymers of agar, agarose, gelrite, gellan gum, and the like. In some aspects, microbial compositions comprise plastic capsules, emulsions (e.g., water and oil), membranes, and artificial membranes. In some aspects, emulsions or linked polymer solutions comprise microbial compositions of the present disclosure. See Harel and Bennett (U.S. Pat. No. 8,460,726 B2).

In some aspects, microbial compositions of the present disclosure occur in a solid form (e.g., dispersed lyophilized spores) or a liquid form (microbes interspersed in a storage medium). In some aspects, microbial compositions of the present disclosure are added in dry form to a liquid to form a suspension immediately prior to use.

Methods of Producing Biosynthesis Products

The present disclosure provides a method of producing one or more biosynthesis products using a recombinant microorganisms. The biosynthesis products include: 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. In one embodiment, the method comprises cultivating the recombinant microorganism in a culture medium. In one embodiment, the culture medium contains a feedstock comprising a carbon source that the recombinant microorganism can utilize to produce the one or more biosynthesis products. In one embodiment, the carbon source in the culture medium is selected from the group that comprises a hexose, a pentose, or glycerol. In certain embodiments, the carbon source is glycerol. Some embodiments of the present disclosure are presented in FIG. 1, FIG. 2, and FIG. 3, which collectively detail the biosynthetic conversion of a carbon feedstock to one or more of the biosynthesis products.

The present disclosure provides a method of producing a recombinant microorganism that produces 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA from a feedstock comprising an exogenous carbon source. In one embodiment, the method comprises introducing into and/or overexpressing in the recombinant microorganism endogenous and/or exogenous nucleic acid molecules capable of converting a carbon source into 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. In one embodiment, the carbon source may include glycerol and/or monosaccharides.

In one embodiment, endogenous and/or exogenous nucleic acid molecules convert glycerol or a monosaccharide into glyceraldehyde 3-phosphate (G3P). G3P is a common natural intermediary metabolite. In some embodiments, it can be produced from glucose via the glycolysis pathway or from xylose via the pentose phosphate pathway, or from glycerol. In one embodiment, the recombinant microorganism capable of producing 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA utilizes a carbon source that comprises a hexose, a pentose, or glycerol. In certain embodiments, the carbon source is glycerol.

In one embodiment, the present disclosure contemplates methods of producing 2,4-FDCA and the multiple steps and processes for producing 2,4-FDCA. In some embodiments, the present disclosure contemplates the individual methods for producing one or more of 4-HMF, 2,4-furandimethanol, furan-2,4-dicarbaldehyde, 4-(hydroxymethyl)furoic acid, 2-formylfuran-4-carboxylate, and 4-formylfuran-2-carboxylate, that are described in the process of making 2,4-FDCA.

In one embodiment, the recombinant microorganisms of the method are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Corynebacterium glutamicum*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Candida krusei*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Issatchenkia orientalis*, *Sporomusa termitida*, *Moorella glycerini*, *Eubacterium aggregans*, *Treponema azotonutricium*, *Pichia kudriavzevii*, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and *Terrisporobacter glycolicus*.

4-HMF

In one embodiment, the present disclosure comprises converting one or more carbon sources to glyceraldehyde 3-phosphate (G3P); converting G3P to (5-formylfuran-3-yl) methyl phosphate (Step A); converting (5-formylfuran-3-yl) methyl phosphate to 4-hydroxymethylfurfural (4-HMF) (Step B).

In one embodiment, the disclosure is drawn to a method of producing a recombinant microorganism of any one of the embodiments disclosed herein comprising an endogenous and/or exogenous nucleic acid molecules capable of converting a carbon source to glyceraldehyde 3-phosphate (G3P). In one embodiment, glycerol is converted to glycerol-3-phopshate by at least one endogenous or exogenous nucleic acid molecule encoding a glycerol kinase. In one embodiment, glycerol-3-phosphate is converted to dihydroxyacetone phosphate (DHAP) by at least one endogenous or exogenous nucleic acid molecule encoding a glycerol-3-phosphate dehydrogenase. In one embodiment, glycerol is converted to dihydroxyacetone by at least one endogenous or exogenous nucleic acid molecule encoding a glycerol dehydrogenase. In one embodiment, dihydroxyacetone is converted to dihydroxyacetone phosphate (DHAP) by at least one endogenous or exogenous nucleic acid molecule encoding a dihydroxyacetone kinase. In one embodiment, DHAP is converted to G3P by at least one endogenous or exogenous nucleic acid molecule encoding a triose phosphate isomerase. See Zhang et al. (2010).

In one embodiment, the disclosure is drawn to a method of producing a recombinant microorganism of any one of the embodiments of disclosed herein comprising at least one endogenous or exogenous nucleic acid molecule encoding a (5-formylfuran-3-yl)methyl phosphate synthase that catalyzes the conversion of G3P to (5-formylfuran-3-yl)methyl phosphate. In one embodiment, the (5-formylfuran-3-yl) methyl phosphate synthase is classified as EC number 4.2.3.153. In some embodiments the EC 4.2.3.153 (5-formylfuran-3-yl)methyl phosphate synthase can be derived from the gene mfnB. In some embodiments, mfnB can be derived from *Methanocaldococcus jannaschii*. In some embodiments, the (5-formylfuran-3-yl)methyl phosphate synthase can be derived from enzyme candidates listed at Table 1. In some embodiments, the (5-formylfuran-3-yl)methyl phosphate synthase is homologous or similar to the enzymes listed at Table 1. In some embodiments, an (5-formylfuran-3-yl)methyl phosphate synthase enzyme is evolved or engineered to improve its catalytic efficiency, markedly kcat.

In one embodiment, the disclosure is drawn to a method of producing a recombinant microorganism of any one of the embodiments disclosed herein comprising at least one endogenous or exogenous nucleic acid molecule encoding a phosphatase that catalyzes the conversion of (5-formylfuran-3-yl)methyl phosphate to (4-HMF). In one embodiment, the phosphatase is classified as haloacid dehalogenase (Koonin et al. J. Mol. Biol. 244(1). 1994). In some aspects, the phosphatase of reaction b is endogenous to the host (Offley et al. Curr. Gen. 65. 2019). In some aspects, the phosphatase enzyme endogenous to the host is overexpressed. In some cases a heterologous phosphatase able to perform the desired reaction is used and is selected from an alkaline phosphatase, acid phosphatase, fructose-bisphosphatase, sugar-phosphatase, or sugar-terminal-phosphatase. In some embodiments, the phosphatase can be derived from enzyme candidates listed at Table 2. In some embodiments, the phosphatase is homologous or similar to the enzymes listed at Table 2. In some embodiments, an phosphatase enzyme is evolved or engineered to improve its catalytic efficiency and or specificity for the conversion of (5-formylfuran-3-yl)methyl phosphate to (4-HMF).

Accordingly, in one embodiment, the disclosure is drawn to a method of producing a recombinant microorganism that comprises endogenous and/or exogenous nucleic acid molecules capable of converting a carbon source to glyceraldehyde 3-phosphate (G3P); at least one endogenous or exogenous nucleic acid molecule encoding a (5-formylfuran-3-yl)methyl phosphate synthase that catalyzes the conversion of G3P to (5-formylfuran-3-yl)methyl phosphate; at least one endogenous or exogenous nucleic acid molecule encoding a phosphatase that catalyzes the conversion of (5-formylfuran-3-yl)methyl phosphate to 4-HMF.

2,4-FDCA

In one embodiment, methods of the disclosure convert G3P to 2,4-FDCA via several enzymatically-catalyzed successive steps. In one embodiment, the present disclosure comprises converting one or more carbon sources to glyceraldehyde 3-phosphate (G3P); converting G3P to (5-formylfuran-3-yl)methyl phosphate (Step A); converting (5-formylfuran-3-yl)methyl phosphate to 4-hydroxymethylfurfural (4-HMF) (Step B); converting 4-HMF to 2,4 FDCA directly (Step C) or or through the production of intermediates, as converting 4-HMF to furan-2,4-dicarbaldehyde (Step D) and/or 4-(hydroxymethyl)furoic acid (Step E); converting furan-2,4-dicarbaldehyde to 4-formylfuran-2-carboxylate (Step G) and/or 2-formylfuran-4-carboxylate (Step F) and/or converting 4-(hydroxymethyl)furoic acid to 4-formylfuran-2-carboxylate (Step H); converting 4-formylfuran-2-carboxylate to 2,4-FDCA (Step J) and/or converting 2-formylfuran-4-carboxylate to 2,4-FDCA (Step I). In a further embodiment, the one or more carbon sources may include glycerol or a monosaccharide.

Accordingly, in one embodiment, provided herein is a method of producing a recombinant microorganism that comprises an endogenous and/or exogenous nucleic acid molecules capable of converting a carbon source to glyceraldehyde 3-phosphate (G3P); at least one endogenous or exogenous nucleic acid molecule encoding a (5-formylfuran-3-yl)methyl phosphate synthase that catalyzes the conversion of G3P to (5-formylfuran-3-yl)methyl phosphate; at least one endogenous or exogenous nucleic acid molecule encoding a phosphatase that catalyzes the conversion of (5-formylfuran-3-yl)methyl phosphate to (4-HMF); at least one endogenous or exogenous nucleic acid molecule encoding a dehydrogenase or an oxidase or a peroxygenase that catalyzes the conversion of 4-HMF to 2,4 FDCA directly or through the production of intermediates, as furan-2,4-dicarbaldehyde and/or 4-(hydroxymethyl)furoic acid; at least one endogenous or exogenous nucleic acid molecule encoding a dehydrogenase or an oxidase or a peroxygenase that catalyzes the conversion of furan-2,4-dicarbaldehyde to 4-formylfuran-2-carboxylate and/or 2-formylfuran-4-carboxylate and/or the conversion of 4-(hydroxymethyl)furoic acid to 4-formylfuran-2-carboxylate; at least one endogenous or exogenous nucleic acid molecule encoding a dehydrogenase or an oxidase or a peroxygenase that catalyzes the conversion of 2-formylfuran-4-carboxylate to 2,4-FDCA and/or 4-formylfuran-2-carboxylate to 2,4-FDCA.

In one embodiment, the recombinant microorganism of any one of the embodiments of the method disclosed herein comprise an endogenous and/or exogenous nucleic acid molecules capable of converting a carbon source to glyceraldehyde 3-phosphate (G3P). In one embodiment, glycerol is converted to glycerol-3-phopshate by at least one endogenous or exogenous nucleic acid molecule encoding a glycerol kinase. In one embodiment, glycerol-3-phosphate is converted to dihydroxyacetone phosphate (DHAP) by at least one endogenous or exogenous nucleic acid molecule encoding a glycerol-3-phosphate dehydrogenase. In one embodiment, glycerol is converted to dihydroxyacetone by at least one endogenous or exogenous nucleic acid molecule encoding a glycerol dehydrogenase. In one embodiment, dihydroxyacetone is converted to dihydroxyacetone phosphate (DHAP) by at least one endogenous or exogenous nucleic acid molecule encoding a dihydroxyacetone kinase. In one embodiment, DHAP is converted to G3P by at least one endogenous or exogenous nucleic acid molecule encoding a triose phosphate isomerase.

In one embodiment, the recombinant microorganism of any one of the embodiments of the method disclosed herein comprise at least one endogenous or exogenous nucleic acid molecule encoding a (5-formylfuran-3-yl)methyl phosphate synthase that catalyzes the conversion of G3P to (5-formylfuran-3-yl)methyl phosphate. In one embodiment, the (5-formylfuran-3-yl)methyl phosphate synthase is classified as EC number 4.2.3.153. In some embodiments the EC 4.2.3.153 (5-formylfuran-3-yl)methyl phosphate synthase can be derived from the gene mfnB. In some embodiments, mfnB can be derived from *Methanocaldococcus jannaschii*. In some embodiments, EC 4.2.3.153 can be derived from homologs of mfnB In one embodiment, the recombinant microorganism of any one of the embodiments of the method disclosed herein comprise at least one endogenous or exogenous nucleic acid molecule encoding a phosphatase that catalyzes the conversion of (5-formylfuran-3-yl)methyl phosphate to (4-HMF). In one embodiment, the phosphatase is classified as EC number 3.1.3. In one embodiment, the phosphatase EC number 3.1.3 phosphatase is selected from an alkaline phosphatase (EC number 3.1.3.1), acid phosphatase (EC number 3.1.3.2), fructose-bisphosphatase (EC number 3.1.3.11), sugar-phosphatase (EC number 3.1.3.23), or sugar-terminal-phosphatase (EC number 3.1.3.58). In one embodiment, the kinase is classified as EC number 2.7.1. In one embodiment, the kinase EC number 2.7.1 is selected from fructokinase (EC number 2.7.1.4), ribokinase (EC number 2.7.1.15), ribulokinase (EC number 2.7.1.16), xylulokinase (EC number 2.7.1.17), or D-ribulokinase (EC number 2.7.1.47).

In one embodiment, the recombinant microorganism of any one of the embodiments of the method disclosed herein comprise at least one endogenous or exogenous nucleic acid molecule encoding a dehydrogenase, or a oxidase, or a peroxygenase that catalyzes the conversion of 4-HMF to furan-2,4-dicarbaldehyde. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments of the method disclosed herein comprise at least one endogenous or exogenous nucleic acid molecule encoding a dehydrogenase, or a oxidase, or a peroxygenase that catalyzes the conversion of 4-HMF to 4-(hydroxymethyl)furoic acid. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments of the method disclosed herein comprise at least one endogenous or exogenous nucleic acid molecule encoding a dehydrogenase, or a oxidase, or a peroxygenase that catalyzes the conversion of furan-2,4-dicarbaldehyde to 4-formylfuran-2-carboxylate and/or to 2-formylfuran-4-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments of the method disclosed herein comprise at least one endogenous or exogenous nucleic acid molecule encoding a dehydrogenase, or a oxidase, or a peroxygenase that catalyzes the conversion of 4-(hydroxymethyl)furoic acid to 4-formylfuran-2-carboxylate. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the dehydrogenase EC number 1.1.1 is. In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, the recombinant microorganism of any one of the embodiments of the method disclosed herein comprise at least one endogenous or exogenous nucleic acid molecule encoding a dehydrogenase, or a oxidase, or a peroxygenase that catalyzes the conversion of 4-formyl-furan-2-carboxylate and/or 2-formylfuran-4-carboxylate to 2,4-FDCA. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment the dehydrogenases can be derived from enzyme candidates listed at Table 3. In some embodiments, the dehydrogenases are homologous or similar to the enzymes listed at Table 3. In some embodiments, a dehydrogenases is evolved or engineered to improve its catalytic efficiency against its desirable substrate.

In one embodiment, the oxidase is classified as EC number 1.1.3. In one embodiment, the oxidase EC number 1.1.3 is 5-(hydroxymethylfurfural oxidase (EC number 1.1.3.47). In some embodiments the HMF oxidase can be derived from the gene hmfH. In some embodiments, HMF oxidase can be derived from *Methylovorus* sp. MP688 or *Cupriavidus basilensis*. See Dijkman and Fraaije (2014). Applied Environmental Microbiology, 80.3:1082-1090) and Koopman et al. (2010. PNAS, 107(11):4919-4924). In one embodiment, the HMF oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015). In some embodiments, the HMF oxidase can be derived from enzyme candidates listed at Table 4. In some embodiments, the HMF oxidase is homologous or similar to the enzymes listed at Table 4. In some embodiments, the HMF oxidase enzyme is evolved or engineered to improve its catalytic efficiency.

2,4-furandimethanol

In one embodiment, the present disclosure is drawn to a method of producing a recombinant microorganism capable of producing 2,4-furandimethanol from a carbon source. Some embodiments of the present disclosure are presented in FIG. 1, FIG. 2, and FIG. 3, which collectively detail the biosynthetic conversion of a carbon feedstock to 2,4-furandimethanol.

In one embodiment, the bioproduction of 2,4-furandimethanol from 4-HMF is catalyzed by a dehydrogenase encoded by the microorganism. In one embodiment, the dehydrogenase is classified as EC number 1.1.1. In one embodiment, the dehydrogenase EC number 1.1.1 is selected from alcohol dehydrogenase (EC number 1.1.1.1). In one embodiment, the dehydrogenase EC number 1.1.1 is selected from alcohol dehydrogenase (NADP+) (EC number 1.1.1.2). In one embodiment, the dehydrogenase EC number 1.1.1 is selected from D-xylose reductase (EC number 1.1.1.90). In one embodiment, the dehydrogenase EC number 1.1.1 is selected from aryl-alcohol dehydrogenase (EC number 1.1.1.91). In one embodiment the dehydrogenases can be derived from enzyme candidates listed at Table 5. In some embodiments, the dehydrogenases are homologous or similar to the enzymes listed at Table 5. In some embodiments, a dehydrogenases is evolved or engineered to improve its catalytic efficiency for 4-HMF reduction to 2,4-furandimethanol.

In some aspects, 2,4-furandimethanol is produced enzymatically, in the absence of microbes. In some aspects, 2,4-furandimethanol is produced enzymatically in one or more vessels. In some aspects, the one or more vessels are substantially free of microbes. In some aspects, the enzymatic production of 2,4-furandimethanol is performed in the same step-wise fashion as described with in the methods utilizing recombinant microorganisms, but substantially free of microorganisms or in the absence of microorganisms. In some aspects, the enzymes utilized in the enzymatic production of 2,4-furandimethanol are isolated from microbes, recombinant or otherwise, and provided to their corresponding substrates for the stepwise production of the intermediates utilized to produce 2,4-furandimethanol. In some aspects, one or more of the steps of the methods are performed in the same vessel. In some aspects, once the desired product is produced as a result of the individual method steps described herein, the product is isolated and purified and then utilized as the substrate in the next step of the method of producing 2,4-furandimethanol.

Furan-2,4-dicarbaldehyde

In one embodiment, the present disclosure is drawn to a method of producing a recombinant microorganism capable of producing furan-2,4-dicarbaldehyde from a carbon source. Some embodiments of the present disclosure are presented in FIG. 1, FIG. 2, and FIG. 3, which collectively detail the biosynthetic conversion of a carbon feedstock to furan-2,4-dicarbaldehyde.

In one embodiment, step D in FIG. 2 is a single step reaction utilizing 4-HMF as a substrate. In one embodiment, the bioproduction of furan-2,4-dicarbaldehyde from 4-HMF is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, an oxidase, or a peroxygenase that catalyzes the conversion of 4-HMF to furan-2,4-dicarbaldehyde. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. See Dijkman and Fraaije (2014) and Koopman et al. (2010). In one embodiment, the oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015).

In some aspects, furan-2,4-dicarbaldehyde is produced enzymatically, in the absence of microbes. In some aspects, furan-2,4-dicarbaldehyde is produced enzymatically in one or more vessels. In some aspects, the one or more vessels are substantially free of microbes. In some aspects, the enzymatic production of furan-2,4-dicarbaldehyde is performed in the same step-wise fashion as described with in the methods utilizing recombinant microorganisms, but substantially free of microorganisms or in the absence of microorganisms. In some aspects, the enzymes utilized in the enzymatic production of furan-2,4-dicarbaldehyde are isolated from microbes, recombinant or otherwise, and provided to their corresponding substrates for the stepwise production of the intermediates utilized to produce furan-2, 4-dicarbaldehyde. In some aspects, one or more of the steps of the methods are performed in the same vessel. In some aspects, once the desired product is produced as a result of the individual method steps described herein, the product is isolated and purified and then utilized as the substrate in the next step of the method of producing furan-2,4-dicarbaldehyde.

4-(hydroxymethyl)furoic acid

In one embodiment, the present disclosure is drawn to a method of producing a recombinant microorganism capable of producing 4-(hydroxymethyl)furoic acid from a carbon source. Some embodiments of the present disclosure are presented in FIG. 1, FIG. 2, and FIG. 3, which collectively detail the biosynthetic conversion of a carbon feedstock to 4-(hydroxymethyl)furoic acid.

In one embodiment, step E in FIG. 2 is a single step reaction utilizing 4-HMF as a substrate. In one embodiment, the bioproduction of 4-(hydroxymethyl)furoic acid from 4-HMF is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-HMF to 4-(hydroxymethyl)furoic acid. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In some aspects, 4-(hydroxymethyl)furoic acid is produced enzymatically, in the absence of microbes. In some aspects, 4-(hydroxymethyl)furoic acid is produced enzymatically in one or more vessels. In some aspects, the one or more vessels are substantially free of microbes. In some aspects, the enzymatic production of 4-(hydroxymethyl) furoic acid is performed in the same step-wise fashion as described with in the methods utilizing recombinant microorganisms, but substantially free of microorganisms or in the absence of microorganisms. In some aspects, the enzymes utilized in the enzymatic production of 4-(hydroxymethyl) furoic acid are isolated from microbes, recombinant or otherwise, and provided to their corresponding substrates for the stepwise production of the intermediates utilized to produce 4-(hydroxymethyl)furoic acid. In some aspects, one or more of the steps of the methods are performed in the same vessel. In some aspects, once the desired product is produced as a result of the individual method steps described herein, the product is isolated and purified and then utilized as the substrate in the next step of the method of producing 4-(hydroxymethyl)furoic acid.

2-formylfuran-4-carboxylate

In one embodiment, the present disclosure is drawn to a method of producing a recombinant microorganism capable of producing 2-formylfuran-4-carboxylate from a carbon source. Some embodiments of the present disclosure are presented in FIG. 1, FIG. 2, and FIG. 3, which collectively detail the biosynthetic conversion of a carbon feedstock to 2-formylfuran-4-carboxylate.

In one embodiment, step F in FIG. 2 is a single step reaction utilizing furan-2,4-dicarbaldehyde as a substrate. In one embodiment, the bioproduction of 2-formylfuran-4-carboxylate from furan-2,4-dicarbaldehyde is catalyzed by one or more enzymes represented by EC numbers 1.2.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 2-formylfuran-4-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In some aspects, 2-formylfuran-4-carboxylate is produced enzymatically, in the absence of microbes. In some aspects, 2-formylfuran-4-carboxylate is produced enzymatically in one or more vessels. In some aspects, the one or more vessels are substantially free of microbes. In some aspects, the enzymatic production of 2-formylfuran-4-carboxylate is performed in the same step-wise fashion as described with in the methods utilizing recombinant microorganisms, but substantially free of microorganisms or in the absence of microorganisms. In some aspects, the enzymes utilized in the enzymatic production of 2-formylfuran-4-carboxylate are isolated from microbes, recombinant or otherwise, and provided to their corresponding substrates for the stepwise production of the intermediates utilized to produce 2-formylfuran-4-carboxylate. In some aspects, one or more of the steps of the methods are performed in the same vessel. In some aspects, once the desired product is produced as a result of the individual method steps described herein, the product is isolated and purified and then utilized as the substrate in the next step of the method of producing 2-formylfuran-4-carboxylate.

4-formylfuran-2-carboxylate

In one embodiment, the present disclosure is drawn to a method of producing a recombinant microorganism capable of producing 4-formylfuran-2-carboxylate from a carbon source. Some embodiments of the present disclosure are presented in FIG. 1, FIG. 2, and FIG. 3, which collectively detail the biosynthetic conversion of a carbon feedstock to 4-formylfuran-2-carboxylate.

In one embodiment, step G in FIG. 2 is a single step reaction utilizing furan-2,4-dicarbaldehyde as a substrate. In one embodiment, the bioproduction of 4-formylfuran-2-carboxylate from furan-2,4-dicarbaldehyde is catalyzed by one or more enzymes represented by EC numbers 1.2.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of furan-2,4-dicarbaldehyde to 4-formylfuran-2-carboxylate. In one embodiment, the dehydrogenase is classified as EC number 1.2.1. In one embodiment, the dehydrogenase EC number 1.2.1 selected from aldehyde dehydrogenase (NAD+) (EC number 1.2.1.3) or aldehyde dehydrogenase (NADP+) (EC number 1.2.1.4) or aldehyde dehydrogenase [NAD(P)+] (EC number 1.2.1.5) or 4-(γ-glutamylamino)butanal dehydrogenase (EC number 1.2.1.99). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. In one embodiment, the oxidase EC number 1.1.3 is aryl-alcohol oxidase (EC number 1.1.3.7). In one embodiment, the peroxygenase is classified as EC number 1.11.2. In one embodiment, the peroxygenase EC number 1.11.2 is unspecific peroxygenase (EC number 1.11.2.1).

In one embodiment, step H in FIG. 2 is a single step reaction utilizing 4-(hydroxymethyl)furoic acid as a substrate. In one embodiment, the bioproduction of 4-formyl-furan-2-carboxylate from 4-(hydroxymethyl)furoic acid is catalyzed by one or more enzymes represented by EC numbers 1.1.1.-, 1.1.3.-, and 1.11.2.-.

In one embodiment, the recombinant microorganism of any one of the embodiments disclosed herein comprises at least one endogenous or exogenous nucleic acid molecule encoding a dehydrogenase, or a oxidase, or a peroxygenase that catalyzes the conversion of 4-(hydroxymethyl)furoic acid to 4-formylfuran-2-carboxylate. In one embodiment, the dehydrogenase is classified as EC number 1.1.1. In one embodiment, the dehydrogenase EC number 1.1.1 selected from alcohol dehydrogenase (EC number 1.1.1.1), or alcohol dehydrogenase (NADP+) (EC number 1.1.1.2), or D-xylose reductase (EC number 1.1.1.307), or aryl-alcohol dehydrogenase (EC number 1.1.1.90), or aryl-alcohol dehydrogenase (NADP+) (EC number 1.1.1.91). In one embodiment, the oxidase is classified as EC number 1.1.3. In one embodiment, the oxidase EC number 1.1.3 is 5-(hydroxymethylfurfural oxidase (EC number 1.1.3.47). In some embodiments the EC 1.1.3.47 oxidase can be derived from the gene hmfH. In some embodiments, hmfH can be derived from *Methylovorus* sp. MP688 or *Cupriavidus basilensis*. See Dijkman and Fraaije (2014) and Koopman et al. (2010). In one embodiment, the oxidase EC number 1.1.3 is aryl-alcohol oxidase (EC number 1.1.3.7). See Carro et al. (2015). In one embodiment, the peroxygenase is classified as EC number 1.11.2. In one embodiment, the peroxygenase EC number 1.11.2 is unspecific peroxygenase (EC number 1.11.2.1). See Carro et al. (2015).

In some aspects, 4-formylfuran-2-carboxylate is produced enzymatically, in the absence of microbes. In some aspects, 4-formylfuran-2-carboxylate is produced enzymatically in one or more vessels. In some aspects, the one or more vessels are substantially free of microbes. In some aspects, the enzymatic production of 4-formylfuran-2-carboxylate is performed in the same step-wise fashion as described with in the methods utilizing recombinant microorganisms, but substantially free of microorganisms or in the absence of microorganisms. In some aspects, the enzymes utilized in the enzymatic production of 4-formylfuran-2-carboxylate are isolated from microbes, recombinant or otherwise, and provided to their corresponding substrates for the stepwise production of the intermediates utilized to produce 4-form-ylfuran-2-carboxylate. In some aspects, one or more of the steps of the methods are performed in the same vessel. In some aspects, once the desired product is produced as a result of the individual method steps described herein, the product is isolated and purified and then utilized as the substrate in the next step of the method of producing 4-formylfuran-2-carboxylate.

The present disclosure provides methods and recombinant microorganisms capable of producing high yields of one or more of 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. In one embodiment one molecule of glucose and two molecules of ATP are converted into one molecule of 2,4-FDCA and three molecules of NAD(P)H according to the net equation 1:

$$1 \text{ glucose} + 2 \text{ ATP} \rightarrow 1 \text{ 2,4-FDCA} + 3 \text{ NAD(P)H} \qquad \text{Equation 1}$$

The net reaction results in a mass yield of about 0.87 grams of 2,4-FDCA per gram of glucose. This yield is equivalent to 75% of the maximal thermodynamic yield of 1.16 grams of 2,4-FDCA per gram of glucose. In some embodiments, the yield of 2,4-FDCA can be about 0.4, 0.5, 0.6, 0.7, 0.8, 0.9, 1.0, 1.1, 1.16 grams per gram of glucose.

In one embodiment one molecule of glucose, two molecules of ATP and three molecules of oxygen are converted into one molecule of 2,4-FDCA and three molecules of hydrogen peroxide ($H_2O_2$) according to the net equation 2:

$$1 \text{ glucose} + 2 \text{ ATP} + 3 \text{ O}_2 \rightarrow 1 \text{ 2,4-FDCA} + 3 \text{ H}_2\text{O}_2 \qquad \text{Equation 2}$$

In one embodiment two molecules of glycerol and two molecules of ATP are converted into one molecule of 2,4-FDCA and five molecules of NAD(P)H according to the net equation 3:

$$2 \text{ glycerol} + 2 \text{ ATP} \rightarrow 1 \text{ 2,4-FDCA} + 5 \text{ NAD(P)H} \qquad \text{Equation 3}$$

The net reaction results in a mass yield of about 0.85 grams of 2,4-FDCA per gram of glycerol. This yield is equivalent to 64% of the maximal thermodynamic yield of 1.32 grams of 2,4-FDCA per gram of glycerol. In some embodiments, the yield of 2,4-FDCA can be about 0.4, 0.5, 0.6, 0.7, 0.8, 0.9, 1.0, 1.1, 1.2, 1.3, 1.32 grams per gram of glycerol.

In one embodiment two molecules of glycerol, two molecules of ATP and three molecules of oxygen are converted into one molecule of 2,4-FDCA and three molecules of hydrogen peroxide according to the net equation 4:

$$2\ glycerol + 2\ ATP + 3\ O_2 \rightarrow 1\ 2,4\text{-FDCA} + 3\ H_2O_2 \qquad \text{Equation 4}$$

Methods of Producing and Isolating Biosynthesis Product Monomers and/or Polymers In some aspects, modified microbes of the present disclosure are modified such that the microbes produce 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA monomers. In some aspects, modified microbes of the present disclosure are modified such that the microbes produce polymers derived from 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. In some aspects, a method of producing the biosynthesis product monomers and/or polymers comprises growing/fermenting one or more microbes of the present disclosure under conditions sufficient to produce the biosynthesis product monomers and/or polymers, and isolating/collecting the resulting 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA and/or polymers thereof. In some aspects, the biosynthesis monomers will polymerize into polymers in vivo. In some aspects, the production of the biosynthesis monomers and polymers is proportional to the number of bacteria utilized in the microbial fermentation process. In some aspects, the bacteria are grown in a reaction chamber. Once a desired number of bacteria have been achieved, the spent media is subjected to a process for the isolating the biosynthesis product monomers and/or polymers. In some aspects, the microbes are lysed and the cellular debris is pelleted out of solution in a centrifuge. In some aspects, the biosynthesis product monomers and/or polymers are collected from the cell pellet fraction or the liquid fraction with the aid of a solvent extraction process or a gradient ultra-centrifugation process. In some aspects, the biosynthesis product polymer can be isolated by filtration.

In some aspects, a biosynthesis product monomer is produced by cultivating the recombinant microorganism in a culture medium containing a feedstock providing a carbon source until the monomer is produced. In some aspects, the feedstock comprises one or more hexose, one or more pentose, or a combination thereof. In some aspects, the monomer is extracted from the culture medium and polymerized in the presence of a catalyst. The present disclosure provides a method of producing a polymer from biosynthesis product produced by the recombinant microorganisms and methods of the disclosure. In one embodiment the one or more biosynthesis products are catalytically polymerized with a diol to form a polymer. The diol can be selected from ethylene glycol, 1,3-propanediol, 1,2-propanediol, 1,4-butanediol, 1,3-butanediol, 2,3-butanediol, 1,5-pentanediol, or 1,6-hexanediol.

In some aspects, the biosynthesis product monomer is catalyzed in the presence of a catalyst selected from a titanium-based catalyst, germanium-based catalyst, magnesium-based catalyst, silicon-based catalyst, aluminum-based catalyst, or an antimony-based catalyst. In some aspects, the catalyst is selected from: antimony acetate, antimony trioxide, germanium dioxide, tetra-isopropyl titanate, and tetra-n-butyl titanate.

In some aspects, the biosynthesis product-derived polymer is polymerized in vivo by a pha synthase. In some aspects, the biosynthesis product-derived monomer is polymerized ex vivo by a pha synthase.

In some aspects, the biosynthesis product 4-HMF is extracted from the culture medium and transformed, in the presence of a catalyst, into one or more of the other biosynthesis products as reported in the state of the art. See Van Putten et al. (2013. Hydroxymethylfurfural, a Versatile Platform Chemical Made from Renewable Resources. *Chemical Reviews*, 113.3:1499-1597).

In some aspects, the biosynthesis product 4-HMF is extracted from the culture medium and transformed, in the presence of a catalyst, into 2,4-dimethylfuran. See Deng et al. (2013. Linked Strategy for the Production of Fuels via Formose Reaction. *Scientific Reports*, 3:1244).

In some aspects, any one or more of the biosynthesized products produced by the methods and compositions described herein are extracted from the culture medium in which they are biosynthesized and are transformed in the presence of a chemical or biological catalyst(s).

In some aspects, the transformation of the biosynthesized products in the presence of a chemical or biological catalyst (s) is performed in the absence of microorganisms. In some aspects, the the transformation of the biosynthesized products in the presence of a biological catalyst(s) is performed in the absence of microorganisms and in the presence of one or more enzymes isolated and purified from one or more microorganisms.

In some aspects, the chemical catalyst or catalysts are any one or more of the chemicals that are known to be utilized in non-biological synthesis of 2,4-furandimethanol, furan-2,4-dicarbaldehyde, 4-(hydroxymethyl)furoic acid, 2-formylfuran-4-carboxylate, 4-formylfuran-2-carboxylate, and/or 2,4-FDCA.

In some aspects, the biological catalyst or catalysts are any one or more of the enzymes described herein for reaction steps C, D, E, F, G, H, I, or J in FIG. 2.

In some aspects, the transformation of biosynthesized 4-HMF into 2,4-furandimethanol occurs in a composition substantially free of microorganisms and in the presence of a chemical or biological catalyst described herein, such as the biological catalysts of EC 1.1.1.-.

In some aspects, the transformation of biosynthesized 4-HMF into furan-2,4-dicarbaldehyde occurs in a composition substantially free of microorganisms and in the presence of a chemical or biological catalyst described herein, such as the biological catalysts of EC 1.1.1.-, EC 1.1.3.-, and/or EC 1.11.2.-.

In some aspects, the transformation of biosynthesized 4-HMF into 4-(hydroxymethyl)furoic acid) occurs in a composition substantially free of microorganisms and in the presence of a chemical or biological catalyst described herein, such as the biological catalysts of EC 1.1.1.-, EC 1.1.3.-, and/or EC 1.11.2.-.

In some aspects, the transformation of biosynthesized 2,4-furandimethanol into 2-formylfuran-4-carboxylate occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, the transformation of biosynthesized furan-2,4-dicarbaldehyde into 2-formylfuran-4-carboxylate occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, the transformation of biosynthesized furan-2,4-dicarbaldehyde into 4-formylfuran-2-carboxylate occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, the transformation of biosynthesized 4-(hydroxymethyl)furoic acid into 4-formylfuran-3-carboxylate occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, the transformation of biosynthesized 2-formylfuran-4-carboxylate into 2,4-FDCA occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, the transformation of biosynthesized 4-formylfuran-2-carboxylate into 2,4-FDCA occurs in a composition substantially free of microorganisms and in the presence of a chemical or biological catalyst described herein, such as the biological catalysts of EC 1.2.1.-, EC 1.1.3.-, and/or EC 1.11.2.-.

In some aspects, any one or more of the transformations described above can be combined with another transformation such that the product of the first transformation is the substrate for the product of the second transformation.

In some aspects, any one or more of the transformations described above can be combined with another transformation such that the product of the first transformation is the substrate for the product of the second transformation, whose product is the substrate for the product of the third transformation.

Biological Processes for Producing the Biosynthesis Products

The present disclosure provides a biological process for producing one or more of the biosynthesis products described herein; 4-HMF, 2,4-furandimethanol, furan-2,4-dicarbaldehyde, 4-(hydroxymethyl)furoic acid, 2-formylfuran-4-carboxylate, 4-formylfuran-2-carboxylate, and 2,4-FDCA. In some embodiments, the process comprises: providing to at least one bioreactor one or more recombinant microorganisms engineered to express one or more enzymes involved in the biosynthesis of glyceraldehyde 3-phosphate (G3P) from one or more biosynthesis pathways and one or more of the biosynthesis products from G3P and a feedstock comprising an exogenous carbon source; cultivating the one or more recombinant microorganisms in one or more stages in a culture medium comprising the feedstock; fermenting the resulting culture in one or more stages under aerobic, microaerobic and/or anaerobic conditions; and recovering from the bioreactor the one or more biosynthesis products after the fermentation step.

In some embodiments of the biological process, the one or more biosynthesis products are recovered continuously prior to exhaustion of the culture medium or the feedstock. In some embodiments, the biosynthesis products are recovered in batches prior to exhaustion of the culture medium or the feedstock. In some embodiments, the one or more recombinant microorganisms are derived from a parental microorganism selected from the group consisting of *Clostridium* sp., *Clostridium ljungdahlii, Clostridium autoethanogenum, Clostridium ragsdalei, Eubacterium limosum, Butyribacterium methylotrophicum, Moorella thermoacetica, Corynebacterium glutamicum, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Candida krusei, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Issatchenkia orientalis, Sporomusa termitida, Moorella glycerini, Eubacterium aggregans, Treponema azotonutricium, Pichia kudriavzevii, Escherichia coli, Saccharomyces cerevisiae, Pseudomonas putida, Bacillus sp, Corynebacterium sp., Yarrowia lipolytica, Scheffersomyces stipitis,* and *Terrisporobacter glycolicus.*

In some embodiments of the biological process, the feedstock comprises C6 carbohydrates and/or C5 carbohydrates. In some embodiments, the feedstock comprises monosaccharides, disaccharides, oligosaccharides, polysaccharides, or combinations thereof.

In some embodiments of the biological process, the cultivating and fermenting steps occur in the same stage. In some embodiments, the cultivating and fermenting steps occur in separate stages. In some embodiments, the cultivating and fermenting steps occur in separate bioreactors. In some embodiments, the cultivating and fermenting steps occurs in the same bioreactor. In some embodiments, the bioreactor operates under aerobic, microaerobic, or anaerobic conditions; or a combination thereof.

In some embodiments, the one or more stages receive the culture and/or culture media as a batch, a fed-batch, or a continuous mode feed. In some embodiments, the cultivating stage receives the culture and/or culture media as a batch, a fed-batch, or a continuous mode feed, and any subsequent stages operate as a batch, a fed-batch, or a continuous mode feed.

In some embodiments, the culture medium comprises carbon (C) that is provided from C5 carbohydrates, C6 carbohydrates, and/or disaccharides. In some embodiments, the culture medium comprises essential nutrients including nitrogen (N), phosphorus (P), magnesium (Mg), and iron (Fe).

In some embodiments, wherein a ratio of C:N in the cultivating step is at least 10:1. In some embodiments, wherein a ratio of C:P in the cultivating step is at least 5:1. In some embodiments, a ratio of C:Mg in the cultivating step is at least 50:1. In some embodiments, a ratio of C:Fe in the cultivating step is at least 300:1.

In some embodiments, the cultivating step operates from 5 up to 100 hours for the cultivation of the cells of the one or more recombinant microorganisms. In some embodiments, the culture in the fermenting step comprises about 1% to about 30% of the cell mass, which is transferred from the cultivating step in the culture medium with the one or more substrates. In some embodiments, a total amount of the feedstock provided to the fermenting step ranges from about 100 kg/m$^3$ to about 800 kg/m$^3$.

In some embodiments, a ratio of C:N in the fermenting step is at least 50:1. In some embodiments, a ratio of C:P in the fermenting step is at least 20:1. In some embodiments, a ratio of C:Mg in the fermenting step is at least 200:1. In some embodiments, a ratio of C:Fe in the fermenting step is at least 800:1. In some embodiments, the fermenting step operates from 10 up to 300 hours for fed-batch operation and up to 300 hours for continuous operation.

EXAMPLES

Example 1: Expression and Purification of Methyl Phosphate Synthase

The expression and purification of enzymes used in enzymatic assays was carried out under the following conditions: Genes coding 27 (5-formylfuran-3-yl)methyl phosphate synthases candidates (Table 1) were synthetized by GenScript and cloned in expression vector pET28a in NdeI and BamHI restriction sites. The expression vector was transformed into *E. coli* BL21 (DE3) and the transformant was stored in 15% glycerol until use for enzyme expression.

The stored transformant was inoculated into 50 mL of TB broth containing kanamycin at 37° C. with agitation for 16 h to prepare a seed culture. The seed culture was added to 300 mL of TB broth containing kanamycin with initial OD (600 nm) of 0.2, the culture was then incubated at 37° C. with agitation until OD (600 nm) reached 0.6-0.8 at which point 1 mM IPTG was added to induce expression overnight at 18° C. with agitation.

Figure 4:
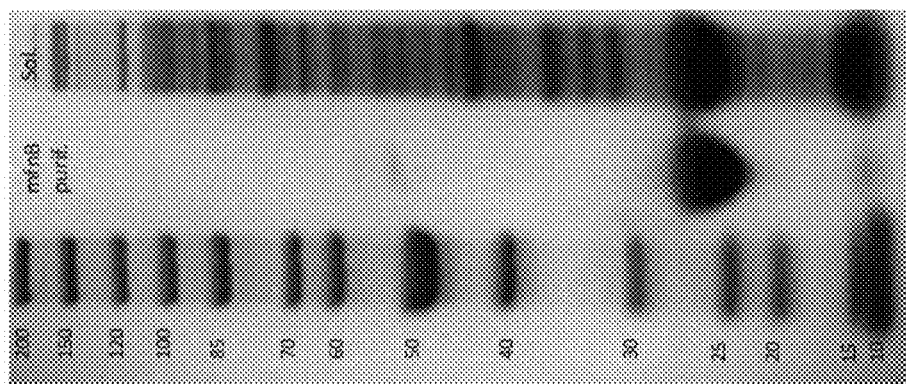
FIG. 4 is an illustrative SDS-PAGE image of expressed and purified 5-formylfuran-3-yl)methyl phosphate synthase candidate, MfnB1.

Following overnight expression, the cells were centrifuged at 6000× rpm for 30 min and the pellet cell was suspended in cold lysis buffer (20 mM phosphate buffer and 500 mM NaCl pH 7.4) before ultrasonic disruption. The cell lysate was again centrifuged at 8000 rpm for 30 min at 4° C. and filtered before purification with affinity chromatography. The column utilized was a HisTrap FF Crude (GE Healthcare) for his-tagged protein purification. The purified protein was bound and washed in the column with binding buffer A (20 mM phosphate buffer, 20 mM imidazole, 500 mM NaCl, 1 mM PMSF and beta-mercaptoethanol, pH 7.4) and eluted in a gradient of elution buffer B (20 mM phosphate buffer, 500 mM imidazole, 500 mM NaCl, 1 mM PMSF and beta-mercaptoethanol, pH 7.4). Then using a PD-10 column the buffer was changed to a 50 mM Tris-HCl pH 7.4. Candidates expression and purification were analyzed on 12% polyacrylamide gel by electrophoresis, as illustrated at FIG. 4.

Example 2: (5-formylfuran-3-yl)methyl phosphate Production from G3P

The (5-formylfuran-3-yl)methyl phosphate production from glyceraldehyde-3-phosphate (G3P) by enzyme candidates described in Table 1 was demonstrated in vitro by incubating approximately 450 µg of purified candidates with a 1 mL solution containing 5 mM of glyceraldehyde-3-phosphate (Sigma) in 20 mM Tris-HCl, 200 mM NaCl (pH 7.4) buffer. The reaction was incubated at 37° C. for 2 hours. Reaction vessels without synthases or substrate (G3P) were used as negative controls. The reaction was monitored by UV-Vis using a spectrophotometer (SpectraMax M5, Molecular Devices), accordingly to the 5-formylfuran-3-yl) methyl phosphate Molar absorption coefficient (ε) 280 nm. Product formation was also confirmed by HPLC analysis.

The chromatographic quantitative analysis of (5-formylfuran-3-yl)methyl phosphate production was performed in a HPLC-DAD (Thermo Ultimate 3000) equipped with an Aminex HPX-87H Biorad column (300×7.8 mm). The column was maintained at 50° C. and the mobile phase used was a 5 mM $H_2SO_4$ solution with flow rate of 0.75 mL/min (isocratic gradient mode).

Figure 5:
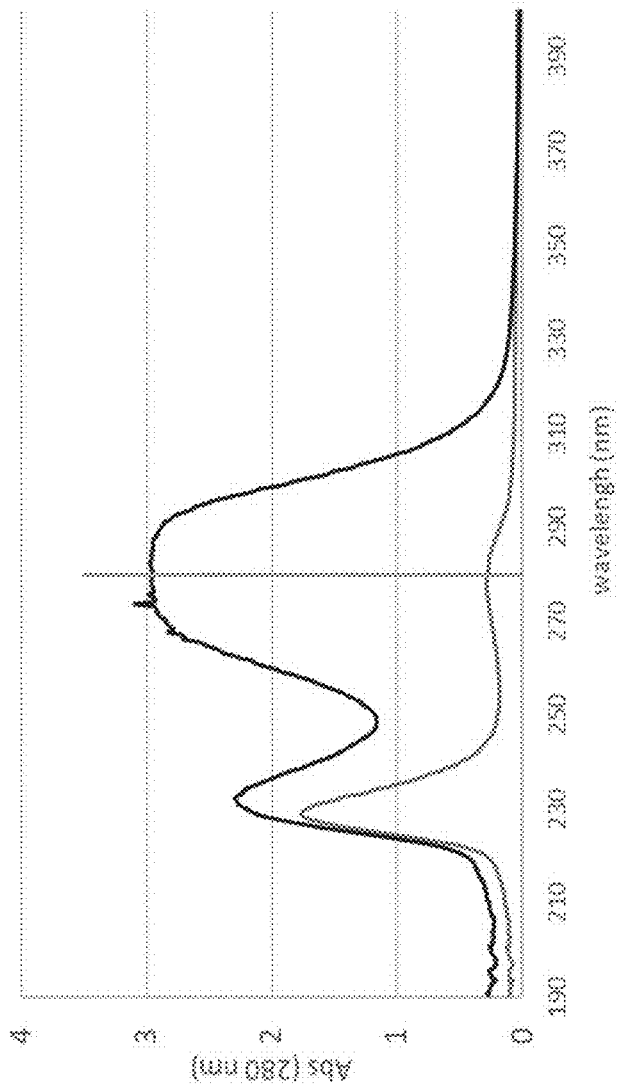
FIG. 5 is a representative UV spectra showing a negative control sample (grey) and methyl phosphate synthase reaction (black) showing (5-formylfuran-3-yl)methyl phosphate produced from G3P.
Figure 6:
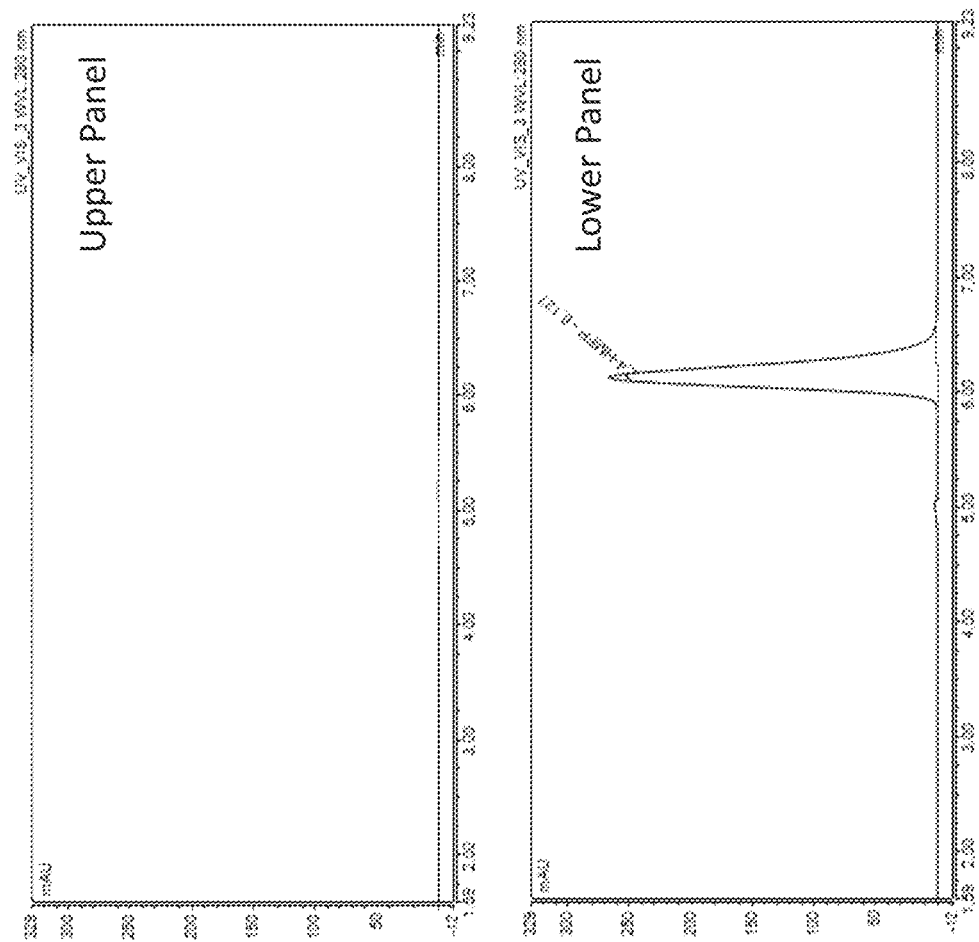
FIG. 6 is a representative UV spectra showing (5-formylfuran-3-yl)methyl phosphate production from G3P by methyl phosphate synthases at $t_0$ (Upper panel) and $t_{2h}$ (Lower panel).

As shown in Table 6, FIG. 5, and FIG. 6, G3P was successfully converted into (5-formylfuran-3-yl)methyl phosphate by methyl phosphate synthases. In FIG. 5, the negative control sample (grey line) shows a low absorbance at 280, indicating little to no presence of the (5-formylfuran-3-yl)methyl phosphate in comparison to the reaction containing the methyl phosphate synthase (black line), indicating that the synthase catalyzed the formation of the (5-formylfuran-3-yl)methyl phosphate from G3P; these results are summarized in Table 6. FIG. 6 shows detectable (5-formylfuran-3-yl)methyl phosphate in the reaction containing synthase (Lower Panel) but not in the negative control reaction (Upper Panel). Table 7 contains a list of methyl phosphate synthase candidates that positively tested for the production of (5-formylfuran-3-yl)methyl phosphate from G3P.

TABLE 6

Absorbance obtained at 280 nm for methyl phosphate synthase production of (5-formylfuran-3-yl)methyl phosphate from G3P.

|  | Absorbance at 280 nm |
|---|---|
| Methyl phosphate synthase positive reaction (MfnB1 candidate) | 2.97 |
| Negative control | 0.26 |

TABLE 7

(5-formylfuran-3-yl)methyl phosphate synthases candidates that positively tested for catalyzing the production of (5-formylfuran-3-yl)methyl phosphate production from G3P.

| Name | Organism |
|---|---|
| MfnB 1 | *Methanocaldococcus jannaschii* |
| MfnB 2 | *Methanocaldococcus fervens* |
| MfnB 3 | *Methanocaldococcus vulcanius* |
| MfnB 4 | *Methanocaldococcus infernos* |
| MfnB 5 | *Methanothermococcus okinawensis* |
| MfnB 6 | *Methanococcales archaeon* HHB |
| MfnB 7 | *Methanobrevibacter smithii* |
| MfnB 8 | *Methanobacterium* sp. PtaB.Bin024 |
| MfnB 9 | *Methanopyrus* sp. KOL6 |
| MfnB 10 | *Candidatus Argoarchaeum ethanivorans* |
| MfnB 12 | *Methanobrevibacter arboriphilus* |
| MfnB 13 | *Methanococcus maripaludis* |
| MfnB 14 | *Methanococcus vannielii* |
| MfnB 15 | *Methanosarcina acetivorans* |
| MfnB 16 | *Methanosarcina barkeri* |
| MfnB 17 | *Methylorubrum extorquens* |
| MfnB 18 | *Methylobacterium* sp. |
| MfnB 19 | *Methanosarcina mazei* |
| MfnB 20 | *Methyloversatilis universalis* |
| MfnB 22 | *Streptomyces cattleya* NRRL 8057 |
| MfnB 23 | *Streptomyces coelicolor* |
| MfnB 24 | *Streptomyces* EFF88969 |
| MfnB 25 | *Streptomyces griséus* |
| MfnB 26 | *Streptomyces* sp. DH-12 |
| MfnB 27 | *Streptomyces venezuelae* |

Example 3: Production of 4-hydroxymethylfurfural (4-HMF) from (5-formylfuran-3-yl)methyl phosphate The production of 4-HMF from (5-formylfuran-3-yl) methyl phosphate using phosphatases was demonstrated using commercially available phosphatase, *E. coli* lysates, and yeast lysates to demonstrate their capability to produce 2,4-HMF from (5-formylfuran-3-yl)methyl phosphate. The substrate (5-formylfuran-3-yl)methyl phosphate was produced by (5-formylfuran-3-yl)methyl phosphate synthases as described at Example 2.

The chromatographic quantitative analysis of (5-formylfuran-3-yl)methyl phosphate and 4-HMF production was performed in a HPLC-DAD (Thermo Ultimate 3000) equipped with an Aminex HPX-87H Biorad column (300× 7.8 mm). The column was maintained at 50° C. and the mobile phase used was a 5 mM $H_2SO_4$ solution with flow rate of 0.75 mL/min (isocratic gradient mode). Both compounds were detected at 280 nm.

Figure 7:
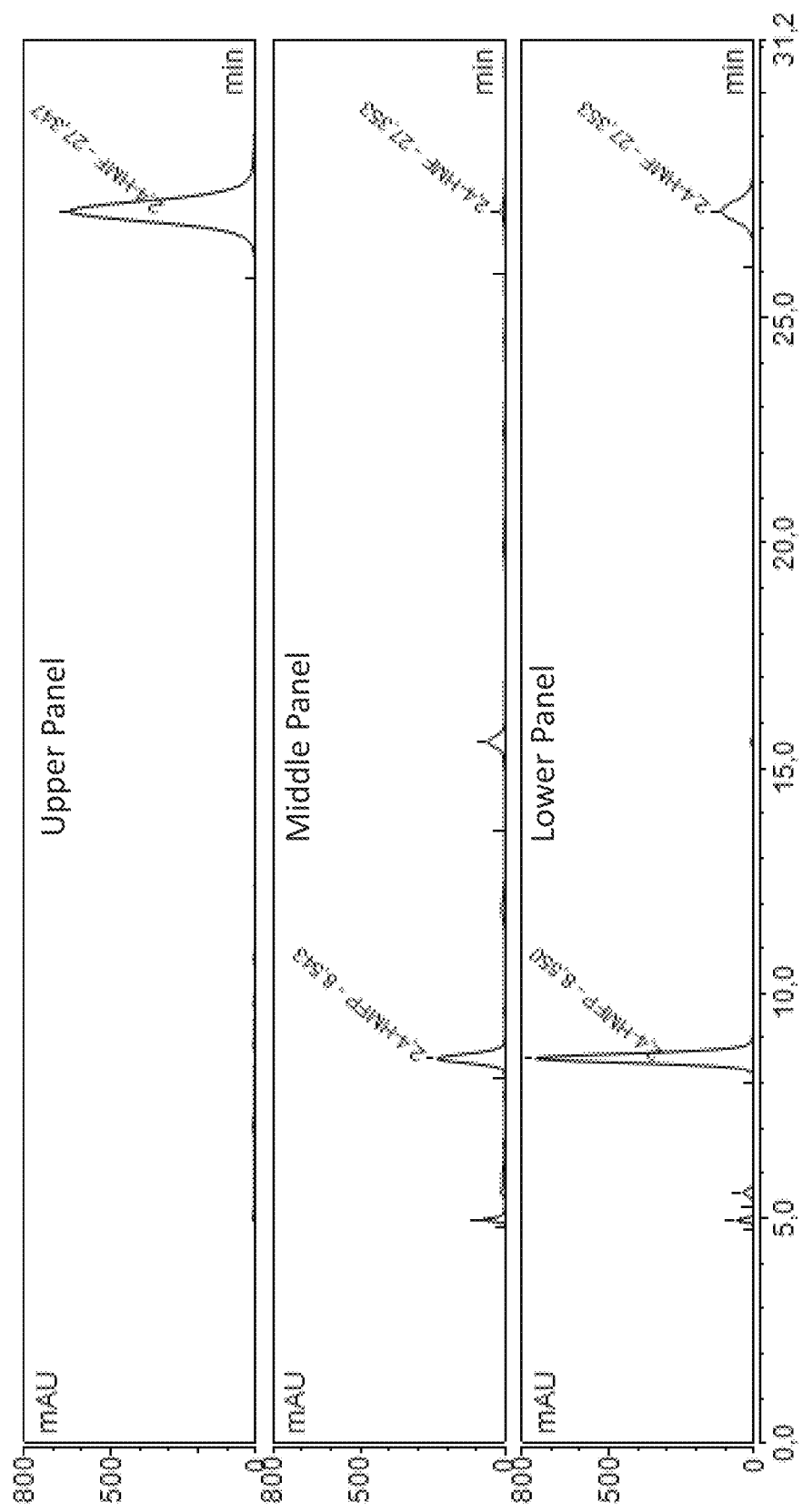
FIG. 7 is a representative UV spectra showing 4-HMF production from (5-formylfuran-3-yl)methyl phosphate by phosphatase (Upper Panel), E. coli lysates (Middle Panel), and yeast lysates (Lower Panel).

To carry out the reaction demonstrating the production of 4-HMF from (5-formylfuran-3-yl)methyl phosphate using a commercially available phosphatase, 2 µL of alkaline phosphatase from bovine intestinal mucosa (Sigma) was added to 1 mL of reaction vessel from Example 2, containing approximately 1-2 mM of (5-formylfuran-3-yl)methyl phosphate. The reaction was incubated at 37° C. for 1 h and initial and final samples were analyzed by HPLC-DAD. As shown in FIG. 7 (Upper Panel) and Table 8, the commercially available phosphatase was able to perform the full conversion of (5-formylfuran-3-yl)methyl phosphate to 4-HMF.

TABLE 8

Peak area of (5-formylfuran-3-yl)methyl phosphate produced using methyl phosphate synthase.

| | Area (mAU*min) |
|---|---|
| Methyl phosphate synthase positive reaction | 62,1544 |
| Negative control | 0 |

To carry out the reaction demonstrating the production of 4-HMF from (5-formylfuran-3-yl)methyl phosphate using phosphatases in an *E. coli* lysate, a strain of *E. coli* MG1655 was inoculated into 200 mL of LB broth at 37° C. with agitation overnight. The culture was centrifuged at 4000 rpm for 15 min and the pellet suspended in 20 mL of 20 mM HEPES buffer pH 7.4 resulting in an OD of 70. The lysis was performed by ultrasonic disruption. 1 mL of the *E. coli* lysate was mixed with 1 mL of reaction from Example 2 and incubated overnight at 37° C. with agitation. Samples were analyzed by HPLC-DAD at 280 nm for production of 4-HMF.

To carry out the reaction demonstrating the production of 4-HMF from (5-formylfuran-3-yl)methyl phosphate using phosphatases in a yeast lysate, a strain of *Saccharomyces cerevisiae* was inoculated into 200 mL of YPD broth at 30° C. with agitation overnight. The culture was centrifuged at 4000 rpm for 15 min and the pellet suspended in 20 mL of 20 mM HEPES buffer pH 7.4 resulting in an OD of 120. Cell lysis was performed by ultrasonic disruption. 1 mL of the yeast lysate was mixed with 1 mL of reaction from example 2 and incubated overnight at 30° C. with agitation. Samples were analyzed by HPLC-DAD at 280 nm for production of 4-HMF.

As shown in FIG. 7 (Middle Panel) and FIG. 7 (Lower Panel) and Table 9, both *E. coli* and yeast lysates showed endogenous phosphatase activity able to perform the conversion of (5-formylfuran-3-yl)methyl phosphate to 4-HMF.

TABLE 9

4-HMF production from (5-formylfuran-3-yl)methyl phosphate with commercially available phosphatase after 1 hour incubation and *E. coli* l and yeast lysates after overnight incubation at 37° C. and 30° C., respectively.

| Sample | (5-formylfuran-3-yl) methyl phosphate area (mAU*min) | 4-HMF area (mAU*min) |
|---|---|---|
| Sigma phosphatase | n.a. | 385,3242 |
| *E. coli* lysate reaction | 57,2574 | 5,6535 |
| Yeast lysate reaction | 187,9746 | 67,0542 |
| *E. coli* negative control reaction (absence of 5-formylfuran-3-yl) methyl phosphate substrate) | n.a. | n.a. |
| Yeast negative control reaction (absence of 5-formylfuran-3-yl) methyl phosphate substrate) | 22,1085 | 4,0767 |

Example 4: Expression of 4-HMF oxidases Enzymes

Genes coding 7 4-HMF oxidases enzymes candidates (Table 4) were synthesized by GenScript and cloned in expression vector pET28a in NdeI and BamHI restriction sites. The expression vector was transformed into *E. coli* BL21 (DE3) and the transformant was stored in 15% glycerol until use for enzyme expression.

The stored transformant was inoculated into 50 mL of TB broth containing kanamycin at 37° C. with agitation for 16 h to prepare a seed culture. The seed culture was added to 300 mL of TB broth containing kanamycin with initial OD (600 nm) of 0.2, the culture was then incubated at 37° C. with agitation until OD (600 nm) reached 0.6-0.8 at which point 1 mM IPTG was added to induce expression overnight at 18° C. with agitation.

Figure 8:
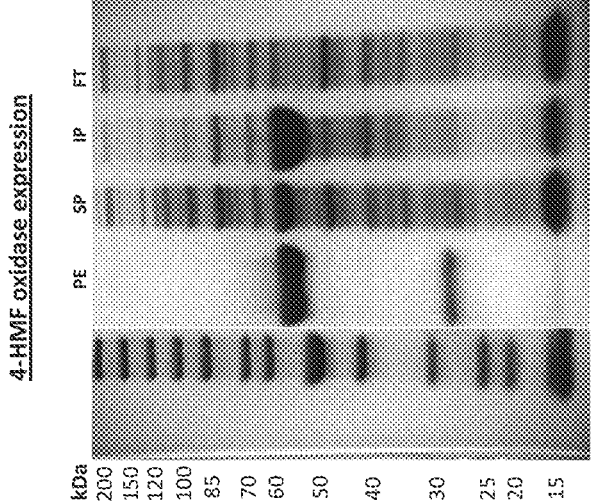
FIG. 8 is an illustrative SDS-PAGE image of the expressed the 4-HMF oxidase candidate, HmfH1, in purified form (PE), soluble phase before purification (SP), in the insoluble phase (IP), and the flow through (FT) after purification.

Following overnight expression, the cells were centrifuged at 6000× rpm for 30 min, the cell pellet was suspended in cold lysis buffer (20 mM phosphate buffer and 500 mM NaCl pH 7.4) before ultrasonic disruption. The cell lysate was again centrifuged at 8000× rpm for 30 min at 4° C. and filtered before purification with affinity chromatography. The column utilized was a HisTrap FF Crude (GE Healthcare) for the his-tagged protein purification. The purified protein was bound and washed in the column with binding buffer A (20 mM phosphate buffer, 20 mM imidazole, 500 mM NaCl, 1 mM PMSF and beta-mercaptoethanol, pH 7.4) and eluted in a gradient of elution buffer B (20 mM phosphate buffer, 500 mM imidazole, 500 mM NaCl, 1 mM PMSF and beta-mercaptoethanol, pH 7.4). Then, using a PD-10 column, the buffer was changed to a 50 mM Tris-HCl pH 7.4. Candidates expression and purification were analyzed on 12% polyacrylamide gel by electrophoresis, as illustrated at FIG. 8.

Example 5: Production of 2,4-FDCA from 2,4-HMF by HmfH oxidases

The 2,4-FDCA production from 2,4-HMF by enzyme candidates described in Table 4 was demonstrated in vitro by incubating approximately 100 µg of purified HmfH oxidase candidates with a 1 mL of reaction vessel from Example 3 (using the commercially available phosphatase), containing approximately 1 mM 4-HMF. The reaction was incubated at 30° C. for 16 hours and both initial and final samples analyzed by HPLC-DAD. Samples were injected in HPLC-DAD and the production of 2,4-FDCA and its intermediates confirmed by GC-MS.

The quantitative analysis of 2,4-FDCA was performed using HPLC-DAD (Thermo Ultimate 3000) equipped with an Aminex HPX-87H Biorad column (300×7.8 mm). The column was maintained at 50° C. The mobile phase used was a 5 mM $H_2SO_4$ solution with flow rate of 0.6 mL/min with isocratic gradient mode. The molecule was detected at 245 nm.

For GC-MS identification, initial and final samples were stopped by adding 6M HCl to reduce pH to 2-3. The products were liquid/liquid extracted using ethyl acetate and dried with $Na_2SO_4$ to remove water traces. The extracted material was then evaporated in a speedvac and derivatized using bis-(trimethylsilyl)trifluoroacetamide at 60° C. for 2 h. The samples were injected in a gas chromatograph with HP-5MS column (Agilent, 30 m×0.25 mm ID, 0.25 um film thickness) coupled with a quadrupole mass detector (ISQ, Thermo). The oven program started at 110° C. for 2 min with increasing ramp of 20° C./min until 300° C. that was held for 3 min. Helium was used as carrier gas at a flow rate of 1.2 mL/min. 2,4-FDCA was identified by comparing their mass spectra with those in literature. (Ref: Carro, Juan, et al. "5-hydroxymethylfurfural conversion by fungal aryl-alcohol oxidase and unspecific peroxygenase." The FEBS journal 282.16 (2015): 3218-3229.) 4-formylfuran-2-carboxylate (2,4-FFCA) and furan-2,4-dicarbaldehyde (2,4-DFF) were also identified by their mass spectra.

Figure 9:
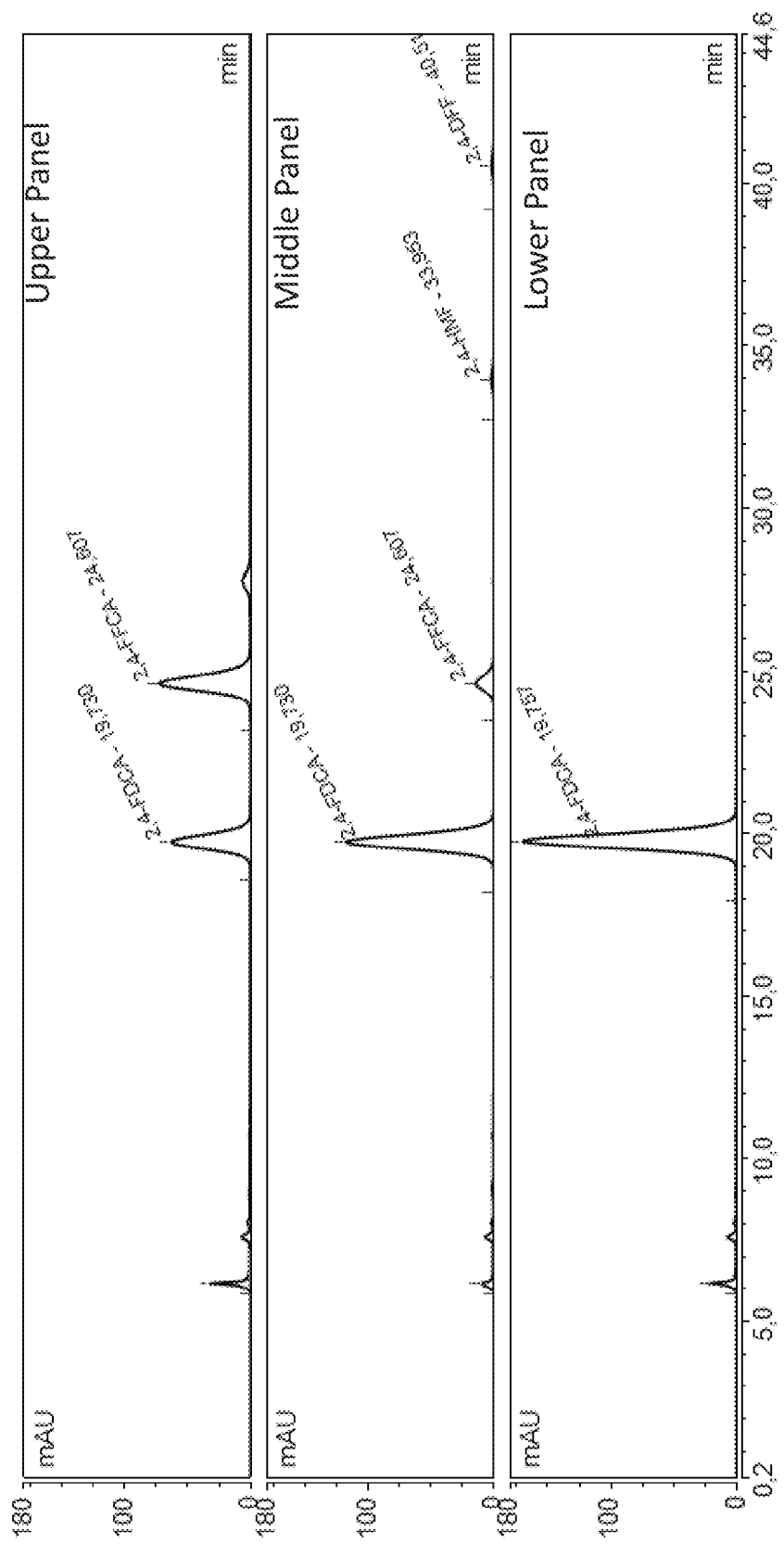
FIG. 9 is a representative UV spectra showing 2,4 FDCA production from 4-HMF by 4-HMF oxidase candidates HmfH1 (Upper Panel), HmfH6 (Middle Panel), and HmfH7 (Lower Panel) after 16 hours incubation. Reaction intermediates 4-formylfuran-2-carboxylate (2,4-FFCA) and furan-2,4-dicarbaldehyde (2,4-DFF) were also identified and quantified. The chromatographic separation was performed by HPLC-DAD.
Figure 10:
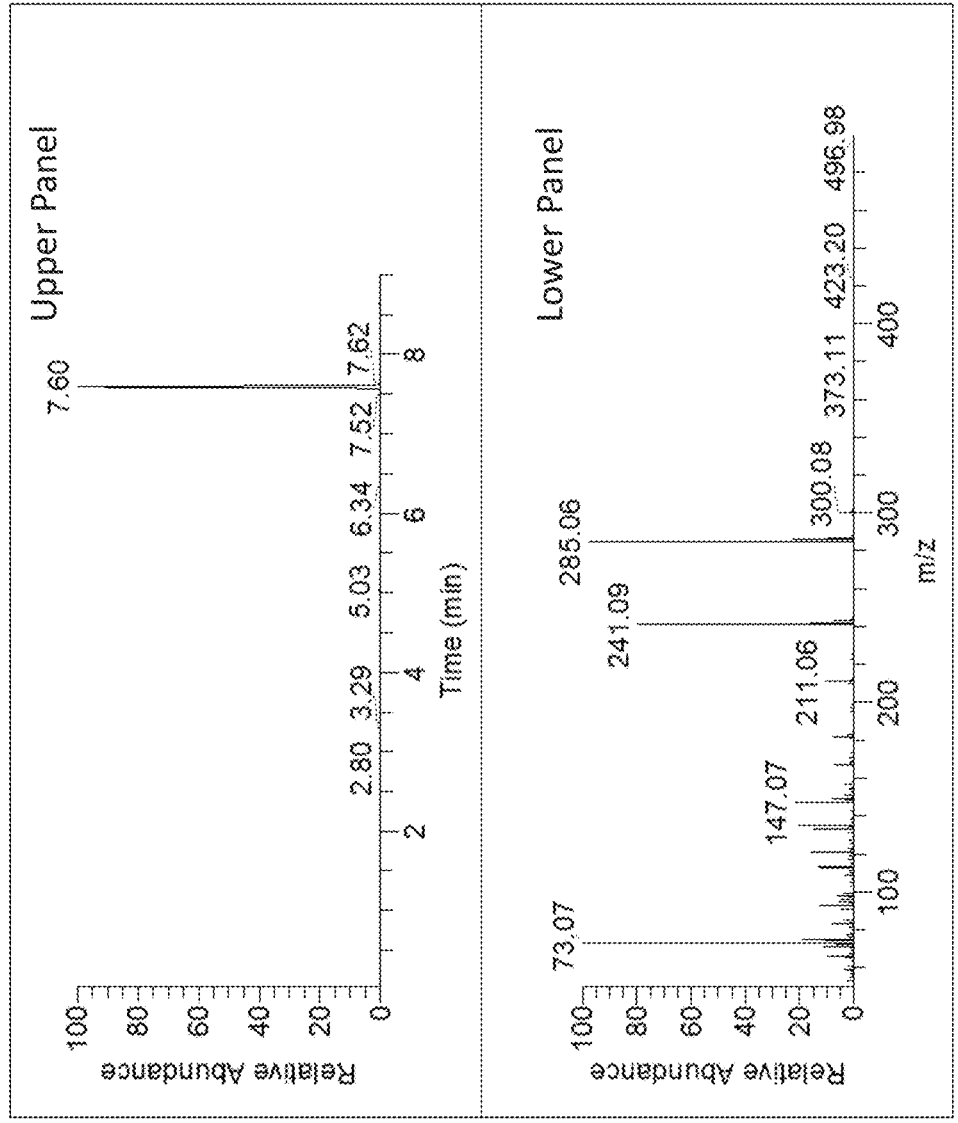
FIG. 10 is a representative GC-MS chromatogram (Upper Panel) and mass spectrum (Lower Panel) showing identification of 2,4-FDCA produced from 4-HMF with hMFh7.
Figure 11:
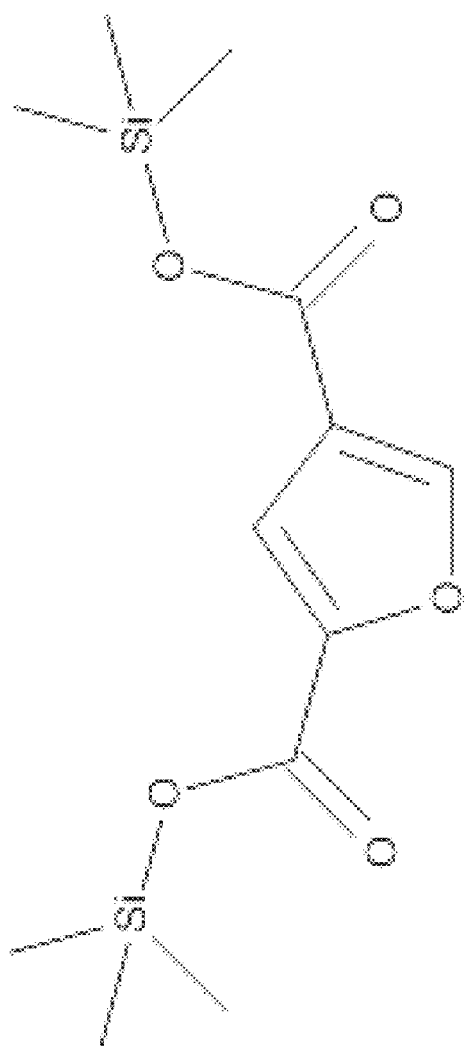
FIG. 11 is a representation of silylated 2,4-FDCA.

As shown in Table 10 and FIG. 9, FIG. 10, and FIG. 11, the conversion of 4-HMF into 2,4-FDCA was successfully demonstrated with 4-HMF oxidases, especially with enzyme HmfH7 that was able to fully convert 2,4-HMF into 2,4-FDCA.

FIG. 9 (Upper Panel) shows the chromatogram of HmfH1, FIG. 9 (Middle Panel) the chromatogram of HmfH6 and FIG. 9 (Lower Panel) the chromatogram of HmfH7. FIG. 10 (Upper Pannel) shows the relative abundance of the products obtained in GC-MS and the mass spectra (Lower Panel) of silylated 2,4-FDCA (FIG. 11).

TABLE 10

2,4 FDCA production from 4-HMF with 4-HMF oxidases candidates after 16 hours incubation. The reaction intermediates 4-formylfuran-2-carboxylate (2,4-FFCA) and furan-2,4-dicarbaldehyde (2,4-DFF) were also identified and quantified[a].

| Reaction Condition | 2,4-HMF area (mAU*min) | 2,4-FDCA area (mAU*min) | 2,4-FFCA area (mAU*min) | 2,4-DFF area (mAu*min) |
|---|---|---|---|---|
| negative control reaction | 100 | n.a. | n.a. | n.a. |
| HmfH1 | n.a. | 34,2154 | 42,5550 | n.a. |
| HmfH6 | 1,4416 | 63,9778 | 8,1581 | 1,5700 |
| HmfH7 | n.a. | 93,0784 | n.a. | n.a. |

[a]Negative control reaction was performed in similar assay condition but in absence of HMF-oxidase enzymes.

Example 6: Production of 2,4-furandimethanol from 4-HMF—Reaction C

Purified enzymes were produced as described at Example 1.

Production of 2,4-furandimethanol from 4-HMF by enzyme candidates described in Table 5 was demonstrated in vitro by incubating approximately 20 μg of purified enzyme candidates in 100 mM potassium phosphate buffer (pH 7) with 0.5 mM NAD(P)H or NADH. The reactions were started by the addition of 0.5 mM 4-HMF obtained as shown in Example 3. The decrease of NAD(P)H was monitored at 340 nm during 40 min at 37° C. on a UV-Vis spectrophotometer (SpectraMax M5, Molecular Devices). Product formation was also confirmed by HPLC and GC-MS analysis (Data not shown). Reaction vessels without enzymes or substrate (4-HMF) were used as negative controls.

Figure 12:
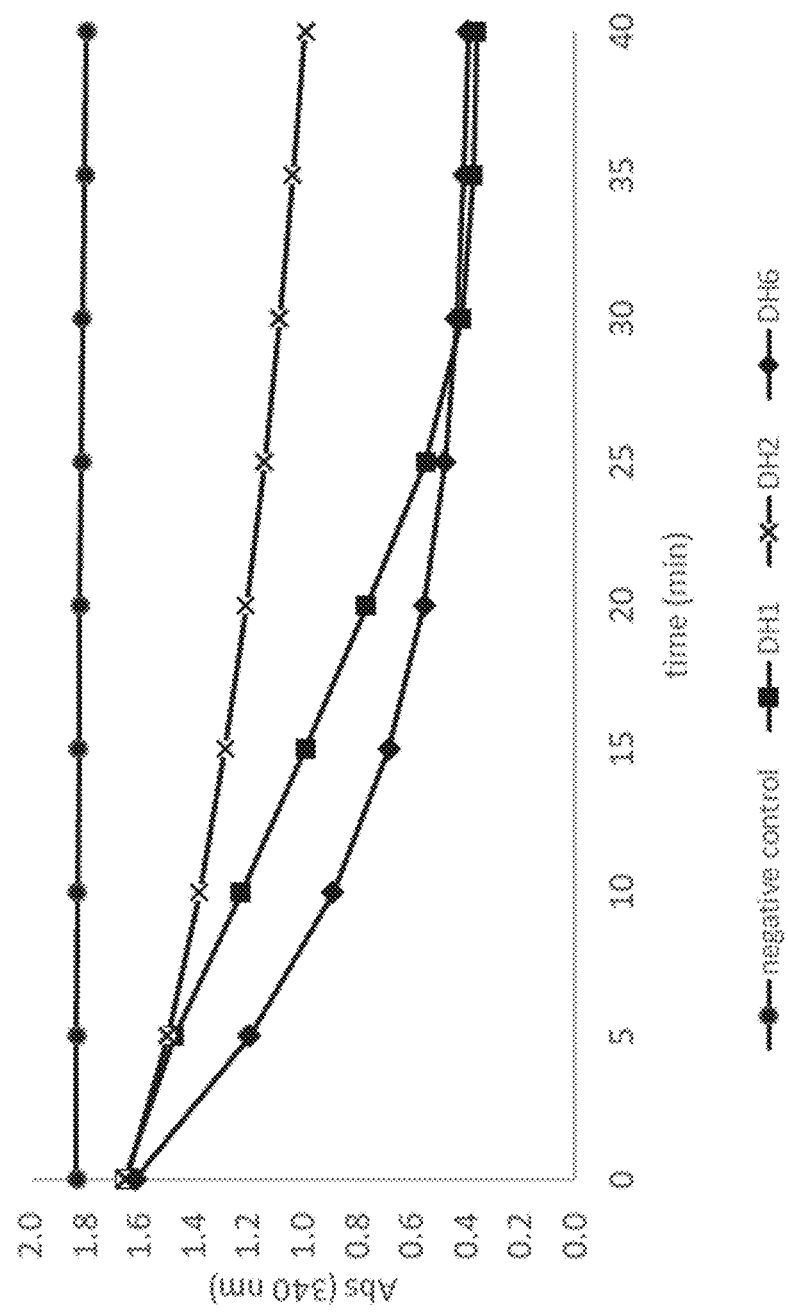
FIG. 12 is a representative plot showing NAD(P)H depletion due to its oxidation during the reduction of 2,4-HMF to 2,4-furandimethanol by 4-HMF dehydrogenase candidates DH1, DH2, or DH6.

As demonstrated in FIG. 12, enzymes candidates DH1, DH2 and DH6 promoted reduction of 2,4-HMF to 2,4-furandimethanol, measured by its oxidation of NAD(P)H to NAD(P)+.

Example 7: Production of furan-2,4-dicarbaldehyde from 4-HMF—Reaction D

Purified enzymes were produced as described in Example 1. The furan-2,4-dicarbaldehyde production from 4-HMF by enzyme candidates described at Table 3 was demonstrated in vitro by incubating approximately 20 μg of purified enzyme candidates in 100 mM potassium phosphate buffer (pH 7) with 0.5 mM NAD(P)+ or NAD+. The reactions started by the addition of 0.5 mM 4-HMF obtained as shown in Example 3. The increase of NAD(P)H was monitored at 340 nm during 40 min at 37° C. on a UV-Vis spectrophotometer (SpectraMax M5, Molecular Devices). Product formation was also confirmed by HPLC and GC-MS analysis (Data not shown). Reaction vessels without enzymes or substrate (4-HMF) were used as negative controls.

Figure 13:
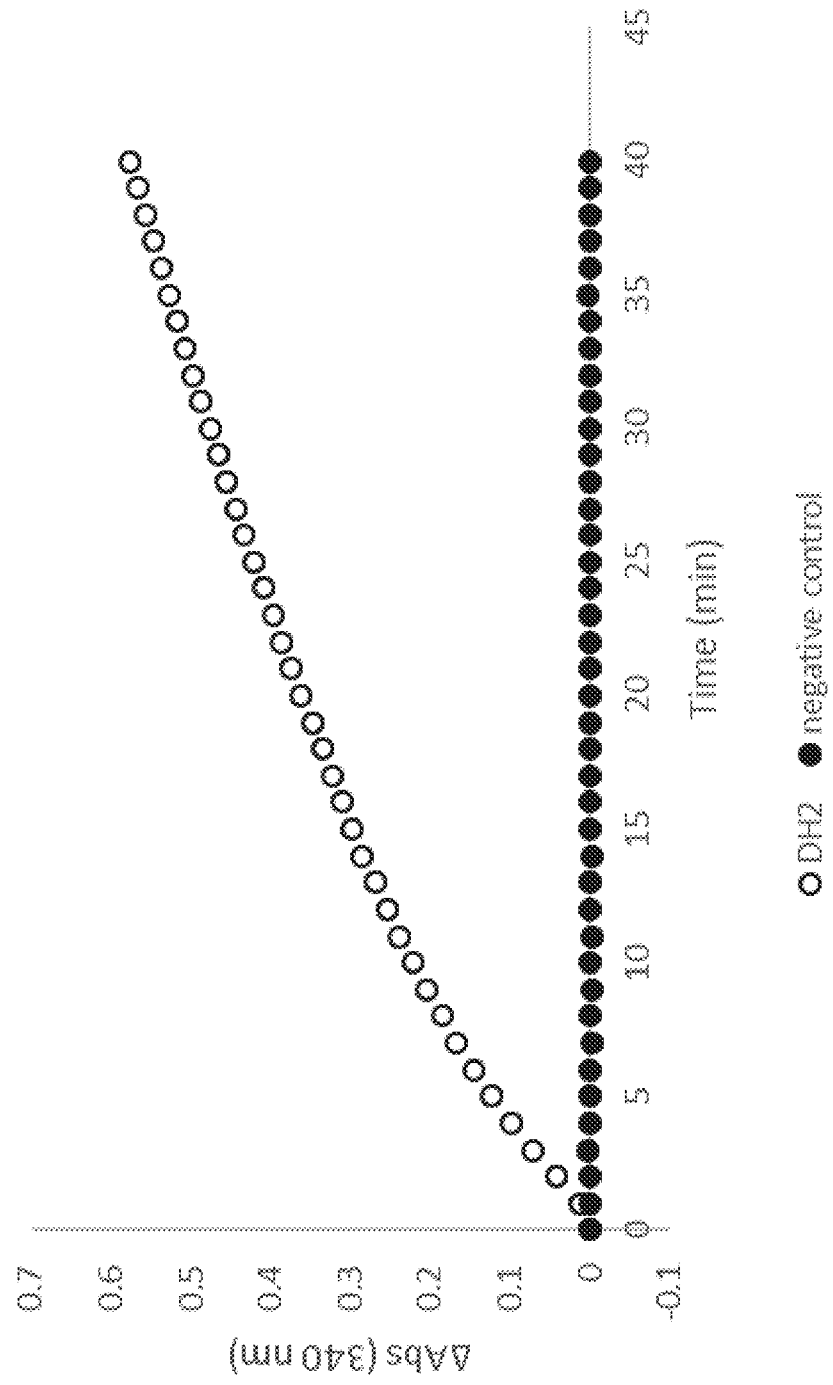
FIG. 13 is a representative plot showing NAD(P)H formation due to reduction of the cofactor and oxidation of the 2,4-HMF substrate to furan-2,4-dicaraldehyde.

As demonstrated for enzyme DH2, selected dehydrogenases are able to oxidate 4-HMF to furan-2,4-dicarbaldehyde in vitro. The data shown in FIG. 13 was plotted after subtraction of the baseline signal and highlights the absorbance increase and consequently the reduction of NAD(P)H and oxidation of 2,4-HMF to furan-2,4-dicarbaldehyde when using the enzyme DH2.

Example 8: Production of 4-(hydroxymethyl)furoic acid from 2,4-HMF—Reaction E

Purified aldehyde dehydrogenase enzymes were produced as described at Example 1. The 4-(hydroxymethyl)furoic acid production from 4-HMF by aldehyde dehydrogenase candidates described at Table 3 was demonstrated in vitro by incubating approximately 20 μg of purified enzyme candidates in 100 mM potassium phosphate buffer (pH 7) with 0.5 mM NAD(P)+ or NAD+. The reactions started by the addition of 0.5 mM 4-HMF obtained as shown in example 3. The increase of NAD(P)H was monitored at 340 nm during 40 min at 37° C. on a UV-Vis spectrophotometer (SpectraMax M5, Molecular Devices). Product formation was also confirmed by HPLC and GC-MS analysis (Data not shown). Reaction vessels without enzymes or substrate (4-HMF) were used as negative controls.

Figure 14:
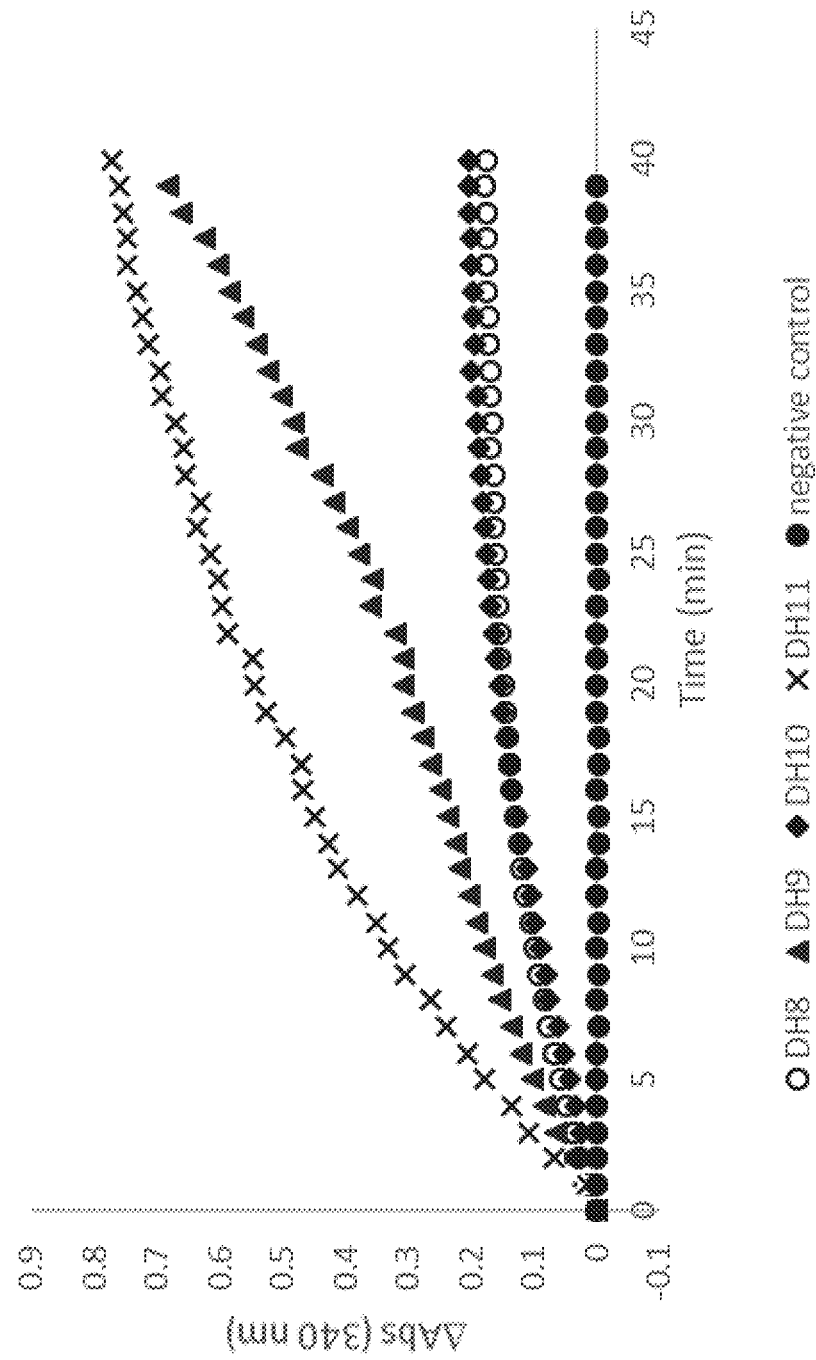
FIG. 14 is a representative plot showing NAD(P)H formation due to reduction of the cofactor and oxidation of the 2,4-HMF substrate to 4-(hydroxymethyl)furoic acid by aldehyde dehydrogenase candidates, DH8, DH9, DH10, and DH11.

As representatively demonstrated for enzymes DH8, DH9, DH10 and DH11, selected aldehyde dehydrogenases are able to oxidate 4-HMF to 4-(hydroxymethyl)furoic acid in vitro (FIG. 14). The data shown in FIG. 14 was plotted after subtraction of the baseline signal and highlights the absorbance increase and consequently the reduction of NAD(P)H and oxidation of 2,4-HMF to 4-(hydroxymethyl)furoic acid when using the respected aldehyde dehydrogenases.

Example 9: One Pot Reaction for the Production of 2,4-FDCA from 4-HMF

Purified aldehyde dehydrogenase enzymes and alcohol dehydrogenase enzymes produced as described at Example 1. The one pot oxidative reaction for 2,4-FDCA production from 4-HMF was performed using DH8 as the representative aldehyde dehydrogenase and DH6 as the representative alcohol dehydrogenase.

To carry out the reaction, 2 mL of a reaction mixture from Example 3 containing 0.5 mM of 2,4-HMF and 1 mM of NAD(P)H were added 20 uM of purified enzyme candidates DH8 and DH6. Positive control reactions were prepared as shown in Table 11. Two negative controls were prepared one without the enzymes and another one without the substrate. The reaction was incubated at 30° C. for 16 hours and both initial and final samples analyzed by HPLC-DAD. Samples were injected in HPLC-DAD and the production of 2,4-FDCA was confirmed in GC-MS using the following method.

The quantitative analysis of 2,4-FDCA was performed using HPLC-DAD (Thermo Ultimate 3000) equipped with an Aminex HPX-87H Biorad column (300×7.8 mm). The column was maintained at 50° C. The mobile phase used was a 5 mM $H_2SO_4$ solution with flow rate of 0.6 mL/min with isocratic gradient mode. The molecule was detected at 245 nm.

For GC-MS identification, initial and final samples were stopped by adding 6M HCl to reduce pH to 2-3. The products were liquid/liquid extracted using ethyl acetate and dried with $Na_2SO_4$ to remove water traces. The extracted material was then evaporated in a speedvac and derivatized using bis-(trimethylsilyl)trifluoroacetamide at 60° C. for 2 h. The samples were injected in a gas chromatograph with HP-5MS column (Agilent, 30 m×0.25 mm ID, 0.25 um film thickness) coupled with a quadrupole mass detector (ISQ, Thermo). The oven program started at 110° C. for 2 min with increasing ramp of 20° C./min until 300° C. that was hold for 3 min. Helium was used as carrier gas at a flow rate of 1.2 mL/min. 2,4-FDCA was identified by comparing their mass spectra with those in literature. (Ref: Carro, Juan, et al. "5-hydroxymethylfurfural conversion by fungal aryl-alcohol oxidase and unspecific peroxygenase." The FEBS journal 282.16 (2015): 3218-3229.) 4-formylfuran-2-carboxylate (2,4-FFCA) and furan-2,4-dicarbaldehyde (2,4-DFF) were also identified by their mass spectra.

Figure 15:
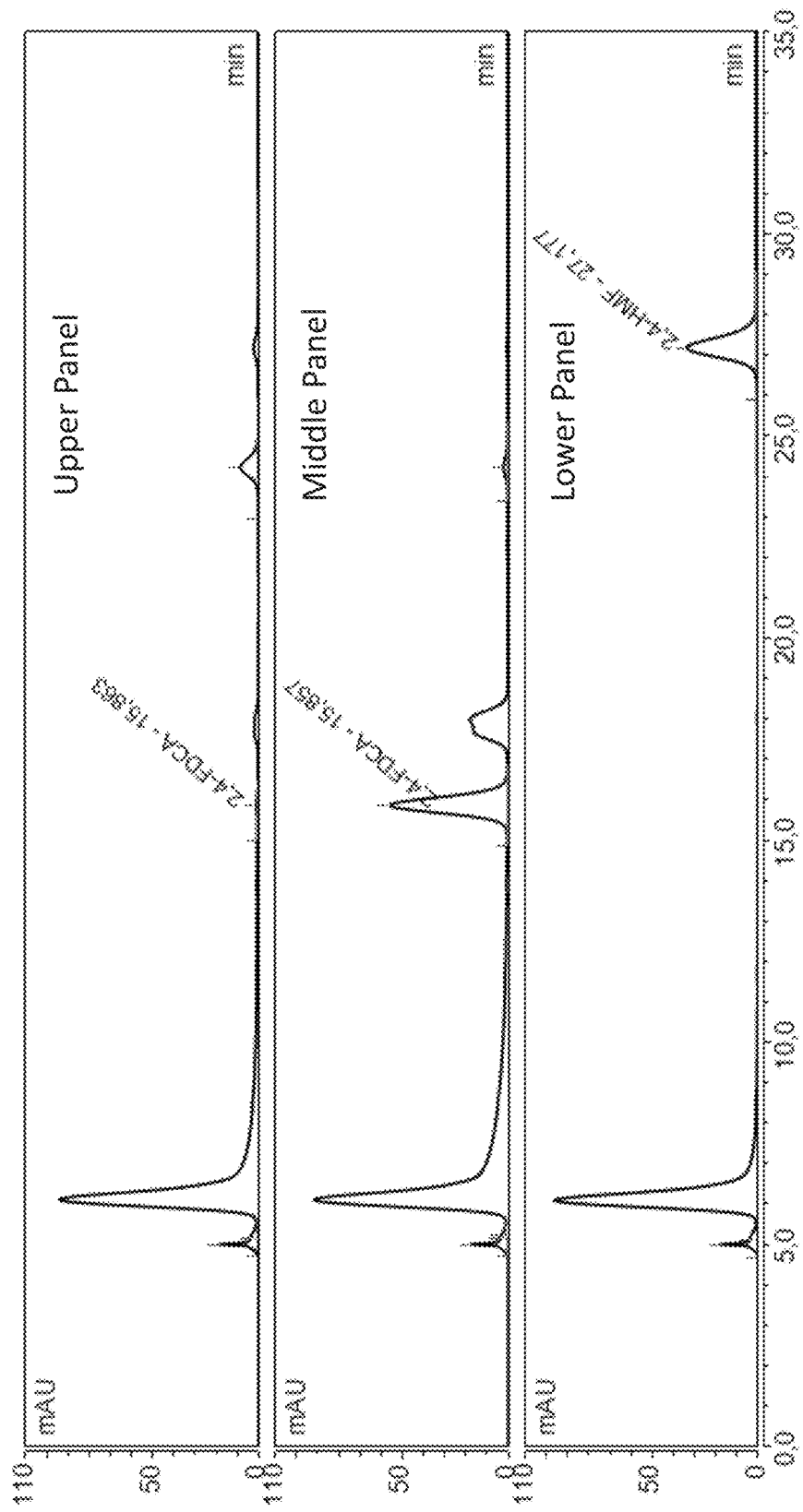
FIG. 15 is a representative chromatogram showing 2,4-FDCA production from 4-HMF by the combination of an aldehyde dehydrogenase (DH8) and an alcohol dehydrogenase (DH6). Negative control reaction (Upper Panel) performed without 4-HMF substrate. Reaction with DH8, DH6, and 4-HMF substrate (Middle Panel). Negative control reaction (Lower Panel) performed without DH6 and DH8 enzymes.

As shown in Table 11 and FIG. 15 (Middle Panel), the conversion of 4-HMF into 2,4-FDCA was successfully demonstrated with the synergic action/combination of an aldehyde dehydrogenase (DH8) and an alcohol dehydrogenase (DH6).

TABLE 11

2,4 FDCA production (2,4 FDCA peak area) from 4-HMF by the synergic action/combination of an aldehyde dehydrogenase (DH8) and an alcohol dehydrogenase (DH6) after 16 hours incubation.

| Reaction Condition | 2,4-FDCA area (mAU*min) |
| --- | --- |
| Positive reaction with enzymes DH8 + DH6 | 26,1823 |
| Negative control - No enzyme | 0,3357 |
| Negative control - No substrate | n.a. |

Example 10. In Vivo Production of 2,4-FDCA from Glucose

A plasmid containing the MfnB 1 gene (Table 1) under the control of the OXB20 promoter was constructed in a pET28a backbone. A second plasmid containing two 4-HMF oxidase genes (HmfH6 and HmfH7 (Table 4)) under the control of OXB20 promoter was constructed in a pZS*13 backbone. The plasmids were constructed using In-fusion commercial kit and were confirmed by sequencing. An *E. coli* K12 strain MG1655 (F-, λ-, rph-1, ilvG-, rfb-50, ΔgapA::gapN (UniProtKB-Q59931), ΔglcDEFGB, ΔaraFGH, ΔxylFGH, ΔfucO was used as production host.

Figure 16:
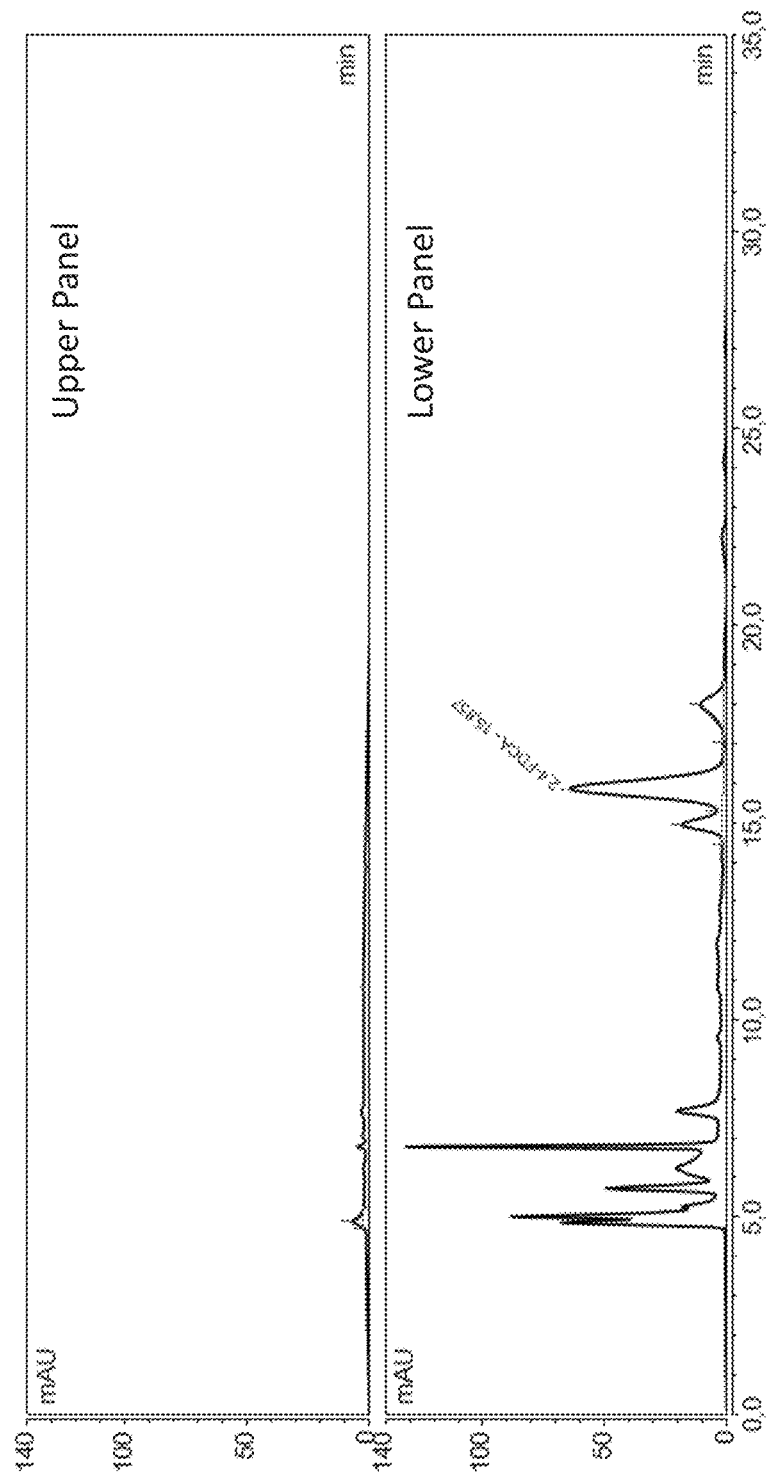
FIG. 16 is a representative chromatogram showing the 2,4-FDCA production in vivo from glucose fermentation at $t_0$ (Upper Panel) and $t_{48h}$ (Lower Panel).

The in vivo production of 2,4-FDCA from glucose was evaluated in shake flask fermentations in triplicate, using a defined media composed by 2.2 g·L$^{-1}$ KH$_2$PO$_4$, 9.4 g·L$^{-1}$ K$_2$HPO$_4$, 1.3 g·L$^{-1}$ (NH$_4$)$_2$SO$_4$, 10 mg·L$^{-1}$ thiamine, 320 mg·L$^{-1}$ EDTA-NaOH, 2 mg·L$^{-1}$ CoCl$_2$.6H$_2$O, 10 mg·L$^{-1}$ MnSO$_4$.H$_2$O, 5 mg·L$^{-1}$ CuSO$_4$.5H$_2$O, 2 mg·L$^{-1}$ H$_3$BO$_3$, 2 mg·L$^{-1}$ Na$_2$MoO$_4$.2H$_2$O, 54 mg·L$^{-1}$ ZnSO$_4$.7H$_2$O, 1 mg·L$^{-1}$ NiSO$_4$.6H$_2$O, 100 mg·L$^{-1}$ citrate Fe (III), 100 mg·L$^{-1}$ CaCl$_2$.2H$_2$O, 0.3 g·L$^{-1}$ MgSO$_4$.H$_2$O. Carbon source was provided by 10 g/L glucose and nitrogen sulphate was used as nitrogen source. Erlenmeyer flasks were inoculated with the recombinant strain to an initial OD of 0.1, and incubated at 37° C., 225 rpm for 48 hours. Analysis of supernatant in 48 h by HPLC indicated the production of 14±2 mg/L 2,4-FDCA (FIG. 16).

The invention claimed is:

1. A method of producing 2,4-furandicarboxylic acid (2,4-FDCA) comprising fermenting a recombinant microorganism in a culture medium containing a carbon source, wherein the recombinant microorganism expresses the following:
   (a) endogenous or exogenous nucleic acid molecules capable of converting a carbon source to glyceraldehyde 3-phosphate (G3P);
   (b) at least one exogenous or exogenous nucleic acid molecule encoding a (5-formylfuran-3-yl)methyl phosphate synthase that catalyzes the conversion of G3P from (a) to (5-formylfuran-3-yl)methyl phosphate;
   (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); and
   (d) at least one endogenous or exogenous nucleic acid molecule encoding a peroxygenase, dehydrogenase, or a oxidase that catalyzes independently or in combination the oxidation of 4-HMF from (c) to 2,4-FDCA, directly or through the production of intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

2. The method of claim 1, wherein the carbon source comprises a hexose, a pentose, glycerol, $CO_2$, sucroses or combinations thereof.

3. The method of claim 1, wherein the recombinant microorganism is derived from a parental microorganism selected from the group consisting of Clostridium sp., Clostridium ljungdahlii, Clostridium autoethanogenum, Clostridium ragsdalei, Eubacterium limosum, Butyribacterium methylotrophicum, Moorella thermoacetica, Corynebacterium glutamicum, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Candida krusei, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Issatchenkia orientalis, Sporomusa termitida, Moorella glycerini, Eubacterium aggregans, Treponema azotonutricium, Pichia kudriavzevii, Escherichia coli, Saccharomyces cerevisiae, Pseudomonas putida, Bacillus sp, Corynebacterium sp., Yarrowia lipolytica, Scheffersomyces stipitis, and Terrisporobacter glycolicus.

4. The method of claim 1, wherein the 2,4-FDCA is recovered or isolated by a process selected from distillation, membrane-based separation, gas stripping, precipitation, solvent extraction, expanded bed adsorption, or a combination thereof.

5. A method of producing a polymer comprising: (1) fermenting a recombinant microorganism in a culture medium containing a carbon source until 2,4-furandicarboxylic acid (2,4-FDCA) monomer is produced; and (2) polymerizing the 2,4-FDCA monomer to produce the polymer; wherein the recombinant microorganism expresses the following:
- (a) endogenous or exogenous nucleic acid molecules capable of converting a carbon source to glyceraldehyde 3-phosphate (G3P);
- (b) at least one exogenous nucleic acid molecule encoding a (5-formylfuran-3-yl)methyl phosphate synthase that catalyzes the conversion of G3P from (a) to (5-formylfuran-3-yl)methyl phosphate;
- (c) at least one endogenous or exogenous nucleic acid molecule encoding a phosphatase that catalyzes the conversion of (5-formylfuran-3-yl)methyl phosphate from (b) to 4-hydroxymethylfurfural (4-HMF); and
- (d) at least one endogenous or exogenous nucleic acid molecule encoding a peroxygenase, dehydrogenase, or a oxidase that catalyzes independently or in combination the oxidation of 4-HMF from (c) to 2,4-FDCA, directly or through the production of intermediates furan-2,4-dicarbaldehyde, 4-(hydroxymethyl)furoic acid, 4-formylfuran-2-carboxylate, 4-formylfuran-2-carboxylate, and/or 2-formylfuran-4-carboxylate.

6. The method of claim 5, wherein the polymer is a polyester.

7. The method of claim 6, wherein the polyester is produced from the polymerization of the 2,4-FDCA monomer with a diol.

8. The method of claim 7, wherein the diol is selected from: ethylene glycol, 1,3-propanediol, 1,2-propanediol, 1,4-butanediol, 1,3-butanediol, 2,3-butanediol, 1,5-pentanediol, or 1,6-hexanediol.

9. The method of claim 6, wherein the 2,4-FDCA and a diol are catalytically polymerized using a catalyst in a non-biological process.

10. The method of claim 9, wherein the catalyst is selected from: a titanium-based catalyst, a germanium-based catalyst, a magnesium-based catalyst, a silicon-based catalyst, an aluminum-based catalyst, or an antimony-based catalyst.

11. The method of claim 9, wherein the catalyst is selected from: antimony acetate, antimony trioxide, germanium dioxide, tetra-isopropyl titanate, or tetra-n-butyl titanate.

12. The method of claim 5, wherein the carbon source comprises a hexose, a pentose, glycerol, $CO_2$, sucroses or combinations thereof.

13. The method of claim 5, wherein the recombinant microorganism is derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Corynebacterium glutamicum*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Candida krusei*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Issatchenkia orientalis*, *Sporomusa termitida*, *Moorella glycerini*, *Eubacterium aggregans*, *Treponema azotonutricium*, *Pichia kudriavzevii*, *Escherichia coli*, *Saccharomyces cerevisiae*, *Pseudomonas putida*, *Bacillus* sp, *Corynebacterium* sp., *Yarrowia lipolytica*, *Scheffersomyces stipitis*, and *Terrisporobacter glycolicus*.

14. The method of claim 5, further comprising recovering or isolating the produced 2,4-FDCA monomer by a process selected from distillation, membrane-based separation, gas stripping, precipitation, solvent extraction, expanded bed adsorption, or a combination thereof prior to polymerizing the 2,4-FDCA monomer.

* * * * *